US011492341B2

(12) United States Patent
Leit de Moradei et al.

(10) Patent No.: US 11,492,341 B2
(45) Date of Patent: Nov. 8, 2022

(54) ACLY INHIBITORS AND USES THEREOF

(71) Applicant: Nimbus Artemis, Inc., Cambridge, MA (US)

(72) Inventors: Silvana Marcel Leit de Moradei, Burlington, MA (US); Kevin Kreutter, Arlington, MA (US); H. James Harwood, Ledyard, CT (US); Eric Therrien, Bronx, NY (US)

(73) Assignee: Nimbus Artemis, Inc., Cambridge, MA (US)

( * ) Notice: Subject to any disclaimer, the term of this patent is extended or adjusted under 35 U.S.C. 154(b) by 0 days.

(21) Appl. No.: 16/684,644

(22) Filed: Nov. 15, 2019

(65) Prior Publication Data
US 2020/0157076 A1 May 21, 2020

Related U.S. Application Data

(60) Provisional application No. 62/877,582, filed on Jul. 23, 2019, provisional application No. 62/768,735, filed on Nov. 16, 2018.

(51) Int. Cl.
| | | |
|---|---|---|
| *C07D 401/12* | (2006.01) | |
| *C07D 205/04* | (2006.01) | |
| *C07D 207/48* | (2006.01) | |
| *C07D 239/92* | (2006.01) | |
| *C07D 491/107* | (2006.01) | |
| *C07D 487/04* | (2006.01) | |
| *C07D 295/26* | (2006.01) | |
| *C07D 211/96* | (2006.01) | |
| *C07D 217/08* | (2006.01) | |
| *C07D 417/04* | (2006.01) | |
| *C07D 241/04* | (2006.01) | |
| *C07D 241/50* | (2006.01) | |
| *C07D 403/06* | (2006.01) | |
| *C07D 403/04* | (2006.01) | |
| *C07D 409/12* | (2006.01) | |
| *C07D 401/04* | (2006.01) | |
| *C07D 401/14* | (2006.01) | |
| *C07D 403/10* | (2006.01) | |
| *C07D 209/08* | (2006.01) | |

(52) U.S. Cl.
CPC ......... *C07D 401/12* (2013.01); *C07D 205/04* (2013.01); *C07D 207/48* (2013.01); *C07D 209/08* (2013.01); *C07D 211/96* (2013.01); *C07D 217/08* (2013.01); *C07D 239/92* (2013.01); *C07D 241/04* (2013.01); *C07D 241/50* (2013.01); *C07D 295/26* (2013.01); *C07D 401/04* (2013.01); *C07D 401/14* (2013.01); *C07D 403/04* (2013.01); *C07D 403/06* (2013.01); *C07D 403/10* (2013.01); *C07D 409/12* (2013.01); *C07D 417/04* (2013.01); *C07D 487/04* (2013.01); *C07D 491/107* (2013.01)

(58) Field of Classification Search
CPC ... C07D 401/12; C07D 205/04; C07D 207/48
See application file for complete search history.

(56) References Cited

U.S. PATENT DOCUMENTS

| | | | |
|---|---|---|---|
| 2004/0162276 A1 | 8/2004 | Tabart et al. | |
| 2010/0075963 A1 | 3/2010 | Lehr et al. | |
| 2011/0245315 A1 | 10/2011 | Chen et al. | |
| 2014/0288126 A1* | 9/2014 | Adams | A61P 13/12 |
| | | | 514/339 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802. (Year: 1995).*
Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*
Patani et al. ("Bioisosterism: A Rational Approach in Drug Design." Chem. Rev., 1996, 96 (8), pp. 3147-3176). (Year: 1996).*
Abu-Elheiga et al., "Acetyl-CoA carboxylase 2 mutant mice are protected against obesity and diabetes induced by high-fat/high-carbohydrate diets," Proc. Natl. Acad. Sci. USA, 2003, vol. 100, No. 18, pp. 10207-10212.
Abu-Elheiga et al., "Mutant mice lacking acetyl-CoA carboxylase 1 are embryonically lethal," Proc. Natl. Acad. Sci. USA, 2005, vol. 102, No. 34, pp. 12011-12016.
Ballantyne et al., "ETC-1002 Lowers LDL-C and beneficially modulates other cardio-metabolic risk factors in hypercholesterolemic subjects with either normal or eleveated triglycerides," J. Am. Coll. Cardiol, 2012, vol. 59, No. 13, Supplement, E1625.
Barafiano et al., "The ketogenic diet: uses in epilepsy and other neurologic illnesses," Curr. Treat. Opin. Neurol., 2008, vol. 10, No. 6, pp. 410-419.
Beckers et al. "Chemical Inhibition of Acetyl-CoA Carboxylase Induces Growth Arrest and Cytotoxicity Selectivity in Cancer Cells," Cancer Res., 2007, vol. 67, No. 17, pp. 8180-8187.
Berge et al., "Pharmaceutical salts", J. Pharmaceutical Sciences, 1977, vol. 66, No. 1, pp. 1-19.
Berkhout et al., "The effect of (−)-hydroxycitrate on the activity of the low-density-lipoprotein receptor and 3-hydroxy-3-methylglutaryl-CoA reductase levels in the human hepatoma cell line Hep G2," Biochem J, 1990, vol. 272, No. 1, pp. 181-186.
Brunet et al., "BRCA1 and Acetyl-CoA Carboxylase: The Metabolic Syndrome of Breast Cancer," Molecular Carcinogenesis, 2008, vol. 47, No. 2, pp. 157-163.

(Continued)

*Primary Examiner* — Jeffrey S Lundgren
*Assistant Examiner* — Chris E Simmons
(74) *Attorney, Agent, or Firm* — Andrea L. C. Reid; Joseph W. Arico; Dechert LLP

(57) ABSTRACT

The present invention provides compounds useful as inhibitors of ATP citrate lyase (ACLY), compositions thereof, and methods of using the same.

8 Claims, No Drawings

(56) References Cited

OTHER PUBLICATIONS

Brusselmans et al. "RNA Interference-Mediated Silencing of the Acetyl-CoA-Carboxylase-alpha Gene Induces Growth Inhibition and Apoptosis of Prostate Cancer Cells" Cancer Res., 2005, vol. 65, No. 15, pp. 6719-6725.
Cairns et al., "Regulation of Cancer Cell Metabolism," Nat Rev Cancer, 2011, vol. 11, No. 2, pp. 85-95.
Chajès et al., "Acetyl-CoA Carboxylase alpha Is Essential to Breast Cancer Cell Survival," Cancer Res., 2006, vol. 66, No. 10, 5287-5294.
Cheng et al., "Synthesis and structure-activity relationship of small-molecule malonyl coenzyme A decarboxylase inhibitors," J. Med. Chem., 2006, vol. 49, No. 5, pp. 1517-1525.
Chiaradonna et al., "From Cancer Metabolism to New Biomarkers and Drug Targets," Biotechnology Advances, 2012, vol. 30, No. 1, pp. 30-51.
Costantini et al., "Hypometabolism as a therapeutic target in Alzheimer's disease," BMC Neurosci., 2008, vol. 9, Suppl. 2, S16, 9 pages.
Ference et al., "Genetic target validation for ATP-Citrate Lyase inhibition," J. Am. Col. Cardio, 2017, vol. 69, Suppl. 11, 1655.
Furler et al., "The ACC inhibitor CP-640186 acutely increases muscle fatty acid clearance independent of glucose clearance and cellular energy demand," 2006, Diabetes, 55: A333.
Harwood et al., "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals," J. Biol. Chem., 2003, vol. 278, pp. 37099-37111.
Harwood Jr., "Treating the metabolic syndrome: Acetyl-CoA carboxylase inhibition," Expert Opin Ther Targets, 2005, vol. 9, pp. 267-281.
Hatzivassiliou et al., "ATP citrate lyase inhibition can suppress tumor cell growth," Cancer Cell, 2005, vol. 8, No. 4, pp. 311-321.
Henderson et al., "Ketone bodies as a therapeutic for Alzheimer's disease," Neurotherapeutics, 2008, vol. 5, No. 3, pp. 470-480.
Infantino et al., "ATP-citrate lyase is essential for macrophage inflammatory response," Biochemical and Biophysical Research Communications, 2009, vol. 440, No. 1, pp. 105-111.
International Search Report and Written Opinion for Application No. PCT/US2019/061589, dated Jan. 23, 2020 (8 pages).
Kolwicz Jr. et al. "Cardiac-specific deletion of acetyl CoA carboxylase 2 prevents metabolic remodeling during pressure-overload hypertrophy," Circ. Res., 2012, vol. 111, No. 6, pp. 728-738.
Lawitz et al., "Acetyl-CoA carboxylase (ACC) inhibitor GS-0976 leads to suppression of hepatic de novo lipogenesis and significant improvements in MRI-PDFF, MRE, and markers of fibrosis after 12 weeks of therapy in patients with NASH," J Hepatol, 2017, vol. 66, No. 1, p. S34.
Makowski et al. "Role of LKB1 in Lung Cancer Development" British Journal of Cancer, 2008, 99, pp. 683-688.
Migita et al., "ATP Citrate Lyase: Activation and Therapeutic Implications in Non-Small Cell Lung Cancer," Cancer Research, 2008, vol. 68, No. 20, pp. 8547-8554.
Olsen et al., "Fatty acid synthesis is a therapeutic target in human liposarcoma," International J. of Oncology, 2010, vol. 36, No. 5, pp. 1309-1314.

Pearce et al., "The role of ATP citrate-lyase in the metabolic regulation of plasma lipids. Hypolipidaemic effects of SB-204990, a lactone prodrug of the potent ATP citrate-lyase inhibitor SB-201076," Biochem J, 1998, vol. 34, No. 1, pp. 113-119.
Petti et al., "AMPK activators inhibit the proliferation of human melanomas bearing the activated MAPK pathway," Melanoma Research, 2012, vol. 22, No. 5, pp. 341-350.
Pietrocolo et al., "Acetyl coenzyme A: a central metabolite and second messenger," Cell Metabolism, 2015, vol. 21, No. 6, pp. 805-821.
Pubchem. CID 10356663. Oct. 25, 2006, pp. 1-12. Retrieved from the Internet <URL: https://pubchem.ncbi.nlm.nih.gov/compound/10356663>.
Pubchem. CID 315017. Mar. 26, 2005, pp. 1-21. Retrieved from the Internet <URL: https://pubchem.ncbi.nlm.nih.gov/compound/315017>.
Saha et al., "Reversal of insulin resistance in rat muscle by the acetyl-CoA carboxylase inhibitor CP-640186," 2006, Diabetes, 55: A288.
Savage et al., "Reversal of diet-induced hepatic steatosis and hepatic insulin resistance by antisense oligonucleotide inhibitors of acetyl-CoA carboxylases 1 and 2," J. Clin. Invest., 2006, vol. 116, No. 3, pp. 817-824.
Steide et al., "Acetyl-coenzyme A carboxylase inhibition reduces de novo lipogenesis in overweight male subjects: A randomized, double-blind, crossover study," Hepatology, 2017, vol. 66, No. 2, pp. 324-334.
Svensson et al. "Lipid Synthesis Is a Metabolic Liability of Non-Small Cell Lung Cancer," Cold Spring Harbor Symp Quant Biol, 2017, vol. 81, pp. 93-103.
Tong et al., "Acetyl-coenzyme A carboxylases: Versatile targets for drug discovery," J. Cellular Biochem., 2006, vol. 99, No. 6, pp. 1476-1488.
Tong et al., "Acetyl-coenzyme A carboxylase: crucial metabolic enzyme and attractive target for drug discovery," Cell and Molecular Life Sciences, 2005, vol. 62, No. 16, pp. 1784-1803.
Varis et al., "Targets of Gene Amplification and Overexpression at 17q in Gastric Cancer," Cancer Research, 2002, vol. 62, pp. 2625-2629.
Wang et al., "Deficiency in hepatic ATP-citrate lyase affects VLDL-triglyceride mobilization and liver fatty acid composition in mice," J Lipid Research, 2010, vol. 51, No. 9, pp. 2516-2526.
Wang et al., "Abrogation of hepatic ATP-citrate lyase protects against fatty liver and ameliorates hyperglycemia in leptin receptor-deficient mice," Hepatology, 2009, vol. 49, No. 4, pp. 1166-1175.
Wang et al., "Acetyl-CoA Carboxylase-alpha Inhibitor TOFA Induces Human Cancer Cell Apoptosis," Biochem Biophys Res Commun., 2009, vol. 385, No. 3, pp. 302-306.
Yancy et al., "Metastatic progression and gene expression between breast cancer cell lines from African American and Caucasian women," J Carcinog, 2007, vol. 6, No. 8, 12 pages.
Zhang et al., "Cullin3-KLHL25 ubiquitin ligase targets ACLY for degradation to inhibit lipid synthesis and tumor progression," Genes and Development, 2016, vol. 30, pp. 1956-1970.
Zhao et al., "ATP-citrate lyase controls a glucose-to-acetate metabolic switch," Cell Reports, 2016, vol. 17, No. 4, pp. 1037-1052.

* cited by examiner

ACLY INHIBITORS AND USES THEREOF

RELATED APPLICATIONS

This application claims the benefit of U.S. Provisional application 62/768,735, filed on Nov. 16, 2018, and U.S. Provisional application 62/877,582, filed on Jul. 23, 2019, the contents of each of which are incorporated herein in their entireties.

BACKGROUND OF THE INVENTION

ATP citrate lyase (ACLY) is a homotetrameric enzyme that catalyzes the ATP dependent cleavage of citrate into acetyl coenzyme A (acetyl-CoA) and oxaloacetate (OAA). Acetyl-CoA is an important cellular metabolite and second messenger, thus ACLY enzymatic activity is positioned at the nexus of intermediary metabolism. The acetyl-CoA forming reaction is initiated upon phosphorylation of ACLY at histidine 760, which then catalyzes the formation of citryl phosphate followed by the formation of a citryl-CoA intermediate after a CoA attack. Finally, the citryl-CoA intermediate is cleaved, and acetyl-CoA and OAA are released. ACLY derived acetyl-CoA serves as the carbon source for the production of cholesterol in the mevalonate pathway and fatty acids (FA) in the de novo lipogenesis (DNL) pathway, and is also required for protein acetylation, thus linking cellular metabolism with the epigenome and gene regulation. Acetyl-CoA production therefore functions as a key metabolic checkpoint used by cells to coordinate cellular metabolism in response to nutrients and plays a key role in sterol and lipid production in a number of tissues. Thus, direct inhibition of ACLY activity may have important therapeutic implications for treating a wide range of diseases including hypercholesteremia and cardiovascular disease (CVD), obesity, diabetes, insulin resistance, fatty liver disease, metabolic syndrome and cancer.

SUMMARY OF THE INVENTION

It has now been found that compounds of this invention, and pharmaceutically acceptable compositions thereof, are effective as inhibitors of ATP citrate lyase (ACLY). Such compounds have the general formula I:

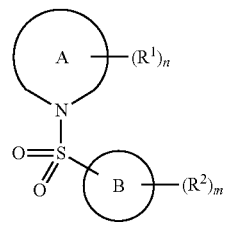

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of the production of sterols or lipids. Such diseases, disorders, or conditions include those described herein.

Compounds provided by this invention are also useful for the study of ACLY enzymes in biological and pathological phenomena; the study of intracellular signal transduction pathways occurring in lipogenic tissues; and the comparative evaluation of new ACLY inhibitors or other regulators of fatty acid levels in vitro or in vivo.

DETAILED DESCRIPTION OF CERTAIN EMBODIMENTS

1. General Description of Compounds of the Invention

In certain embodiments, the present invention provides a compound of formula I:

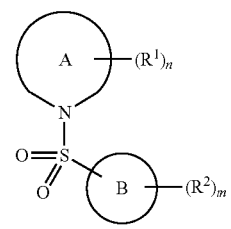

or a pharmaceutically acceptable salt thereof, wherein:

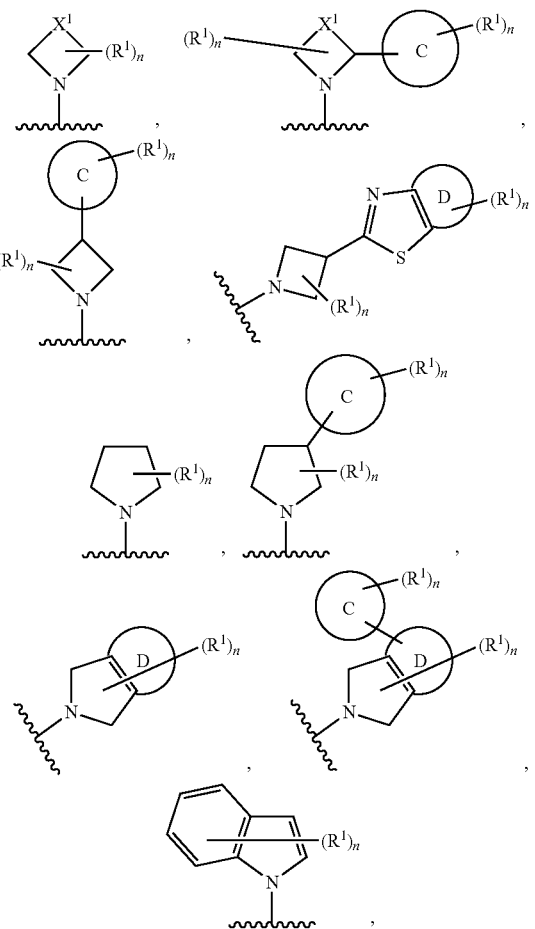

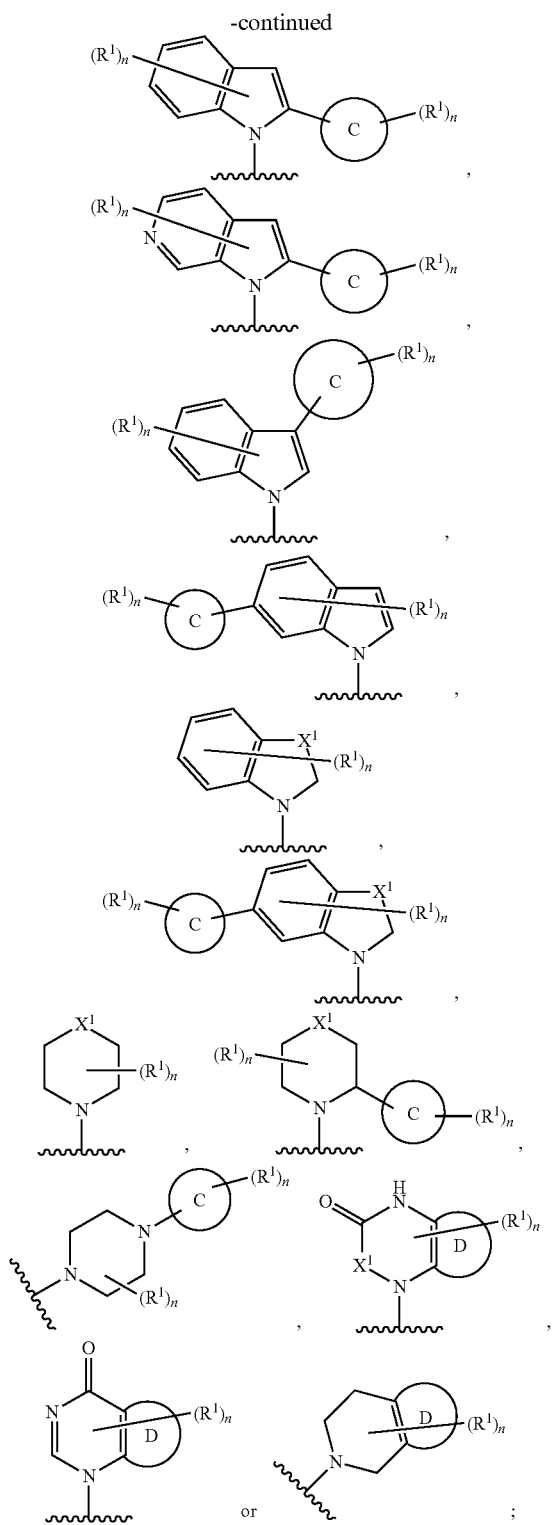

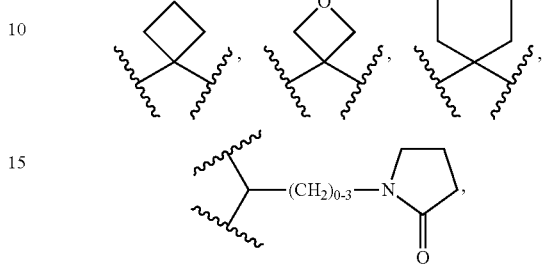

Ring D is a fused ring selected from benzo or 5-6 membered heteroaro-having 1-2 heteroatoms independently selected from nitrogen, oxygen, and sulfur;

$X^1$ is a bivalent moiety selected from —$CH_2$—, —CH($R^1$)—, —C($R^1$)$_2$—, —C(O)—, or —O—;

each $R^1$ is independently hydrogen, —$R^3$, halogen, —CN, —$NO_2$, —OR, —SR, —$NR_2$, —S(O)$_2$R, —S(O)$_2$$NR_2$, —S(O)R, —C(O)R, —C(O)OR, —C(O)$NR_2$, —C(O)N(R)OR, —OC(O)R, —OC(O)$NR_2$, —OPh, —C(R)$_2$Ph, —C(R)$_2$OR, —C(R)$_2$C(O)OR, —C(R)$_2$C(O)$NR_2$, —$CH_2$C(R)$_2$C(O)OR, —$CH_2$C(R)$_2$C(O)$NR_2$, —$CH_2$OPh, —N(R)C(O)OR, —N(R)C(O)R, —N(R)C(O)$NR_2$, —N(R)S(O)$_2$R, or —N(R)S(O)$_2$$NR_2$;

or two instances of $R^1$ are optionally taken together to form an oxo;

or $R^1$ at N forms an N-oxide;

each R is independently hydrogen, or an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

each $R^2$ is independently hydrogen, —$R^3$, halogen, —CN, —$NO_2$, —OR, —OC(R)$_2$Ph, —SR, —$NR_2$, —S(O)$_2$R, —S(O)$_2$$NR_2$, —S(O)R, —C(O)R, —C(O)OR, —C(O)$NR_2$, —C(O)N(R)OR, —OC(O)R, —OC(O)$NR_2$, —C(R)$_2$OR, —C(R)$_2$C(O)OR, —C(R)$_2$C(O)$NR_2$, —$CH_2$C(R)$_2$C(O)OR, —$CH_2$C(R)$_2$C(O)$NR_2$, —N(R)C(O)OR, —N(R)C(O)R, —N(R)C(O)$NR_2$, —N(R)S(O)$_2$R, or —N(R)S(O)$_2$$NR_2$;

or two instances of $R^2$ are optionally taken together to form an oxo;

each $R^3$ is independently an optionally substituted group selected from $C_{1-6}$ aliphatic, phenyl, a 3-7 membered saturated or partially unsaturated carbocyclic ring, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, 2, 3, or 4; and each m is 0, 1, 2, 3, or 4.

Ring A is a mono-, bi-, or tricyclic ring selected from

Ring B is a ring selected from phenyl or 5-6 membered heteroaryl having 1-3 heteroatoms independently selected from nitrogen, oxygen, and sulfur;

Ring C is a ring selected from phenyl or 5-6 membered heteroaryl having 1-3 heteroatoms independently selected from nitrogen, oxygen, and sulfur;

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

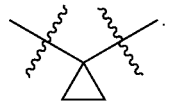 [SMILES: *C1(*)CC1]

As used herein, the term "cyclobutylenyl" refers to a bivalent cyclobutyl group of the following structure:

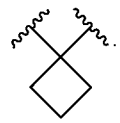 [SMILES: *C1(*)CCC1]

As used herein, the term "oxetanyl" refers to a bivalent oxetanyl group of the following structure:

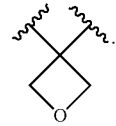

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl", "heteroaro-", and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl", "heteroaro-", and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —$O$—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —$CH=CHPh$, which may be substituted with $R°$; —$(CH_2)_{0-4}O(CH_2)_{0-1}$-pyridyl which may be substituted with $R°$; —$NO_2$; —$CN$; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)$O$—$N(R°)_2$; or —$(C_{1-4}$ straight or branched)alkylene)$C(O)O$—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —$CN$, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

3. Description of Exemplary Embodiments

In certain embodiments, the present invention provides inhibitors of ACLY. In some embodiments, such compounds include those of formula I:

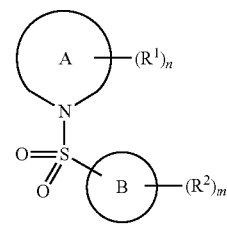

I or a pharmaceutically acceptable salt thereof, wherein:
Ring A is a mono-, bi-, or tricyclic ring selected from

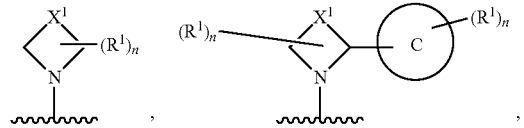

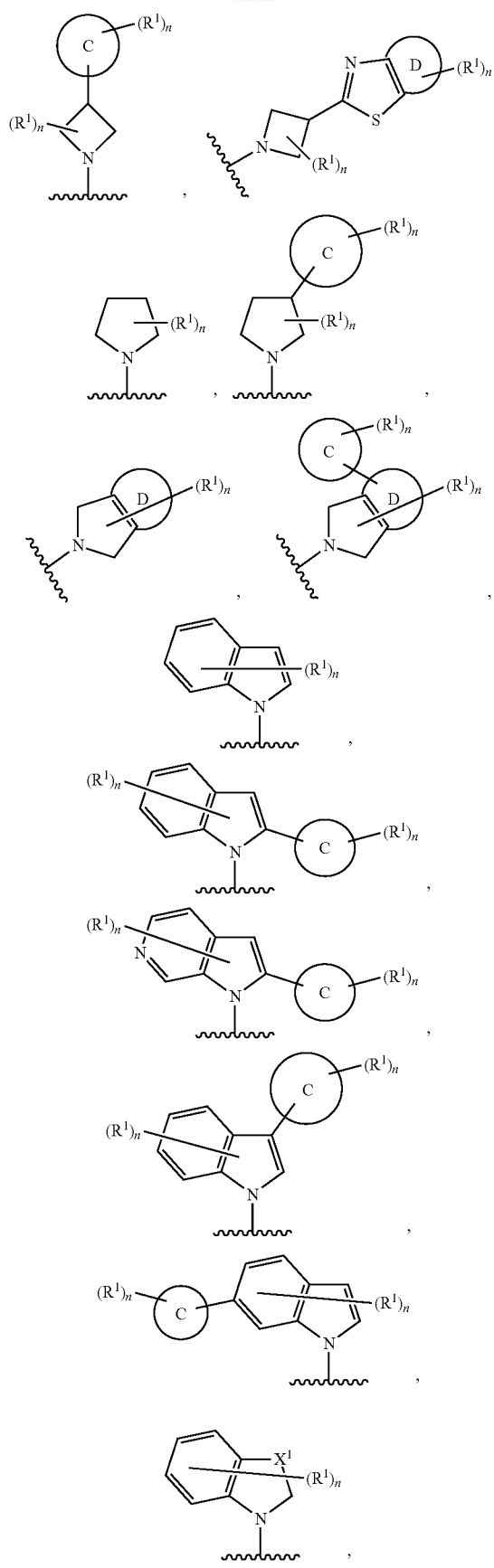

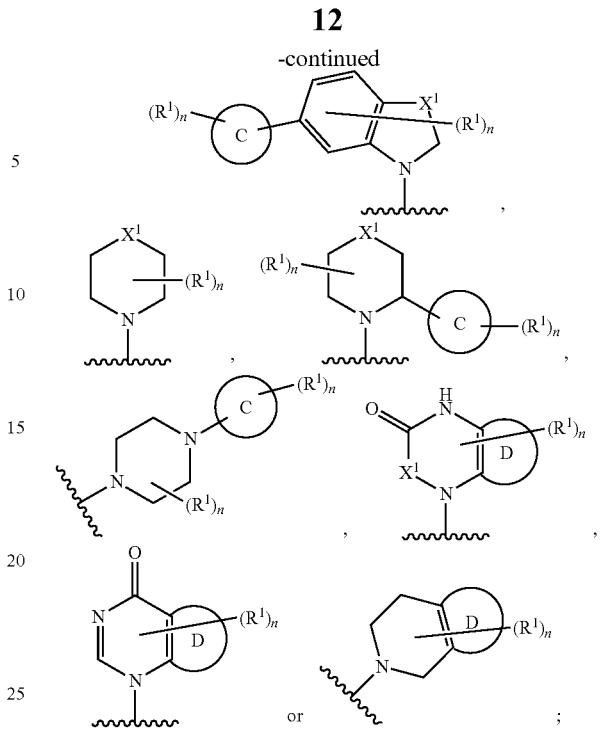

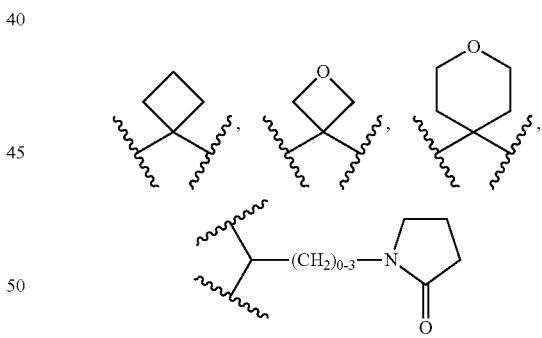

Ring B is a ring selected from phenyl or 5-6 membered heteroaryl having 1-3 heteroatoms independently selected from nitrogen, oxygen, and sulfur;

Ring C is a ring selected from phenyl or 5-6 membered heteroaryl having 1-3 heteroatoms independently selected from nitrogen, oxygen, and sulfur;

Ring D is a fused ring selected from benzo or 5-6 membered heteroaro-having 1-2 heteroatoms independently selected from nitrogen, oxygen, and sulfur;

$X^1$ is a bivalent moiety selected from —$CH_2$—, —CH($R^1$)—, —C($R^1$)$_2$—, —C(O)—, or —O—;

each $R^1$ is independently hydrogen, —$R^3$, halogen, —CN, —$NO_2$, —OR, —SR, —$NR_2$, —S(O)$_2$R, —S(O)$_2$$NR_2$, —S(O)R, —C(O)R, —C(O)OR, —C(O)$NR_2$, —C(O)N(R)OR, —OC(O)R, —OC(O)$NR_2$, —OPh, —C(R)$_2$Ph, —C(R)$_2$OR, —C(R)$_2$C(O)OR, —C(R)$_2$C(O)$NR_2$, —$CH_2$C(R)$_2$C(O)OR, —$CH_2$C(R)$_2$C(O)$NR_2$, —$CH_2$OPh, —N(R)C(O)OR, —N(R)C(O)R, —N(R)C(O)$NR_2$, —N(R)S(O)$_2$R, or —N(R)S(O)$_2$$NR_2$;

or two instances of $R^1$ are optionally taken together to form an oxo;

or $R^1$ at N forms an N-oxide;

each R is independently hydrogen, or an optionally substituted group selected from $C_{1-6}$ aliphatic, a 3-7 membered saturated or partially unsaturated carbocyclic ring, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

each $R^2$ is independently hydrogen, $-R^3$, halogen, $-CN$, $-NO_2$, $-OR$, $-OC(R)_2Ph$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-C(R)_2OR$, $-C(R)_2C(O)OR$, $-C(R)_2C(O)NR_2$, $-CH_2C(R)_2C(O)OR$, $-CH_2C(R)_2C(O)NR_2$, $-N(R)C(O)OR$, $-N(R)C(O)R$, $-N(R)C(O)NR_2$, $-N(R)S(O)_2R$, or $-N(R)S(O)_2NR_2$;

or two instances of $R^2$ are optionally taken together to form an oxo;

each $R^3$ is independently an optionally substituted group selected from $C_{1-6}$ aliphatic, phenyl, a 3-7 membered saturated or partially unsaturated carbocyclic ring, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, 2, 3, or 4; and each m is 0, 1, 2, 3, or 4.

In some embodiments, such compounds include those of formula I':

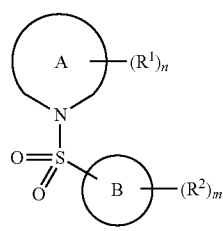

or a pharmaceutically acceptable salt thereof, wherein:
Ring A is a mono-, bi-, or tricyclic ring selected from

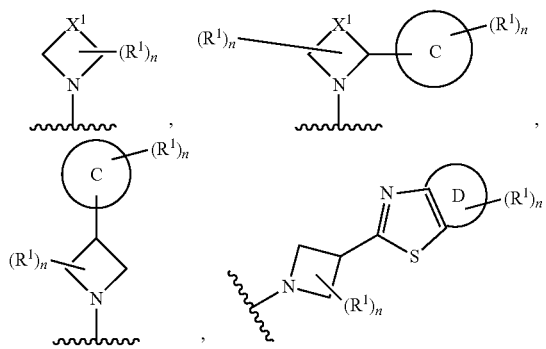

-continued

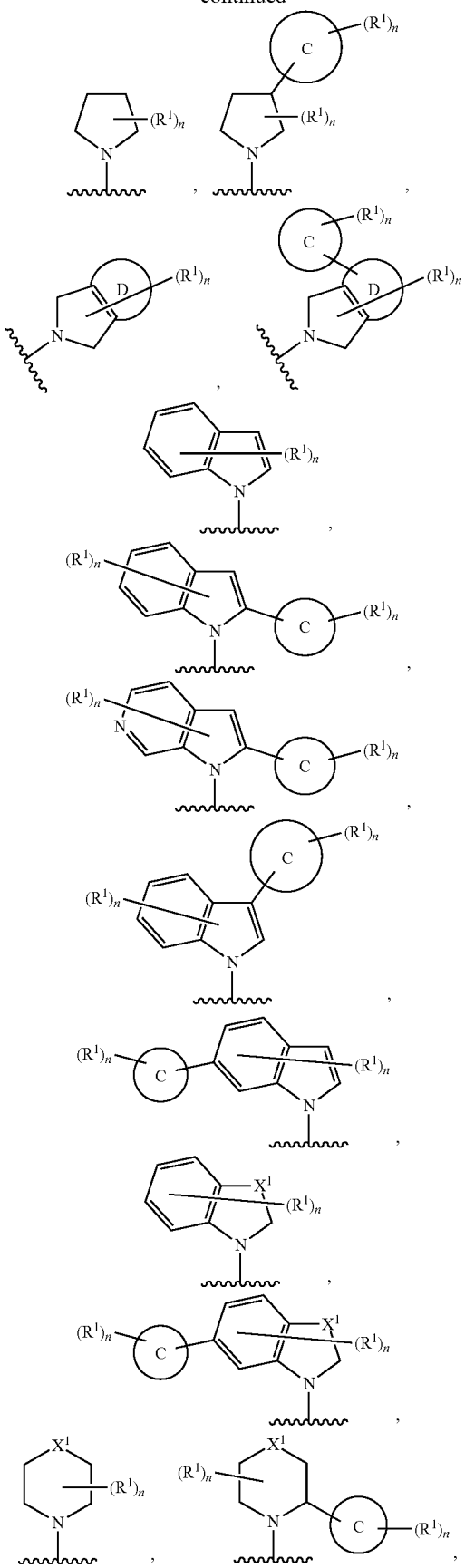

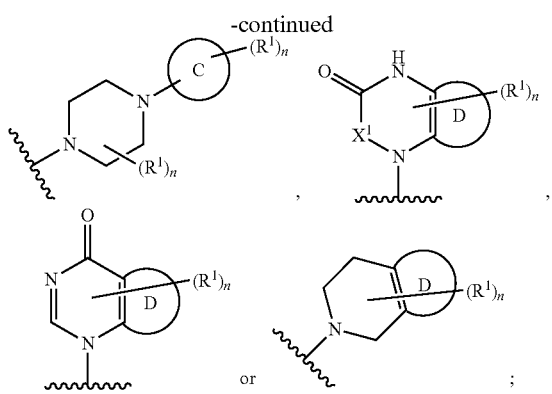

Ring B is a ring selected from phenyl or 5-6 membered heteroaryl having 1-3 heteroatoms independently selected from nitrogen, oxygen, and sulfur;

Ring C is a ring selected from phenyl, 5-6 membered heteroaryl having 1-3 heteroatoms independently selected from nitrogen, oxygen, and sulfur, or a 8-10 member bicyclic heteroaryl having 1-3 heteroatoms independently selected from nitrogen, oxygen, and sulfur;

Ring D is a fused ring selected from benzo or 5-6 membered heteroaro-having 1-2 heteroatoms independently selected from nitrogen, oxygen, and sulfur;

$X^1$ is a bivalent moiety selected from —CH$_2$—, —CH(R$^1$)—, —C(R$^1$)$_2$—, —C(O)—,

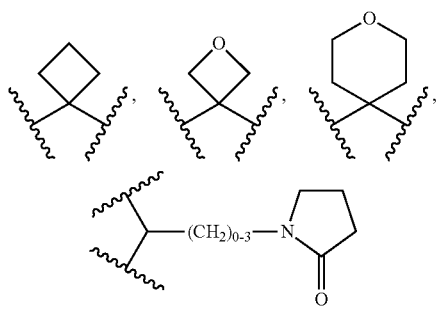

or —O—;

each R$^1$ is independently hydrogen, —R$^3$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —OPh, —C(R)$_2$Ph, —C(R)$_2$OR, —C(R)$_2$C(O)OR, —C(R)$_2$C(O)NR$_2$, —CH$_2$C(R)$_2$C(O)OR, —CH$_2$C(R)$_2$C(O)NR$_2$, —CH$_2$OPh, —N(R)C(O)OR, —N(R)C(O)R, —N(R)C(O)NR$_2$, —N(R)S(O)$_2$R, or —N(R)S(O)$_2$NR$_2$;

or two instances of R$^1$ are optionally taken together to form an oxo;

or R$^1$ at N forms an N-oxide;

each R is independently hydrogen, or an optionally substituted group selected from C$_{1-6}$ aliphatic, a 3-7 membered saturated or partially unsaturated carbocyclic ring, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or het-eroaryl ring having 0-3 heteroatoms, in addition to the nitrogen, independently selected from nitrogen, oxygen, and sulfur.

each R$^2$ is independently hydrogen, —R$^3$, halogen, —CN, —NO$_2$, —OR, —OC(R)$_2$Ph, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —C(R)$_2$OR, —C(R)$_2$C(O)OR, —C(R)$_2$C(O)NR$_2$, —CH$_2$C(R)$_2$C(O)OR, —CH$_2$C(R)$_2$C(O)NR$_2$, —N(R)C(O)OR, —N(R)C(O)R, —N(R)C(O)NR$_2$, —N(R)S(O)$_2$R, or —N(R)S(O)$_2$NR$_2$;

or two instances of R$^2$ are optionally taken together to form an oxo;

each R$^3$ is independently an optionally substituted group selected from C$_{1-6}$ aliphatic, phenyl, a 3-7 membered saturated or partially unsaturated carbocyclic ring, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, 2, 3, or 4; and each m is 0, 1, 2, 3, or 4.

As defined above and described herein, Ring A is a mono-, bi-, or tricyclic ring selected from

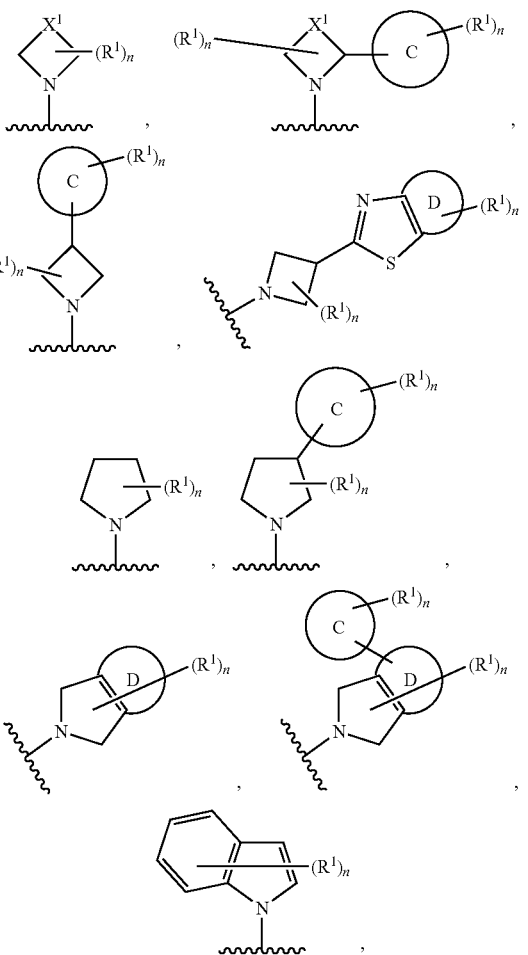

-continued
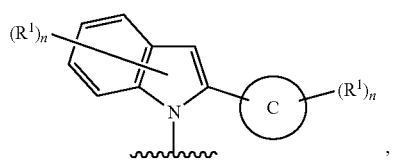,
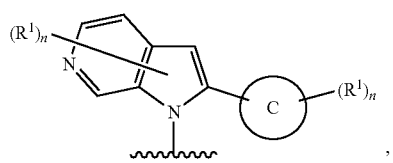,
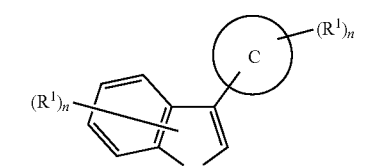,
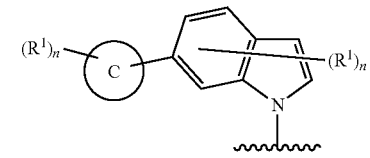,
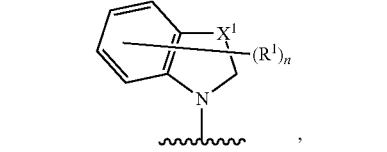,
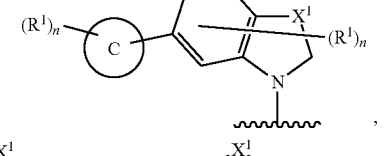,
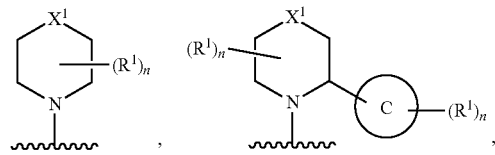,
,
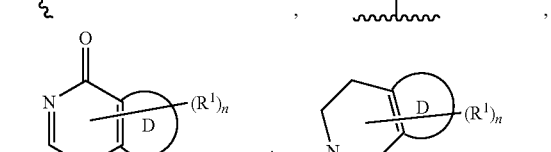 or 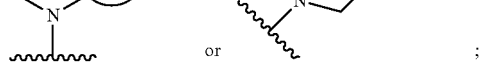;
In some embodiments, Ring A is
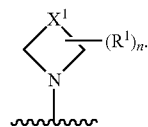
In some embodiments, Ring A is
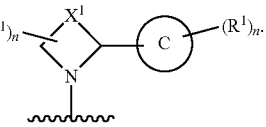
In some embodiments, Ring A is
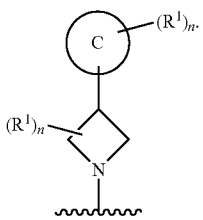
In some embodiments, Ring A is
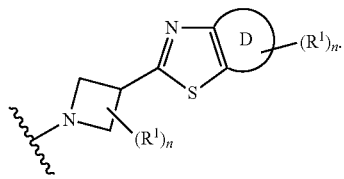
In some embodiments, Ring is
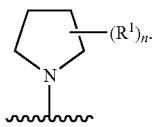
In some embodiments, Ring A is
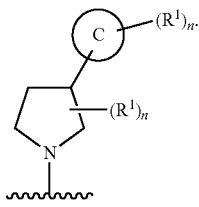

19
In some embodiments, Ring A is
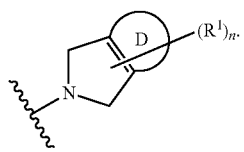
In some embodiments, Ring A is
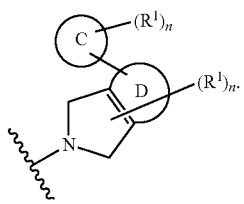
In some embodiments, Ring A is
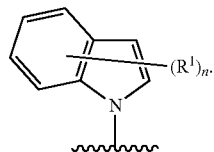
In some embodiments, Ring A is
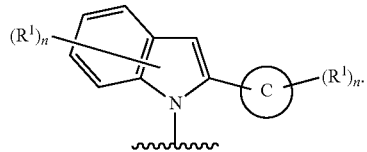
In some embodiments, Ring A is
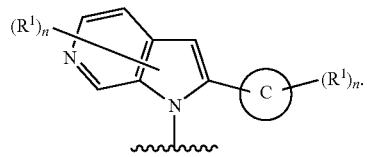
In some embodiments, Ring A is
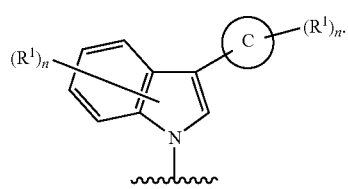
20
In some embodiments, Ring A is
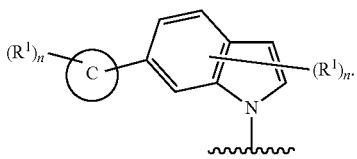
In some embodiments, Ring A is
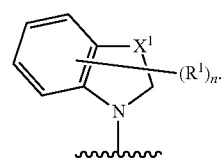
In some embodiments, Ring A is
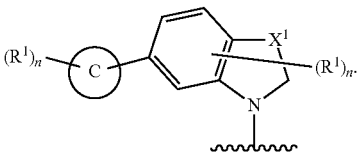
In some embodiments, Ring A is
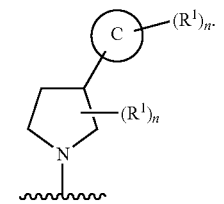
In some embodiments, Ring A is
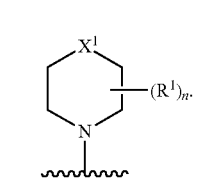
In some embodiments, Ring A is
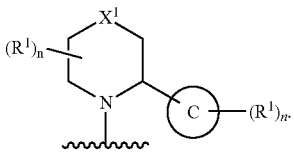

In some embodiments, Ring A is

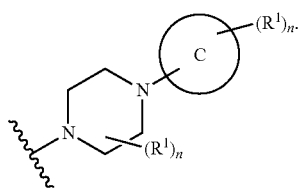

In some embodiments, Ring A is

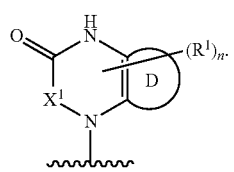

In some embodiments, Ring A is

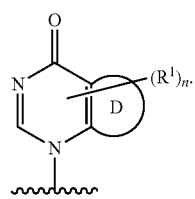

In some embodiments, Ring A is

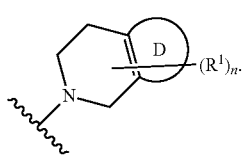

In some embodiments, Ring A is selected from those depicted in Table 1, below.

As defined above and described herein, Ring B is a ring selected from phenyl or 5-6 membered heteroaryl having 1-3 heteroatoms independently selected from nitrogen, oxygen, and sulfur.

In some embodiments, Ring B is phenyl. In some embodiments, Ring B is a 5-6 membered heteroaryl ring having 1-3 heteroatoms independently selected from nitrogen, oxygen or sulfur.

In some embodiments, Ring B is selected from those depicted in Table 1, below.

As defined above and described herein, Ring C is a ring selected from phenyl or 5-6 membered heteroaryl having 1-3 heteroatoms independently selected from nitrogen, oxygen, and sulfur.

In some embodiments, Ring C is a phenyl. In some embodiments, Ring C is a 5-6 membered heteroaryl ring having 1-3 heteroatoms independently selected from nitrogen, oxygen or sulfur.

In some embodiments, Ring C is selected from those depicted in Table 1, below.

As defined above and described herein, Ring D is a fused ring selected from benzo or 5-6 membered heteroaro-having 1-2 heteroatoms independently selected from nitrogen, oxygen, and sulfur.

In some embodiments, Ring D is a fused benzo. In some embodiments, Ring D is a fused 5-6 membered heteroaro-ring having 1-2 heteroatoms independently selected from nitrogen, oxygen or sulfur.

In some embodiments, Ring D is selected from those depicted in Table 1, below.

As defined above and described herein, $X^1$ is a bivalent moiety selected from —$CH_2$—, —$CH(R^1)$—, —$C(R^1)_2$—, —$C(O)$—,

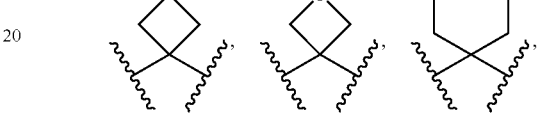

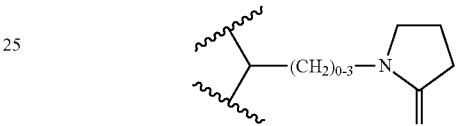

or —O—.

In some embodiments, $X^1$ is —$CH_2$—. In some embodiments, $X^1$ is —$CH(R^1)$—. In some embodiments, $X^1$ is —$C(R^1)_2$—. In some embodiments, $X^1$ is —$C(O)$—. In some embodiments, $X^1$ is

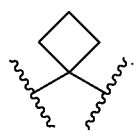 [SMILES: *C1(*)CCC1]

In some embodiments, $X^1$ is

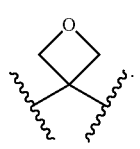 [SMILES: *C1(*)COC1]

In some embodiments, $X^1$ is

In some embodiments, X$^1$ is

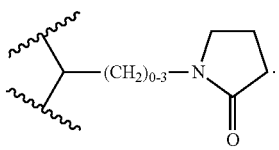 [SMILES: *C(*)CN1CCCC1=O]

In some embodiments, X$^1$ is

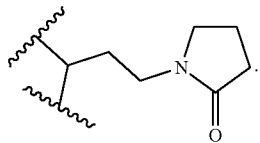 [SMILES: *C(*)CCN1CCCC1=O]

In some embodiments, X$^1$ is —O—.

In some embodiments, X$^1$ is selected from those depicted in Table 1, below.

As defined above and described herein, each R$^1$ is independently hydrogen, —R$^3$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —OPh, —C(R)$_2$Ph, —C(R)$_2$OR, —C(R)$_2$C(O)OR, —C(R)$_2$C(O)NR$_2$, —CH$_2$C(R)$_2$C(O)OR, —CH$_2$C(R)$_2$C(O)NR$_2$, —CH$_2$OPh, —N(R)C(O)OR, —N(R)C(O)R, —N(R)C(O)NR$_2$, —N(R)S(O)$_2$R, or —N(R)S(O)$_2$NR$_2$, or two instances of R$^1$ are optionally taken together to form an oxo, or R$^1$ at N forms an N-oxide;

In some embodiments, R$^1$ is hydrogen. In some embodiments, R$^1$ is —R$^3$. In some embodiments, R$^1$ is halogen. In some embodiments, R$^1$ is —CN. In some embodiments, R$^1$ is —NO$_2$. In some embodiments, R$^1$ is —OR. In some embodiments, R$^1$ is —SR. In some embodiments, R$^1$ is —NR$_2$. In some embodiments, R$^1$ is —S(O)$_2$R. In some embodiments, R$^1$ is —S(O)$_2$NR$_2$, In some embodiments, R$^1$ is —S(O)R. In some embodiments, R$^1$ is —C(O)R. In some embodiments, R$^1$ is —C(O)OR. In some embodiments, R$^1$ is —C(O)NR$_2$. In some embodiments, R$^1$ is —C(O)N(R)OR. In some embodiments, R$^1$ is —OC(O)R. In some embodiments, R$^1$ is —OC(O)NR$_2$. In some embodiments, R$^1$ is —OPh. In some embodiments, R$^1$ is —C(R)$_2$Ph. In some embodiments, R$^1$ is —C(R)$_2$OR. In some embodiments, R$^1$ is —C(R)$_2$C(O)OR. In some embodiments, R$^1$ is —C(R)$_2$C(O)NR$_2$. In some embodiments, R$^1$ is —CH$_2$C(R)$_2$C(O)OR. In some embodiments, R$^1$ is —CH$_2$C(R)$_2$C(O)NR$_2$. In some embodiments, R$^1$ is —CH$_2$OPh. In some embodiments, R$^1$ is —N(R)C(O)R. In some embodiments, R$^1$ is —N(R)C(O)OR. In some embodiments, R$^1$ is —N(R)C(O)NR$_2$. In some embodiments, R$^1$ is —N(R)S(O)$_2$R. In some embodiments, R$^1$ is —N(R)S(O)$_2$NR$_2$. In some embodiments, two instances of R$^1$ are optionally taken together to form an oxo. In some embodiments, R$^1$ at N forms an N-oxide.

In some embodiments, each R$^\bullet$ is independently selected from —CH$_3$, -cyclopropyl, —C(CH$_3$)$_2$OH, —CH$_2$CO$_2$H, —CN, —F, —Cl, —Br, —I, —N(H)C(O)CH$_3$, —OH, —OMe, —OCF$_3$, —CO$_2$H, —CO$_2$CH$_3$, —C(O)NH$_2$, —C(O)N(CH$_3$)$_2$,

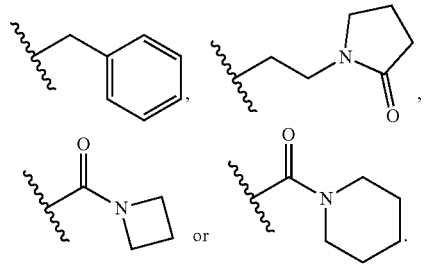

In some embodiments, R$^1$ is independently —CH$_3$. In some embodiments, R$^1$ is independently-cyclopropyl. In some embodiments, R$^1$ is independently —C(CH$_3$)$_2$OH. In some embodiments, R$^1$ is independently —CH$_2$CO$_2$H. In some embodiments, R$^1$ is independently —CN. In some embodiments, R$^1$ is independently —F. In some embodiments, R$^1$ is independently —Cl. In some embodiments, R$^1$ is independently —Br. In some embodiments, R$^1$ is independently —I. In some embodiments, R$^1$ is independently —N(H)C(O)CH$_3$. In some embodiments, R$^1$ is independently —OH. In some embodiments, R$^1$ is independently —OCH$_3$. In some embodiments, R$^1$ is independently —OCF$_3$. In some embodiments, R$^1$ is independently —CO$_2$H. In some embodiments, R$^1$ is independently —CO$_2$CH$_3$. In some embodiments, R$^1$ is independently —C(O)NH$_2$. In some embodiments, R$^1$ is independently —C(O)N(CH$_3$)$_2$. In some embodiments, R$^1$ is independently

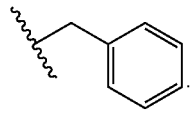 [SMILES: *Cc1ccccc1]

In some embodiments, R$^1$ is independently

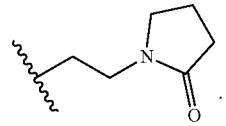 [SMILES: *CCN1CCCC1=O]

In some embodiments, R$^1$ is independently

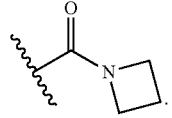 [SMILES: *C(=O)N1CCC1]

In some embodiments, R$^1$ is independently

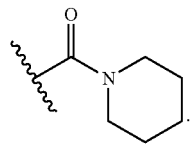 [SMILES: *C(=O)N1CCCCC1]

In some embodiments, R$^1$ is independently —C(O)OEt. In some embodiments, R$^1$ is independently —C(O)OMe. In some embodiments, R$^1$ is independently —C(O)NHOH.

In some embodiments, R¹ is independently —OCH₂OMe. In some embodiments, R¹ is independently —CF₃.

In some embodiments, R¹ is selected from those depicted in Table 1, below.

As defined above and described herein, each R is independently hydrogen, or an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is optionally substituted C₁₋₆ aliphatic. In some embodiments, R is optionally substituted phenyl. In some embodiments, R is an optionally substituted 4-7 membered saturated or partially unsaturated heterocyclic ring having 1-2 heteroatoms independently selected from nitrogen, oxygen, and sulfur. In some embodiments, R is an optionally substituted 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined above and described herein, each R² is independently hydrogen, —R³, halogen, —CN, —NO₂, —OR, —OC(R)₂Ph, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —C(R)₂OR, —C(R)₂C(O)OR, —C(R)₂C(O)NR₂, —CH₂C(R)₂C(O)OR, —CH₂C(R)₂C(O)NR₂, —N(R)C(O)OR, —N(R)C(O)R, —N(R)C(O)NR₂, —N(R)S(O)₂R, or —N(R)S(O)₂NR₂, or two instances of R² are optionally taken together to form an oxo.

In some embodiments, R² is hydrogen. In some embodiments, R² is —R³. In some embodiments, R² is halogen. In some embodiments, R² is —CN. In some embodiments, R² is —NO₂. In some embodiments, R² is —OR. In some embodiments, R² is —OC(R)₂Ph. In some embodiments, R² is —SR. In some embodiments, R² is —NR₂. In some embodiments, R² is —S(O)₂R. In some embodiments, R² is —S(O)₂NR₂. In some embodiments, R² is —S(O)R. In some embodiments, R² is —C(O)R. In some embodiments, R² is —C(O)OR. In some embodiments, R² is —C(O)NR₂. In some embodiments, R² is —C(O)N(R)OR. In some embodiments, R² is —C(R)₂OR. In some embodiments, R² is —C(R)₂C(O)OR. In some embodiments, R² is —C(R)₂C(O)NR₂. In some embodiments, R² is —CH₂C(R)₂C(O)OR. In some embodiments, R² is —CH₂C(R)₂C(O)NR₂. In some embodiments, R² is —OC(O)R. In some embodiments, R² is —OC(O)NR₂. In some embodiments, R² is —N(R)C(O)R. In some embodiments, R² is —N(R)C(O)OR. In some embodiments, R² is —N(R)C(O)NR₂. In some embodiments, R² is —N(R)S(O)₂R. In some embodiments, R² is —N(R)S(O)₂NR₂. In some embodiments, two instances of R² are optionally taken together to form an oxo.

In some embodiments, each R² is independently selected from —CH₃, -cyclopropyl, —C(CH₃)₂OH, —CH₂CO₂H, —CN, —F, —Cl, —Br, —I, —N(H)C(O)CH₃, —OH, —OCH₃, —OCF₃, —CO₂H, —CO₂CH₃, —C(O)NH₂, —C(O)N(CH₃)₂,

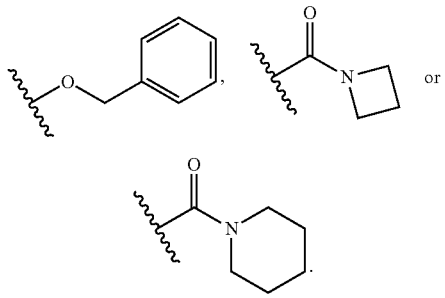

In some embodiments, R² is independently —CH₃. In some embodiments, R² is independently-cyclopropyl. In some embodiments, R² is independently —C(CH₃)₂OH. In some embodiments, R² is independently —CH₂CO₂H. In some embodiments, R² is independently —CN. In some embodiments, R² is independently —F. In some embodiments, R² is independently —Cl. In some embodiments, R² is independently —Br. In some embodiments, R² is independently —I. In some embodiments, R² is independently —N(H)C(O)CH₃. In some embodiments, R² is independently —OH. In some embodiments, R² is independently —OCH₃. In some embodiments, R² is independently —OCF₃. In some embodiments, R² is independently —CO₂H. In some embodiments, R² is independently —CO₂CH₃. In some embodiments, R² is independently —C(O)NH₂. In some embodiments. R² is independently —C(O)N(CH₃)₂. In some embodiments, R² is

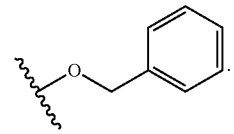 [SMILES: *OCc1ccccc1]

In some embodiments, R² is independently

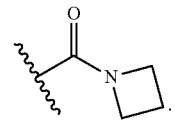

In some embodiments, R² is independently

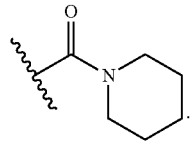 [SMILES: *C(=O)N1CCCCC1]

In some embodiments, R² is independently selected from —C(O)OEt, -Ph, or

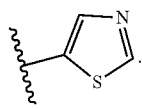

In some embodiments, $R^2$ is independently —C(O)OEt. In some embodiments, $R^2$ is independently -Ph. In some embodiments, $R^2$ is independently

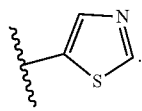

In some embodiments, $R^2$ is selected from those depicted in Table 1, below.

As defined above and described herein, each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ is an optionally substituted $C_{1-6}$ aliphatic. In some embodiments, $R^3$ is an optionally substituted phenyl. In some embodiments, $R^2$ is an optionally substituted 4-7 membered saturated or partially unsaturated heterocyclic ring having 1-2 heteroatoms independently selected from nitrogen, oxygen, and sulfur. In some embodiments, $R^3$ is an optionally substituted 5-6 membered heteroaryl ring having 1-4 heteroatoms independently selected from nitrogen, oxygen, and sulfur.

In some embodiments, $R^3$ is selected from those depicted in Table 1, below.

As defined above and described herein, each n is 0, 1, 2, 3, or 4.

In some embodiments, n is 0. In some embodiments, n is 1. In some embodiments, n is 2. In some embodiments, n is 3. In some embodiments, n is 4.

In some embodiments, each n is selected from those depicted in Table 1, below.

As defined above and described herein, each m is 0, 1, 2, 3, or 4.

In some embodiments, m is 0. In some embodiments, m is 1. In some embodiments, m is 2. In some embodiments, m is 3. In some embodiments, m is 4.

In some embodiments, each m is selected from those depicted in Table 1, below.

In some embodiments, Ring C is

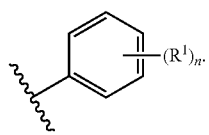

In some embodiments, Ring C is

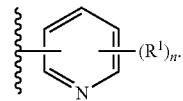

In some embodiments, Ring C is

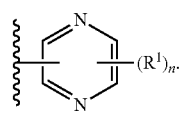

In some embodiments, Ring C is

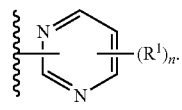

In some embodiments, Ring C is

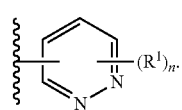

In some embodiments, Ring C is

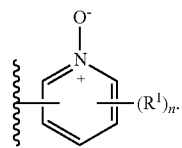

In some embodiments, Ring C is

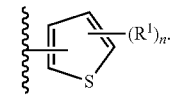

In some embodiments, Ring C is

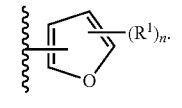

In some embodiments, Ring C is

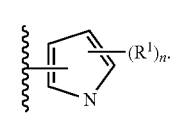

In some embodiments, Ring C is

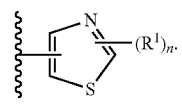

In some embodiments, Ring C is

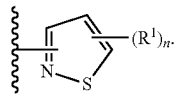

In some embodiments, Ring C is

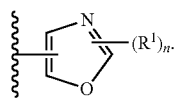

In some embodiments, Ring C is

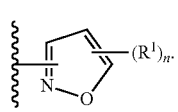

In some embodiments, Ring C

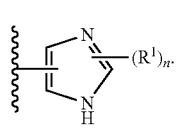

In some embodiments, Ring C is

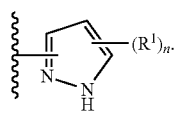

In some embodiments, Ring C is

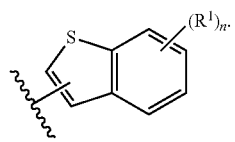

In some embodiments, Ring D is

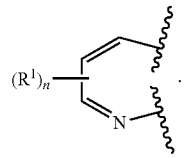

In some embodiments, Ring D is

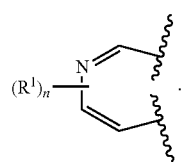

In some embodiments, Ring D is

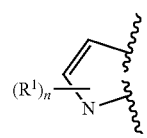

In some embodiments, Ring D is

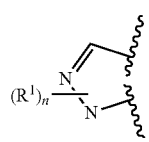

In some embodiments, Ring D is

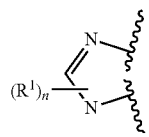

In some embodiments, Ring D is

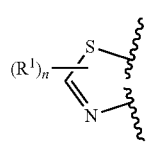

In some embodiments, Ring D is

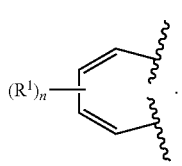

In some embodiments, Ring D is

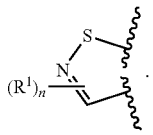

In some embodiments, Ring D is

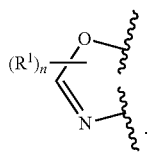

In some embodiments, Ring D is

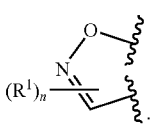

In some embodiments, Ring A and Ring C are

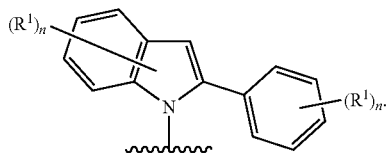

In some embodiments, Ring A and Ring C are

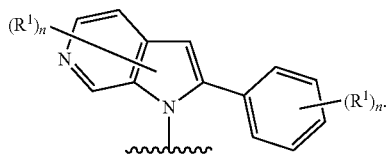

In some embodiments, Ring A and Ring C are

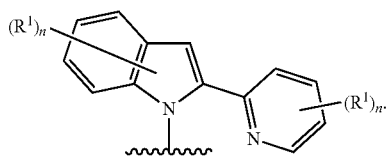

In some embodiments, Ring A and Ring C are

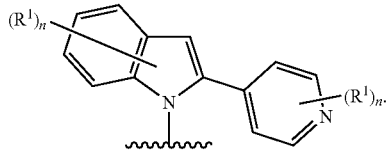

In some embodiments, Ring A and Ring C are

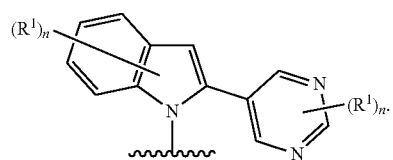

In some embodiments, Ring A and Ring C are

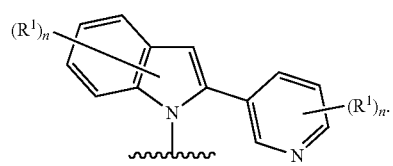

In some embodiments, Ring A and Ring C are

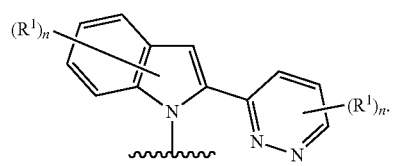

In some embodiments, Ring A and Ring C are

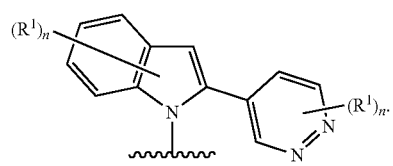

In some embodiments, Ring A and Ring C are

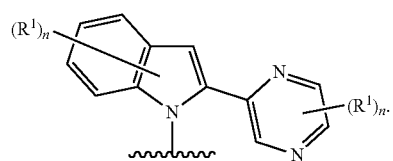

In some embodiments, Ring A and Ring C are

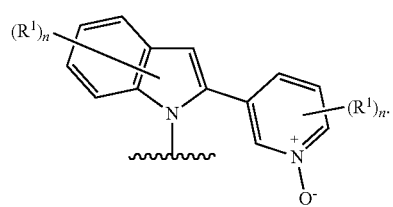

In some embodiments, Ring A and Ring C are

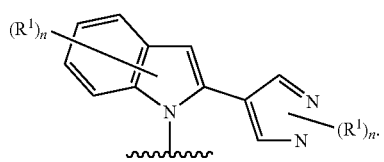

In some embodiments, Ring A and Ring C are

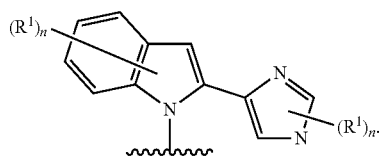

In some embodiments, Ring A and Ring C are

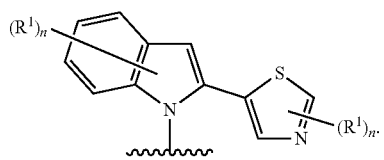

In some embodiments, Ring A and Ring C are

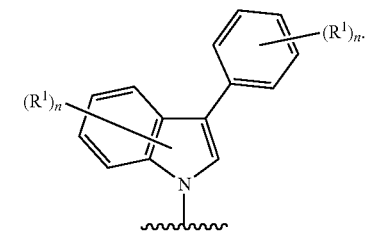

In some embodiments, Ring A and Ring C are

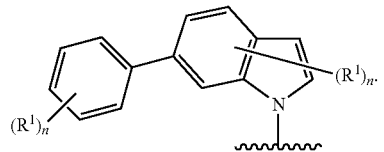

In some embodiments, Ring A, $X^1$, and Ring C are

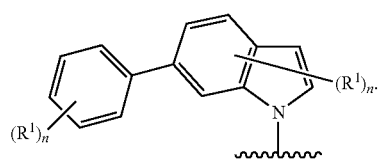

In some embodiments, Ring A and Ring C are

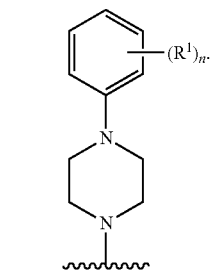

In some embodiments, Ring A, $X^1$, and Ring C are

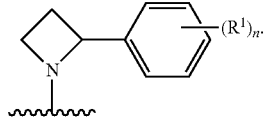

In some embodiments, Ring A, $X^1$, and Ring C are

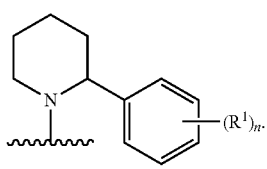

In some embodiments, Ring A, $X^1$, and Ring C are

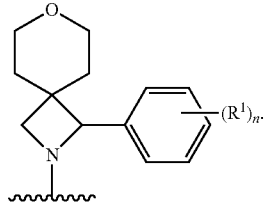

In some embodiments, Ring A and Ring C are

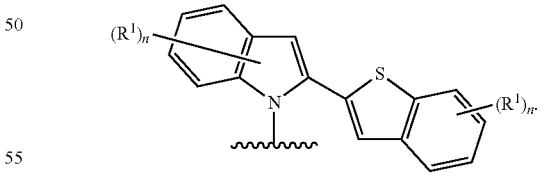

In some embodiments, Ring A and Ring D are

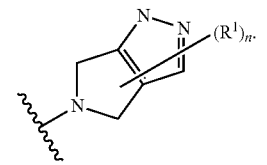

In some embodiments, Ring A, Ring C, and Ring D are

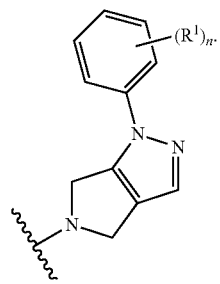

In some embodiments, Ring A and Ring D are

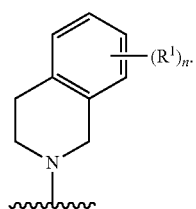

In some embodiments, Ring A and Ring D are

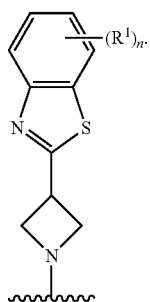

In some embodiments, Ring A, $X^1$, and Ring D are

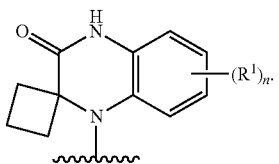

In some embodiments, Ring A and $X^1$ are

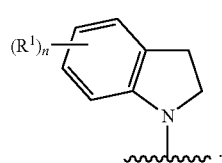

In some embodiments, Ring A is

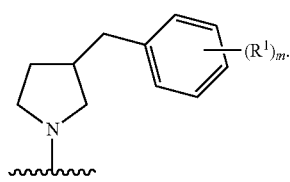

In some embodiments, Ring A and Ring C are

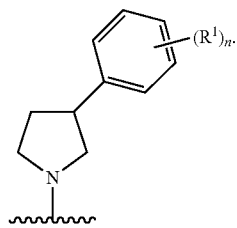

In some embodiments, Ring A and $X^1$ are

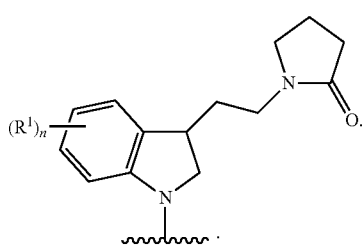

In some embodiments, Ring A and $X^1$ are

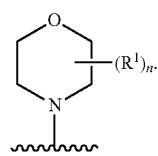

In some embodiments, Ring A and $X^1$ are

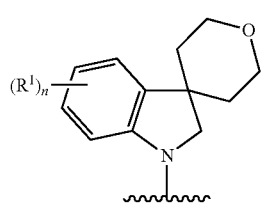

In some embodiments, Ring A and X¹ are

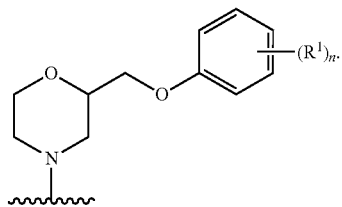

In some embodiments, Ring A and Ring C are

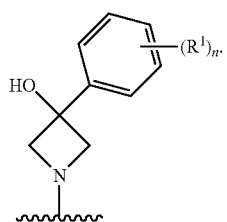

In some embodiments, Ring A is

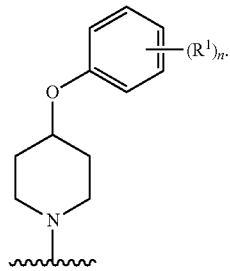

In some embodiments, Ring A and Ring C are

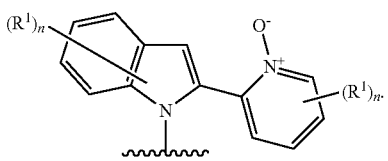

In specific embodiments, Ring A, Ring C, and R¹ substituents are

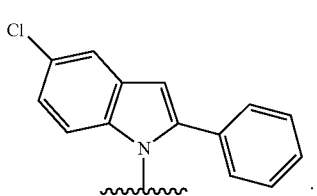

In specific embodiments, Ring A, X¹ and Ring C are

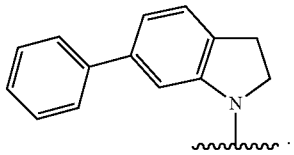 [SMILES: *N1CCc2ccc(-c3ccccc3)cc21]

In specific embodiments, Ring A and Ring C are

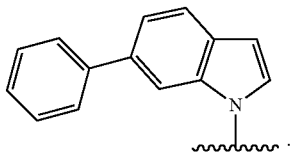 [SMILES: *n1ccc2ccc(-c3ccccc3)cc21]

In specific embodiments, Ring A and X¹ are

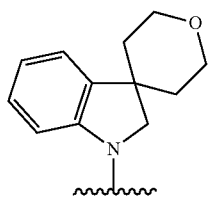

In specific embodiments, Ring A, Ring C, and Ring D are

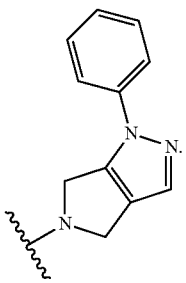 [SMILES: *N1Cc2cnn(-c3ccccc3)c2C1]

In specific embodiments, Ring A, X¹, and R¹ substituents are

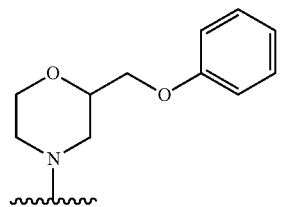

In specific embodiments, Ring A, Ring C, and R¹ substituents are

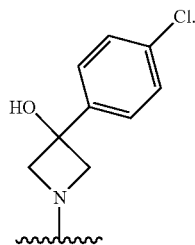

In specific embodiments, Ring A and R¹ substituents are

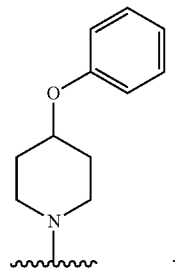

In specific embodiments, Ring A, Ring C, and R¹ substituents are

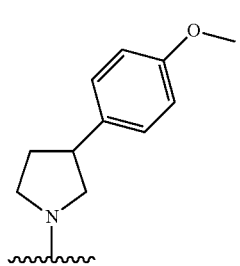

In specific embodiments, Ring A, X¹, Ring C, and R¹ substituents are

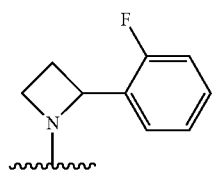

In specific embodiments, Ring A, Ring D, and R¹ substituents are

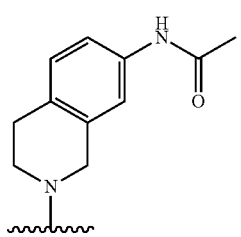

In specific embodiments, Ring A, X¹, and R¹ substituents are

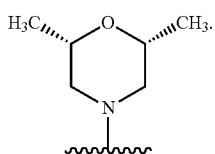 [SMILES: *N1C[C@@H](C)O[C@@H](C)C1]

In specific embodiments, Ring A and Ring D are

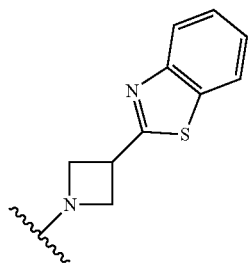

In specific embodiments, Ring A, Ring C, and R¹ substituents are

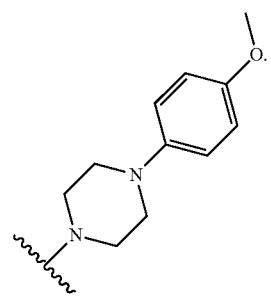 [SMILES: *N1CCN(c2ccc(OC)cc2)CC1]

In specific embodiments, Ring A, X¹, and R¹ substituents are

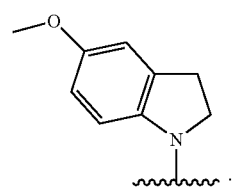 [SMILES: *N1CCc2cc(OC)ccc21]

In specific embodiments, Ring A is

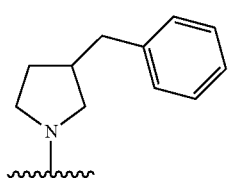

In specific embodiments, Ring A, X¹, and Ring C are

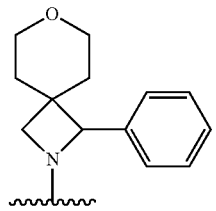

In specific embodiments, Ring A and X¹ are

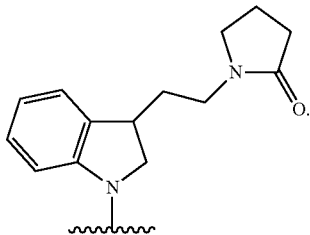 [SMILES: *N1CC(CCN2CCCC2=O)c2ccccc21]

In specific embodiments, Ring A, X¹, Ring D, and R¹ substituents are

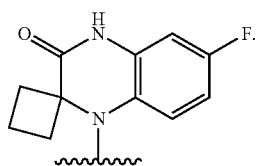 [SMILES: *N1c2ccc(F)cc2NC(=O)C12CCC2]

In specific embodiments, Ring A, X¹, and Ring C are

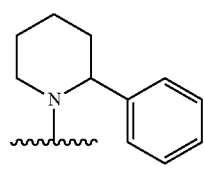

In specific embodiments, Ring A and Ring C are

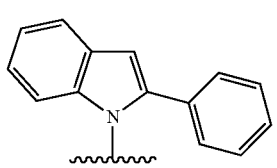

In specific embodiments, Ring A, Ring C, and R¹ substituents are

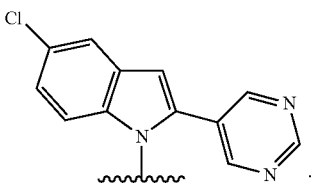 [SMILES: *n1c(-c2cncnc2)cc2cc(Cl)ccc21]

In specific embodiments, Ring A, Ring C, and R¹ substituents are

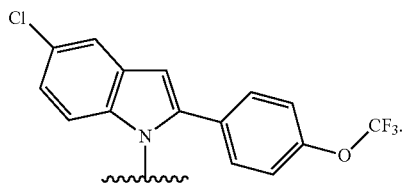 [SMILES: *n1c(-c2ccc(OC(F)(F)F)cc2)cc2cc(Cl)ccc21]

In specific embodiments, Ring A, Ring C, and R¹ substituents are

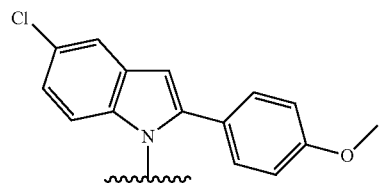

In specific embodiments, Ring A, Ring C, and R¹ substituents are

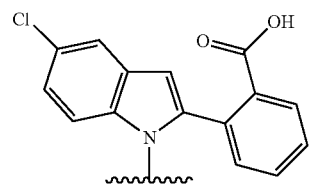

In specific embodiments, Ring A, Ring C, and R¹ substituents are

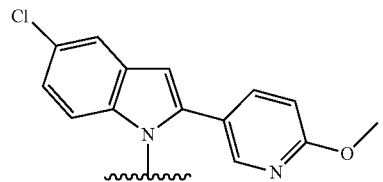

In specific embodiments, Ring A and Ring C are

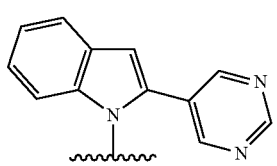

In specific embodiments, Ring A and R¹ substituents are

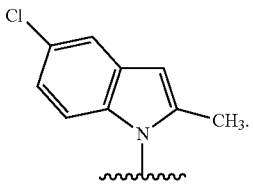 [SMILES: *n1c(C)cc2cc(Cl)ccc21]

In specific embodiments, Ring A, Ring C, and R¹ substituents are

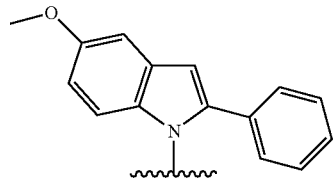

In specific embodiments, Ring A, Ring C, and R¹ substituents are

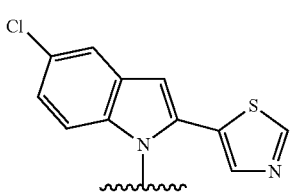

In specific embodiments, Ring A, Ring C, and R¹ substituents are

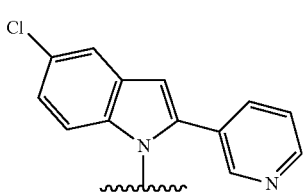

In specific embodiments, Ring A, Ring C, and R¹ substituents are

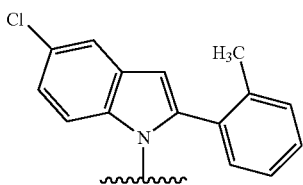

In specific embodiments, Ring A and R¹ substituents are

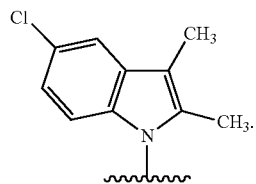 [SMILES: *n1c(C)c(C)c2cc(Cl)ccc21]

In specific embodiments, Ring A, Ring C, and R¹ substituents are

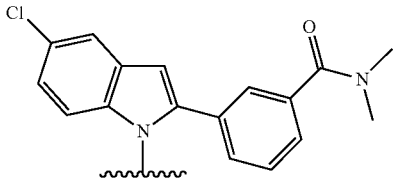

In specific embodiments, Ring A, Ring C, and R¹ substituents are

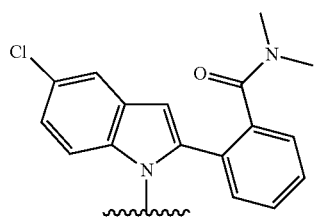

In specific embodiments, Ring A and R¹ substituents are

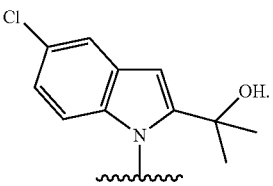 [SMILES: *n1c(C(C)(C)O)cc2cc(Cl)ccc21]

In specific embodiments, Ring A, Ring C, and R¹ substituents are

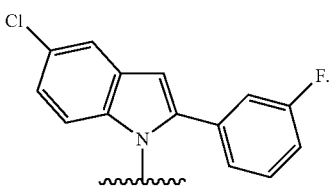 [SMILES: *n1c(-c2cccc(F)c2)cc2cc(Cl)ccc21]

In specific embodiments, Ring A and R¹ substituents are

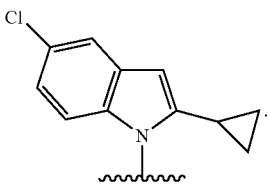 [SMILES: *n1c(C2CC2)cc2cc(Cl)ccc21]

In specific embodiments, Ring A, Ring C, and R¹ substituents are

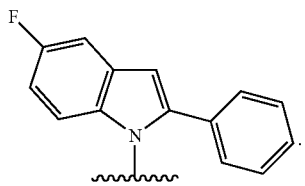 [SMILES: *n1c(-c2ccccc2)cc2cc(F)ccc21]

In specific embodiments, Ring A, Ring C, and R¹ substituents are

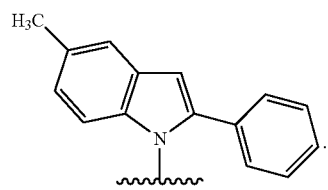 [SMILES: *n1c(-c2ccccc2)cc2cc(C)ccc21]

In specific embodiments, Ring A, Ring C, and R¹ substituents are

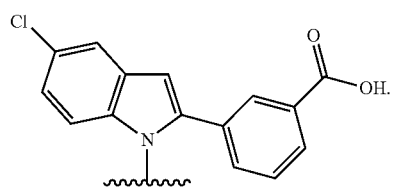 [SMILES: *n1c(-c2cccc(C(=O)O)c2)cc2cc(Cl)ccc21]

In specific embodiments, Ring A, Ring C, and R¹ substituents are

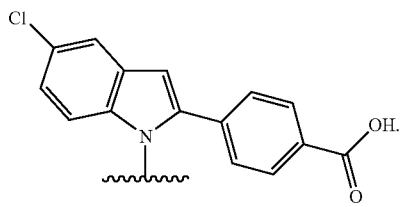 [SMILES: *n1c(-c2ccc(C(=O)O)cc2)cc2cc(Cl)ccc21]

In specific embodiments, Ring A and R¹ substituents are

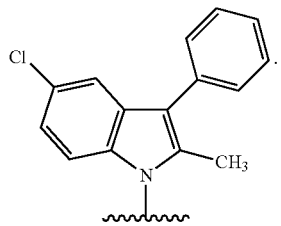 [SMILES: *n1c(C)c(-c2ccccc2)c2cc(Cl)ccc21]

In specific embodiments, Ring A, Ring C, and R¹ substituents are

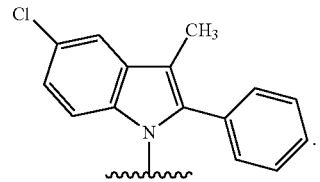 [SMILES: *n1c(-c2ccccc2)c(C)c2cc(Cl)ccc21]

In specific embodiments, Ring A, Ring C, and R¹ substituents are

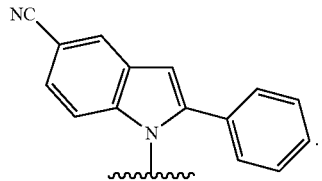 [SMILES: *n1c(-c2ccccc2)cc2cc(C#N)ccc21]

In specific embodiments, Ring A, Ring C, and R¹ substituents are

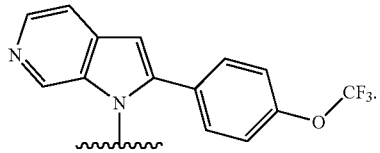 [SMILES: *n1c(-c2ccc(OC(F)(F)F)cc2)cc2ccncc21]

In specific embodiments, Ring A, Ring C, and R¹ substituents are

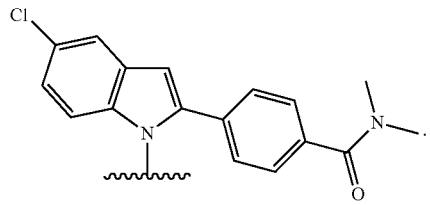 [SMILES: *n1c(-c2ccc(C(=O)N(C)C)cc2)cc2cc(Cl)ccc21]

In specific embodiments, Ring A, Ring C, and R¹ substituents are

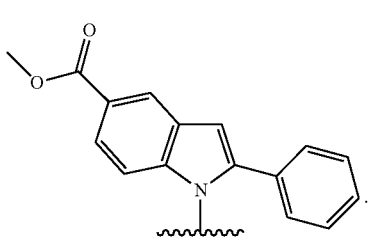 [SMILES: *n1c(-c2ccccc2)cc2cc(C(=O)OC)ccc21]

In specific embodiments, Ring A, Ring C, and R¹ substituents are

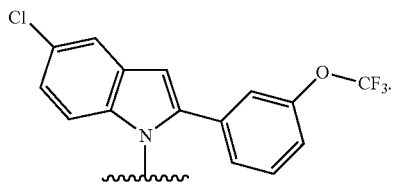 [SMILES: *n1c(-c2cccc(OC(F)(F)F)c2)cc2cc(Cl)ccc21]

In specific embodiments, Ring A, Ring C, and R¹ substituents are

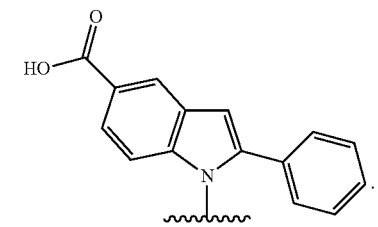 [SMILES: *n1c(-c2ccccc2)cc2cc(C(=O)O)ccc21]

In specific embodiments, Ring A, Ring C, and R¹ substituents are

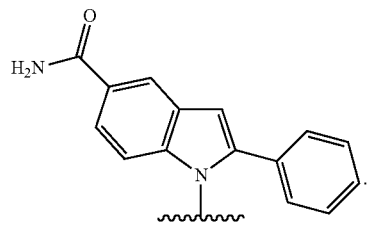 [SMILES: *n1c(-c2ccccc2)cc2cc(C(N)=O)ccc21]

In specific embodiments, Ring A, Ring C, and R¹ substituents are

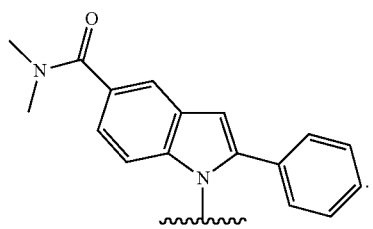 [SMILES: *n1c(-c2ccccc2)cc2cc(C(=O)N(C)C)ccc21]

In specific embodiments, Ring A and R¹ substituents are

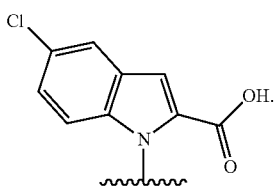 [SMILES: *n1c(C(=O)O)cc2cc(Cl)ccc21]

In specific embodiments, Ring A, Ring C, and R¹ substituents are

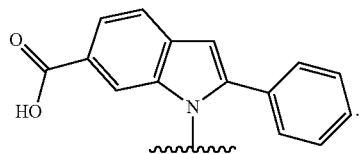 [SMILES: *n1c(-c2ccccc2)cc2ccc(C(=O)O)cc21]

In specific embodiments, Ring A, Ring C, and R¹ substituents are

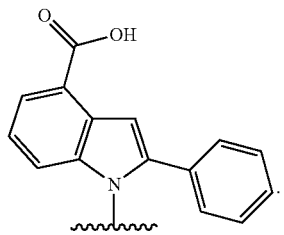 [SMILES: *n1c(-c2ccccc2)cc2c(C(=O)O)cccc21]

In specific embodiments, Ring A, Ring C, and R¹ substituents are

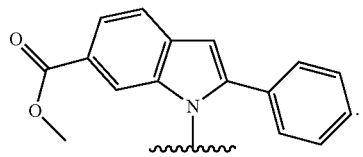 [SMILES: *n1c(-c2ccccc2)cc2ccc(C(=O)OC)cc21]

In specific embodiments, Ring A and R¹ substituents are

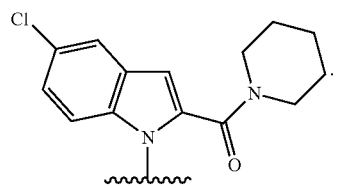 [SMILES: *n1c(C(=O)N2CCCCC2)cc2cc(Cl)ccc21]

In specific embodiments, Ring A, Ring C, and R¹ substituents are

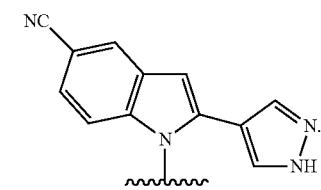 [SMILES: *n1c(-c2cn[nH]c2)cc2cc(C#N)ccc21]

In specific embodiments, Ring A, Ring C, and R[1] substituents are

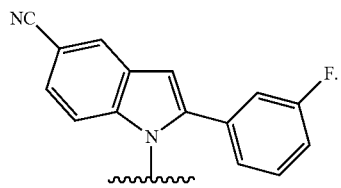 [SMILES: *n1c(-c2cccc(F)c2)cc2cc(C#N)ccc21]

In specific embodiments, Ring A, Ring C, and R[1] substituents are

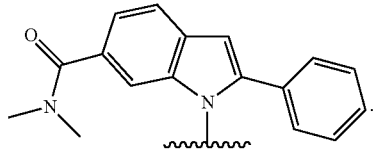 [SMILES: *n1c(-c2ccccc2)cc2ccc(C(=O)N(C)C)cc21]

In specific embodiments, Ring A, Ring C, and R[1] substituents are

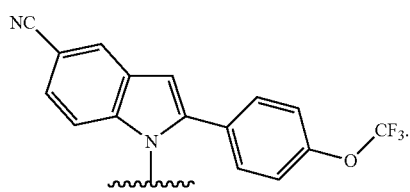 [SMILES: *n1c(-c2ccc(OC(F)(F)F)cc2)cc2cc(C#N)ccc21]

In specific embodiments, Ring A and R[1] substituents are

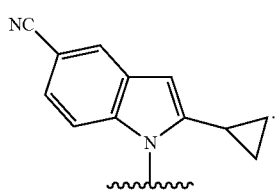 [SMILES: *n1c(C2CC2)cc2cc(C#N)ccc21]

In specific embodiments, Ring A, Ring C, and R[1] substituents are

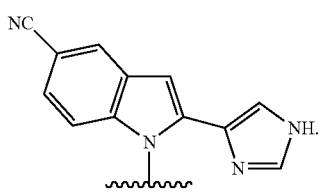 [SMILES: *n1c(-c2c[nH]cn2)cc2cc(C#N)ccc21]

In specific embodiments, Ring A, Ring C, and R[1] substituents are

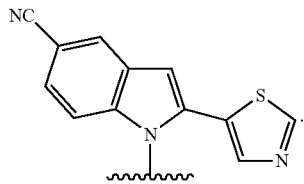 [SMILES: *n1c(-c2cncs2)cc2cc(C#N)ccc21]

In specific embodiments, Ring A, Ring C, and R[1] substituents are

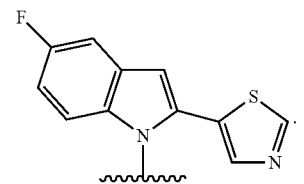 [SMILES: *n1c(-c2cncs2)cc2cc(F)ccc21]

In specific embodiments, Ring A and R[1] substituents are

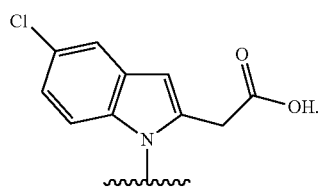 [SMILES: *n1c(CC(=O)O)cc2cc(Cl)ccc21]

In specific embodiments, Ring A, Ring C, and R[1] substituents are

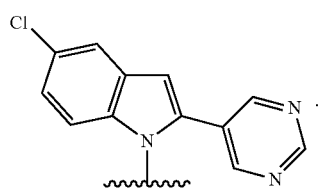

In specific embodiments, Ring A, Ring C, and R[1] substituents are

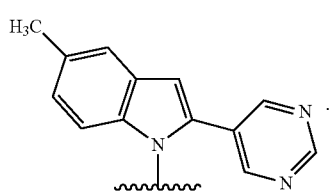 [SMILES: *n1c(-c2cncnc2)cc2cc(C)ccc21]

In specific embodiments, Ring A, Ring C, and R¹ substituents are

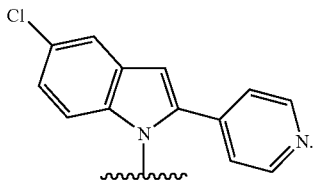

In specific embodiments, Ring A, Ring C, and R¹ substituents are

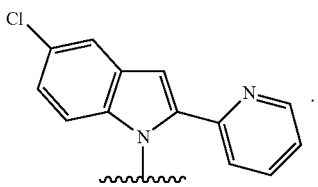

In specific embodiments, Ring A, Ring C, and R¹ substituents are

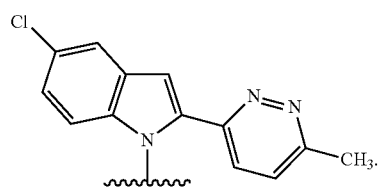 [SMILES: *n1c(-c2ccc(C)nn2)cc2cc(Cl)ccc21]

In specific embodiments, Ring A, Ring C, and R¹ substituents are

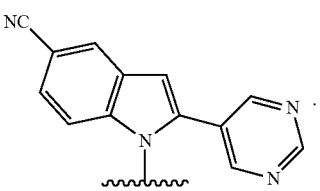 [SMILES: *n1c(-c2cncnc2)cc2cc(C#N)ccc21]

In specific embodiments, Ring A, Ring C, and R¹ substituents are

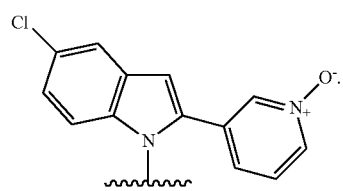

In specific embodiments, Ring A, Ring C, and R¹ substituents are

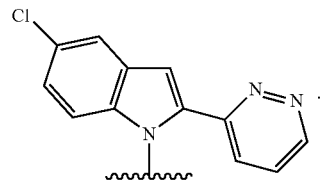 [SMILES: *n1c(-c2cccnn2)cc2cc(Cl)ccc21]

In specific embodiments, Ring A, Ring C, and R¹ substituents are

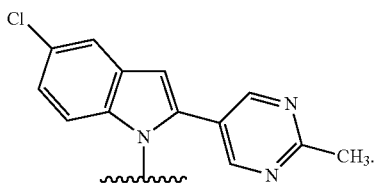 [SMILES: *n1c(-c2cnc(C)nc2)cc2cc(Cl)ccc21]

In specific embodiments, Ring A, Ring C, and R¹ substituents are

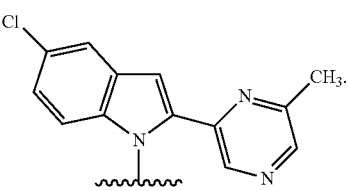 [SMILES: *n1c(-c2cncc(C)n2)cc2cc(Cl)ccc21]

In specific embodiments, Ring A, Ring C, and R¹ substituents are

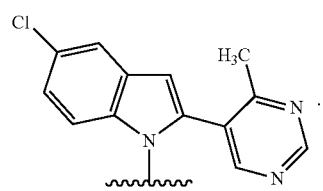

In specific embodiments, Ring A, Ring C, and R¹ substituents are

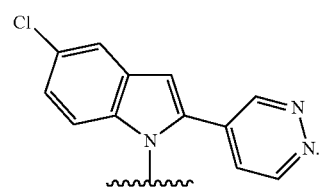

In specific embodiments, Ring A, Ring C, and R¹ substituents are

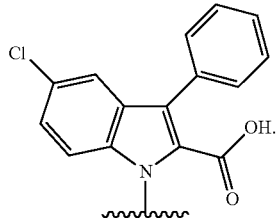 [SMILES: *n1c(C(=O)O)c(-c2ccccc2)c2cc(Cl)ccc21]

In specific embodiments, Ring A, Ring C, and R¹ substituents are

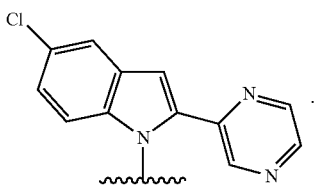

In specific embodiments, Ring A and R¹ substituents are

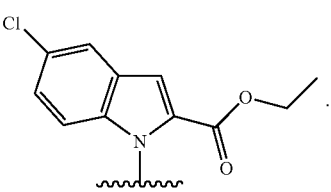 [SMILES: *n1c(C(=O)OCC)cc2cc(Cl)ccc21]

In specific embodiments, Ring A, Ring C, and R¹ substituents are

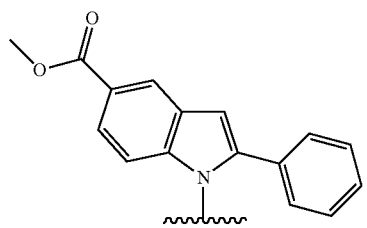

In specific embodiments, Ring A and R¹ substituents are

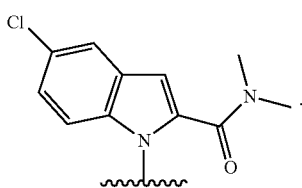 [SMILES: *n1c(C(=O)N(C)C)cc2cc(Cl)ccc21]

In specific embodiments, Ring A, Ring C, and R¹ substituents are

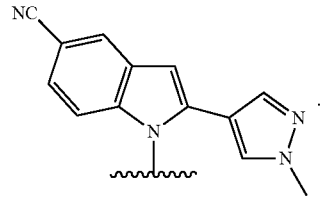 [SMILES: *n1c(-c2cnn(C)c2)cc2cc(C#N)ccc21]

In specific embodiments, Ring A, Ring C, and R¹ substituents are

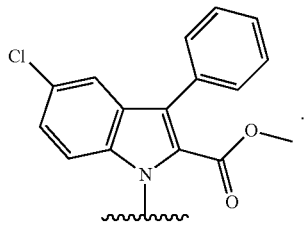 [SMILES: *n1c(C(=O)OC)c(-c2ccccc2)c2cc(Cl)ccc21]

In specific embodiments, Ring A, Ring C, and R¹ substituents are

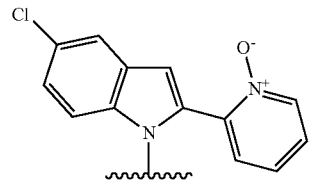

In specific embodiments, Ring A, Ring C, and R¹ substituents are

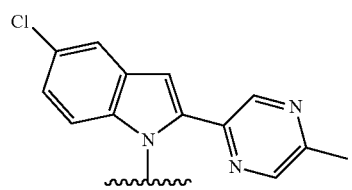

In specific embodiments, Ring A and R¹ substituents are

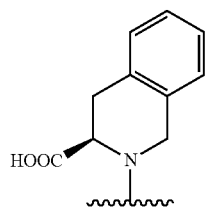

In specific embodiments, Ring A and R¹ substituents are

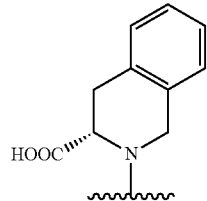

In specific embodiments, Ring A and R¹ substituents are

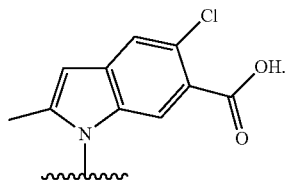 [SMILES: *n1c(C)cc2cc(Cl)c(C(=O)O)cc21]

In specific embodiments, Ring A and R¹ substituents are

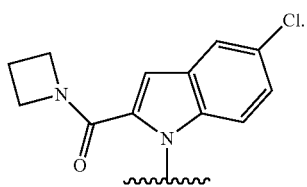 [SMILES: *n1c(C(=O)N2CCC2)cc2cc(Cl)ccc21]

In specific embodiments, Ring A and R¹ substituents are

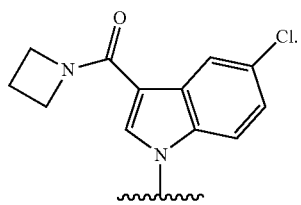 [SMILES: *n1cc(C(=O)N2CCC2)c2cc(Cl)ccc21]

In specific embodiments, Ring A and R¹ substituents are

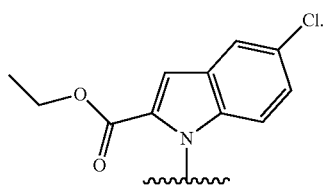 [SMILES: *n1c(C(=O)OCC)cc2cc(Cl)ccc21]

In specific embodiments, Ring A and R¹ substituents are

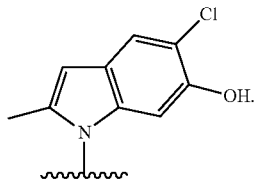 [SMILES: *n1c(C)cc2cc(Cl)c(O)cc21]

In specific embodiments, Ring A and R¹ substituents are

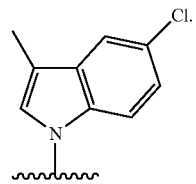 [SMILES: *n1cc(C)c2cc(Cl)ccc21]

In specific embodiments, Ring A and R¹ substituents are

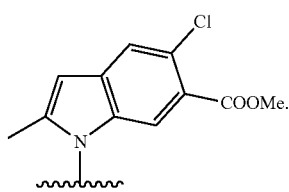 [SMILES: *n1c(C)cc2cc(Cl)c(C(=O)OC)cc21]

In specific embodiments, Ring A and R¹ substituents are

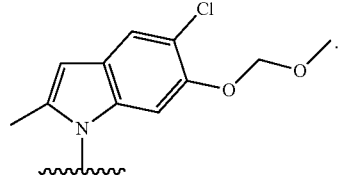

In specific embodiments, Ring A, Ring C, and R¹ substituents are

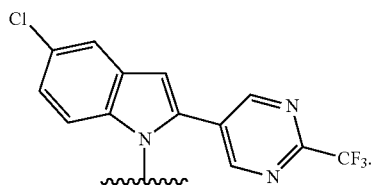 [SMILES: *n1c(-c2cnc(C(F)(F)F)nc2)cc2cc(Cl)ccc21]

In specific embodiments, Ring A, Ring C, and R¹ substituents are

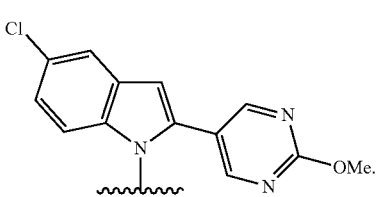 [SMILES: *n1c(-c2cnc(OC)nc2)cc2cc(Cl)ccc21]

In specific embodiments, Ring A, Ring C, and R¹ substituents are

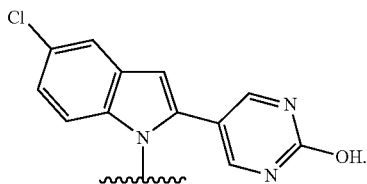 [SMILES: *n1c(-c2cnc(O)nc2)cc2cc(Cl)ccc21]

In specific embodiments, Ring A, Ring C, and R¹ substituents are

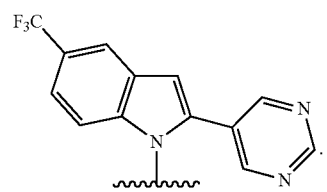 [SMILES: *n1c(-c2cncnc2)cc2cc(C(F)(F)F)ccc21]

In specific embodiments, Ring A, Ring C, and R¹ substituents are

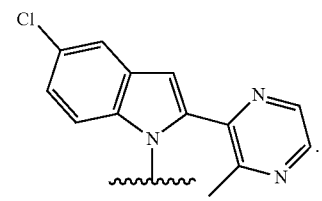 [SMILES: *n1c(-c2nccnc2C)cc2cc(Cl)ccc21]

In specific embodiments, Ring A, Ring C, and R¹ substituents are

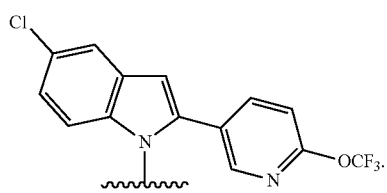 [SMILES: *n1c(-c2ccc(OC(F)(F)F)nc2)cc2cc(Cl)ccc21]

In specific embodiments, Ring A, Ring C, and R¹ substituents are

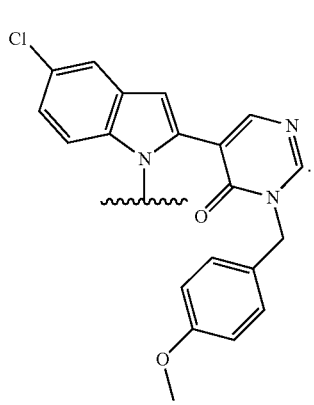 [SMILES: *n1c(-c2cncn(Cc3ccc(OC)cc3)c2=O)cc2cc(Cl)ccc21]

In specific embodiments, Ring A, Ring C, and R¹ substituents are

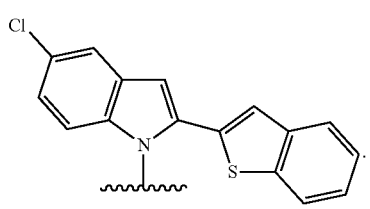 [SMILES: *n1c(-c2cc3ccccc3s2)cc2cc(Cl)ccc21]

In specific embodiments, Ring A, Ring C, and R¹ substituents are

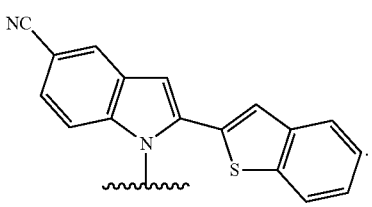 [SMILES: *n1c(-c2cc3ccccc3s2)cc2cc(C#N)ccc21]

In specific embodiments, Ring A, Ring C, and R¹ substituents are

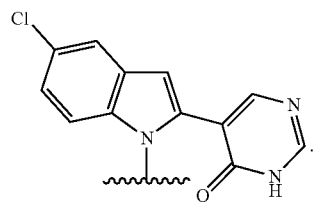 [SMILES: *n1c(-c2cnc[nH]c2=O)cc2cc(Cl)ccc21]

In specific embodiments, Ring A, Ring C, and R¹ substituents are

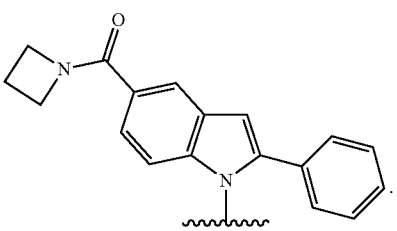 [SMILES: *n1c(-c2ccccc2)cc2cc(C(=O)N3CCC3)ccc21]

In specific embodiments, Ring A, Ring C, and R¹ substituents are

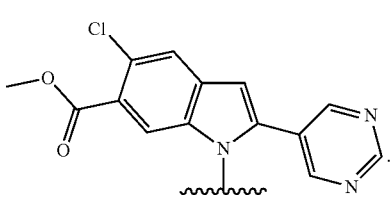 [SMILES: *n1c(-c2cncnc2)cc2cc(Cl)c(C(=O)OC)cc21]

In specific embodiments, Ring A, Ring C, and R¹ substituents are

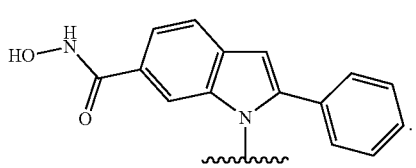 [SMILES: *n1c(-c2ccccc2)cc2ccc(C(=O)NO)cc21]

In specific embodiments, Ring A, Ring C, and R¹ substituents are

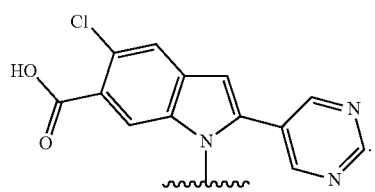 [SMILES: *n1c(-c2cncnc2)cc2cc(Cl)c(C(=O)O)cc21]

In specific embodiments, Ring A, Ring C, and R¹ substituents are

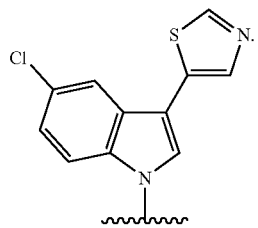 [SMILES: *n1cc(-c2cncs2)c2cc(Cl)ccc21]

In some embodiments, Ring B is

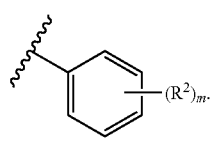

In some embodiments, Ring B is

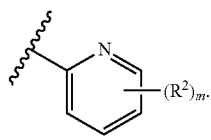

In some embodiments, Ring B is

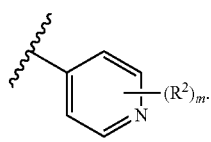

In some embodiments, Ring B is

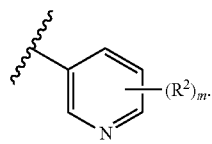

In some embodiments, Ring B is

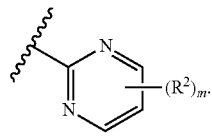

In some embodiments, Ring B is

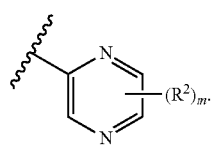

In some embodiments, Ring B is

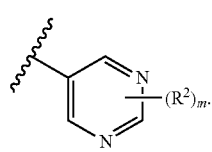

In some embodiments, Ring B is

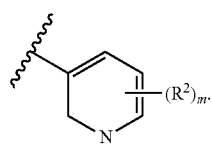

In some embodiments, Ring B is

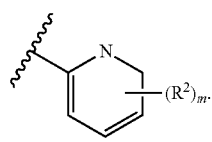

In some embodiments, Ring B is

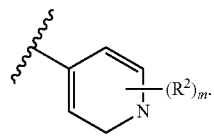

In some embodiments, Ring B is

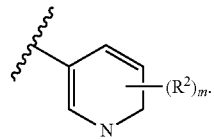

In some embodiments, Ring B and some R² substituents are

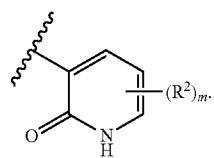

In some embodiments, Ring B and some R² substituents are

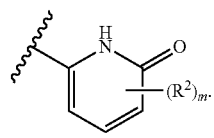

In some embodiments, Ring B and some R² substituents are

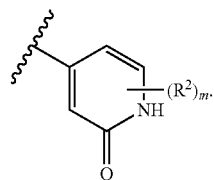

In some embodiments, Ring B and some R² substituents are

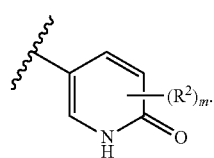

In some embodiments, Ring B is

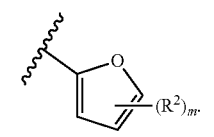

In some embodiments, Ring B is

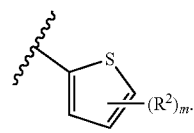

In some embodiments, Ring B is

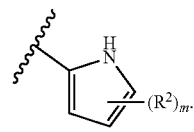

In some embodiments, Ring B is

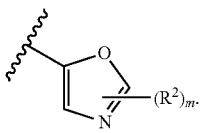

In some embodiments, Ring B is

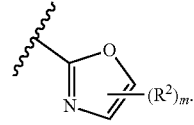

In some embodiments, Ring B is

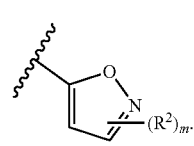

In some embodiments, Ring B is

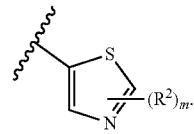

In some embodiments, Ring B is

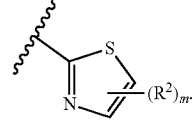

In some embodiments, Ring B is

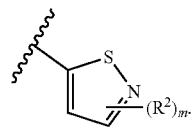

In some embodiments, Ring B is

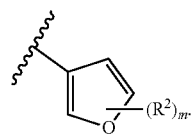

In some embodiments, Ring B is

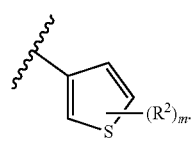

In some embodiments, Ring B is

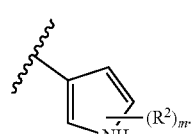

In some embodiments, Ring B is

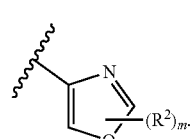

In some embodiments, Ring B is

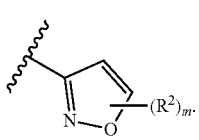

In some embodiments, Ring B is

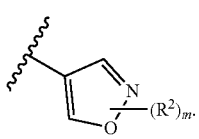

In some embodiments, Ring B is

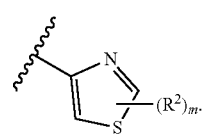

In some embodiments, Ring B is

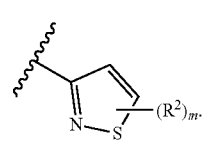

In some embodiments, Ring B is

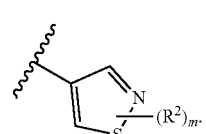

In some embodiments, Ring B is

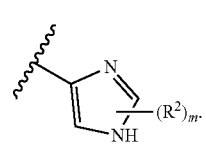

In some embodiments, Ring B is

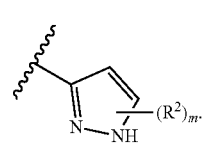

In some embodiments, Ring B is

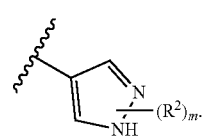

In some embodiments, Ring B is

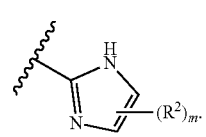

In specific embodiments, Ring B and its R² substituents are

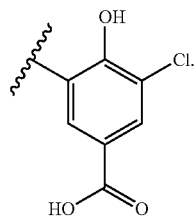 [SMILES: *c1cc(C(=O)O)cc(Cl)c1O]

In some embodiments, Ring B and its R² substituents are

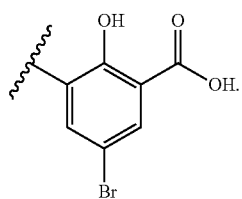 [SMILES: *c1cc(Br)cc(C(=O)O)c1O]

In some embodiments, Ring B is

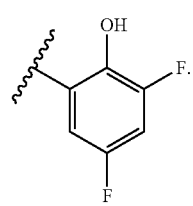 [SMILES: *c1cc(F)cc(F)c1O]

In some embodiments, Ring B and its R² substituents are

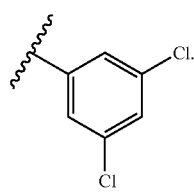 [SMILES: *c1cc(Cl)cc(Cl)c1]

In some embodiments, Ring B and its R² substituents are

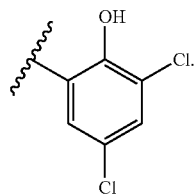 [SMILES: *c1cc(Cl)cc(Cl)c1O]

In some embodiments, Ring B and its R² substituents are

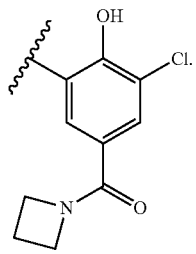 [SMILES: *c1cc(C(=O)N2CCC2)cc(Cl)c1O]

In some embodiments, Ring B and its R² substituents are

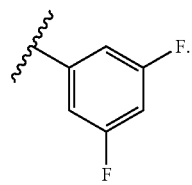 [SMILES: *c1cc(F)cc(F)c1]

In some embodiments, Ring B and its R² substituents are

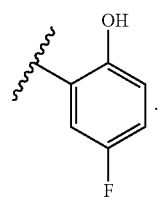 [SMILES: *c1cc(F)ccc1O]

In some embodiments, Ring B and its R² substituents are

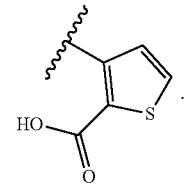

In some embodiments, Ring B and its R² substituents are

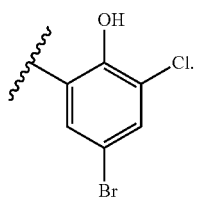 [SMILES: *c1cc(Br)cc(Cl)c1O]

In some embodiments, Ring B and its R² substituents are

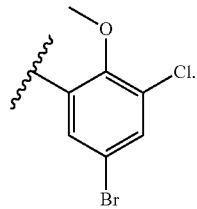 [SMILES: *c1cc(Br)cc(Cl)c1OC]

In some embodiments, Ring B and its R² substituents are

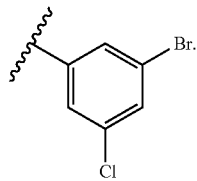 [SMILES: *c1cc(Cl)cc(Br)c1]

In some embodiments, Ring B and its R² substituents are

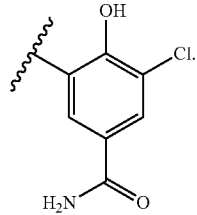 [SMILES: *c1cc(C(N)=O)cc(Cl)c1O]

In some embodiments, Ring B and its R² substituents are

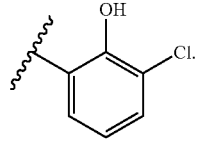 [SMILES: *c1cccc(Cl)c1O]

In some embodiments, Ring B and its R² substituents are

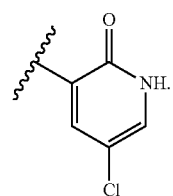 [SMILES: *c1cc(Cl)c[nH]c1=O]

In some embodiments, Ring B and its R² substituents are

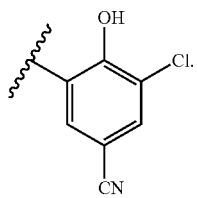 [SMILES: *c1cc(C#N)cc(Cl)c1O]

In some embodiments, Ring B and its R² substituents are

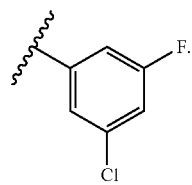 [SMILES: *c1cc(F)cc(Cl)c1]

In some embodiments, Ring B and its R² substituents are

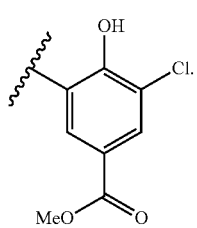 [SMILES: *c1cc(C(=O)OC)cc(Cl)c1O]

some embodiments, Ring B and its R² substituents are

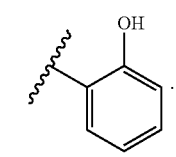 [SMILES: *c1ccccc1O]

In some embodiments, Ring B and its R² substituents are

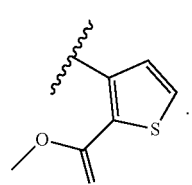

In some embodiments, Ring B and its R² substituents are

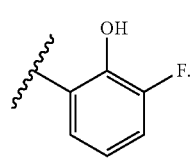 [SMILES: *c1cccc(F)c1O]

In some embodiments, Ring B and its R² substituents are

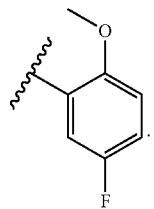 [SMILES: *c1cc(F)ccc1OC]

In some embodiments, Ring B and its R² substituents are

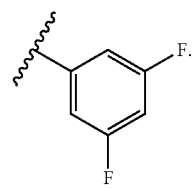 [SMILES: *c1cc(F)cc(F)c1]

In some embodiments, Ring B and its R² substituents are

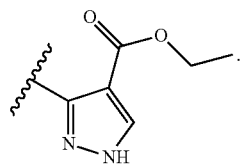 [SMILES: *c1n[nH]cc1C(=O)OCC]

In some embodiments, Ring B and its R² substituents are

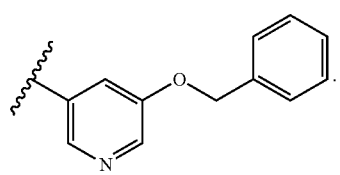 [SMILES: *c1cncc(OCc2ccccc2)c1]

In some embodiments, Ring B and its R² substituents are

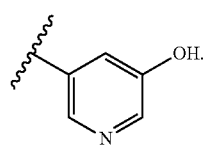 [SMILES: *c1cncc(O)c1]

In some embodiments, Ring B and its R² substituents are

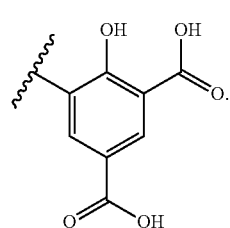 [SMILES: *c1cc(C(=O)O)cc(C(=O)O)c1O]

In some embodiments, Ring B and its R² substituents are

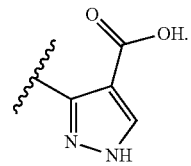 [SMILES: *c1n[nH]cc1C(=O)O]

In some embodiments, Ring B is

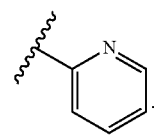 [SMILES: *c1ccccn1]

In some embodiments, Ring B and its R² substituents are

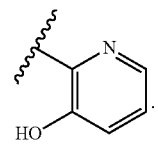

In some embodiments, Ring B and its R² substituents are

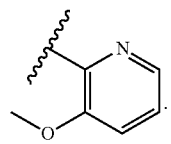 [SMILES: *c1ncccc1OC]

In some embodiments, Ring B and its R² substituents are

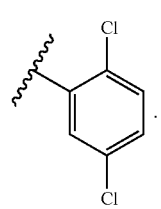

In some embodiments, Ring B and its R² substituents are

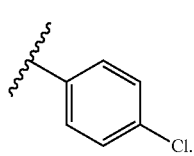 [SMILES: *c1ccc(Cl)cc1]

In some embodiments, Ring B and its R² substituents are

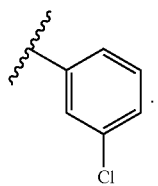 [SMILES: *c1cccc(Cl)c1]

In some embodiments, Ring B and its R² substituents are

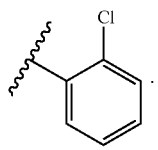 [SMILES: *c1ccccc1Cl]

In some embodiments, Ring B and its R² substituents are

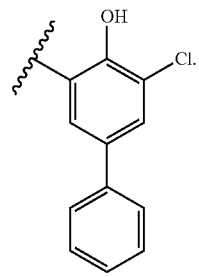 [SMILES: *c1cc(-c2ccccc2)cc(Cl)c1O]

In some embodiments, Ring B and its R² substituents are

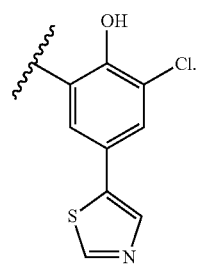 [SMILES: *c1cc(-c2cncs2)cc(Cl)c1O]

In some embodiments, Ring B and its R² substituents are

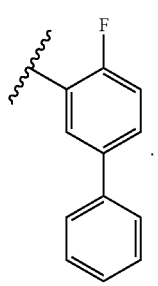 [SMILES: *c1cc(-c2ccccc2)ccc1F]

In certain embodiments, the invention provides a compound provided in Table 1.

TABLE 1

| Compound # | Structure |
|---|---|
| I-1 | 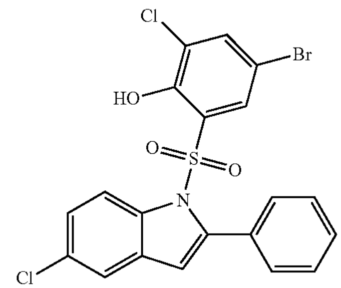 [SMILES: O=S(=O)(c1cc(Br)cc(Cl)c1O)n1c(-c2ccccc2)cc2cc(Cl)ccc21] |
| I-2 | 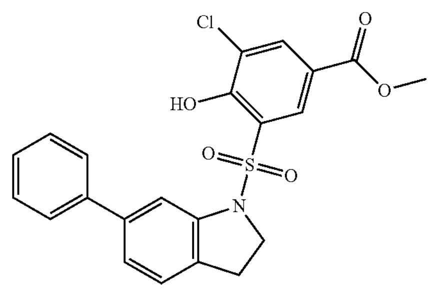 [SMILES: COC(=O)c1cc(Cl)c(O)c(S(=O)(=O)N2CCc3ccc(-c4ccccc4)cc32)c1] |
| I-3 | 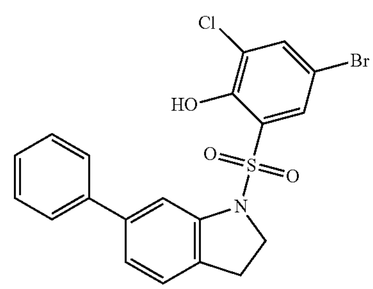 [SMILES: O=S(=O)(c1cc(Br)cc(Cl)c1O)N1CCc2ccc(-c3ccccc3)cc21] |
| I-4 | 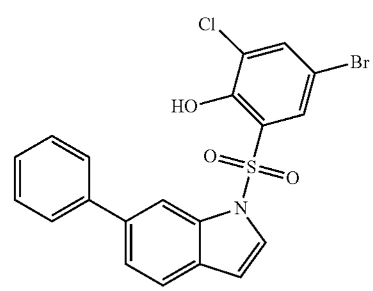 [SMILES: O=S(=O)(c1cc(Br)cc(Cl)c1O)n1ccc2ccc(-c3ccccc3)cc21] |
| I-5 | 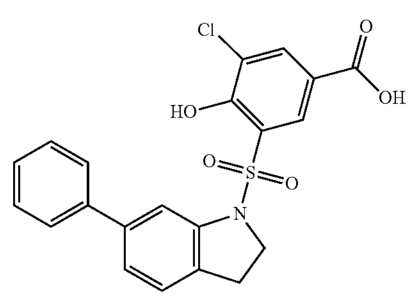 [SMILES: O=C(O)c1cc(Cl)c(O)c(S(=O)(=O)N2CCc3ccc(-c4ccccc4)cc32)c1] |

TABLE 1-continued
| Compound # | Structure |
|---|---|
| I-6 | 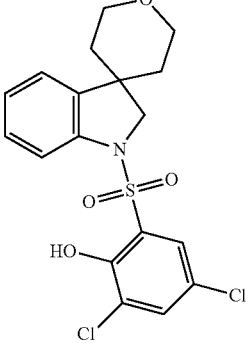 |
| I-7 | 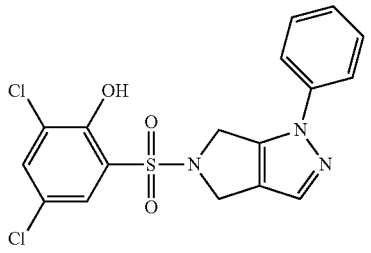 [SMILES: O=S(=O)(c1cc(Cl)cc(Cl)c1O)N1Cc2cnn(-c3ccccc3)c2C1] |
| I-8 | 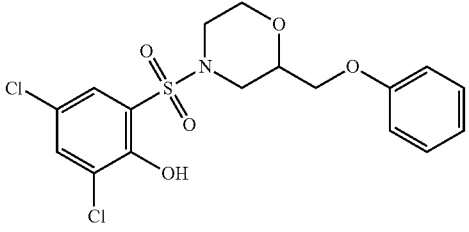 [SMILES: O=S(=O)(c1cc(Cl)cc(Cl)c1O)N1CCOC(COc2ccccc2)C1] |
| I-9 | 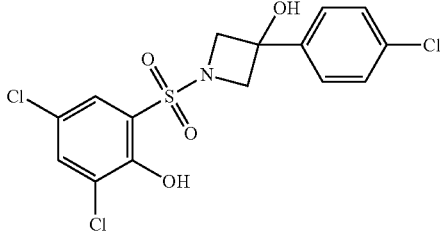 [SMILES: O=S(=O)(c1cc(Cl)cc(Cl)c1O)N1CC(O)(c2ccc(Cl)cc2)C1] |
| I-10 | 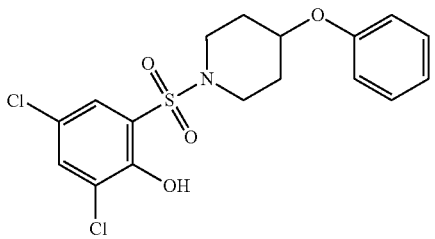 [SMILES: O=S(=O)(c1cc(Cl)cc(Cl)c1O)N1CCC(Oc2ccccc2)CC1] |
| I-11 | 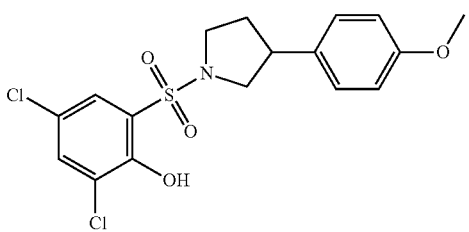 [SMILES: COc1ccc(C2CCN(S(=O)(=O)c3cc(Cl)cc(Cl)c3O)C2)cc1] |
| I-12 | 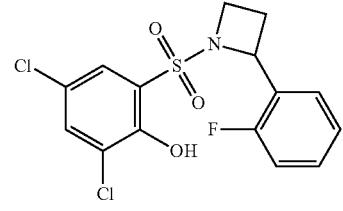 [SMILES: O=S(=O)(c1cc(Cl)cc(Cl)c1O)N1CCC1c1ccccc1F] |
| I-13 | 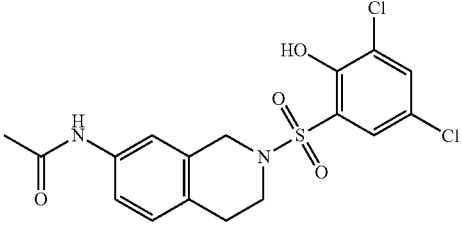 [SMILES: CC(=O)Nc1ccc2c(c1)CN(S(=O)(=O)c1cc(Cl)cc(Cl)c1O)CC2] |
| I-14 | 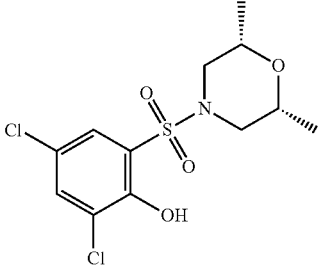 [SMILES: C[C@@H]1CN(S(=O)(=O)c2cc(Cl)cc(Cl)c2O)C[C@H](C)O1] |
| I-15 | 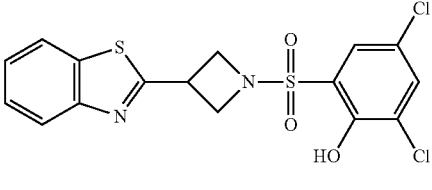 [SMILES: O=S(=O)(c1cc(Cl)cc(Cl)c1O)N1CC(c2nc3ccccc3s2)C1] |
| I-16 | 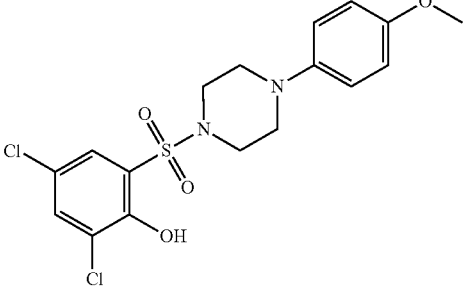 |
| I-17 | 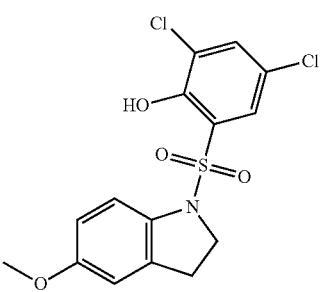 [SMILES: COc1ccc2c(c1)CCN2S(=O)(=O)c1cc(Cl)cc(Cl)c1O] |

TABLE 1-continued
| Compound # | Structure |
|---|---|
| I-18 | 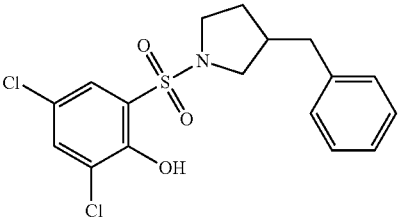 [SMILES: O=S(=O)(c1cc(Cl)cc(Cl)c1O)N1CCC(Cc2ccccc2)C1] |
| I-19 | 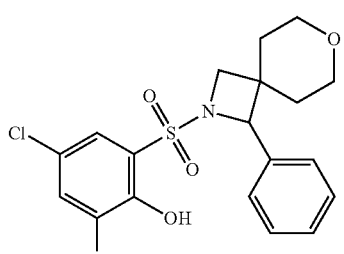 |
| I-20 | 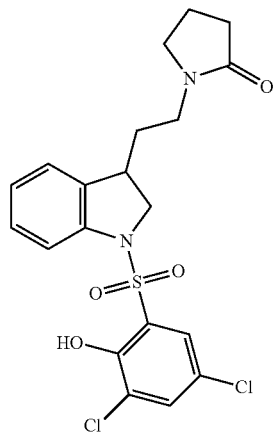 [SMILES: O=C1CCCN1CCC1CN(S(=O)(=O)c2cc(Cl)cc(Cl)c2O)c2ccccc21] |
| I-21 | 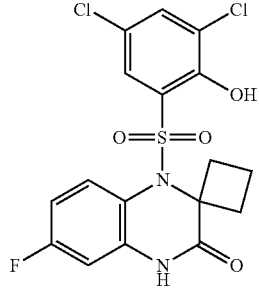 |
| I-22 | 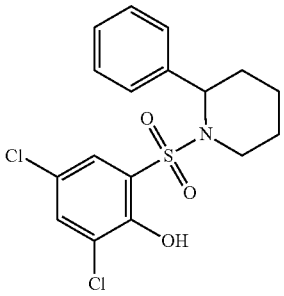 [SMILES: O=S(=O)(c1cc(Cl)cc(Cl)c1O)N1CCCCC1c1ccccc1] |
TABLE 1-continued
| Compound # | Structure |
|---|---|
| I-23 | 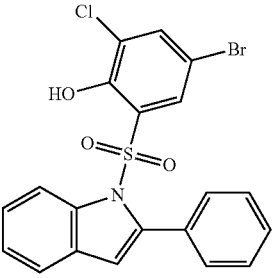 |
| I-24 | 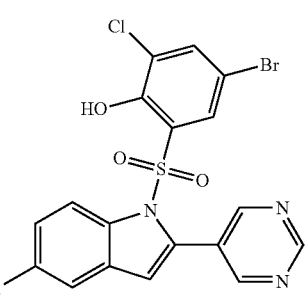 |
| I-25 | 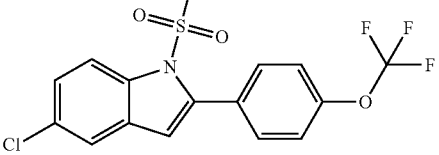 |
| I-26 | 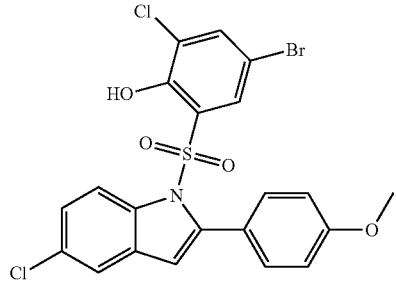 [SMILES: COc1ccc(-c2cc3cc(Cl)ccc3n2S(=O)(=O)c2cc(Br)cc(Cl)c2O)cc1] |
| I-27 | 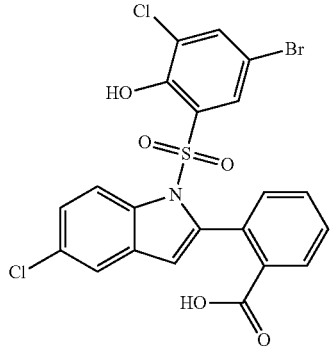 [SMILES: O=C(O)c1ccccc1-c1cc2cc(Cl)ccc2n1S(=O)(=O)c1cc(Br)cc(Cl)c1O] |

TABLE 1-continued
| Compound # | Structure |
|---|---|
| I-28 | 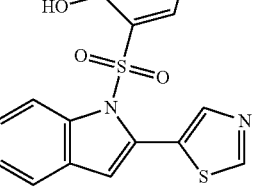 |
| I-29 | |
| I-30 | |
| I-31 | |
| I-32 | |† |
| I-33 | 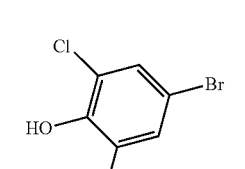 |
| I-34 | 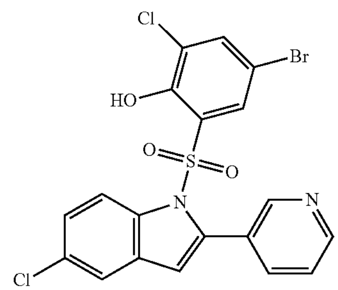 [SMILES: O=S(=O)(c1cc(Br)cc(Cl)c1O)n1c(-c2cccnc2)cc2cc(Cl)ccc21] |
| I-35 | 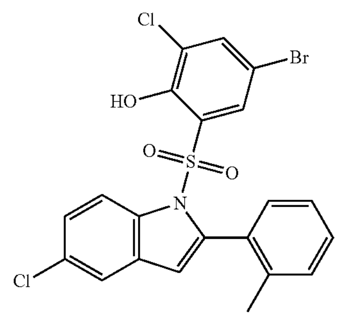 [SMILES: Cc1ccccc1-c1cc2cc(Cl)ccc2n1S(=O)(=O)c1cc(Br)cc(Cl)c1O] |
| I-36 | 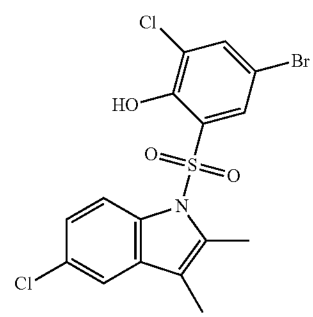 [SMILES: Cc1c(C)n(S(=O)(=O)c2cc(Br)cc(Cl)c2O)c2ccc(Cl)cc12] |
| I-37 | 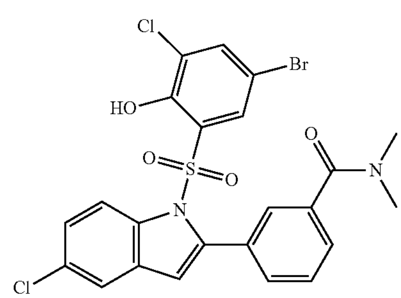 [SMILES: CN(C)C(=O)c1cccc(-c2cc3cc(Cl)ccc3n2S(=O)(=O)c2cc(Br)cc(Cl)c2O)c1] |

TABLE 1-continued

| Compound # | Structure |
|---|---|
| I-38 | 3-chloro-5-bromo-2-hydroxyphenylsulfonyl attached to N of 5-chloroindole with 2-(2-(N,N-dimethylcarbamoyl)phenyl) substituent |
| I-39 | 3-chloro-5-bromo-2-hydroxyphenylsulfonyl attached to N of 5-chloroindole with 2-(2-hydroxypropan-2-yl) substituent |
| I-40 | 3-chloro-5-bromo-2-hydroxyphenylsulfonyl attached to N of 5-chloroindole with 2-(3-fluorophenyl) substituent |
| I-41 | 3-chloro-5-bromo-2-hydroxyphenylsulfonyl attached to N of 5-chloroindole with 2-cyclopropyl substituent |
| I-42 | 3-chloro-5-bromo-2-hydroxyphenylsulfonyl attached to N of 5-fluoroindole with 2-phenyl substituent |
| I-43 | 3-chloro-5-bromo-2-hydroxyphenylsulfonyl attached to N of 5-methylindole with 2-phenyl substituent |
| I-44 | 3-chloro-5-bromo-2-hydroxyphenylsulfonyl attached to N of 5-chloroindole with 2-(3-carboxyphenyl) substituent |
| I-45 | 3-chloro-5-bromo-2-hydroxyphenylsulfonyl attached to N of 5-chloroindole with 2-(4-carboxyphenyl) substituent |
| I-46 | 3-chloro-5-bromo-2-hydroxyphenylsulfonyl attached to N of 5-chloro-2-methyl-3-phenylindole |
| I-47 | 3-chloro-5-bromo-2-hydroxyphenylsulfonyl attached to N of 5-chloro-3-methyl-2-phenylindole |

TABLE 1-continued

| Compound # | Structure |
|---|---|
| I-48 | 1-(3-bromo-5-chloro-2-hydroxyphenylsulfonyl)-2-phenyl-1H-indole-5-carbonitrile |
| I-49 | 3-bromo-5-chloro-2-hydroxyphenyl 2-(4-(trifluoromethoxy)phenyl)-1H-pyrrolo[2,3-c]pyridin-1-yl sulfone |
| I-50 | 4-(1-((3-bromo-5-chloro-2-hydroxyphenyl)sulfonyl)-5-chloro-1H-indol-2-yl)-N,N-dimethylbenzamide |
| I-51 | 5-chloro-1-((3,5-difluoro-2-hydroxyphenyl)sulfonyl)-2-(4-(trifluoromethoxy)phenyl)-1H-indole |
| I-52 | azetidin-1-yl(3-chloro-5-((5-chloro-2-phenyl-1H-indol-1-yl)sulfonyl)-4-hydroxyphenyl)methanone |
| I-53 | methyl 1-((3-bromo-5-chloro-2-hydroxyphenyl)sulfonyl)-2-phenyl-1H-indole-5-carboxylate |
| I-54 | 5-chloro-1-((3,5-dichloro-2-hydroxyphenyl)sulfonyl)-2-(3-(trifluoromethoxy)phenyl)-1H-indole |
| I-55 | 1-((3-bromo-5-chloro-2-hydroxyphenyl)sulfonyl)-2-phenyl-1H-indole-5-carboxylic acid |
| I-56 | 1-((3-bromo-5-chloro-2-hydroxyphenyl)sulfonyl)-N,N-dimethyl-2-phenyl-1H-indole-5-carboxamide |

TABLE 1-continued

| Compound # | Structure |
|---|---|
| I-57 | 3,5-dichloro-2-hydroxyphenylsulfonyl on N of 5-carboxamido-2-phenylindole |
| I-58 | 3,5-dichlorophenylsulfonyl on N of 5-chloro-2-(4-carboxyphenyl)indole |
| I-59 | 3,5-dichloro-2-hydroxyphenylsulfonyl on N of 5-chloro-2-(4-carboxyphenyl)indole |
| I-60 | 3,5-dichloro-2-hydroxyphenylsulfonyl on N of 5-chloro-2-(4-(N,N-dimethylcarbamoyl)phenyl)indole |
| I-61 | 3,5-difluoro-2-hydroxyphenylsulfonyl on N of 5-chloro-2-phenylindole |
| I-62 | 3,5-dichlorophenylsulfonyl on N of 5-chloro-2-carboxyindole |
| I-63 | 3-chloro-2-hydroxyphenylsulfonyl on N of 5-chloro-2-phenylindole |
| I-64 | (5-chloro-2-oxo-1,2-dihydropyridin-3-yl)sulfonyl on N of 5-chloro-2-(4-(trifluoromethoxy)phenyl)indole |
| I-65 | (5-chloro-2-oxo-1,2-dihydropyridin-3-yl)sulfonyl on N of 5-chloro-2-phenylindole |
| I-66 | 3,5-dichloro-2-hydroxyphenylsulfonyl on N of 5-chloro-2-carboxyindole |

TABLE 1-continued

| Compound # | Structure |
|---|---|
| I-67 | (structure) |
| I-68 | (structure) |
| I-69 | (structure) |
| I-70 | (structure) |
| I-71 | (structure) |
| I-72 | (structure) |
| I-73 | (structure) |
| I-74 | (structure) |
| I-75 | (structure) |
| I-76 | (structure) |

TABLE 1-continued
| Compound # | Structure |
|---|---|
| I-77 | 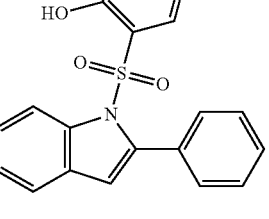 |
| I-78 | 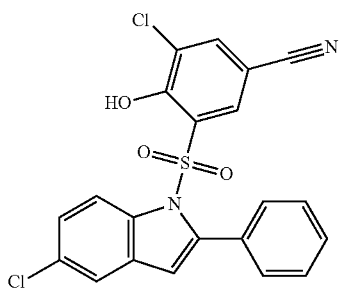 [SMILES: N#Cc1cc(Cl)c(O)c(S(=O)(=O)n2c(-c3ccccc3)cc3cc(Cl)ccc32)c1] |
| I-79 | 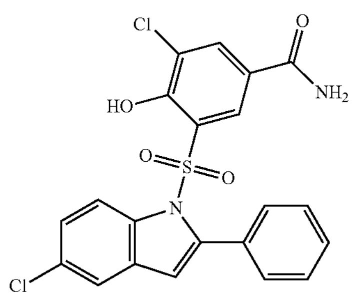 [SMILES: NC(=O)c1cc(Cl)c(O)c(S(=O)(=O)n2c(-c3ccccc3)cc3cc(Cl)ccc32)c1] |
| I-80 | 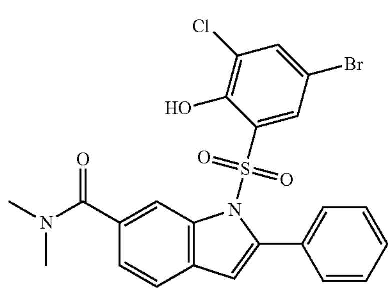 [SMILES: CN(C)C(=O)c1ccc2cc(-c3ccccc3)n(S(=O)(=O)c3cc(Br)cc(Cl)c3O)c2c1] |
| I-81 | 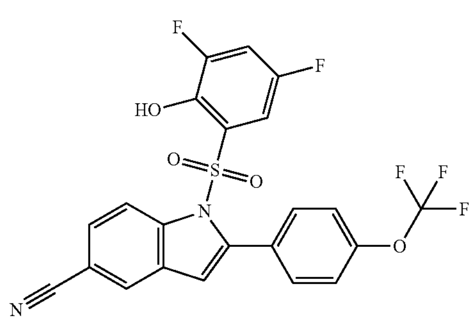 [SMILES: N#Cc1ccc2c(c1)cc(-c1ccc(OC(F)(F)F)cc1)n2S(=O)(=O)c1cc(F)cc(F)c1O] |
TABLE 1-continued
| Compound # | Structure |
|---|---|
| I-82 | 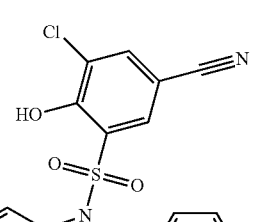 |
| I-83 | 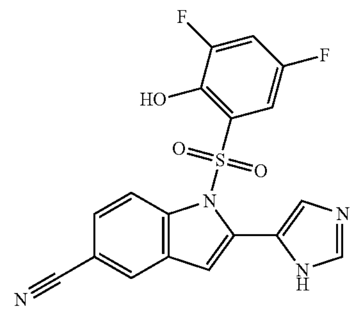 [SMILES: N#Cc1ccc2c(c1)cc(-c1cnc[nH]1)n2S(=O)(=O)c1cc(F)cc(F)c1O] |
| I-84 | 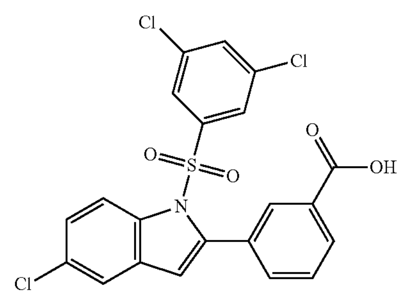 [SMILES: O=C(O)c1cccc(-c2cc3cc(Cl)ccc3n2S(=O)(=O)c2cc(Cl)cc(Cl)c2)c1] |
| I-85 | 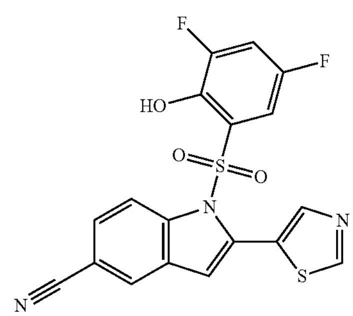 [SMILES: N#Cc1ccc2c(c1)cc(-c1cncs1)n2S(=O)(=O)c1cc(F)cc(F)c1O] |
| I-86 | 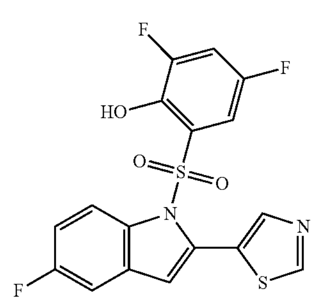 [SMILES: O=S(=O)(c1cc(F)cc(F)c1O)n1c(-c2cncs2)cc2cc(F)ccc21] |

TABLE 1-continued

| Compound # | Structure |
|---|---|
| I-87 | (structure) |
| I-88 | (structure) |
| I-89 | (structure) |
| I-90 | (structure) |
| I-91 | (structure) |
| I-92 | (structure) |
| I-93 | (structure) |
| I-94 | (structure) |
| I-95 | (structure) |
| I-96 | (structure) |

TABLE 1-continued

| Compound # | Structure |
|---|---|
| I-97 | (2,4-difluoro-3-hydroxyphenyl)sulfonyl-5-cyano-2-(pyrimidin-5-yl)indole |
| I-98 | (2,4-difluoro-3-hydroxyphenyl)sulfonyl-5-chloro-2-(pyridin-3-yl N-oxide)indole |
| I-99 | (2,4-difluoro-3-hydroxyphenyl)sulfonyl-5-chloro-2-(pyridazin-3-yl)indole |
| I-100 | (2,4-difluoro-3-hydroxyphenyl)sulfonyl-5-chloro-2-(2-methylpyrimidin-5-yl)indole |
| I-101 | (2,4-difluoro-3-hydroxyphenyl)sulfonyl-5-chloro-2-(5-methylpyrazin-2-yl)indole |
| I-102 | (2,4-difluoro-3-hydroxyphenyl)sulfonyl-5-chloro-2-(4-methylpyrimidin-5-yl)indole |
| I-103 | (2,4-difluoro-3-hydroxyphenyl)sulfonyl-5-chloro-2-(pyridazin-4-yl)indole |
| I-104 | (3,5-dichlorophenyl)sulfonyl-5-chloro-3-phenyl-indole-2-carboxylic acid |
| I-105 | (2,4-difluoro-3-hydroxyphenyl)sulfonyl-5-chloro-2-(pyrazin-2-yl)indole |

TABLE 1-continued

| Compound # | Structure |
|---|---|
| I-106 | 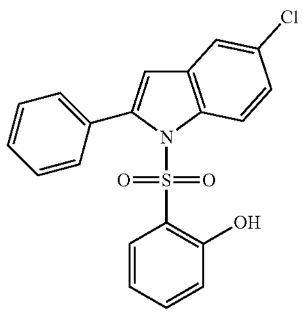 [SMILES: O=S(=O)(c1ccccc1O)n1c(-c2ccccc2)cc2cc(Cl)ccc21] |
| I-107 | 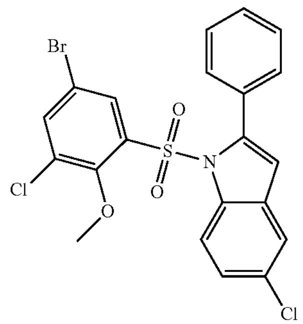 [SMILES: COc1c(Cl)cc(Br)cc1S(=O)(=O)n1c(-c2ccccc2)cc2cc(Cl)ccc21] |
| I-108 | 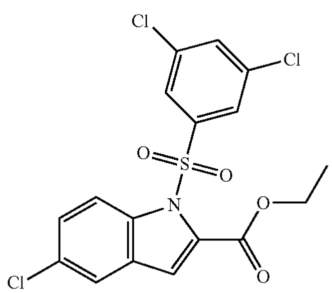 [SMILES: CCOC(=O)c1cc2cc(Cl)ccc2n1S(=O)(=O)c1cc(Cl)cc(Cl)c1] |
| I-109 | 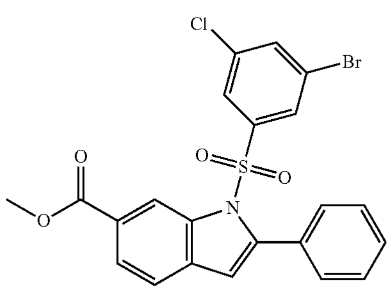 [SMILES: COC(=O)c1ccc2cc(-c3ccccc3)n(S(=O)(=O)c3cc(Cl)cc(Br)c3)c2c1] |
| I-110 | 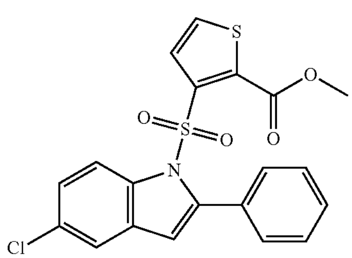 [SMILES: COC(=O)c1sccc1S(=O)(=O)n1c(-c2ccccc2)cc2cc(Cl)ccc21] |
| I-111 | |
| I-112 | |
| I-113 | |
| I-114 | |
| I-115 | |

TABLE 1-continued

| Compound # | Structure |
|---|---|
| I-116 | 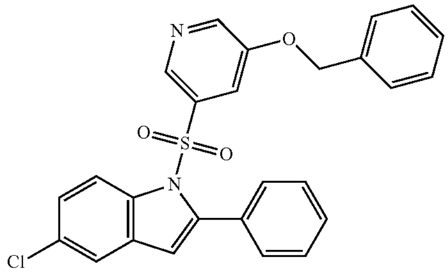 [SMILES: O=S(=O)(c1cncc(OCc2ccccc2)c1)n1c(-c2ccccc2)cc2cc(Cl)ccc21] |
| I-117 | 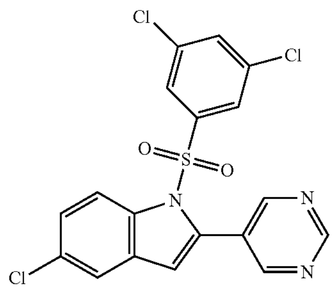 [SMILES: O=S(=O)(c1cc(Cl)cc(Cl)c1)n1c(-c2cncnc2)cc2cc(Cl)ccc21] |
| I-118 | 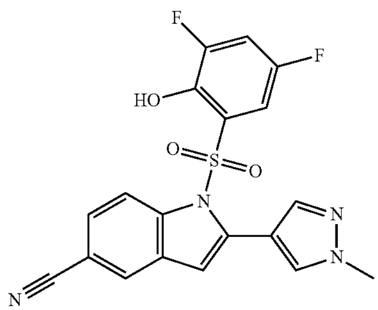 [SMILES: Cn1cc(-c2cc3cc(C#N)ccc3n2S(=O)(=O)c2cc(F)cc(F)c2O)cn1] |
| I-119 | 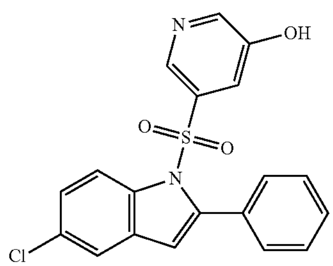 [SMILES: O=S(=O)(c1cncc(O)c1)n1c(-c2ccccc2)cc2cc(Cl)ccc21] |
| I-120 | 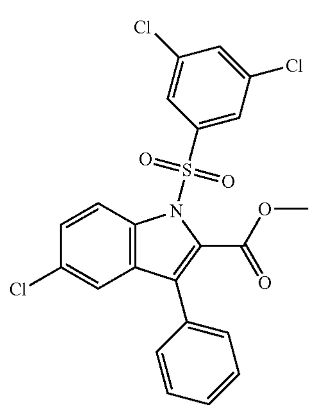 [SMILES: COC(=O)c1c(-c2ccccc2)c2cc(Cl)ccc2n1S(=O)(=O)c1cc(Cl)cc(Cl)c1] |
| I-121 | 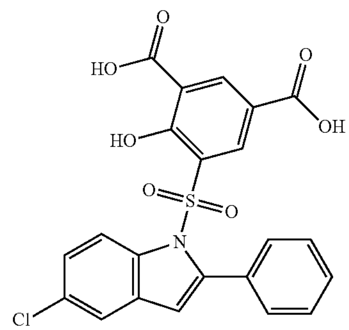 [SMILES: O=C(O)c1cc(C(=O)O)c(O)c(S(=O)(=O)n2c(-c3ccccc3)cc3cc(Cl)ccc32)c1] |
| I-122 | 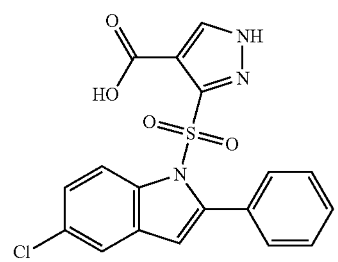 [SMILES: O=C(O)c1c[nH]nc1S(=O)(=O)n1c(-c2ccccc2)cc2cc(Cl)ccc21] |
| I-123 | 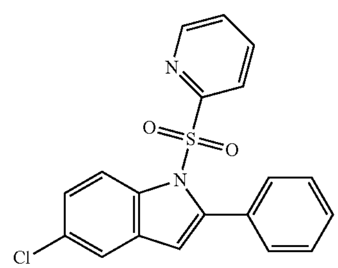 [SMILES: O=S(=O)(c1ccccn1)n1c(-c2ccccc2)cc2cc(Cl)ccc21] |
| I-124 | 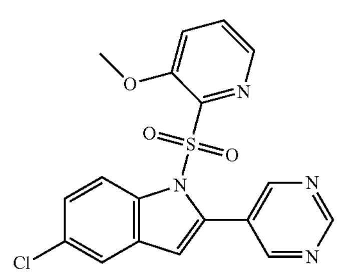 [SMILES: COc1cccnc1S(=O)(=O)n1c(-c2cncnc2)cc2cc(Cl)ccc21] |
| I-125 | 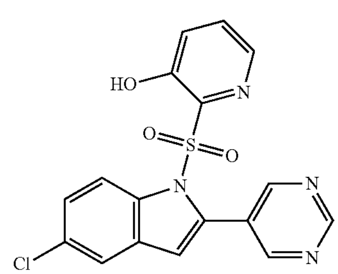 [SMILES: O=S(=O)(c1ncccc1O)n1c(-c2cncnc2)cc2cc(Cl)ccc21] |

TABLE 1-continued

| Compound # | Structure |
|---|---|
| I-126 | (structure) |
| I-127 | (structure) |
| I-135 | (structure) |
| I-136 | (structure) |
| I-137 | (structure) |
| I-138 | (structure) |
| I-139 | (structure) |
| I-140 | (structure) |
| I-141 | (structure) |

TABLE 1-continued

| Compound # | Structure |
|---|---|
| I-142 | (structure) |
| I-143 | (structure) |
| I-144 | (structure) |
| I-145 | (structure) |
| I-146 | (structure) |
| I-147 | (structure) |
| I-148 | (structure) |
| I-149 | (structure) |
| I-150 | (structure) |
| I-151 | (structure) |

TABLE 1-continued

| Compound # | Structure |
|---|---|
| I-152 | 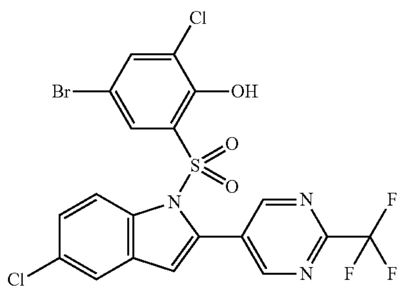 [SMILES: O=S(=O)(c1cc(Br)cc(Cl)c1O)n1c(-c2cnc(C(F)(F)F)nc2)cc2cc(Cl)ccc21] |
| I-153 | 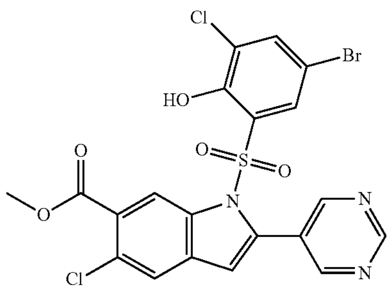 [SMILES: COC(=O)c1cc2c(cc1Cl)cc(-c1cncnc1)n2S(=O)(=O)c1cc(Br)cc(Cl)c1O] |
| I-154 | 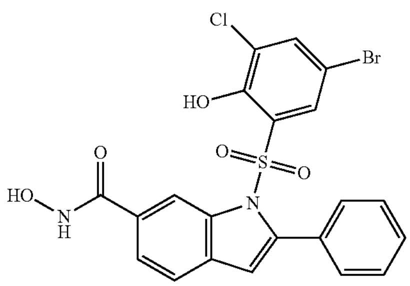 [SMILES: O=C(NO)c1ccc2cc(-c3ccccc3)n(S(=O)(=O)c3cc(Br)cc(Cl)c3O)c2c1] |
| I-155 | 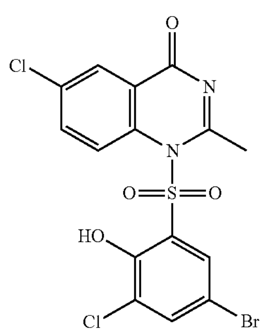 [SMILES: Cc1nc(=O)c2cc(Cl)ccc2n1S(=O)(=O)c1cc(Br)cc(Cl)c1O] |
| I-156 | 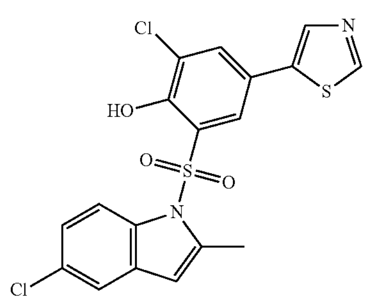 [SMILES: Cc1cc2cc(Cl)ccc2n1S(=O)(=O)c1cc(-c2cncs2)cc(Cl)c1O] |
| I-157 | |
| I-158 | |
| I-159 | |
| I-160 | |
| I-161 | |

TABLE 1-continued

| Compound # | Structure |
|---|---|
| I-162 | (structure) |
| I-163 | (structure) |
| I-164 | (structure) |
| I-165 | (structure) |

4. Uses, Formulation and Administration

Pharmaceutically Acceptable Compositions

According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit ACLY, in a biological sample or in a patient. In certain embodiments, the amount of compound in compositions of this invention is such that is effective to measurably inhibit ACLY, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ACLY.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In mammals ACLY is most abundantly expressed in the liver and white adipose tissue. It also exhibits low levels of expression in brain, heart, small intestine and muscles as well as pancreatic beta cells [Wang, Q., et al. 2010. J Lipid Research 285, 2516-2526]. While its cellular localization is mostly cytosolic, ACLY has also been detected in nuclei of different mammalian cells and may be involved in the compartmentalized production of acetyl-CoA. Within cells, ACLY functions as a critical link between glucose metabolism and FA and cholesterol synthesis. In the cytoplasm, glucose-derived citrate is transformed into acetyl-CoA by ACLY. Acetyl-CoA functions as the essential substrate for the cholesterol and FA synthesis pathways [Pietrocolo, F., et al. 2015. Cell Metabolism 805-821]. In the fatty acid synthesis pathway, acetyl-CoA is carboxylated into malonyl-CoA by acetyl-CoA carboxylase (ACC). Next, fatty-acid-synthase (FASN) performs condensation of acetyl-CoA and malonyl-CoA to produce the long-chain fatty acid palmitate, and the subsequent synthesis of endogenously derived FA's occurs in the pathway. Alternatively, ACLY derived acetyl-CoA is shunted into the mevalonate pathway and functions as a precursor for the synthesis of cholesterol as well as a number of intermediates required for posttranslational modification of a variety of proteins. Additionally, acetyl-CoA can also be used for acetylation of histone and non-histone proteins, and thus regulates global chromatin architecture and gene transcription in metabolic cells and tissues.

Given its critical role in promoting FA and cholesterol biosynthesis, ACLY inhibition has been considered an attractive target for lipid lowering. Reduced intracellular cholesterol synthesis triggers a feedback response involving sterol response element binding protein 2 (SREBP2) mediated upregulation of the low-density lipoprotein receptor (LDL), such that cells require more cholesterol scavenging from circulating LDL particles, thus reducing LDL-C and the potential of atherosclerotic cardiovascular disease (AS-CVD). ACLY inhibition is predicted to not only reduce intracellular cholesterol synthesis but to also promote the effects of LDL mediated LDL-C clearance, and this is supported by in vitro studies of ACLY in human livers [Berkhout, T A., et al. 1990. Biochem J 272, 181-186]. Interestingly, single nucleotide polymorphisms (SNPs) in the ACLY gene region have been shown to correlate with lowered LDL-C levels and also associated with a shift in plasma biomarkers such as apolipoprotein B (ApoB), high density lipoprotein C (HDL-C), C reactive protein (CRP) and triglycerides, analogous to LDL-C lowering polymorphisms in hydroxy-3-methylglutaryl-CoA reductase (HMGR) and the effects of statins [Ference, B A. 2017. J. Am. Col. Cardio 69 (Suppl 11) 1655]. Furthermore, lower LDL-C levels mediated by ACLY SNPs was found to be causally associated with a reduction in ASCVD risk [Ference, B A. 2017. J. Am. Col. Cardio 69 (Suppl 11) 1655]. Thus, ACLY inhibitors might be useful as LDL-C lowering drugs that reduce the risk of ASCVD. In fact, recent clinical evidence suggests that pharmacological inhibition of ACLY by bempedoic acid (BA) can promote dose dependent LDL-C lowering and proportional reductions in several plasma biomarkers associated with ASCVD risk [Ballantyne, C. M., et al. 2012. J. Am. Coll. Cardiol 59, E1625-E1625]. Additionally, the robust cholesterol lowering effects and decreases in plasma triglycerides that have been reported suggest that pharmacologic ACLY inhibitors may also have utility as anti-obesity drugs [Pearce, N.J., et al. 1998. Biochem J 34, 113-119].

ACLY blockade leads to a dramatic reduction in de novo FA production. Thus, shutdown of FA synthesis resulting from ACLY inhibition may have therapeutic benefits for a number of other lipid related metabolic diseases and disease outcomes associated with metabolic syndrome. In the liver, accumulation of lipids leads to liver steatosis and the onset of fatty liver disease (non-alcoholic fatty liver disease, NAFLD). Progression of NAFLD into the more severe form of non-alcoholic steatohepatitis (NASH) due to excessive lipid accumulation, inflammation, tissue scarring and fibrosis, is a precursor for the development of cirrhosis and hepatocellular carcinoma (HCC), the most common type of liver cancer. ACLY inhibitors are expected to have a dramatic impact on FA metabolism in the liver through DNL inhibition and fatty acid oxidation induction and should therefore inhibit FA accumulation and the development and progression of fatty liver diseases to terminal liver disease states. The therapeutic utility of inhibiting DNL in NASH patients has been recently been described where hepatic ACC inhibition was reported to rapidly reduce DNL, hepatic steatosis and reduce markers of liver fibrosis within 12 weeks [Steide. K., et al. 2017. Hepatology 66, 324-344, Lawitz. E., et al. 2017. J Hepatol 66, S34]. ACLY is positioned one step upstream of ACC in the DNL pathway and controls its activity due to the dependence of ACC on acetyl-CoA production from ACLY. Thus, ACLY inhibitors should be efficacious at inhibiting DNL in humans. In preclinical studies, liver specific knockdown of ACLY using RNA interference (RNAi) led to reductions in hepatic acetyl-CoA and malonyl-CoA levels as well as lowered expression of lipogenesis, steatosis and gluconeogenesis genes which, importantly, promoted improvements in insulin sensitivity and glucose tolerance in animals [Wang, Q., et al. 2009. Hepatology 49, 1166-1175]. Furthermore, ACLY inhibition or gene silencing by siRNA was shown to reduce a variety of inflammatory mediators in macrophage cells [Infantino. V., et al. 2009. BBRC 440, 105-111], suggesting that ACLY inhibitors may also possess anti-inflammatory properties that could directly lower hepatic inflammation to improve tissue scarring and fibrosis. Thus, the potential for pharmacologic ACLY suppression to reduce DNL, inflammation, fibrosis and to restore insulin sensitivity could have profound therapeutic impacts in fatty liver, dyslipidemia and metabolic disease states.

ACLY inhibitors may also possess therapeutic utility in oncology. Interestingly, upregulation of ACLY expression has been documented in many human cancers including hepatocellular carcinoma, non-small cell lung cancer, breast cancer, colorectal cancer, and prostate cancer [Yancy, H. F., et al. 2007. J Carcinog 6, 8, Varis, A., et al. 2002. Cancer Research 62, 2625-9]. Furthermore, ACLY has also been proposed as a prognostic biomarker in some cancer patients [Migita, T., et al. 2009. Cancer Research 66, 8547-54]. The pro cancer role of ACLY may be related to enhanced DNL associated with its activity and thus the growth and survival advantage that DNL confers over normal cells [Svensson, R U., et al. 2017. Cold Spring Harbor Symp Quant Biol, 81, 93-103]. Thus, direct ACLY inhibition may be effective as an anti-cancer strategy and several lines of evidence suggest this. Inhibition of ACLY by either RNAi or pharmacological inhibitors results in cell cycle arrest and induction of apoptosis in vitro and in vivo [Hatzivassiliou, G., et al. 2005. Cancer Cell 8, 311-321]. Genetic knockout of ACLY in LN229 human glioblastoma cells led to profound defects in FA synthesis, histone acetylation and cellular proliferation [Zhao, S., et al. 2016. Cell Reports 17, 1037-1052]. Furthermore, ACLY knockdown in H1299 and H358 lung cancer cells led to a dramatic reduction in xenograft tumor growth in vivo [Zhang, C., et al. 2016. Genes and Development 30, 1956-1970].

ACLY derived acetyl-CoA is a critical precursor for malonyl-CoA production, which serves as the rate limiting metabolite for FA synthesis. Malonyl-CoA not only serves as the substrate for FA synthesis but also is required to suppress fatty acid oxidation in mitochondria. Hence, ACLY inhibition is expected to reduce cytosolic acetyl-CoA and Malonyl-CoA production, which will simultaneously reduce de novo lipid synthesis and promote the oxidation of existing fat. This dual effect on lipid metabolism raises the possibility that ACLY inhibitors will be substantially more effective in reducing excess fat than other mechanisms, and coupled to the effect of cholesterol synthesis inhibition, ACLY inhibitors are expected to be far superior than current therapies. Furthermore, ACLY inhibitors will impact insulin sensitivity, plasma and tissue triglycerides, and fasting plasma glucose as a consequence of whole-body and tissue-specific fat mass reduction, without the need for poly-pharmacy.

As ACLY inhibition is expected to reduce cytosolic acetyl-CoA, it is expected to have an impact on the enzyme immediately downstream of ACLY, Acetyl-CoA carboxylase. Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle [Harwood, 2005].

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation [Tong and Harwood, *J. Cellular Biochem.* 99: 1476, 2006]. This compartmentalization of malonyl-CoA results from a combination of synthesis proximity [Abu-Elheiga et al., PNAS (USA) 102: 12011, 2005] and the rapid action of malonyl-CoA decarboxylase [Cheng et al., *J. Med. Chem.* 49:1517, 2006].

Simultaneous suppression of the enzymatic activities of ACC1 and ACC2 via ACLY offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of inhibition of ACC activity as an important therapeutic target for treating obesity, diabetes, insulin resistance, and the metabolic syndrome.

Abu-Elheiga et al. [*Proc. Natl. Acad. Sci.* USA 100: 10207-10212, 2003] demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. [*J. Clin. Invest.* 116: 817, 2006], using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. [*J. Biol. Chem.* 278: 37099, 2003] demonstrated that the isozyme-nonselective ACC inhibitor, CP-640186, which equally inhibits ACC1 and ACC2 ($IC_{50}=\sim 60$ nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. [*Diabetes* 55:A288, 2006] demonstrated stimulation of insulin sensitivity in insulin-resistant rat muscle tissue by CP-640186 within 30 min of compound administration, and studies by Furler et al. [*Diabetes* 55:A333, 2006] used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, the suppression of ACC activity via ACLY may both reduce de novo lipid synthesis and promote the oxidation of existing fat. This dual effect on lipid metabolism raises the possibility that ACC suppression via ACLY inhibition will be substantially more effective in reducing excess fat than other mechanisms. Furthermore, ACLY inhibitors will impact insulin sensitivity, plasma and tissue triglycerides, and fasting plasma glucose as a consequence of whole-body and tissue-specific fat mass reduction without the need for poly-pharmacy.

ACLY inhibitors need only access the liver and muscle in the peripheral compartment. Avoiding the CNS will address many of side effects associated with the late-stage obesity programs targeting CNS receptors. ACLY inhibitors are also expected to have superior safety profiles to existing metabolic disease agents. For example, it is unlikely that an ACLY inhibitor will precipitate life-threatening hypoglycemia as is often seen with insulin mimetics, insulin secretagogues, and insulin degradation inhibitors. Also, since ACLY inhibitors will reduce whole-body fat mass, they will be superior to the glitazones that increase whole-body fat mass as part of their mechanism of action.

A peripherally acting agent that causes significant weight loss and improves other metabolic endpoints fits well within the US FDA's requirements for approval of a new obesity agent. However, if an approval for obesity continues to be challenging in 5-7 years, ACLY inhibitors could be approved for familial combined hyperlipidemia and non-alcoholic steatohepatitis (NASH). There are currently no marketed ACLY inhibitors, so an ACLY inhibitor would represent first-in-class therapy for treating obesity and metabolic syndrome.

The activity of a compound utilized in this invention as an inhibitor of ACLY or treatment for obesity, metabolic syndrome, NAFLD, NASH, dyslipidemia, cancer or hypercholesteremia may be assayed in vitro or in vivo. An in vivo assessment of the efficacy of the compounds of the invention may be made using an animal model of aforementioned indications, e.g., a rodent or primate model. Cell-based assays may be performed using a relevant cell line isolated from a tissue that expresses ACLY. Additionally, biochemical, biophysical, molecular and mechanism-based assays, e.g., transcription assays using a purified protein, western blot, northern blot, RT-PCR, luminescence or fluorescence-based enzyme assays etc., may be performed. In vitro assays include assays that determine cell proliferation, protein expression, cytotoxicity, enzyme inhibitory activity, and/or the subsequent functional consequences of treatment of cells with compounds of the invention. Additional in vitro assays may include stable isotope labeling of carbons and radiolabel quantitation in inhibitor treated cells. Additionally, metabolic flux and metabolomics may be used. Alternate in vitro assays quantitate the ability of the inhibitor to bind to protein or nucleic acid molecules within the cell. Inhibitor binding may be measured by radiolabeling the inhibitor prior to binding, isolating the inhibitor/target molecule complex and determining the amount of radiolabel bound. Alternatively, inhibitor binding may be determined by additional biophysical techniques e.g. surface plasma resonance (SPR). Detailed conditions for assaying a compound utilized in this invention as an inhibitor of ACLY are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with ACLY.

In some embodiments, the compounds and compositions, according to the method of the present invention, may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, the compounds and compositions, according to the method of the present invention, may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, Type III dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance.

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with compounds of the present invention include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with compounds of the present invention include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with compounds of the present invention include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-$HT_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), $PYY_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buprorion plus zonisamide (Empatic), pramlintide plus metreleptin, buprorion plus naltrexone (Contrave), phentermine plus topiramate (Qsymia).

In some embodiments, the anti-obesity agents used in combination with compounds of the invention are selected from gut-selective MTP inhibitors (e.g. dirlotapide, mitratapide, implitapide, R56918), CCK-A agonists, 5-$HT_2c$ agonists (e.g. lorcaserin/Belviq), MCR4 agonists, lipase inhibitors (e.g. Cetilistat), $PYY_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, the compounds and compositions, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, the compounds and compositions, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, the compounds and compositions, according to the method of the present invention, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

Compounds of the present invention find special utility in triple negative breast cancer, as the tumor suppressor protein BRCA1 binds and stabilizes the inactive form of ACC, thus upregulating de novo lipid synthesis, resulting in cancer cell proliferation Brunet et al. "BRCA1 and acetyl-CoA carboxylase: the metabolic syndrome of breast cancer" Mol. Carcinog. (2008) 47(2), 157-163.

In some embodiments, the compounds and compositions, according to the method of the present invention, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, the compounds and compositions, according to the method of the present invention, may be administered using any amount and any route of administration effective for treating or lessening the severity of a liver disease. In some embodiments, the liver disease is selected from hepatitis C, hepatocellular carcinoma, familial combined hyperlipidemia and non-alcoholic steatohepatitis (NASH), liver cancer, cholangiocarcinoma, angiosarcoma, hemangiosarcoma, and progressive familial intrahepatic cholestasis.

In some embodiments, the compounds and compositions, according to the method of the present invention, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2:S16; Baranano et al. Curr. Treat. Opin. Neurol. (2008) 10, 410-419).

In some embodiments, the compounds and compositions, according to the method of the present invention, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation by indirect ACC inhibition via ACLY (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting ACLY in a biological sample comprising the step of contacting said biological sample with a compound of this invention, or a composition comprising said compound.

In certain embodiments, the invention relates to a method of modulating fatty acid levels in a biological sample comprising the step of contacting said biological sample with a compound of this invention, or a composition comprising said compound.

The term "biological sample", as used herein, includes, without limitation, cell cultures or extracts thereof biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting ACLY in a patient comprising the step of administering to said patient a compound of the present invention, or a composition comprising said compound.

According to another embodiment, the invention relates to a method of inhibiting fatty acid production, inhibiting sterol production, or both, in a patient comprising the step of administering to said patient a compound of the present invention, or a composition comprising said compound. According to certain embodiments, the invention relates to a method of inhibiting fatty acid production, inhibiting sterol production, or both in a patient, leading to decreasing obesity or alleviating symptoms of metabolic syndrome, comprising the step of administering to said patient a compound of the present invention, or a composition comprising said compound. In other embodiments, the present invention provides a method for treating a disorder mediated by ACLY, in a patient in need thereof, comprising the step of administering to said patient a compound according to the present invention or pharmaceutically acceptable composition thereof. Such disorders are described in detail herein.

In some embodiments the compounds and compositions of the present invention may be used in a method of treating obesity or another metabolic disorder. In certain embodiments the compounds and compositions of the present invention may be used to treat obesity or other metabolic disorder in a mammal. In certain embodiments the mammal is a human patient. In certain embodiments the compounds and compositions of the present invention may be used to treat obesity or other metabolic disorder in a human patient.

In some embodiments the present invention provides a method of treating obesity or another metabolic disorder, comprising administering a compound or composition of the present invention to a patient with obesity or another metabolic disorder. In certain embodiments the method of treating obesity or another metabolic disorder comprises administering compounds and compositions of the present invention to a mammal. In certain embodiments the mammal is a human. In some embodiments the metabolic disorder is dyslipidemia, Type III dyslipidemia, or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfunylureas, thiazolidinediones, antipsychotics, antidepressants, steroids, anticonvulsants (including phenytoin and valproate), pizotifen, or hormonal contraceptives.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments the cancer to be treated by compounds or compositions of the invention is one bearing an activated MAPK pathway. In some embodiments the cancer bearing an activated MAPK pathway is a melanoma. In certain preferred embodiments the cancer treated by compounds or compositions of the invention is one associated with BRCA1 mutation. In an especially preferred embodiment, the cancer treated by compounds or compositions of the invention is a triple negative breast cancer.

In certain embodiments, the disease which can be treated by compounds of the invention are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, gliomaor Huntington's Disease.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of ACLY or antiobesity agent. In some embodiments, a provided compound, or composition thereof, is administered in combination with one or more other therapeutic agents. Such therapeutic agents agents include, but are not limited to agents such as orlistat (Xenical), CNS stimulants, Qsymia, or Belviq.

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphami de, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposi de, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, $C_{225}$, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, MINI, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Oxapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, compounds of the present invention may be administered together with a biguanide selected from metformin, phenformin, or buformin, to a patient in need thereof. In certain embodiments, the patient administered a combination of a compound of the invention and a biguanide is suffering from a cancer, obesity, a liver disease, diabetes or two or more of the above.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, mTOR inhibitors, CPT1 inhibitors, AMPK activators, PCSK9 inhibitors, SREBP site 1 protease inhibitors, HMG CoA-reductase inhibitors, antiemetics (e.g. 5-HT3 receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of formula I can be present in different crystal modifications whose biological activity may differ. They are likewise subject matter of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Reaction Schemes

Chlorosulfonation I.

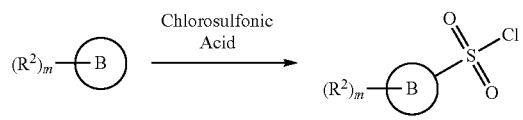

A 3-necked round-bottom flask purged and maintained with an inert atmosphere of nitrogen is charged with aryl compound B (1 eq.) and chlorosulfonic acid. The resulting solution is stirred overnight at between about 65° C. to 115° C. Upon completion the reaction is quenched by the addition of water/ice. The resulting solution is then extracted with ethyl acetate and the combined organic layers are concentrated under vacuum to the target sulfonylchloride.

Chlorosulfonation II.

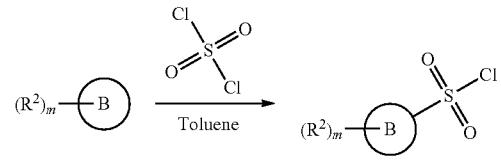

A 3-necked round-bottom flask purged and maintained with an inert atmosphere of nitrogen is charged with aryl compound A (1 eq.), sulfuroyl dichloride (6 eq.), and toluene. The resulting solution is stirred at about 65° C. Upon completion the reaction is quenched by the addition of water/ice. Product sulfonylchloride is collected by filtration or extraction with ethyl acetate.

Sulfonamide Linker Formation.

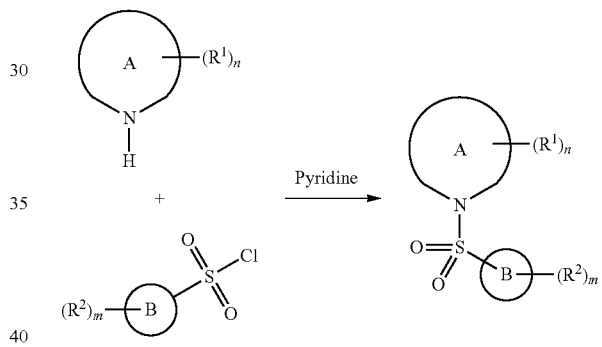

A round-bottom flask is charged with sulfonyl chloride B (1 eq.), amine A (1.2 eq.), pyridine, and DCM. The reaction solution is stirred at room temperature. Upon completion the reaction is quenched by the addition of water and the pH is adjusted with 1M HCl. The resulting solution is extracted with ethyl acetate and the combined organic layers are concentrated under vacuum. The product sulfonamide is then further purified by column chromatography.

Sulfonamide Linker and Indole Formation.

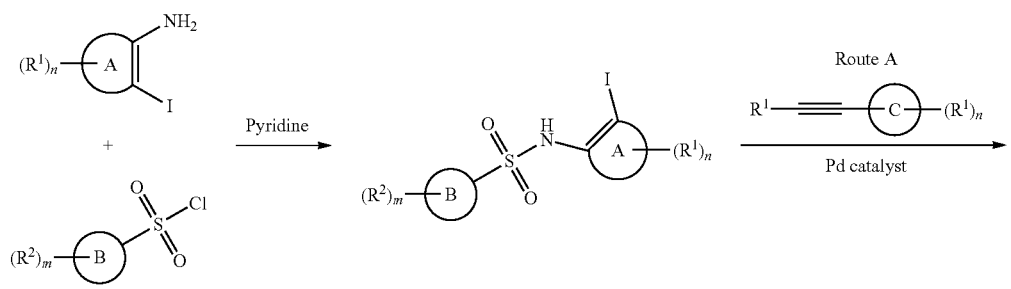

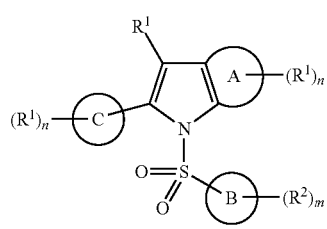
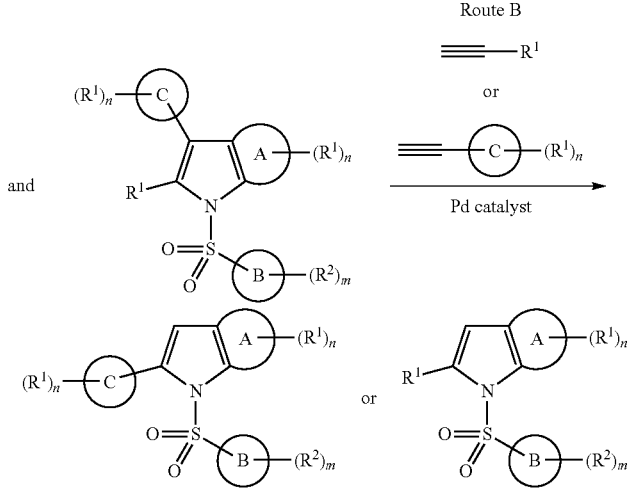

A round-bottom flask is charged with sulfonyl chloride B (1 eq.), amine A (1.2 eq.), pyridine, and DCM. The reaction solution is stirred at room temperature. Upon completion the reaction is quenched by the addition of water and the pH is adjusted with 1M HCl. The resulting solution is extracted with ethyl acetate and the combined organic layers are concentrated under vacuum. The product sulfonamide is then further purified by column chromatography and then added to a sealed vial containing ZnCl$_2$ (0.1 eq.), Et$_3$N (7 eq.), PPh$_3$ (0.25 eq.), Pd/C (0.29 eq.), and an alkyne (1.2 eq.) according to Route A or Route B. The resulting mixture is then heated with stirring to 100-110° C. in an oil bath. Upon completion the reaction the product indole is purified by column chromatography directly or after an aqueous work-up.

Example 1. Synthesis of 4-bromo-2-chloro-6-((5-chloro-2-phenyl-1H-indol-1-yl)sulfonyl)phenol (I-1)

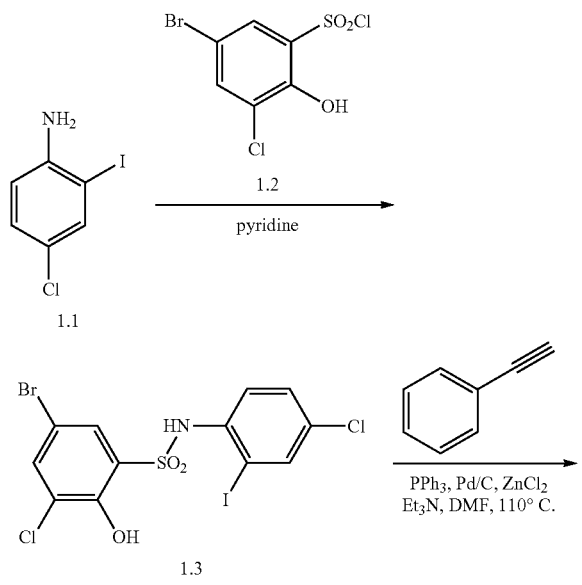

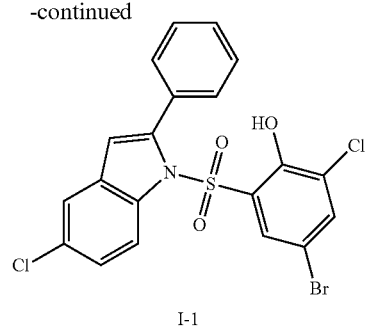

I-1

Synthesis of Compound 1.3.

Into a 50-mL round-bottom flask were placed 4-chloro-2-iodoaniline (1.1, 500 mg, 1.97 mmol, 1equiv), pyridine (10 mL), 5-bromo-3-chloro-2-hydroxybenzene-1-sulfonyl chloride (1.2, 724.3 mg, 2.37 mmol, 1.2 equiv). The resulting solution was stirred overnight at 25° C. The pH value of the solution was adjusted to 7-8 with 1M HCl (aq.). The resulting solution was extracted with ethyl acetate (3×10 mL) the combined organic layers were concentrated under vacuum. The residue was applied onto a silica gel column with ethyl acetate/petroleum ether (1:4). This resulted in 200 mg (17%) of 1.3 as off-white solid. (ES, m/z): [M+H]$^+$ 501.9.

Synthesis of I-1.

Into a 15-mL sealed tube, was placed 1.3 (180 mg, 0.34 mmol, 1 equiv), ethynylbenzene (36.9 mg, 0.36 mmol, 1.05 equiv), PPh$_3$ (22.6 mg, 0.09 mmol, 0.25 equiv), Pd/C (1.8 mg), ZnCl$_2$ (4.7 mg, 0.03 mmol, 0.1 equiv), DMF (5 mL), Et$_3$N (243.8 mg, 2.41 mmol, 7 equiv). The resulting solution was stirred for 3 h at 110° C. The solids were filtered out. The crude product was purified by Flash-Prep-HPLC with the following conditions (IntelFlash-1): Column, C18; mobile phase, ACN/H$_2$O=10% increasing to ACN/H$_2$O=60% within 15 min; Detector, UV 220 nm. This resulted in 70 mg (50%) of I-1 as white solid. LC-MS (ES, m/z): [M+H]$^+$ 496.1. 1 H-NMR (300 MHz, DMSO-d$_6$, ppm): δ 8.04-8.01 (d, J=9 Hz, 1H), 7.78 (s, 1H), 7.68 (s, 1H), 7.44-7.29 (m, 4H), 7.25-7.20 (m, 2H), 7.08-6.91 (m, 1H), 6.68 (s, 1H).

Example 2. Synthesis of 4-bromo-2-chloro-6-((6-phenylindolin-1-yl)sulfonyl)phenol (I-3) and 4-bromo-2-chloro-6-((6-phenyl-1H-indol-1-yl)sulfonyl)phenol (I-4)

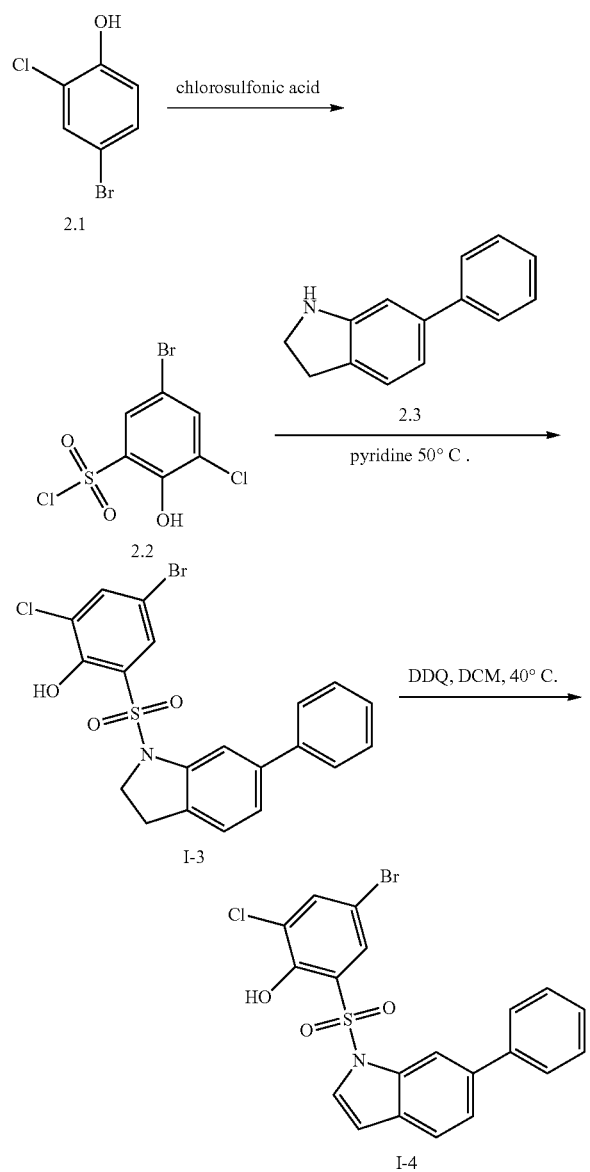

1H-indole (2.3, 638.2 mg, 3.27 mmol, 1 equiv), pyridine (10 mL). The resulting solution was stirred for 16 h at 50° C. in an oil bath. The resulting mixture was diluted with 10 mL of water. The resulting solution was extracted with 3×20 mL of ethyl acetate. The combined organic layers were washed with 2×10 mL of 1M HCl and concentrated under vacuum. The crude mixture was purified by Flash-Prep-HPLC with the following conditions (IntelFlash-1): Column, C18; mobile phase, water:acetonitrile=90:10 increasing to water:acetonitrile=0:100 within 40 min. This resulted in 19.8 mg (1%) of 8.2 as a red solid. (ES, m/z): [M+H]$^+$ 464.0.

Synthesis of I-4.

Into a 50-mL 3-necked round-bottom flask purged and maintained with an inert atmosphere of nitrogen, was placed I-3 (500 mg, 1.08 mmol, 1 equiv), DCM (8 mL), DDQ (488.4 mg, 2.15 mmol, 2 equiv). The resulting solution was stirred for 16 h at 40° C. in an oil bath. The resulting mixture was diluted with 5 mL of water. The resulting solution was extracted with 3×10 mL of dichloromethane and the organic layers combined and concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 40 min. Detector, UV 254 nm. This resulted in 10.3 mg (2%) of I-4 as a grey solid. LC-MS (ES, m/z): [M+H]$^+$ 461.9. 1 H-NMR (300 MHz, DMSO, ppm): δ 8.02 (s, 1H), 7.90 (s, 1H), 7.80 (s, 1H), 7.68-7.53 (m, 4H), 7.45-7.41 (m, 3H), 7.33-7.29 (t, J=7.6 Hz, 1H), 6.61 (s, 1H)

Example 3. Synthesis of 4-bromo-2-chloro-6-((2-phenyl-1H-indol-1-yl)sulfonyl)phenol (I-23)

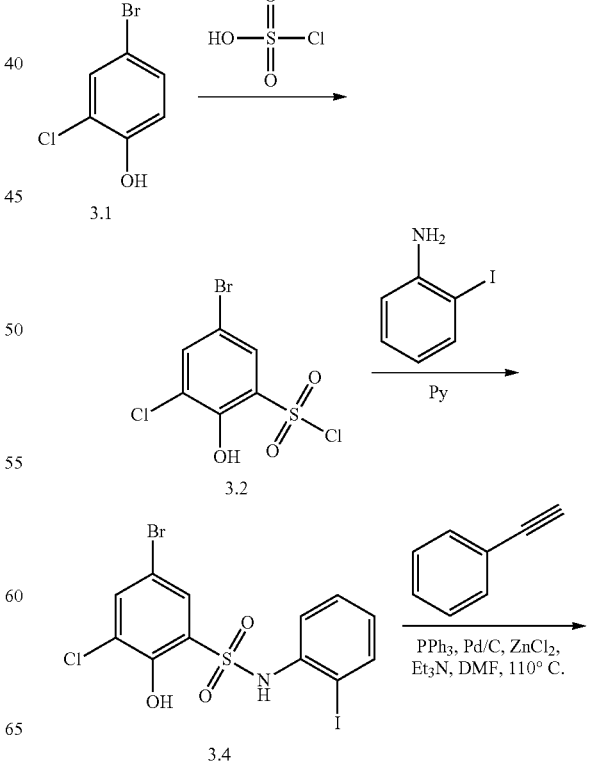

Synthesis of Compound 2.2.

Into a 100-mL 3-necked round-bottom flask were placed 4-bromo-2-chlorophenol (2.1, 5 g, 24.10 mmol, 1 equiv) and O-(chlorosulfonyl)oxidane (15 mL). The resulting solution was stirred for 2 h at room temperature. The reaction was then quenched by the addition of water/ice (40 mL). The resulting solution was extracted with ethyl acetate (2×40 mL) and the combined organic layers were concentrated under vacuum. This resulted in 6.9 g (94%) of 2.2 as brown solid.

Synthesis of I-3.

Into a 100-mL 3-necked round-bottom flask purged and maintained with an inert atmosphere of nitrogen, was placed 2.2 (1000 mg, 3.27 mmol, 1 equiv), 6-phenyl-2,3-dihydro-

Example 4. Synthesis of 4-bromo-2-chloro-6-((5-chloro-2-(pyrimidin-5-yl)-1H-indol-1-yl)sulfonyl)phenol (I-24)

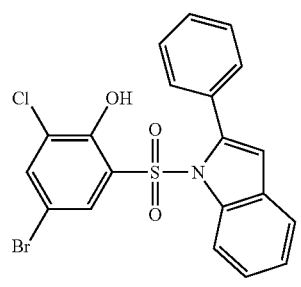

I-23

Synthesis of 3.2.

Into a 250-mL round-bottom flask purged and maintained with an inert atmosphere of nitrogen, was placed 4-bromo-2-chlorophenol (10 g, 48.204 mmol, 1 equiv), sulfurochloridic acid (20 mL). The resulting solution was stirred for 12 h at room temperature. The reaction was then quenched by the addition of 100 mL of water/ice. The resulting solution was extracted with 3×100 mL of ethyl acetate. The resulting mixture was washed with 1×100 mL of brine. The mixture was dried over anhydrous sodium sulfate and concentrated. This resulted in 11 g (75%) of 3.2 as a white solid.

Synthesis of 3.4.

Into a 250-mL round-bottom flask purged and maintained with an inert atmosphere of nitrogen, was placed 3.2 (5 g, 16.343 mmol, 1.00 equiv), 2-iodoaniline (3.58 g, 16.345 mmol, 1.00 equiv), pyridine (50 mL). The resulting solution was stirred for 0.5 h at room temperature. The resulting mixture was concentrated. The residue was applied onto a silica gel column with ethyl acetate/petroleum ether (1:1). This resulted in 2.4 g (30%) of 3.4 as yellow green solid. (ES, m/z): [M+H]$^+$ 487.9.

Synthesis of I-23.

Into a 8-mL round-bottom flask purged and maintained with an inert atmosphere of nitrogen, was placed 3.4 (200 mg, 0.409 mmol, 1 equiv), ethynylbenzene (43.91 mg, 0.430 mmol, 1.05 equiv), PPh$_3$ (26.84 mg, 0.102 mmol, 0.25 equiv), Pd/C (2 mg, 0.019 mmol, 0.05 equiv), ZnCl$_2$ (5.58 mg, 0.041 mmol, 0.10 equiv), Et$_3$N (289.99 mg, 2.866 mmol, 7.00 equiv), DMF (5 mL). The resulting solution was stirred for 12 h at 110° C. in an oil bath. The reaction was then quenched by the addition of 10 mL of water. The resulting solution was extracted with 3×10 mL of ethyl acetate. The resulting mixture was washed with 1×10 mL of brine. The mixture was dried over anhydrous sodium sulfate and concentrated. The crude product was purified by Flash-Prep-HPLC with the following conditions (IntelFlash-1): Column, silica gel; mobile phase, CH$_3$CN/H$_2$O=1:2 increasing to CH$_3$CN/H$_2$O=1:1 within 20 min; Detector, 254 nm. This resulted in 8.7 mg (5%) of I-23 as a white solid. LC-MS (ES, m/z): [M−H]$^-$ 461.8, 1H-NMR (400 MHz, CD$_3$OD, ppm): δ8.18-8.16 (d, J=8 Hz, 1H), 7.61 (s, 1H), 7.57-7.55 (d, J=7.6 Hz, 1H), 7.41-7.37 (m, 1H), 7.34-7.22 (m, 6H), 7.10 (s, 1H), 6.59 (s, 1H).

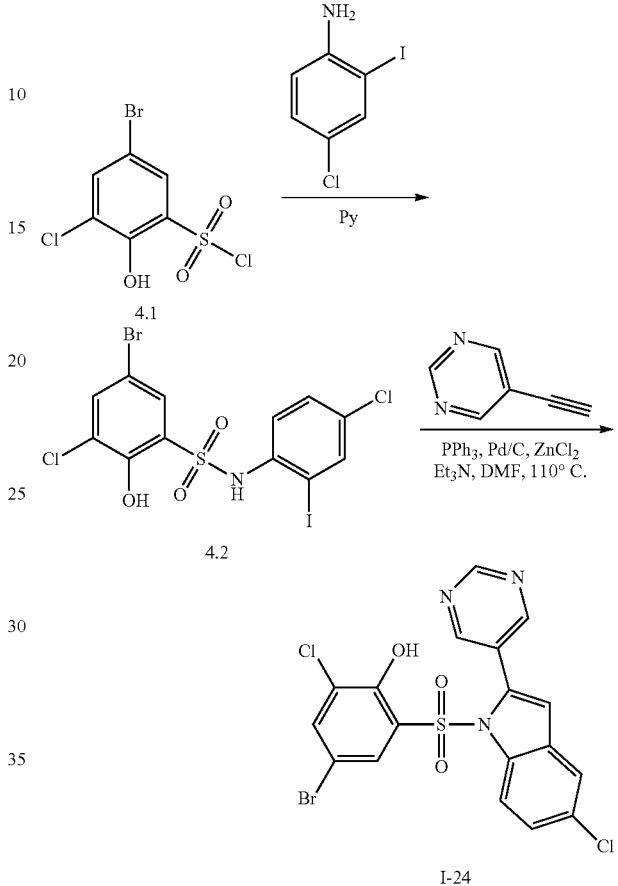

I-24

Synthesis of 4.2.

Into a 250-mL round-bottom flask purged and maintained with an inert atmosphere of nitrogen, was placed 4.1 (5 g, 16.343 mmol, 1 equiv), 4-chloro-2-iodoaniline (4.14 g, 16.343 mmol, 1 equiv), pyridine (50 mL). The resulting solution was stirred for 0.5 h at room temperature. The resulting mixture was concentrated. The residue was applied onto a silica gel column with ethyl acetate/petroleum ether (1:1). This resulted in 2.2 g (26%) of 4.2 as solid. (ES, m/z): [M+H]$^+$ 521.9.

Synthesis of I-24.

Into a 50-mL round-bottom flask purged and maintained with an inert atmosphere of nitrogen, was placed 4.2 (200 mg, 0.382 mmol, 1 equiv), 5-ethynylpyrimidine (47.78 mg, 0.459 mmol, 1.20 equiv), PPh$_3$ (25.08 mg, 0.096 mmol, 0.25 equiv), ZnCl$_2$ (5.21 mg, 0.038 mmol, 0.10 equiv), Et$_3$N (270.89 mg, 2.677 mmol, 7.00 equiv), Pd/C (2 mg, 0.019 mmol, 0.05 equiv), DMF (5 mL). The resulting solution was stirred for 12 h at 110° C. in an oil bath. The solids were filtered out. The resulting solution was extracted with 3×20 mL of ethyl acetate. The resulting mixture was washed with 1×10 mL of brine. The mixture was dried over anhydrous sodium sulfate and concentrated. The residue was applied onto a silica gel column with ethyl acetate/petroleum ether (1:1). This resulted in 11.9 mg (6%) of I-24 as white solid. LC-MS (ES, m/z): [M−H]$^-$ 497.9. 1H-NMR (400 MHz, CD$_3$OD, ppm): δ9.19 (s, 1H), 8.86 (s, 2H), 7.98-7.95 (d, J=8.8 Hz, 1H), 7.66-7.63 (d, J=11.6 Hz, 2H), 7.52 (s, 1H), 7.33-7.31 (d, J=9.2 Hz, 1H), 6.82 (s, 1H).

Example 5. Synthesis of 4-bromo-2-chloro-6-((5-chloro-2-(4-(trifluoromethoxy)phenyl)-1H-indol-1-yl)sulfonyl)phenol (I-25)

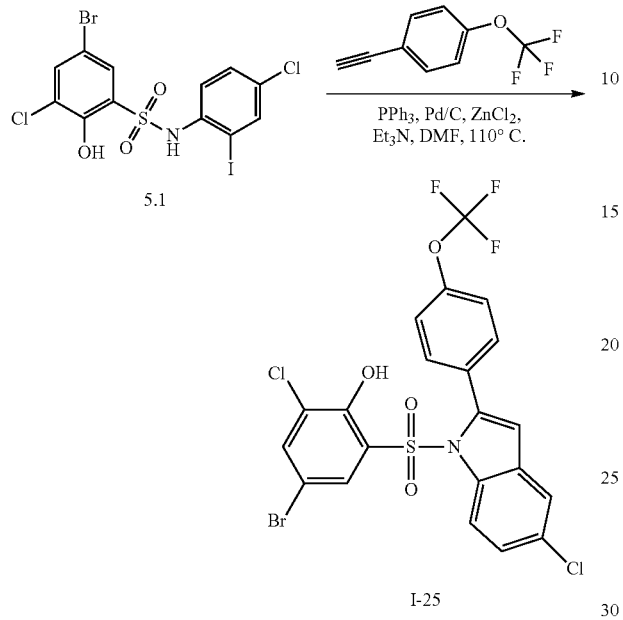

Synthesis of I-25.

Into a 25-mL round-bottom flask purged and maintained with an inert atmosphere of nitrogen, was placed 5.1 (200 mg, 0.382 mmol, 1 equiv), 1-ethynyl-4-(trifluoromethoxy) benzene (85.42 mg, 0.459 mmol, 1.20 equiv), PPh$_3$ (25.08 mg, 0.096 mmol, 0.25 equiv), ZnCl$_2$ (5.21 mg, 0.038 mmol, 0.10 equiv), Et$_3$N (270.89 mg, 2.677 mmol, 7.00 equiv), Pd/C (2 mg, 0.019 mmol, 0.05 equiv), DMF (5 mL). The resulting solution was stirred for 3 h at 110° C. in an oil bath. The reaction was then quenched by the addition of 10 mL of water. The resulting solution was extracted with 3×10 mL of ethyl acetate. The resulting mixture was washed with 1×10 mL of brine. The mixture was dried over anhydrous sodium sulfate and concentrated. The crude product was purified by Flash-Prep-HPLC with the following conditions (IntelFlash-1): Column, silica gel; mobile phase, CH$_3$CN/H$_2$O=1:2 increasing to CH$_3$CN/H$_2$O=1:1 within 20; Detector, 254 nm. This resulted in 39.8 mg (18%) of I-25 as white solid. LC-MS (ES, m/z): [M−H]$^-$ 579.9, 1H-NMR (400 MHz, DMSO-d$_6$, ppm): δ7.99-7.97 (d, J=8.8 Hz, 1H), 7.86 (s, 1H), 7.71 (s, 1H), 7.42-7.33 (m, 5H), 7.22 (s, 1H), 6.81 (s, 1H).

Example 6. Synthesis of 4-bromo-2-chloro-6-((5-chloro-2-(4-methoxyphenyl)-1H-indol-1-yl)sulfonyl)phenol (I-26)

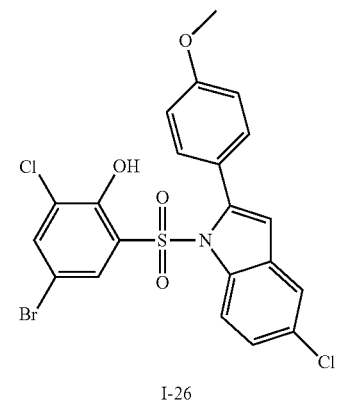

Synthesis of I-26.

Into a 50-mL round-bottom flask purged and maintained with an inert atmosphere of nitrogen, was placed 6.1 (200 mg, 0.382 mmol, 1 equiv), 1-ethynyl-4-methoxybenzene (60.65 mg, 0.459 mmol, 1.2 equiv), ZnCl$_2$ (5.21 mg, 0.038 mmol, 0.1 equiv), DMF (10 mL), Et$_3$N (270.89 mg, 2.677 mmol, 7 equiv), PPh$_3$ (25.08 mg, 0.096 mmol, 0.25 equiv), Pd/C (2 mg, 0.019 mmol, 0.05 equiv). The resulting solution was stirred for 12 hour at 110° C. in an oil bath. The solids were filtered out. The resulting solution was extracted with 3×10 mL of ethyl acetate. The resulting mixture was washed with 1×10 mL of brine. The mixture was dried over anhydrous sodium sulfate and concentrated. The crude product was purified by Flash-Prep-HPLC with the following conditions (IntelFlash-1): Column, silica gel; mobile phase, CH$_3$CN/H$_2$O=1:1 increasing to CH$_3$CN/H$_2$O=2:1 within 20 min; Detector, 254 nm. This resulted in 17.3 mg (8.58%) of I-26 as a white solid. LC-MS (ES, m/z): [M+H]$^+$ 525.9. 1H-NMR (400 MHz, DMSO-d$_6$, ppm): δ 8.06-8.04 (d, J=8.8 Hz, 1H), 7.86 (s, 1H), 7.68-7.67 (d, J=2 Hz, 1H), 7.37-7.36 (d, J=2.4 Hz, 1H), 7.10-7.05 (m, 2H), 7.02-7.01 (d, J=2.4 Hz, 1H), 6.92-6.83 (m, 2H), 6.65 (s, 1H), 3.81 (s, 3H).

Example 7. Synthesis of 2-(1-((5-bromo-3-chloro-2-hydroxyphenyl)sulfonyl)-5-chloro-1H-indol-2-yl)benzoic acid (I-27)

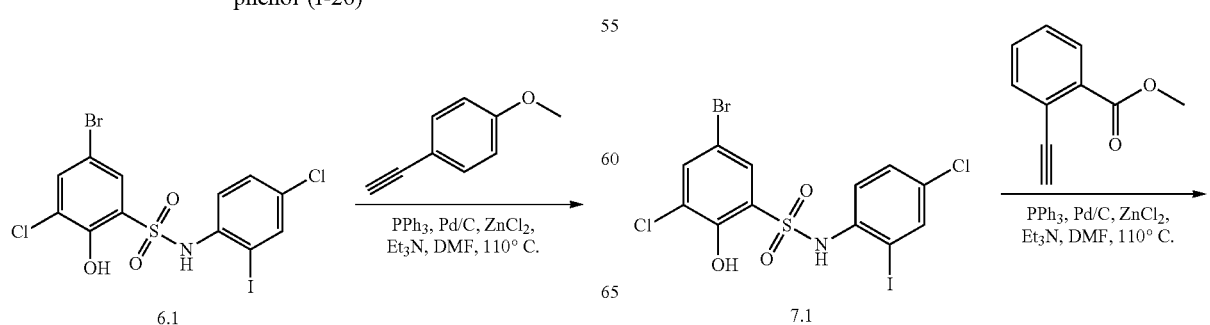

133
-continued

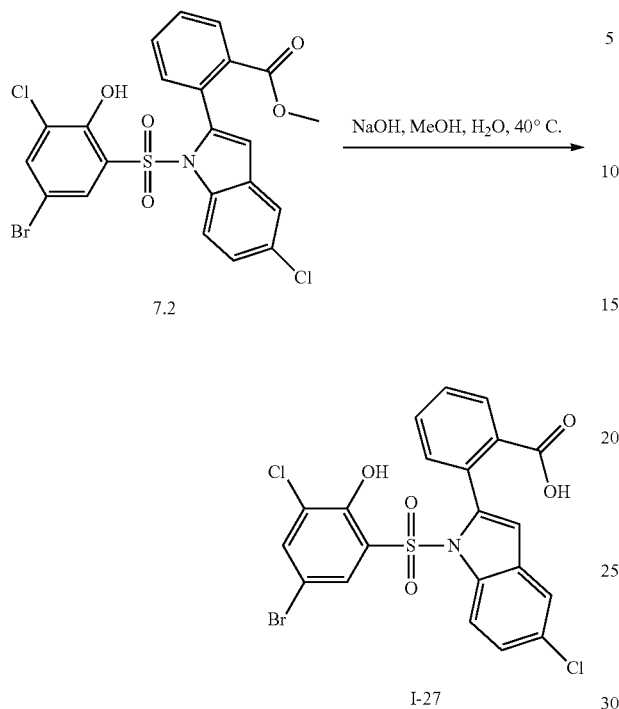

7.2

I-27

134

Example 8. Synthesis of 4-bromo-2-chloro-6-((5-chloro-2-(6-methoxypyridin-3-yl)-1H-indol-1-yl)sulfonyl)phenol (I-28)

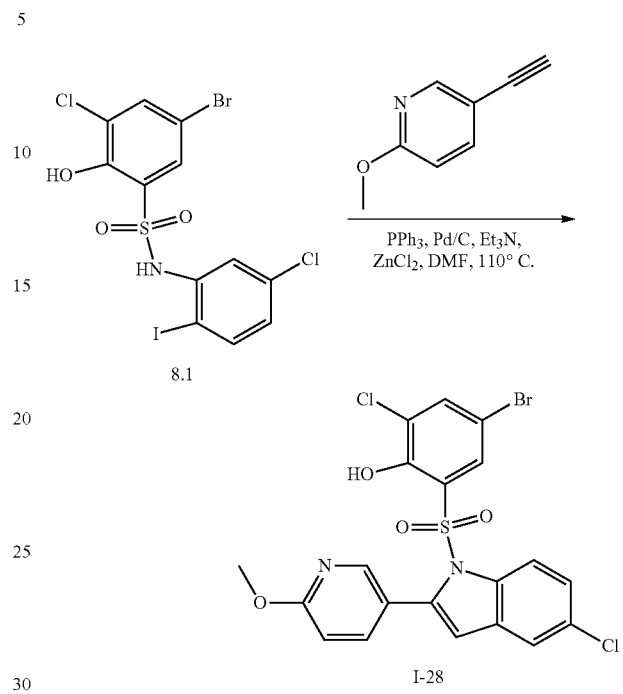

8.1

I-28

Synthesis of 7.2.

Into a 50-mL round-bottom flask purged and maintained with an inert atmosphere of nitrogen, was placed 7.1 (300 mg, 0.574 mmol, 1 equiv), methyl 2-ethynylbenzoate (110.26 mg, 0.688 mmol, 1.2 equiv), PPh₃ (37.62 mg, 0.143 mmol, 0.25 equiv), Pd/C (3 mg, 0.028 mmol, 0.05 equiv), ZnCl₂ (7.82 mg, 0.057 mmol, 0.1 equiv), Et₃N (406.34 mg, 4.016 mmol, 7 equiv), DMF (7.5 mL). The resulting solution was stirred for 12 h at 110° C. in an oil bath. The solids were filtered out. The resulting solution was extracted with 3×10 mL of ethyl acetate. The resulting mixture was washed with 1×10 mL of brine. The mixture was dried over anhydrous sodium sulfate and concentrated. The residue was applied onto a silica gel column with ethyl acetate/petroleum ether (1:2). This resulted in 60 mg (19%) of 7.2 as white solid. LC-MS (ES, m/z): [M+H]⁺ 553.8.

Synthesis of I-27.

Into a 50-mL round-bottom flask were placed 7.2 (60 mg, 0.108 mmol, 1 equiv), MeOH (10 mL), H₂O (2 mL), NaOH (43.22 mg, 1.081 mmol, 10 equiv). The resulting solution was stirred for 12 h at 40° C. in an oil bath. The pH value of the solution was adjusted to 5 with hydrochloric acid (1 mol/L). The resulting solution was extracted with 3×20 mL of ethyl acetate, dried over anhydrous sodium sulfate and concentrated. The crude product was purified by Flash-Prep-HPLC with the following conditions (IntelFlash-1): Column, silica gel; mobile phase, CH₃CN/H₂O=1:1 increasing to CH₃CN/H₂O=2:1 within 20 min; This resulted in 18.0 mg (31%) of I-27 as a white solid. LC-MS (ES, m/z): [M−H]⁻ 539.9. 1H-NMR (400 MHz, DMSO-d₆, ppm): δ7.94-7.91 (d, J=9.2 Hz, 1H), 7.82 (s, 1H), 7.63 (s, 1H), 7.49-7.42 (m, 2H), 7.31-7.29 (d, J=8.8 Hz, 2H), 7.21-7.08 (m, 3H), 6.92 (s, 1H), 6.48 (s, 1H).

Synthesis of I-28. Into a 50-mL round-bottom flask purged and maintained with an inert atmosphere of nitrogen, was placed 8.1 (200 mg, 0.382 mmol, 1 equiv), 5-ethynyl-2-methoxypyridine (61.11 mg, 0.459 mmol, 1.20 equiv), PPh₃ (25.08 mg, 0.096 mmol, 0.25 equiv), Pd/C (2 mg, 0.019 mmol, 0.05 equiv), Et₃N (270.89 mg, 2.677 mmol, 7.00 equiv), ZnCl₂ (5.21 mg, 0.038 mmol, 0.10 equiv), DMF (5 mL). The resulting solution was stirred for 12 h at 110° C. in an oil bath. The solids were filtered out. The resulting mixture was concentrated. The residue was applied onto a silica gel column with ethyl acetate/petroleum ether (1:1). This resulted in 56.4 mg (28%) of 1-28 as a white solid. LC-MS (ES, m/z): [M−H]⁻ 526.8. 1H-NMR (400 MHz, CD₃OD, ppm): δ 8.16-8.14 (d, J=8.8 Hz, 1H), 7.80 (s, 1H), 7.60-7.58 (d, J=8.4 Hz, 1H), 7.57-7.55 (d, J=10 Hz, 2H), 7.28-7.26 (d, J=8.8 Hz, 1H), 7.04 (s, 1H), 6.76-6.74 (d, J=8.4 Hz, 1H), 6.57 (s, 1H), 3.96 (s, 3H).

Example 9. Synthesis of 4-bromo-2-chloro-6-((2-(pyrimidin-5-yl)-1H-indol-1-yl)sulfonyl)phenol (I-29)

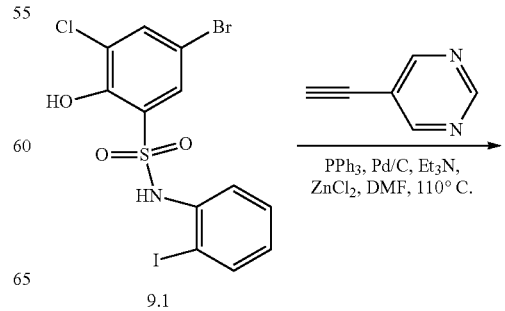

9.1

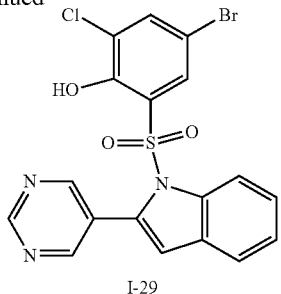

I-29

Synthesis of I-29. Into a 50-mL round-bottom flask purged and maintained with an inert atmosphere of nitrogen, was placed 9.1 (200 mg, 0.409 mmol, 1 equiv), 5-ethynylpyrimidine (51.15 mg, 0.491 mmol, 1.20 equiv), PPh₃ (26.84 mg, 0.102 mmol, 0.25 equiv), Pd/C (2 mg, 0.019 mmol, 0.05 equiv), Et₃N (289.99 mg, 2.866 mmol, 7.00 equiv), ZnCl₂ (5.58 mg, 0.041 mmol, 0.10 equiv), DMF (5 mL). The resulting solution was stirred for 12 h at 110° C. in an oil bath. The solids were filtered out. The resulting mixture was concentrated. The residue was applied onto a silica gel column with ethyl acetate/petroleum ether (1:1). This resulted in 39.5 mg (21%) of 1-29 as white solid. (ES, m/z): [M–H]⁻ 463.8, 1H-NMR (400 MHz, DMSO-d6, ppm): δ9.20 (s, 1H), 8.95 (s, 2H), 7.88-7.79 (m, 2H), 7.70-7.65 (m, 2H), 7.37-7.27 (m, 2H), 6.99 (s, 1H).

Example 10. Synthesis of 4-bromo-2-chloro-6-((5-chloro-2-methyl-1H-indol-1-yl)sulfonyl)phenol (I-30)

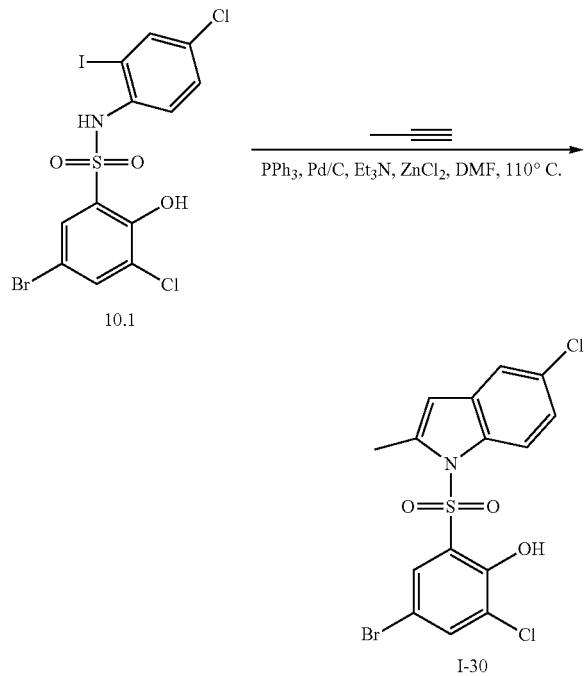

Synthesis of I-30.

Into a 25-mL round-bottom flask purged and maintained with an inert atmosphere of nitrogen, was placed 10.1 (200 mg, 0.382 mmol, 1 equiv), prop-1-yne (22.98 mg, 0.574 mmol, 1.50 equiv), PPh₃ (25.08 mg, 0.096 mmol, 0.25 equiv), Pd/C (2 mg, 0.019 mmol, 0.05 equiv), Et₃N (270.89 mg, 2.677 mmol, 7.00 equiv), ZnCl₂ (5.21 mg, 0.038 mmol, 0.10 equiv), DMF (10 mL). The resulting solution was stirred for 12 h at 110° C. in an oil bath. The solids were filtered out. The resulting solution was extracted with 3×25 mL of ethyl acetate. The resulting mixture was washed with 1×25 mL of brine. The mixture was dried over anhydrous sodium sulfate and concentrated. The residue was applied onto a silica gel column with ethyl acetate/petroleum ether (1:1). This resulted in 27.8 mg (16%) of 1-30 as a white solid. (ES, m/z): [M+H]⁺ 434.9. 1H-NMR (400 MHz, CD₃OD, ppm): δ 8.00 (s, 1H), 7.81-7.79 (d, J=9.2 Hz, 1H), 7.72 (s, 1H), 7.42 (s, 1H), 7.16-7.14 (d, J=8.8 Hz, 1H), 6.37 (s, 1H), 2.59 (s, 3H).

Example 11. Synthesis of 4-bromo-2-chloro-6-((5-methoxy-2-phenyl-1H-indol-1-yl)sulfonyl)phenol (I-31)

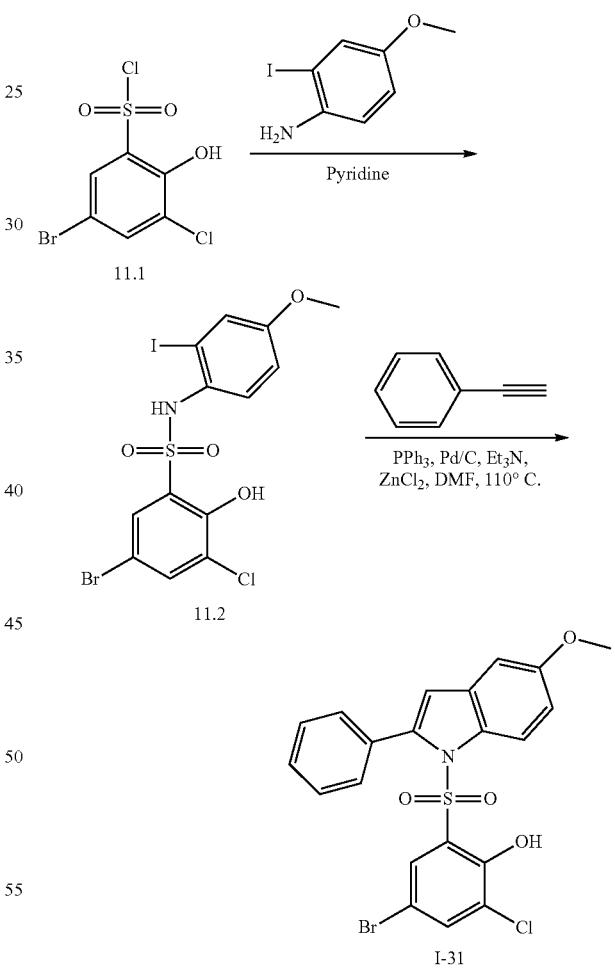

Synthesis of 11.2.

Into a 50-mL round-bottom flask purged and maintained with an inert atmosphere of nitrogen, was placed 5-bromo-3-chloro-2-hydroxybenzene-1-sulfonyl chloride (11.1, 500 mg, 1.634 mmol, 1 equiv), 2-iodo-4-methoxyaniline (407.01 mg, 1.634 mmol, 1.00 equiv), pyridine (10 mL). The resulting solution was stirred for 0.5 hr at room temperature. The resulting mixture was concentrated. The residue was applied onto a silica gel column with ethyl acetate/petroleum ether (1:1). This resulted in 270 mg (32%) of 11.2 as a solid.

Synthesis of I-31.

Into a 25-mL round-bottom flask were placed 11.2 (110 mg, 0.212 mmol, 1 equiv), DMF (1 mL), ethynylbenzene (65.00 mg, 0.636 mmol, 3.00 equiv), $ZnCl_2$ (2.89 mg, 0.021 mmol, 0.10 equiv), $Et_3N$ (150.26 mg, 1.485 mmol, 7.00 equiv), $PPh_3$ (13.91 mg, 0.053 mmol, 0.25 equiv), Pd/C (1.1 mg, 0.010 mmol, 0.05 equiv). The resulting solution was stirred for 12 hr at 110° C. The solids were filtered out. The resulting solution was extracted with 3×20 mL of ethyl acetate and the organic layers combined. The crude product was purified by Flash-Prep-HPLC with the following conditions (IntelFlash-1): Column, silica gel; mobile phase, $CH_3CN/H_2O=1:1$ increasing to $CH_3CN/H_2O=1:2$ within 30 min; Detector, 254/220 nm. This resulted in 64.1 mg of I-31 as an off-white solid. LC-MS (ES, m/z): $[M-H]^-$ 491.9. H-NMR (DMSO, 400 MHz, ppm): δ 12.70 (s, 1H), 67.89-7.87 (d, J=8.8 Hz, 1H), 7.83 (s, 1H), 67.42-7.40 (m, 1H), 7.39-7.31 (m, 2H), 7.27-7.25 (m, 2H), 7.14-7.12 (m, 2H), 6.96-6.93 (m, 1H), 6.66 (s, 1H), 3.80 (s, 3H).

Example 12. Synthesis of 2,4-dichloro-6-((5-chloro-2-(4-(trifluoromethoxy)phenyl)-1H-indol-1-yl)sulfonyl)phenol (I-32)

Synthesis of 12.2.

Into a 25-mL round-bottom flask were placed 4-chloro-2-iodoaniline (0.97 g, 3.824 mmol, 1 equiv), pyridine (10 mL), 3,5-dichloro-2-hydroxybenzene-1-sulfonyl chloride (12.1, 1 g, 3.824 mmol, 1 equiv). The resulting solution was stirred for 10 min at room temperature. The resulting mixture was concentrated. The resulting solution was extracted with 3×20 mL of ethyl acetate. The crude product was purified by Flash-Prep-HPLC with the following conditions (IntelFlash-1): Column, silica gel; mobile phase, $CH_3CN/H_2O=1:1$ increasing to $CH_3CN/H_2O=1:2$ within 30 min; Detector, 254/220 nm. This resulted in 100 mg (5.46%) of 12.2 as a solid.

Synthesis of I-32.

Into a 25-mL round-bottom flask were placed 12.2 (100 mg, 0.209 mmol, 1 equiv), DMF (2 mL, 25.844 mmol, 123.66 equiv), 1-ethynyl-4-(trifluoromethoxy)benzene (116.70 mg, 0.627 mmol, 3 equiv), $ZnCl_2$ (2.85 mg, 0.021 mmol, 0.1 equiv), $Et_3N$ (148.03 mg, 1.463 mmol, 7 equiv), $PPh_3$ (13.70 mg, 0.052 mmol, 0.25 equiv), Pd/C (1.5 mg, 0.014 mmol, 0.07 equiv). The resulting solution was stirred for 12 h at 110° C. in an oil bath. The solids were filtered out. The resulting solution was extracted with 3×20 mL of ethyl acetate concentrated. The crude product was purified by Flash-Prep-HPLC with the following conditions (IntelFlash-1): Column, silica gel; mobile phase, $CH_3CN/H_2O=1:1$ increasing to $CH_3CN/H_2O=1:2$ within 30; Detector, 254/220 nm. This resulted in 6.4 mg (5.71%) of I-32 as a solid. LC-MS (ES, m/z): $[M+H]^+$ 535.7. H-NMR (DMSO, 400 MHz, ppm): δ 11.40 (s, 1H), 7.99-7.97 (d, J=9.2 Hz, 1H), 7.82 (s, 1H) 7.71 (s, 1H), 7.41-7.34 (m, 5H), 7.15-7.14 (d, J=2.8 Hz, 1H), 6.79 (s, 1H).

Example 13. Synthesis of 4-bromo-2-chloro-6-((5-chloro-2-(thiazol-5-yl)-1H-indol-1-yl)sulfonyl)phenol (I-33)

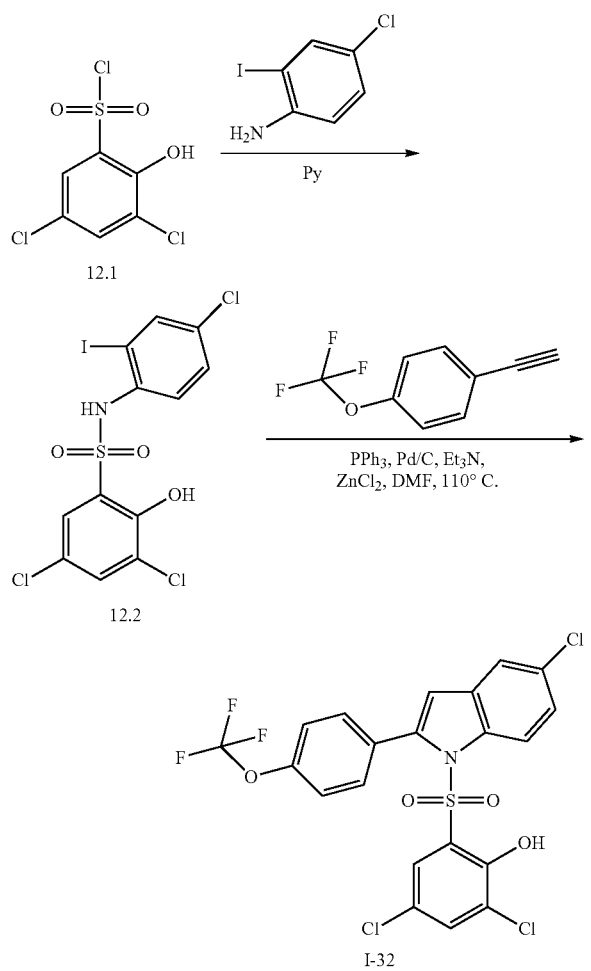

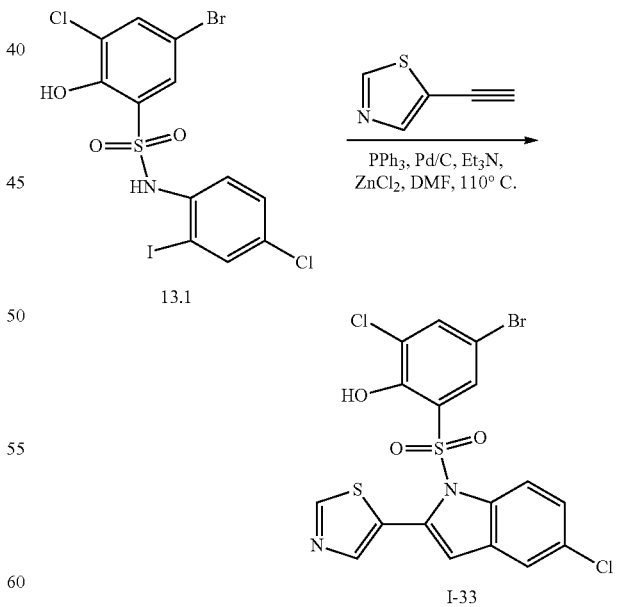

Synthesis of I-33.

Into a 25-mL round-bottom flask were placed PH-NAL-01741-1 (200 mg, 0.382 mmol, 1 equiv), 5-ethynyl-1,3-thiazole (62.61 mg, 0.574 mmol, 1.50 equiv), $PPh_3$ (25.08 mg, 0.096 mmol, 0.25 equiv), Pd/C (2 mg, 0.019 mmol, 0.05 equiv), Et₃N (270.89 mg, 2.677 mmol, 7.00 equiv), ZnCl₂ (5.21 mg, 0.038 mmol, 0.10 equiv), DMF (10 mL, 129.218 mmol, 337.88 equiv). The resulting solution was stirred for 12 hr at 110° C. in an oil bath. The solids were filtered out. The resulting mixture was concentrated. The residue was purified by reverse flash chromatography with the following conditions: column, C18 silica gel; mobile phase, MeOH in water, 10% to 50% gradient in 10 min; detector, UV 254 nm. This resulted in 22.6 mg (11.31%) of I-33 as a white solid. LC-MS (ES, m/z): [M+H]+ 504. H-NMR (DMSO, 400 MHz, ppm): δ 9.18 (s, 1H), 7.99-7.96 (m, 1H), 7.88 (s, 1H), 7.85-7.71 (m, 2H), 7.42-7.39 (m, 1H), 7.29 (s, 1H), 6.96-6.91 (m, 1H).

Example 14. Synthesis of 4-(1-((5-bromo-3-chloro-2-hydroxyphenyl)sulfonyl)-5-chloro-1H-indol-2-yl) benzoic acid (I-45)

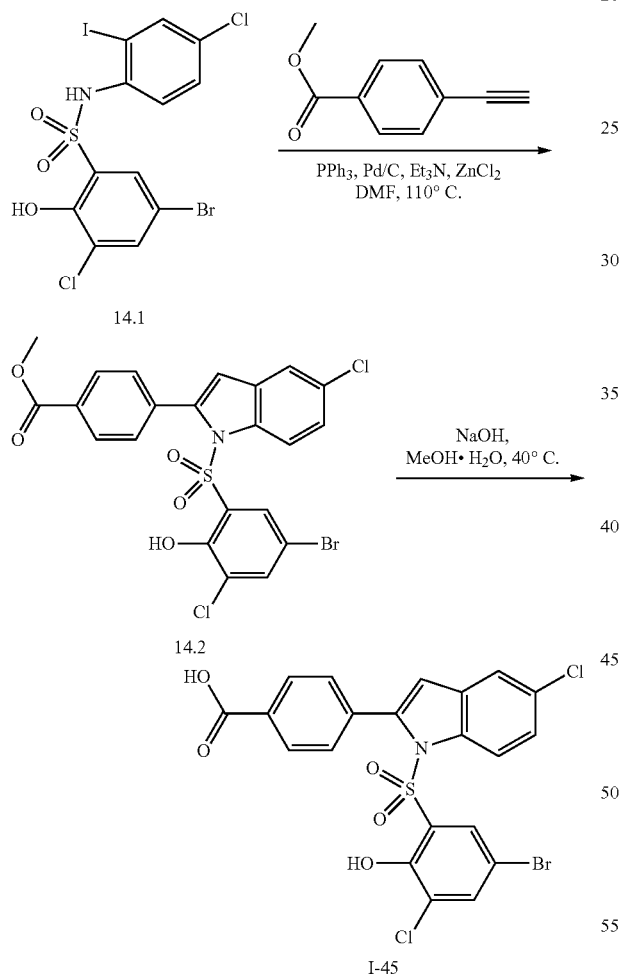

Synthesis of 14.2.

Into a 100-mL 3-necked round-bottom flask were placed 14.1 (2.7 g, 5.163 mmol, 1 equiv), DMF (15 mg), methyl 4-ethynylbenzoate (1.24 g, 7.742 mmol, 1.50 equiv), PPh₃ (0.34 g, 1.291 mmol, 0.25 equiv), ZnCl₂ (0.07 g, 0.516 mmol, 0.10 equiv), Et₃N (3.66 g, 36.140 mmol, 7.00 equiv), Pd/C (200 mg). The resulting solution was stirred for 1 overnight at 100° C. in an oil bath. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254 nm. 2.5 g product was obtained. This resulted in 2.5 g (87.21%) of 14.2 as yellow solid.

Synthesis of I-45.

Into a 20-mL vial, was placed methyl 14.2 (200 mg, 0.360 mmol, 1 equiv), MeOH (10 mL, 246.989 mmol, 685.67 equiv), H₂O (10 mL, 555.084 mmol, 1540.97 equiv), KOH (202.10 mg, 3.602 mmol, 10.00 equiv). The resulting solution was stirred for 2 h at room temperature. The crude product was purified by Flash-Prep-HPLC with the following conditions (IntelFlash-1): Column, silica gel; mobile phase, ACN/H₂O=15% increasing to ACN/H₂O=60% within 20 min; Detector, UV: 254 nm. This resulted in 81.3 mg (41.70%) of I-45 as white solid. LC-MS (ES, m/z): [M−H]⁻ 539.7. H-NMR (400 MHz, DMSO-d6, ppm): δ 12.95 (s, 1H), 7.95-7.85 (m, 3H), 7.69 (s, 1H), 7.50-7.40 (m, 2H), 7.14-6.88 (m, 2H), 7.10 (s, 2H), 6.65 (s, 1H).

Example 15. Synthesis of 4-(1-((5-bromo-3-chloro-2-hydroxyphenyl)sulfonyl)-5-chloro-1H-indol-2-yl)-N,N-dimethylbenzamide (I-50)

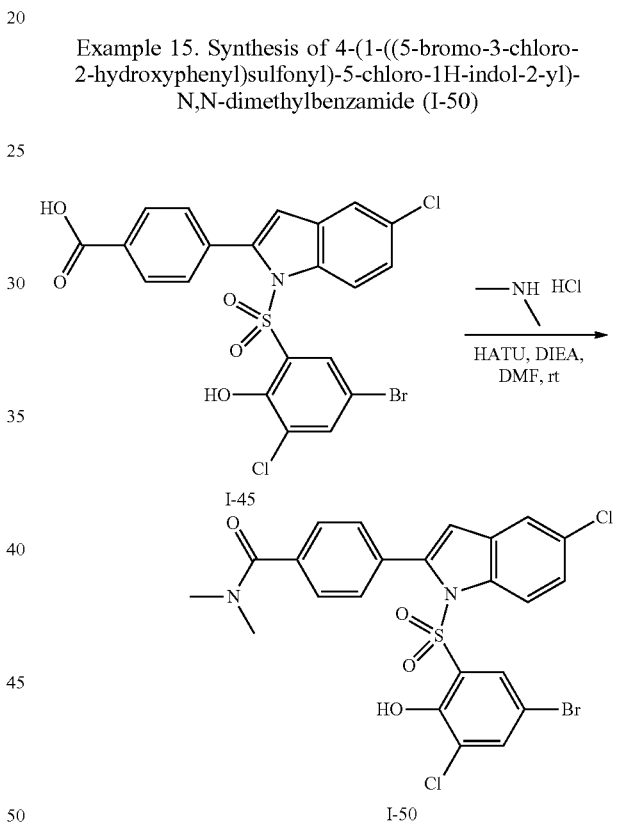

Synthesis of I-50.

Into a 20-mL vial, was placed I-45 (250 mg, 0.462 mmol, 1 equiv), DMF 5 ML, DIEA (179.11 mg, 1.386 mmol, 3 equiv), dimethylamine hydrochloride (75.33 mg, 0.924 mmol, 2 equiv), HATU (526.94 mg, 1.386 mmol, 3 equiv). The resulting solution was stirred for 1 overnight at room temperature. The crude product was purified by Flash-Prep-HPLC with the following conditions (IntelFlash-1): Column, C18 silica gel; mobile phase, ACN/H₂O=15% increasing to ACN/H₂O=60% within 10 min; Detector, UV: 254 nm. This resulted in 175.4 mg (66.82%) of I-50 as off-white solid. LC-MS (ES, m/z): [M−H]− 566.8. H-NMR (300 MHz, DMSO-d₆, ppm): δ 7.96-7.93 (d, J=9.0 Hz, 1H), 7.65 (s, 2H), 7.40-7.05 (m, 7H), 7.01-6.65 (m, 1H), 3.01-2.94 (s, 6H).

Example 16. Synthesis of 5-chloro-3-((5-chloro-2-phenyl-1H-indol-1-yl)sulfonyl)pyridin-2(1H)-one (I-65)

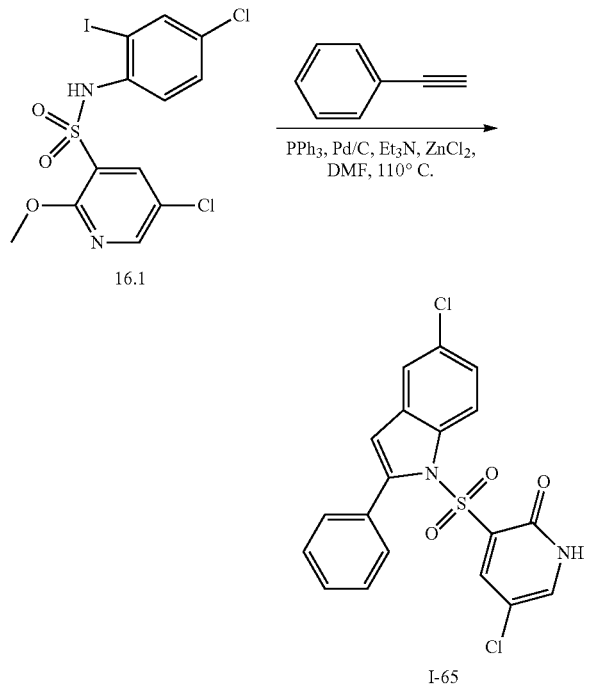

Synthesis of I-65.

Into a 8-mL vial, was placed 16.1 (150 mg, 0.337 mmol, 1 equiv), DMF (2 mL), ZnC12 (4.59 mg, 0.034 mmol, 0.1 equiv), Et3N (238.74 mg, 2.359 mmol, 7 equiv), Pd/C (10 mg), PPh3 (22.10 mg, 0.084 mmol, 0.25 equiv), ethynylbenzene (41.31 mg, 0.404 mmol, 1.20 equiv). The resulting solution was stirred for overnight at 100° C. The crude product was purified by Flash-Prep-HPLC with the following conditions (IntelFlash-1): Column, C18 silica gel; mobile phase, ACN:H$_2$O=15% increasing to ACN:H$_2$O=35% within 12; Detector, 254 nm. 24.3 mg product was obtained. This resulted in 24.3 mg (17.20%) of I-65 as off-white solid. LC-MS (ES, m/z): [M−H]⁻ 416.8. H-NMR (300 MHz, DMSO-d$_6$, ppm): δ 8.02-7.98 (m, 2H), 7.68 (s, 1H), 7.50-7.41 (m, 7H), 6.68 (s, 1H).

Example 17. Synthesis of azetidin-1-yl(3-chloro-5-((5-chloro-2-phenyl-1H-indol-1-yl)sulfonyl)-4-hydroxyphenyl)methanone (I-52)

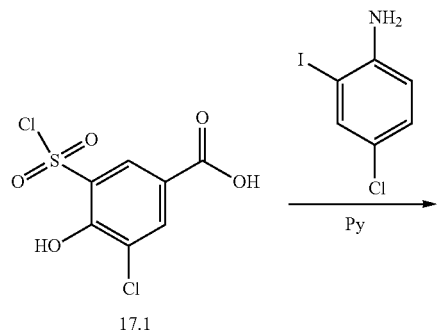

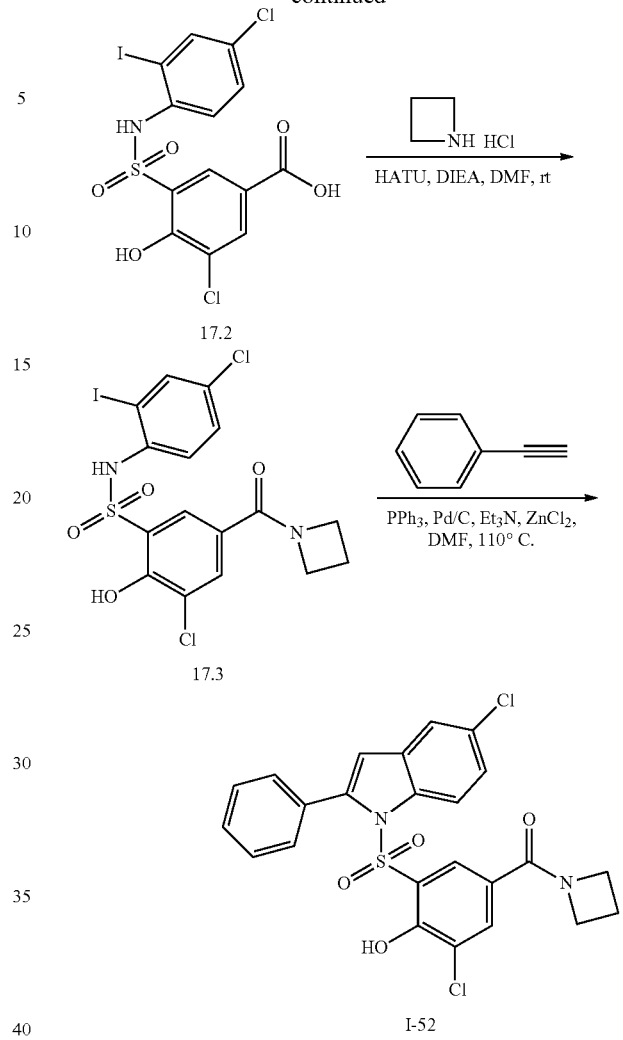

Synthesis of 17.2.

Into a 100-mL round-bottom flask purged and maintained with an inert atmosphere of nitrogen, was placed 3-chloro-5-(chlorosulfonyl)-4-hydroxybenzoic acid (1 g, 3.7 mmol, 1 equiv), 4-chloro-2-iodoaniline (935 mg, 3.7 mmol, 1.00 equiv), pyridine (10 mL). The resulting solution was stirred for 0.5 h at room temperature. The reaction was then quenched by the addition of 100 mL of water/ice. The resulting solution was extracted with 3×100 mL of ethyl acetate. The resulting mixture was washed with 1×100 mL of brine. The mixture was dried over anhydrous sodium sulfate and concentrated. This resulted in 650 mg of 17.2 as a white solid.

Synthesis of 17.3.

Into a 8-mL round-bottom flask were placed 17.2 (200 mg, 0.411 mmol, 1 equiv), DMF (2 mL), azetidine hydrogen chloride (46.36 mg, 0.493 mmol, 1.2 equiv), DIEA (159.06 mg, 1.233 mmol, 3 equiv). The resulting solution was stirred for 12 hr at room temperature. The resulting mixture was concentrated. The residue was applied onto a silica gel column with ethyl acetate/petroleum ether (1:1). This resulted in 145 mg (66%) of 17.3 as off-white solid.

Synthesis of I-52.

Into a 8-mL vial, was placed 17.3 (145 mg, 0.275 mmol, 1 equiv), DMF (8 mL), ethynylbenzene (42.14 mg, 0.413 mmol, 1.5 equiv), PPh3 (18.04 mg, 0.069 mmol, 0.25 equiv), Et3N (194.84 mg, 1.925 mmol, 7 equiv), ZnCl2 (3.75 mg, 0.028 mmol, 0.1 equiv), Pd/C (10 mg). The resulting solution was stirred for 1 overnight at 100° C. The crude product was purified by Flash-Prep-HPLC with the following conditions (IntelFlash-1): Column, C18 silica gel; mobile phase, ACN/H₂O=16% increasing to ACN/H₂O=60% within 10 min; Detector, UV: 254 nm. This resulted in 14 mg (10.15%) of I-52 as white solid. LC-MS (ES, m/z): [M−H]⁻ 498. H-NMR (DMSO, 400 MHz, ppm): δ7.95-7.93 (d, J=8.8 Hz, 1H), 7.68-7.64 (m, 2H), 7.42-7.28 (m, 7H), 7.28-6.95 (m, 1H), 6.62 (s, 1H), 4.15 (s, 4H), 2.30-2.19 (m, 2H).

Example 18. Synthesis of 5-chloro-3-((5-chloro-2-(4-(trifluoromethoxy)phenyl)-1H-indol-1-yl)sulfonyl)pyridin-2(1H)-one (I-64)

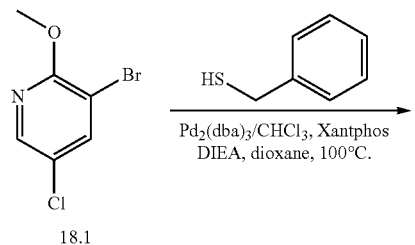

18.1

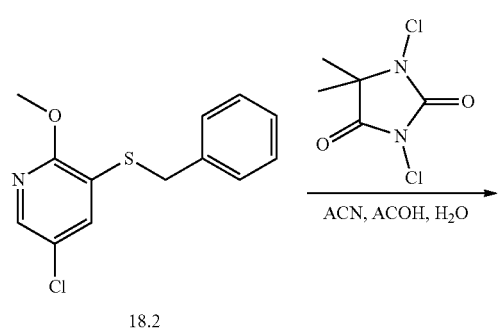

18.2

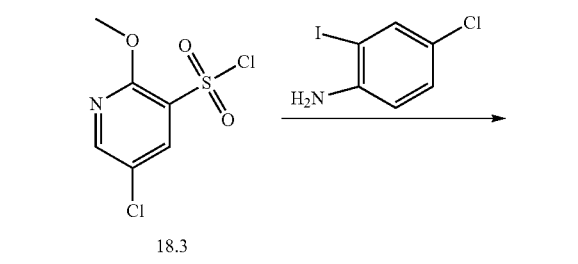

18.3

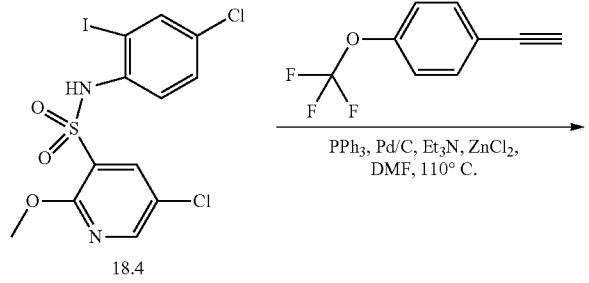

18.4

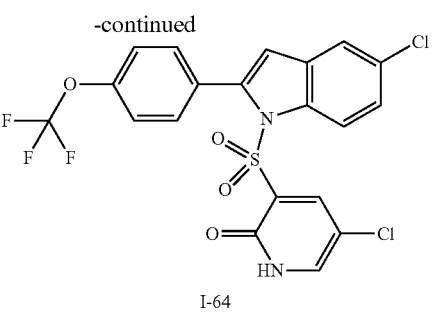

I-64

Synthesis of 18.2.

Into a 250-mL 3-necked round-bottom flask were placed 3-bromo-5-chloro-2-methoxypyridine (2 g, 8.990 mmol, 1 equiv), dioxane (30 mL), DIEA (3.49 g, 26.970 mmol, 3 equiv), Xantphos (1.04 g, 1.798 mmol, 0.2 equiv), phenylmethanethiol (3.35 g, 26.973 mmol, 3.00 equiv). The resulting solution was stirred for 1 overnight at 100° C. in an oil bath. The crude product ( ) was purified by Flash-Prep-HPLC with the following conditions (IntelFlash-1): Column, C18 silica gel; mobile phase, ACN:H₂O=15% increasing to ACN:H₂O=35% within 20; Detector, 254 nm. 2.486 g 18.2 was obtained.

Synthesis of 18.3.

Into a 100-mL 3-necked round-bottom flask were placed 18.2, ACN (20 mL), ACOH (0.25 mL), H₂O (0.5 mL), 1,3-dichloro-5,5-dimethylimidazolidine-2,4-dione (2.76 g, 14.009 mmol, 1.50 equiv). The resulting solution was stirred for 1 hr at room temperature in a water/ice bath. The crude product was purified by Flash-Prep-HPLC with the following conditions (IntelFlash-1): Column, C18 silica gel; mobile phase, ACN:H₂O=15% increasing to ACN:H₂O=45% within 20; Detector, 254 nm. 4.6 g product was obtained. This resulted in 4.6 g (203.14%) of 18.3 as off-white solid.

Synthesis of 18.4.

Into a 100-mL vial, was placed 18.3 (4.4 g, 18.177 mmol, 1 equiv), pyridine (40 mL), 4-chloro-2-iodoaniline (5.53 g, 21.817 mmol, 1.20 equiv). The resulting solution was stirred for 3 hr at room temperature. The crude product was purified by Flash-Prep-HPLC with the following conditions (IntelFlash-1): Column, C18 silica gel; mobile phase, ACN:H₂O=15% increasing to ACN:H₂O=35% within 15; Detector, 254 nm. 1 g product was obtained. This resulted in 1 g (11.98%) of 18.4 as off-white solid.

Synthesis of I-64.

Into a 8-mL vial, was placed 18.4 (150 mg, 0.327 mmol, 1 equiv), DMF (1.5 mL), ZnCl₂ (4.45 mg, 0.033 mmol, 0.1 equiv), Et₃N (231.44 mg, 2.287 mmol, 7 equiv), PPh3 (21.42 mg, 0.082 mmol, 0.25 equiv), 1-ethynyl-4-(trifluoromethoxy)benzene (72.98 mg, 0.392 mmol, 1.20 equiv), Pd/C (10 mg, 0.094 mmol, 0.29 equiv). The resulting solution was stirred for 1 overnight at 100° C. in an oil bath. The crude product was purified by Flash-Prep-HPLC with the following conditions (IntelFlash-1): Column, C18 silica gel; mobile phase, ACN:H₂O=15 increasing to ACN:H₂O=30 within 10; Detector, 254 nm. 25.4 mg product was obtained. This resulted in 25.4 mg (15.45%) of I-64 as white solid. LC-MS (ES, m/z): [M−H]⁻ 500.8. H-NMR (400 MHz, DMSO-d6, ppm): δ 12.85 (s, 1H), 8.15 (s, 1H), 7.94-7.92 (d, J=8.8 Hz, 1H), 7.70 (s, 2H), 7.56-7.54 (d, J=8.4 Hz, 2H), 7.42-7.38 (m, 3H), 7.75 (s, 1H).

Example 19. Synthesis of 2-((5-chloro-2-phenyl-1H-indol-1-yl)sulfonyl)phenol (I-106)

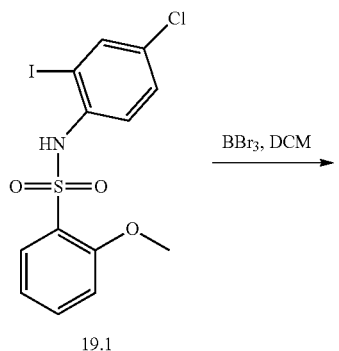

19.1

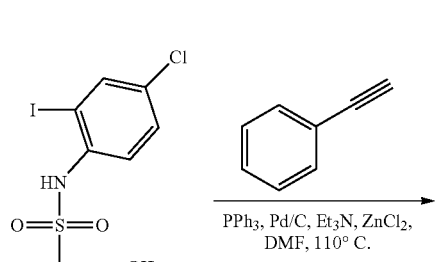

19.2

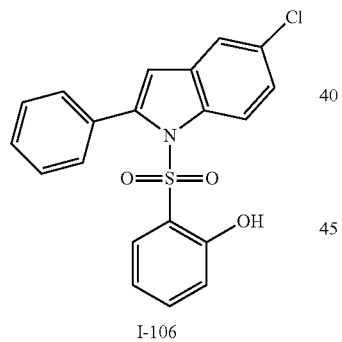

I-106 equiv), ethynylbenzene (56.10 mg, 0.549 mmol, 1.50 equiv), ZnCl2 (4.99 mg, 0.037 mmol, 0.10 equiv), PPh3 (24.01 mg, 0.092 mmol, 0.25 equiv), Pd/C (10 mg). The resulting solution was stirred for 1 overnight at 100° C. The crude product was purified by Flash-Prep-HPLC with the following conditions (IntelFlash-1): Column, C18 silica gel; mobile phase, ACN/H$_2$O=15% increasing to ACN/H$_2$O=60% within 20 min; Detector, UV: 254 nm. 49.5 mg product was obtained. This resulted in 48.5 mg (35.69%) of I-106 as off-white solid. LC-MS (ES, m/z): [M–H]$^-$ 382.3. H-NMR (300 MHz, DMSO-d$_6$, ppm): δ 10.95 (s, 1H), 67.95-7.92 (d, J=12.0 Hz, 1H), 7.64 (s, 1H), 7.41-7.20 (m, 8H), 6.80-6.61 (m, 3H).

Example 20. Synthesis of 1-((5-bromo-3-chloro-2-methoxyphenyl)sulfonyl)-5-chloro-2-phenyl-1H-indole (I-107)

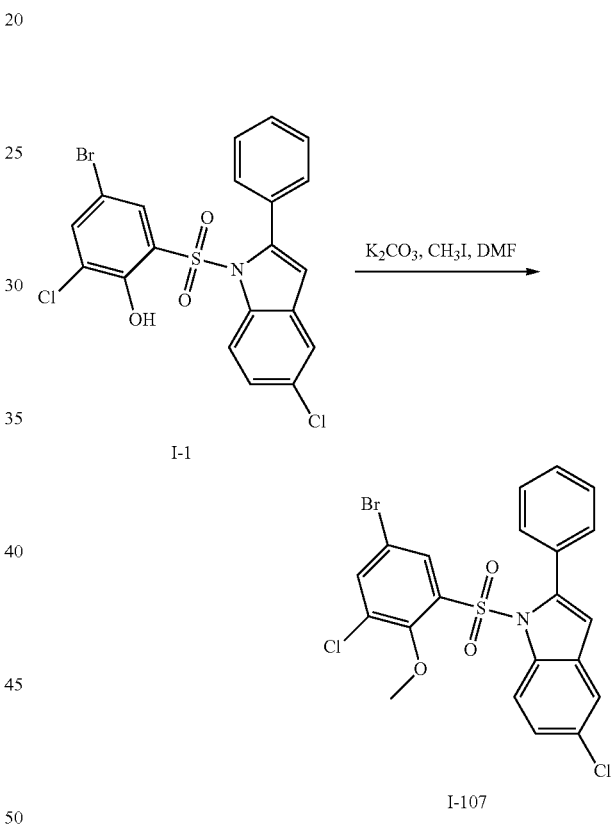

Synthesis of 19.2.

Into a 25-mL round-bottom flask were placed 4-chloro-2-iodoaniline (613.31 mg, 2.420 mmol, 1 equiv), pyridine (5 mL, 0.063 mmol, 0.03 equiv), 2-methoxybenzene-1-sulfonyl chloride (500 mg, 2.420 mmol, 1 equiv). The resulting solution was stirred for 10 min at room temperature. The resulting mixture was concentrated. The pH value of the solution was adjusted to 5-6 with HCl (1 mol/L). The resulting solution was extracted with 3×20 mL of ethyl acetate The crude product was purified by Flash-Prep-HPLC with the following conditions (IntelFlash-1): Column, silica gel; mobile phase, CH$_3$CN/H$_2$O=1:1 increasing to CH$_3$CN/H$_2$O=1:2 within 30; Detector. 792 mg 19.2 was obtained.

Synthesis of I-106.

Into a 20-mL vial, was placed 19.2 (150 mg, 0.366 mmol, 1 equiv), DMF (8 mL), Et3N (259.39 mg, 2.563 mmol, 7.00

Synthesis of I-107. Into a 25-mL round-bottom flask purged and maintained with an inert atmosphere of nitrogen, was placed I-1 (35 mg, 0.07 mmol, 1 equiv), K$_2$CO$_3$ (19.5 mg, 0.14 mmol, 2 equiv), CH$_3$I (12.0 mg, 0.08 mmol, 1.2 equiv), DMF (1 mL). The resulting solution was stirred for 12 h at room temperature. The reaction solution was diluted with 3 mL of water and extracted with 3×5 mL of ethyl acetate. The organic extracts was washed with 5 mL of brine, dried over anhydrous sodium sulfate and concentrated under vacuum. The residue was applied onto a silica gel column with ethyl acetate/petroleum ether (1:5). This resulted in 25.4 mg (71%) of I-107 as a white solid. (ES, m/z): [M–H]$^-$ 509.9, 1H-NMR (400 Mhz, DMSO, ppm): δ8.11 (s, 1H), 8.08-8.06 (d, J=9.2 Hz, 1H), 7.72-7.71 (d, J=2 Hz, 1H), 7.47-7.41 (m, 2H), 7.39-7.35 (t, J=8 Hz, 2H), 7.24-7.22 (d, J=7.2 Hz, 2H), 7.16 (s, 1H), 6.78 (s, 1H), 3.48 (s, 3H).

Example 21. Synthesis of 4-bromo-2-chloro-6-((2-(4-(trifluoromethoxy)phenyl)-1H-pyrrolo[2,3-c]pyridin-1-yl)sulfonyl)phenol (I-49)

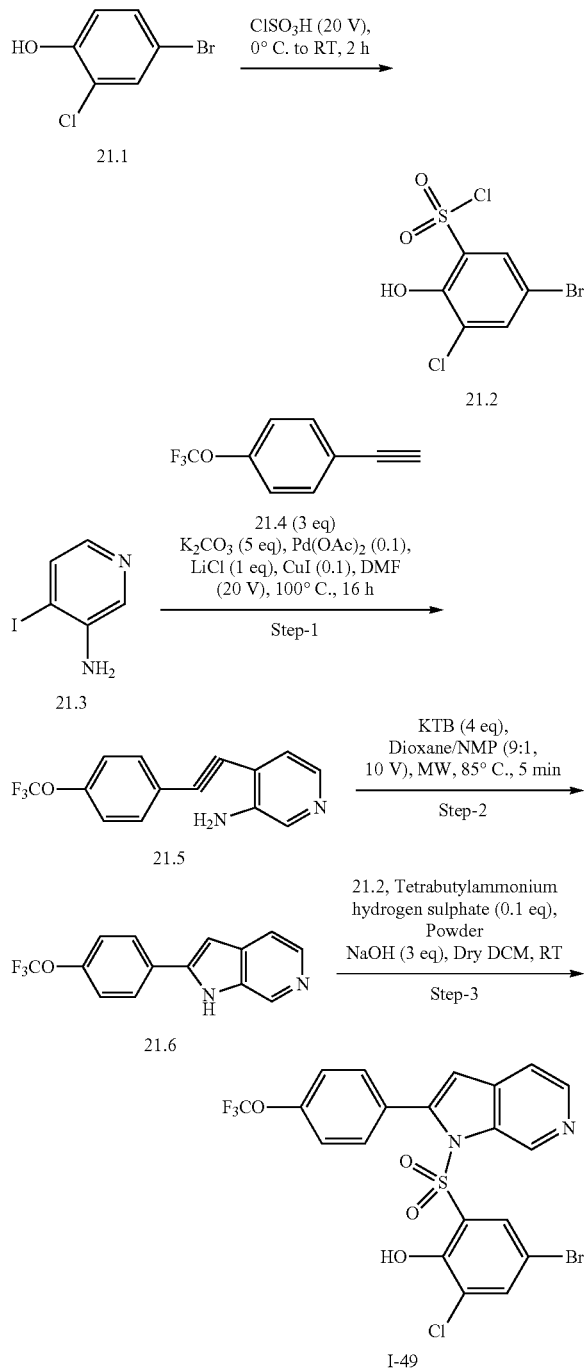

Synthesis of Compound 21.2.

A 250-mL round-bottom flask purged and maintained with an inert atmosphere of nitrogen and charged with 4-bromo-2-chlorophenol (10 g, 48.1 mmol, 1 eq) was added to chlorosulphonic acid (200 mL, 20V) at 0° C. in small portions and reaction mixture was then stirred at room temperature for 2 h. The reaction mixture was quenched by drop wise addition on to crushed ice cautiously and solid precipitated out was filtered, washed with water (500 mL) and hexanes (300 mL), and dried under vacuum to afford 21.2 (13 g, 88.15%). MS (ES): m/z 305.1 [M−H]⁻.

Synthesis of COMPOUND 21.5.

1-ethynyl-4-(trifluoromethoxy)benzene (0.888 g, 4.77 mmol, 3 eq) was added to a suspension of 4-iodopyridin-3-amine (0.350 g, 1.59 mmol, 1 eq), $K_2CO_3$ (1.097 g, 7.91 mmol, 5 eq) and LiCl (0.066 g, 1.59 mmol, 1 eq) in anhydrous DMF (6.5 mL, 20V) in a 30 mL seal tube. Reaction mixture was purged with argon for 10 min and Pd(OAc)$_2$ (0.035 g, 0.159 mmol, 0.1 eq) was added. The purging with argon was continued for another 15 min and tube was sealed with Teflon cap. Reaction mixture was heated at 100° C. for 16 h. After completion of reaction, water (20 mL) was added to reaction mixture and acidified using 10% HCl solution. The reaction mixture was extracted using EtOAc (30 mL×2) and combined organic layer was washed with brine (20 mL), dried over sodium sulphate and concentrated under reduced pressure to obtain crude material. This was further purified by column chromatography and compound was eluted in 55% ethyl acetate in hexane to obtain pure 21.5 (Yield: 0.25 g, 56%). MS (ES): m/z 279.21 [M+H]⁺.

Synthesis of Compound 21.6.

21.5 (0.200 g, 0.718 mmol, 1 eq) was taken in dioxane/NMP (2 mL, 9:1, 10 v) in microwave vial. Potassium tert-butoxide (0.3 g, 2.8 mmol, 4 eq) was added and vial was irradiated in microwave at 80° C. for 5 min. After completion of reaction, water (20 mL) was added to reaction mixture and extracted using EtOAc (30 mL×2), and combined organic layer was washed with brine (20 mL), dried over sodium sulphate and concentrated under reduced pressure to obtain crude material which was purified column chromatography and compound was eluted in 35% ethyl acetate in hexane to obtain pure 21.6 (Yield: 0.159 g, 79%). MS (ES): m/z 279.31 [M+H]⁺.

Synthesis of Compound I-49.

To a stirred solution of 21.6 (0.159 g, 0.539 mmol, 1 eq) in anhydrous DCM (4 mL, 20 V) at 0° C. under nitrogen atmosphere was added powdered NaOH (0.06 g, 1.6 mmol) and tetrabutylammonium hydrogen sulphate (0.018 g, 0.0539 mmol 0.1 eq). Ice bath was removed and the reaction mixture was stirred vigorously at room temperature for an hour. After an hour, solution of 25.2 (0.25 g, 0.82 mmol, 1.5 eq) in anhydrous DCM (4 mL, 20V) was added drop wise at 0° C. After completion of addition cooling bath was removed and reaction mixture was stirred at room temperature for overnight. Water (25 mL) was added to reaction mixture and extracted with DCM (20 mL×2). The combined organic extracts was washed with brine (15 mL) and dried over anhydrous Sodium sulphate, filtered and concentrated under reduced pressure to afford crude product. The compound was purified by reverse phase preparative HPLC carried out using YMC ACTUS C18 (150*20) mm, 5μ column and 5 mM ammonium bicarbonate+0.1% $NH_3$ in water and 100% ACN as mobile phase. The pure fractions were collected and lyophilized to afford pure I-49 (0.028 g, 10%). MS (ES): m/z 547.2 [M+H]⁺, LCMS purity: 100%, ¹H NMR (400 MHz, DMSO-d$_6$) δ 6.86-6.98 (m, 2H), 7.39 (q, J=8.5 Hz, 4H), 7.47 (s, 1H), 7.87 (d, J=5.6 Hz, 1H), 8.44 (d, J=5.6 Hz, 1H), 9.35 (s, 1H).

Example 23. 5-(5-chloro-1-((3,5-difluoro-2-hydroxyphenyl)sulfonyl)-1H-indol-2-yl)-3-(4-methoxybenzyl)pyrimidin-4(3H)-one (I-136)

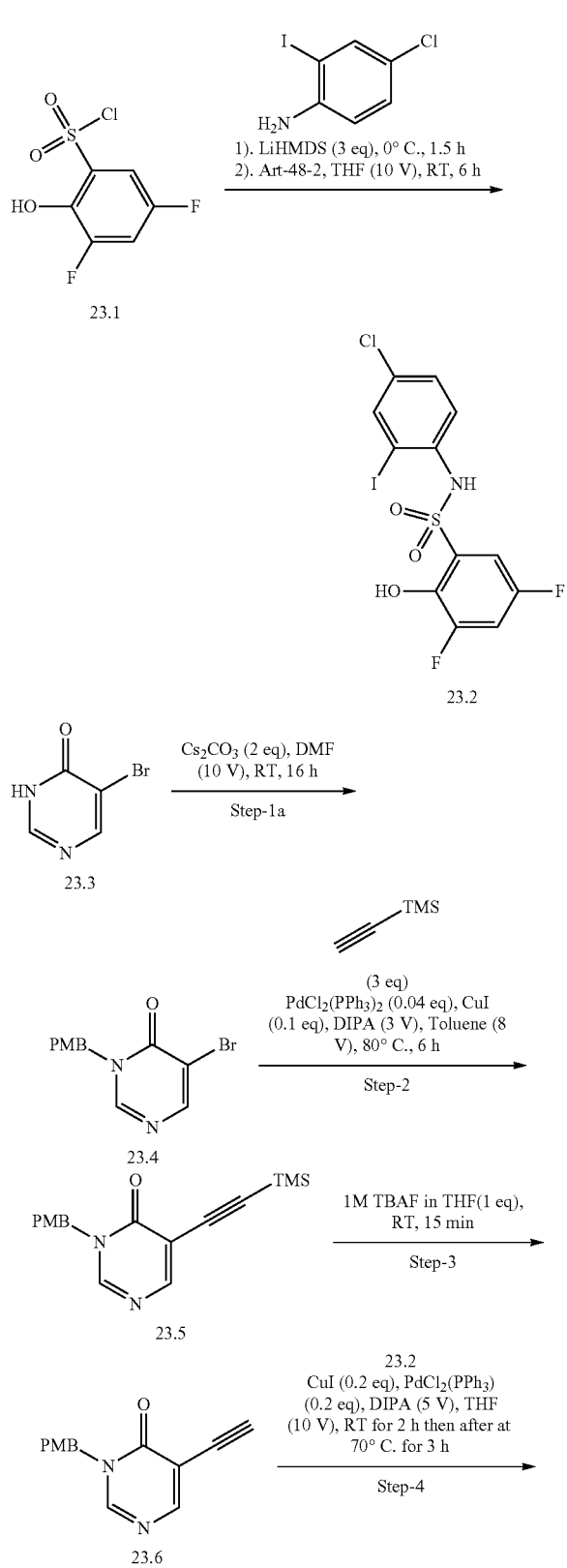

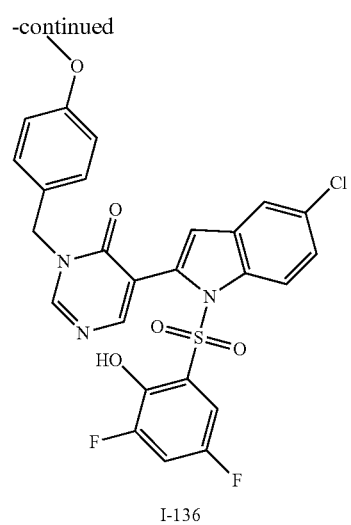

I-136

Synthesis of Compound 23.2:

To a solution of 4-fluoro-2-iodoaniline (1 eq), in anhydrous tetrahydrofuran (10V) was added 1M solution of LiHMDS in THF (3 eq) at −78° C. and stirred for 1.5 h by this time temperature of reaction was rose to 0° C. A solution of 23.1 (1.5 eq) in anhydrous THF (10V) was added drop wise to above reaction mixture at −78° C. The reaction mixture was allowed to warm to room temperature and stirred for 2 h. After completion of reaction, water was added to reaction mixture and extracted using EtOAc. Organic layer was combined, washed with brine solution, dried over sodium sulfate and concentrated under reduced pressure to obtain crude material. The crude reaction mixture was purified by column chromatography and compound was eluted in 20-25% ethyl acetate in hexane to obtain 23.2 (Yield: 30.11%, MS (ES): m/z 444.1$^+$).

Synthesis of Compound 23.4:

Under a nitrogen atmosphere, $Cs_2CO_3$ (3.7 g, 11.4 mmol, 2 eq) was added to the solution of 23.3 (1 g, 5.7 mmol, 1 eq) in DMF (10V) and stirred for 30 min at room temperature. A solution of 1-Chloromethyl-4-methoxybenzene (1.07 g, 6 mmol, 1.2 eq) was added to above solution and stirred at room temperature for 16 h. Water (30 mL) was added to reaction mixture and extracted using EtOAc (40 mL×2) and combined organic layer was washed with brine (20 mL×3), dried over sodium sulphate and concentrated under reduced pressure to obtain crude material. This was further purified by column chromatography and compound was eluted in 50% EtOAc in hexane to afford the desired product 23.4 (0.7 g; Yield: 41%; MS (ES): m/z 294.2 [M−H]$^-$).

Synthesis of Compound 23.5:

Under a nitrogen atmosphere, a reaction vial was changed with 23.4 (1 eq), $PdCl_2(PPh_3)_2$ (0.04 eq.), CuI (0.1 eq) in toluene (10V). DIPA (3V) was added to the reaction and stirred for 2 min at room temperature. After 2 min trimethylsilylacetylene (1.2 eq) was added slowly to the reaction mixture and vial was sealed with Teflon cap. The reaction mixture was stirred at room temperature for 20 h. The progress of the reaction was monitored by TLC. After 20 h, the resulting reaction solution was passed through a celite bed and washed the bed with ethyl acetate (20 mL). Filtrate was collected and evaporation of the solvent gave crude compound which was purified through column chromatography on silica gel and compound was eluted with ethyl acetate in hexane to afford 23.5 (Yield: 80%; MS (ES): m/z 313.3 [M+H]$^+$).

151

Synthesis of Compound 23.6:

Compound 23.5 (1 eq) was dissolved in anhydrous THF (10V) at 0° C. under nitrogen atmosphere. 1.0 M solution of TBAF in THF (1.5 eq) was added slowly to the reaction mixture and stirred at room temperature for 30 min. After 30 min, the solvent was removed under reduced pressure and the obtained crude material was dissolved in dichloromethane and washed with water. The organic layer was collected, washed with brine, dried over sodium sulphate, filtered and concentrated under reduced pressure to afford crude which was purified by column chromatography using silica gel, and compound was eluted with ethyl acetate in hexane to afford the desired product 23.6 (Yield: 78%; MS (ES): m/z 241.2 [M+H]$^+$).

Synthesis of Compound I-136:

PdCl$_2$(PPh$_3$)$_2$ (0.2 eq) and CuI (0.2 eq) were added to a suspension of 23.2 (1 eq), in anhydrous THF (10V) in a 30 mL seal tube. Reaction mixture was purged with argon for 10 min and 23.6 (3 eq) and diisopropylamine (5V) were added. The purging with argon was continued for another 15 min and reaction tube was sealed with Teflon cap. The reaction mixture was stirred for 16 h at room temperature and then after heated at 70° C. for 3 h. Water was added to reaction mixture and acidified using 10% HCl solution. The reaction mixture was extracted using EtOAc (10 mL×2) and combined organic layer was washed with brine, dried over sodium sulphate and concentrated under reduced pressure to obtain crude material. This was further purified by column chromatography and compound was eluted in ethyl acetate in hexane to afford pure compound. Additional purification by reverse phase preparative HPLC was carried out using SUNFIRE C18 (150*19) mm, 5μ column and 0.1% formic acid in water and 100% ACN as mobile phase. The pure fractions were collected and lyophilized to afford pure obtain I-136 (Yield: (0.05 g, 21.57%; MS (ES): m/z 558.3 [M+H]$^+$; LCMS purity: 96.67%; $^1$H NMR (400 MHz, DMSO-d$_6$) δ 3.75 (s, 3H), 5.10 (s, 2H), 6.81 (s, 1H), 6.93 (d, J=8.2 Hz, 2H), 7.35 (d, J=8.5 Hz, 3H), 7.50 (s, 1H), 7.65 (s, 1H), 7.72 (d, J=7.8 Hz, 2H), 7.95 (s, 1H), 8.76 (s, 1H), 11.32 (brs, 1H)).

Example 24. 5-(5-chloro-1-((3,5-difluoro-2-hydroxyphenyl)sulfonyl)-1H-indol-2-yl)pyrimidin-4(3H)-one (I-141)

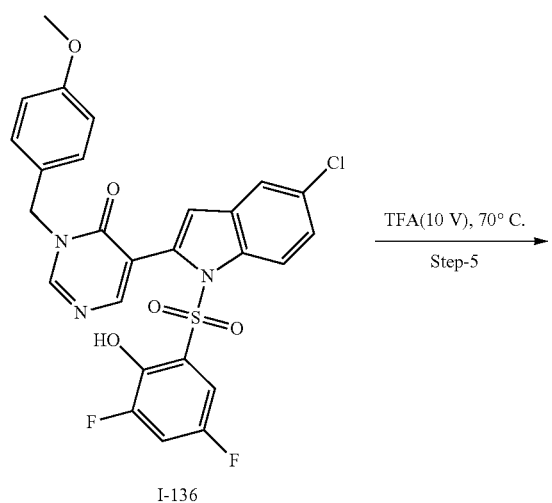

152

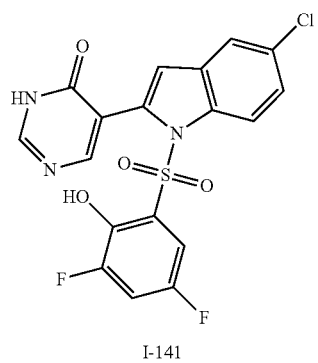

I-141

Synthesis of Compound I-141:

A solution of I-136 (0.1 g) in TFA (10V) was heated at 70° C. for 2 h. The reaction mixture was concentrated under reduced pressure and crude obtained was taken in Sat. Sodium bicarbonate solution (10 mL). The aqueous layer was extracted using EtOAc (10 mL×2) and combined organic layer was washed with brine, dried over sodium sulphate and concentrated under reduced pressure to obtain crude material. This was further purified by column chromatography and compound was eluted in 50% EtOAc in hexane. Additional purification by reverse phase preparative HPLC was carried out using SUNFIRE C18 (150*19) mm, 5μ column and 0.1% formic acid in water and 100% ACN as mobile phase. The pure fractions were collected and lyophilized to afford pure I-141 (0.009 g, Yield: 11.47%; MS (ES): m/z [M−H]$^-$: 436.3; LCMS purity: 100%; $^1$H NMR (400 MHz, DMSO-d$_6$) δ 6.77 (s, 1H), 7.33 (d, J=8.9 Hz, 1H), 7.42 (s, 1H), 7.63 (s, 1H), 7.71-7.75 (m, 2H), 7.94 (s, 1H), 8.29 (s, 1H), 11.35 (brs, 1H), 12.8 (brs, 1H)).

Example 25. 2-((2-(benzo[b]thiophen-2-yl)-5-chloro-1H-indol-1-yl)sulfonyl)-4,6-difluorophenol (I-143)

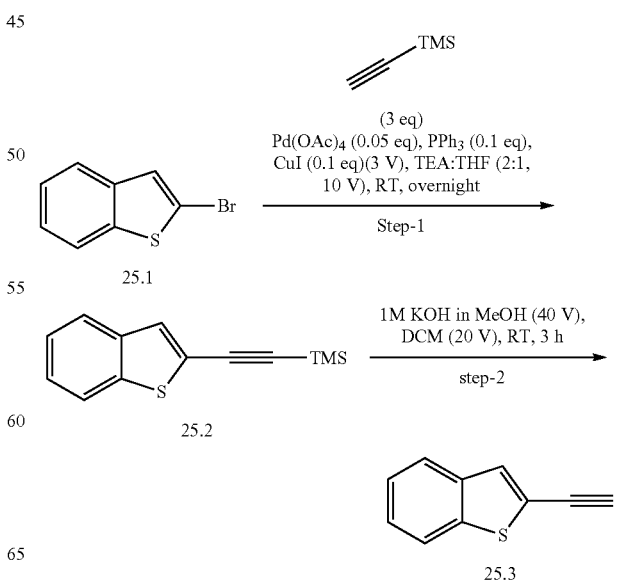

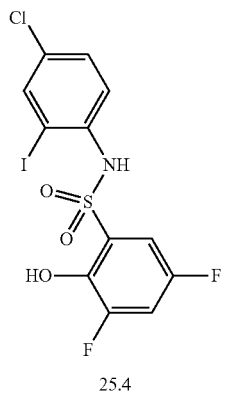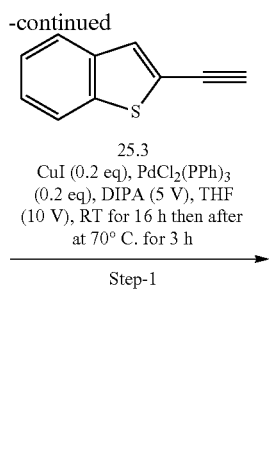

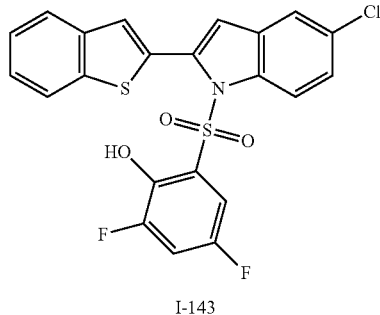

I-143

Synthesis of Compound 25.2.

Palladium acetate (0.104 g, 0.4 mmol, 0.05 eq) and CuI (0.178 g, 0.9 mmol, 0.1 eq) was added to the suspension of 2-bromobenzo[b]thiophene (2 g, 9.3 mmol, 1 eq), Trimethylsilyl acetylene (2.7 g, 27.9 mmol, 3 eq) and Triphenylphosphine (0.249 g, 0.9 mmol, 0.1 eq) in TEA:THF (2:1, 10V) at room temperature in 30 mL seal tube. The reaction mixture was purged with Argon gas for 10 min and sealed with Teflon cap. The reaction mixture was stirred at room temperature for overnight. Water (50 mL) was added to reaction mixture and extracted using EtOAc (50 mL×2) and combined organic layer was washed with brine, dried over sodium sulphate and concentrated under reduced pressure to obtain crude material. This was further purified by column chromatography and compound was eluted in 9% ethyl acetate in hexane to afford pure 25.2 (2 g, Yield: 92%; MS (ES): m/z 231.3 [M+H]$^+$).

Synthesis of Compound 25.3.

1M solution of KOH in methanol (20V) was added to the solution of 25.2 (2 g, 8.6 mmol, 1 eq) in DCM (5V) at room temperature and stirred for 3 h. The volatiles were removed under reduced pressure and crude reaction mixture was purified by column chromatography and compound was eluted in 10% ethyl acetate in hexane to afford pure 25.3 (1.1 g, 80%). MS (ES): m/z 159.2 [M+H]$^+$.

Synthesis of Compound 25.4.

Compound 25.4 was synthesized per the protocol of 23.2.

Synthesis of Compound I-143.

PdCl$_2$(PPh$_3$)$_2$ (0.2 eq) and CuI (0.2 eq) were added to a suspension of 25.3 (1 eq) in anhydrous THF (10V) in a 30 mL seal tube. Reaction mixture was purged with argon for 10 min and 25.4 (3 eq) and diisopropylamine (5V) were added. The purging with argon was continued for another 15 min and reaction tube was sealed with Teflon cap. The reaction mixture was stirred for 16 h at room temperature and then after heated at 70° C. for 3 h. Water was added to reaction mixture and acidified using 10% HCl solution. The reaction mixture was extracted using EtOAc and combined organic layer was washed with brine, dried over sodium sulphate and concentrated under reduced pressure to obtain crude material. This was further purified by column chromatography and compound was eluted with ethyl acetate in hexane to afford pure compound however we could not obtained required purity hence it was again purified by reverse phase preparative HPLC carried out using SUNFIRE C18 (150*19) mm, 5μ column and 0.1% formic acid in water and 100% ACN as mobile phase. The pure fractions were collected and lyophilized to obtain I-143 (0.146 g, Yield: 56%; MS (ES): m/z 474.2 [M−H]$^-$; LCMS purity: 100%; $^1$H NMR (400 MHz, DMSO-d$_6$) δ 6.94-7.05 (m, 2H), 7.44 (s, 1H), 7.38-7.50 (m, 2H), 7.52 (s, 1H), 7.61 (ddd, J=11.0, 8.4, 3.1 Hz, 1H), 7.78 (d, J=2.3 Hz, 1H), 7.94 (ddd, J=18.1, 6.6, 2.9 Hz, 2H), 8.05 (d, J=8.9 Hz, 1H), 11.43 (brs, 1H)).

Example 26. Azetidin-1-yl(1-((5-bromo-3-chloro-2-hydroxyphenyl)sulfonyl)-2-phenyl-1H-indol-6-yl)methanone (I-145)

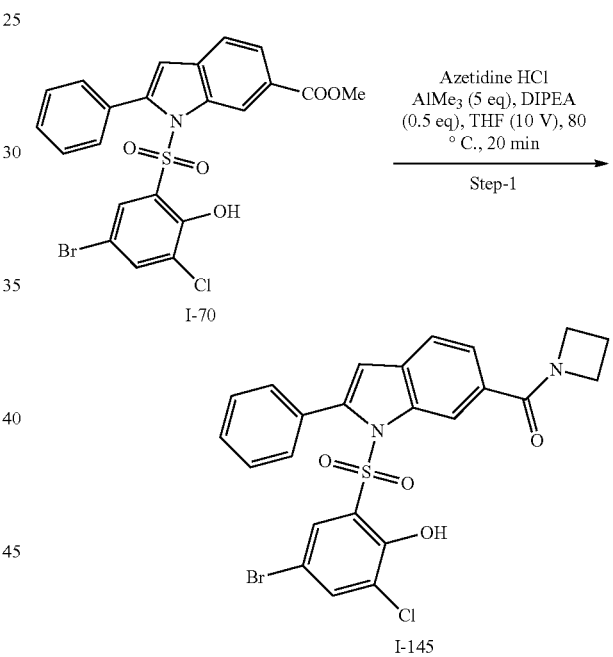

Synthesis of compound I-145.

Under a nitrogen atmosphere, 30 mL reaction vial was charged with 1-70 (0.2 g, 0.384 mmol, 1.0 eq), Azetidine HCl (0.070, 0.769 mmol, 2.0 eq), AlMe$_3$ (0.14 g, 1.92 mmol, 5 eq), DIPEA (0.04 mL, 0.192 mmol, 0.5 eq) in THF (2 mL, 10V) and resulting reaction solution was stirred at 80° C. for 20 min. After 20 min, reaction mixture was quenched with water (20 mL, 100 V) and the resulting solution was extracted with EtOAc (25 mL×2) and combined organic layer was washed with brine, dried over sodium sulphate and concentrated under reduced pressure to obtain crude material which was purified by reverse phase preparative HPLC carried out using X-SELECT PHENYL HEXYL (150*19) mm, 5μ column and 0.1% formic acid in water and 100% ACN as mobile phase. The pure fractions were collected and lyophilized to afford pure I-145 (90 mg, Yield: 42.98%; MS (ES): m/z 547.62 [M+H]$^+$; LCMS purity: 99.33%; $^1$H NMR (400 MHz, DMSO-d$_6$) δ 2.24-2.32 (m, 2H), 4.09 (t, J=7.9 Hz, 2H), 4.32 (t, J=7.5 Hz, 2H), 6.80 (s, 1H), 7.11 (d, J=2.5 Hz, 1H), 7.20 (d, J=7.6 Hz, 2H), 7.33 (t, J=7.5 Hz, 2H), 7.43 (t, J=7.4 Hz, 1H), 7.57 (d, J=8.2 Hz, 1H), 7.68 (d, J=8.1 Hz, 1H), 7.91 (d, J=2.5 Hz, 1H), 8.31 (s, 1H), 11.47 (brs, 1H)).

Example 27. Characterization Data of Further Compounds

Characterization data of further compounds prepared according to the invention are provided in Table 2 below.

TABLE 2

| Compound # | Structure | Characterization Data |
|---|---|---|
| I-34 | 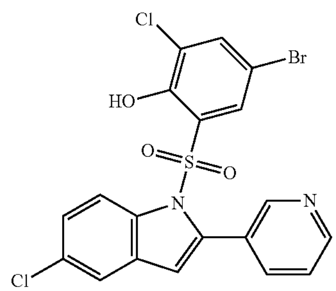 [SMILES: O=S(=O)(c1cc(Br)cc(Cl)c1O)n1c(-c2cccnc2)cc2cc(Cl)ccc21] | [M + H]$^+$: 498.95<br>$^1$H NMR (400 MHz, Chloroform-d) δ 6.67 (s, 1H), 7.36-7.48 (m, 2H), 7.60 (dd, J = 10.9, 2.6 Hz, 3H), 8.05 (dd, J = 20.3, 8.5 Hz, 2H), 8.42 (s, 1H), 8.66 (s, 1H). |
| I-35 | 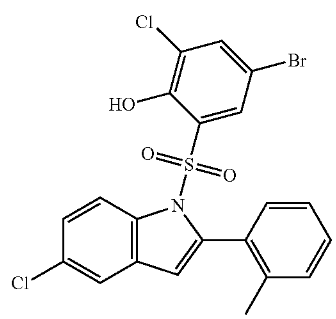 [SMILES: Cc1ccccc1-c1cc2cc(Cl)ccc2n1S(=O)(=O)c1cc(Br)cc(Cl)c1O] | [M + H]$^+$: 510.0<br>$^1$H NMR (400 MHz, Chloroform-d) δ 1.28 (s, 1H), 2.12 (s, 3H), 6.52 (s, 1H), 6.99 (d, J = 7.6 Hz, 1H), 7.14-7.29 (m, 2H), 7.40 (dd, J = 8.9, 2.2 Hz, 2H), 7.60 (dd, J = 21.3, 2.3 Hz, 2H), 7.82 (s, 1H), 8.20 (d, J = 9.0 Hz, 1H). |
| I-36 | 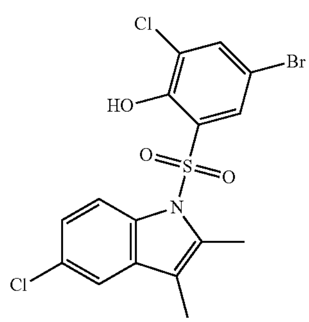 [SMILES: Cc1c(C)n(S(=O)(=O)c2cc(Br)cc(Cl)c2O)c2ccc(Cl)cc12] | [M + H]$^+$: 448<br>$^1$H NMR (400 MHz, DMSO-d$_6$) δ 2.14 (s, 3H), 2.43 (s, 3H), 7.27 (dd, J = 8.8, 2.2 Hz, 1H), 7.57 (d, J = 2.2 Hz, 1H), 7.79 (d, J = 8.8 Hz, 1H), 8.02 (d, J = 3.4 Hz, 2H), 11.56 (brs, 1H). |
| I-37 | 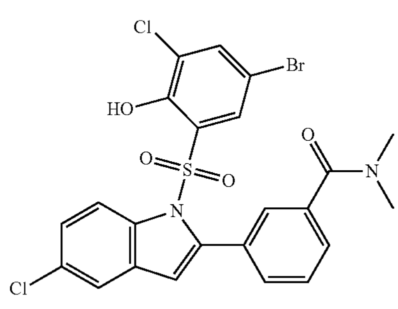 [SMILES: CN(C)C(=O)c1cccc(-c2cc3cc(Cl)ccc3n2S(=O)(=O)c2cc(Br)cc(Cl)c2O)c1] | [M + H]+: 567.4<br>$^1$H NMR (400 MHz, DMSO-d$_6$) δ 3.00 (d, J = 9.1 Hz, 6H), 6.81 (s, 1H), 7.23-7.35 (m, 2H), 7.38-7.51 (m, 4H), 7.73 (s, 1H), 7.92 (s, 1H), 7.99 (d, J = 9.0 Hz, 1H), 11.42 (brs, 1H). |

TABLE 2-continued

| Compound # | Structure | Characterization Data |
|---|---|---|
| I-38 | 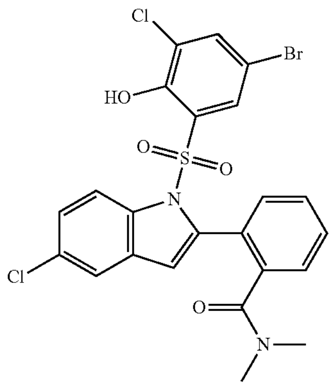 [SMILES: CN(C)C(=O)c1ccccc1-c1cc2cc(Cl)ccc2n1S(=O)(=O)c1cc(Br)cc(Cl)c1O] | [M + H]+: 569.3<br>¹H NMR (400 MHz, Chloroform-d) δ 3.12 (s, 3H), 3.20 (s, 3H), 6.34 (s, 1H), 7.26-7.36 (m, 2H), 7.48-7.59 (m, 4H), 7.80-7.86 (m, 1H), 8.02 (d, J = 9.0 Hz, 1H), 10.99 (brs, 1H). |
| I-39 | 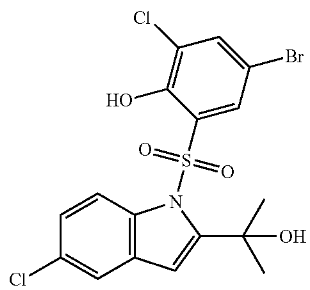 [SMILES: CC(C)(O)c1cc2cc(Cl)ccc2n1S(=O)(=O)c1cc(Br)cc(Cl)c1O] | [M + H]+: 478<br>¹H NMR (400 MHz, DMSO-d₆) δ 1.66 (s, 6H), 6.64 (s, 1H), 7.22 (dd, J = 9.0, 2.3 Hz, 1H), 7.46 (s, 1H), 7.57 (d, J = 2.2 Hz, 1H), 7.68 (dd, J = 23.9, 6.0 Hz, 2H). |
| I-40 | 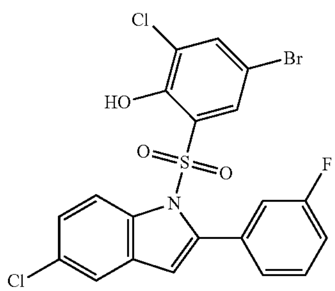 [SMILES: O=S(=O)(c1cc(Br)cc(Cl)c1O)n1c(-c2cccc(F)c2)cc2cc(Cl)ccc21] | [M + H]+: 514<br>¹H NMR (400 MHz, Chloroform-d) δ 6.65 (s, 1H), 7.10-7.26 (m, 4H), 7.42 (d, J = 10.0 Hz, 2H), 7.56 (s, 1H), 7.6 (dd, J = 20.5, 2.3 Hz, 2H), 8.16 (d, J = 8.8 Hz, 1H). |
| I-41 | 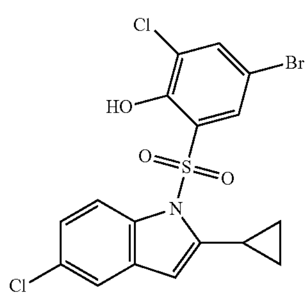 [SMILES: O=S(=O)(c1cc(Br)cc(Cl)c1O)n1c(C2CC2)cc2cc(Cl)ccc21] | [M + H]+: 459.9<br>¹H NMR (400 MHz, DMSO-d₆) δ 0.51 (d, J = 5.4 Hz, 2H), 0.75-0.83 (m, 2H), 2.26 (t, J = 7.8 Hz, 1H), 6.43 (s, 1H), 7.29 (dd, J = 8.9, 2.3 Hz, 1H), 7.55 (d, J = 2.3 Hz, 1H), 7.94 (d, J = 8.9 Hz, 1H), 7.99-8.07 (m, 2H), 11.56 (brs, 1H). |
| I-42 | 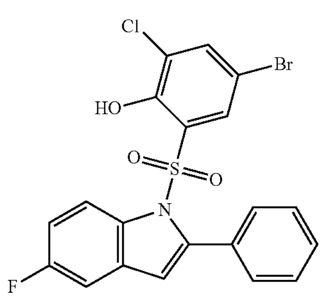 [SMILES: O=S(=O)(c1cc(Br)cc(Cl)c1O)n1c(-c2ccccc2)cc2cc(F)ccc21] | [M + H]+: 479.9<br>¹H NMR (400 MHz, DMSO-d₆) δ 6.75 (s, 1H), 7.11 (d, J = 2.4 Hz, 1H), 7.18-7.28 (m, 3H), 7.34 (t, J = 7.6 Hz, 2H), 7.39-7.49 (m, 2H), 7.91 (d, J = 2.4 Hz, 1H), 8.04 (dd, J = 9.2, 4.5 Hz, 1H), 11.40 (brs, 1H). |

TABLE 2-continued

| Compound # | Structure | Characterization Data |
|---|---|---|
| I-43 | 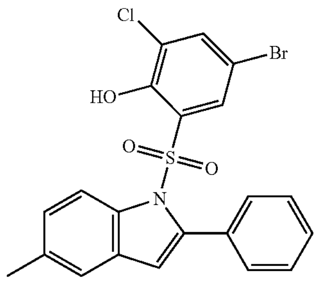 [SMILES: Cc1ccc2c(c1)cc(-c1ccccc1)n2S(=O)(=O)c1cc(Br)cc(Cl)c1O] | [M + H]+: 476.77<br>¹H NMR (400 MHz, DMSO-d$_6$) δ 2.39 (s, 3H), 6.67 (s, 1H), 7.12-7.20 (m, 1H), 7.25 (d, J = 7.1 Hz, 2H), 7.33 (t, J = 7.5 Hz, 2H), 7.38-7.42 (m, 2H), 7.83-7.91 (m, 2H), 11.29 (brs, 1H). |
| I-44 | 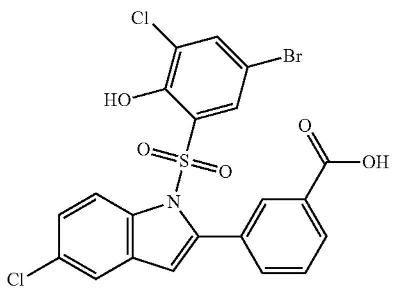 [SMILES: O=C(O)c1cccc(-c2cc3cc(Cl)ccc3n2S(=O)(=O)c2cc(Br)cc(Cl)c2O)c1] | [M + H]+: 539.9<br>¹H NMR (400 MHz, DMSO-d$_6$) δ 6.83 (s, 1H), 7.11 (d, J = 2.5 Hz, 1H), 7.43 (dd, J = 9.0, 2.3 Hz, 1H), 7.54 (dt, J = 15.0, 7.5 Hz, 2H), 7.67 (s, 1H), 7.75 (d, J = 2.1 Hz, 1H), 7.85 (s, 1H), 8.02 (dd, J = 14.6, 8.2 Hz, 2H), 11.51 (brs, 1H), 13.09 (brs, 1H). |
| I-46 | 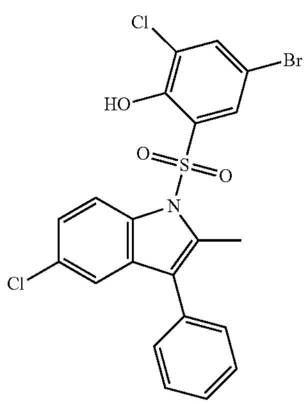 [SMILES: Cc1c(-c2ccccc2)c2cc(Cl)ccc2n1S(=O)(=O)c1cc(Br)cc(Cl)c1O] | [M + H]+: 510.4<br>¹H NMR (400 MHz, DMSO-d$_6$) δ 2.67, (s, 3H), 7.30-7.45 (m, 2H), 7.42-7.50 (m, 3H), 7.55 (t, J = 7.6 Hz, 2H), 7.88 (d, J = 9.3 Hz, 1H), 8.02-8.12 (m, 2H), 11.73 (brs, 1H). |
| I-47 | 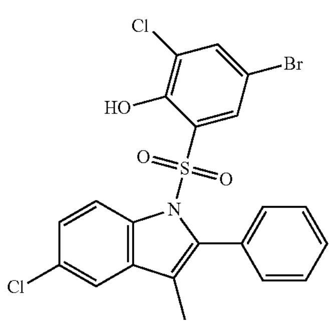 [SMILES: Cc1c(-c2ccccc2)n(S(=O)(=O)c2cc(Br)cc(Cl)c2O)c2ccc(Cl)cc12] | [M + H]+: 510.4<br>¹H NMR (400 MHz, DMSO-d$_6$) δ 1.98 (s, 3H), 6.89-6.95 (m, 1H), 7.03 (d, J = 7.5 Hz, 2H), 7.33 (t, J = 7.6 Hz, 2H), 7.43 (t, J = 7.5 Hz, 2H), 7.72 (s, 1H), 7.90 (s, 1H), 8.08 (d, J = 8.9 Hz, 1H), 11.37 (brs, 1H). |

TABLE 2-continued

| Compound # | Structure | Characterization Data |
|---|---|---|
| I-48 | 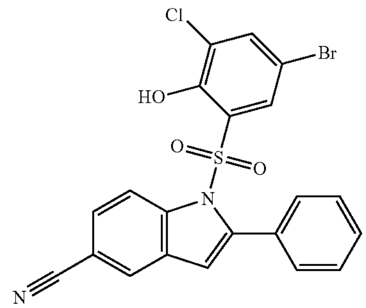 [SMILES: N#Cc1ccc2c(c1)cc(-c1ccccc1)n2S(=O)(=O)c1cc(Br)cc(Cl)c1O] | [M + H]+: 487.26<br>¹H NMR (400 MHz, Chloroform-d) δ 6.67 (s, 1H), 7.10 (d, J = 2.4 Hz, 1H), 7.31 (s, 1H), 7.36-7.46 (m, 3H), 7.52 (t, J = 7.4 Hz, 1H), 7.61 (d, J = 2.3 Hz, 1H), 7.69 (dd, J = 8.8, 1.7 Hz, 1H), 7.92 (s, 1H), 8.37 (d, J = 8.7 Hz, 1H), Phenolic OH not observed. |
| I-51 | 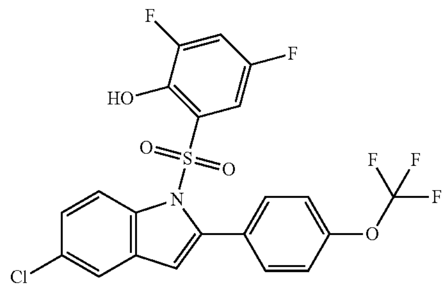 [SMILES: O=S(=O)(c1cc(F)cc(F)c1O)n1c(-c2ccc(OC(F)(F)F)cc2)cc2cc(Cl)ccc21] | [M − H]⁻: 502.05<br>¹H NMR (400 MHz, Chloroform-d) δ 6.65 (s, 1H), 6.64-6.70 (m, 1H), 7.02 (ddd, J = 10.3, 7.7, 3.1 Hz, 1H), 7.33 (s, 2H), 7.42 (dd, J = 8.9, 2.2 Hz, 1H), 7.48-7.58 (m, 3H), 8.15 (d, J = 8.8 Hz, 1H). |
| I-53 | 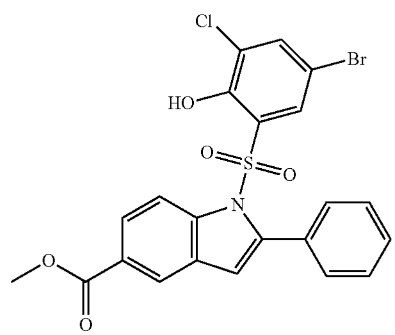 [SMILES: COC(=O)c1ccc2c(c1)cc(-c1ccccc1)n2S(=O)(=O)c1cc(Br)cc(Cl)c1O] | [M + H]+: 520<br>¹H NMR (400 MHz, Chloroform-d) δ 4.00 (s, 3H), 6.73 (s, 1H), 7.15 (d, J = 2.4 Hz, 1H), 7.36-7.49 (m, 4H), 7.51 (d, J = 7.3 Hz, 1H), 7.59 (d, J = 2.5 Hz, 1H), 8.14 (d, J = 8.9 Hz, 1H), 8.30 (d, J = 7.0 Hz, 2H), Phenolic OH not observed. |
| I-54 | 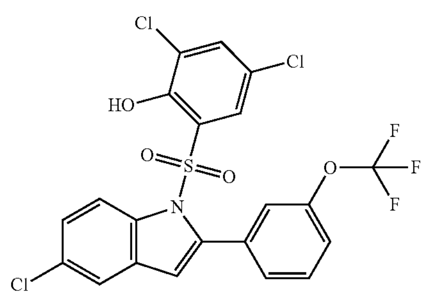 [SMILES: O=S(=O)(c1cc(Cl)cc(Cl)c1O)n1c(-c2cccc(OC(F)(F)F)c2)cc2cc(Cl)ccc21] | [M + H]+: 536.73<br>¹H NMR (400 MHz, DMSO-d₆) δ 6.86 (s, 1H), 7.19 (d, J = 2.7 Hz, 1H), 7.31 (d, J = 6.8 Hz, 2H), 7.38-7.54 (m, 3H), 7.74 (d, J = 2.2 Hz, 1H), 7.83 (d, J = 2.7 Hz, 1H), 8.00 (d, J = 8.9 Hz, 1H), 11.49 (brs, 1H). |
| I-55 | 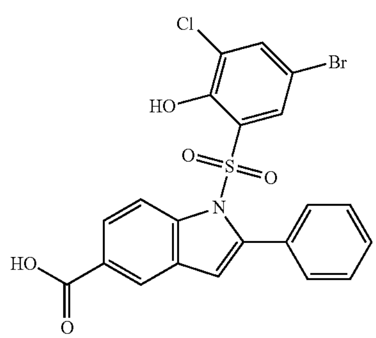 [SMILES: O=C(O)c1ccc2c(c1)cc(-c1ccccc1)n2S(=O)(=O)c1cc(Br)cc(Cl)c1O] | [M + H]+: 505.75<br>¹H NMR (400 MHz, DMSO-d₆) δ 6.89 (s, 1H), 7.09 (d, J = 2.5 Hz, 1H), 7.20 (d, J = 7.5 Hz, 2H), 7.34 (t, J = 7.6 Hz, 2H), 7.44 (t, J = 7.3 Hz, 1H), 7.88-8.00 (m, 2H), 8.15 (d, J = 8.8 Hz, 1H), 8.27 (d, J = 1.7 Hz, 1H), 11.60 (brs, 1H), 12.92 (brs, 1H). |

TABLE 2-continued

| Compound # | Structure | Characterization Data |
|---|---|---|
| I-56 | 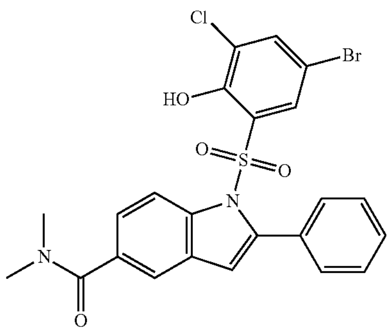 [SMILES: CN(C)C(=O)c1ccc2c(c1)cc(-c1ccccc1)n2S(=O)(=O)c1cc(Br)cc(Cl)c1O] | [M + H]+: 533.82<br>¹H NMR (400 MHz, DMSO-d₆) δ 3.02 (d, J = 8.0 Hz, 6H), 6.80 (s, 1H), 7.09 (s, 1H), 7.21 (d, J = 7.4 Hz, 2H), 7.34 (t, J = 7.7 Hz, 2H), 7.42 (d, J = 8.6 Hz, 2H), 7.70 (s, 1H), 7.91 (s, 1H), 8.10 (d, J = 8.6 Hz, 1H), 11.46, (brs, 1H). |
| I-57 | 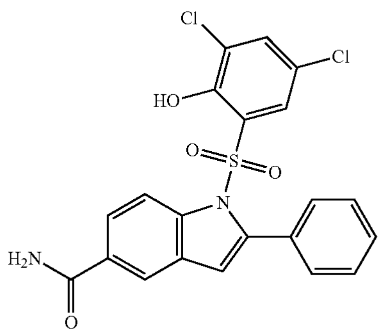 [SMILES: NC(=O)c1ccc2c(c1)cc(-c1ccccc1)n2S(=O)(=O)c1cc(Cl)cc(Cl)c1O] | [M − H]−: 459.6<br>¹H NMR (400 MHz, DMSO-d₆) δ 6.82 (s, 1H), 7.04 (d, J = 2.7 Hz, 1H), 7.22 (d, J = 7.6 Hz, 2H), 7.34 (dd, J = 14.0, 6.4 Hz, 3H), 7.41 (t, J = 7.4 Hz, 1H), 7.79-7.90 (m, 2H), 8.04 (d, J = 9.8 Hz, 2H), 8.16 (s, 1H), 11.39 (s, 1H). |
| I-58 | 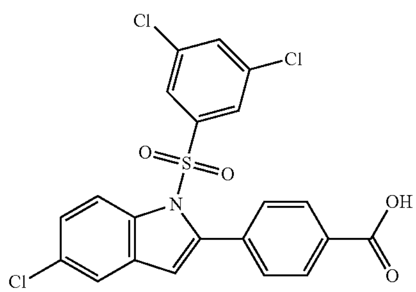 [SMILES: O=C(O)c1ccc(-c2cc3cc(Cl)ccc3n2S(=O)(=O)c2cc(Cl)cc(Cl)c2)cc1] | [M + H]+: 479.74<br>¹H NMR (400 MHz, DMSO-d₆) δ 7.01 (s, 1H), 7.27 (d, J = 1.9 Hz, 2H), 7.50 (dd, J = 8.9, 2.3 Hz, 1H), 7.64 (d, J = 8.0 Hz, 2H), 7.71 (d, J = 2.2 Hz, 1H), 7.98-8.11 (m, 3H), 8.19 (d, J = 8.9 Hz, 1H), 13.23 (brs, 1H). |
| I-59 | 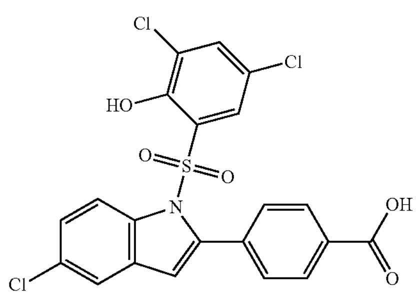 [SMILES: O=C(O)c1ccc(-c2cc3cc(Cl)ccc3n2S(=O)(=O)c2cc(Cl)cc(Cl)c2O)cc1] | [M − H]−: 494.5<br>¹H NMR (400 MHz, DMSO-d₆) δ 6.84 (d, J = 2.9 Hz, 1H), 7.14 (d, J = 3.0 Hz, 1H), 7.41 (d, J = 8.0 Hz, 3H), 7.74 (s, 1H), 7.83 (s, 1H), 7.87-7.97 (m, 2H), 8.00 (dd, J = 9.1, 3.0 Hz, 1H), 11.44 (brs, 1H), 13.11 (brs, 1H). |
| I-60 | 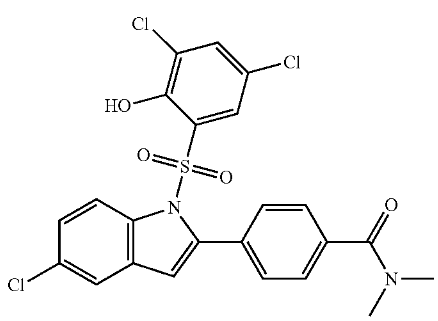 [SMILES: CN(C)C(=O)c1ccc(-c2cc3cc(Cl)ccc3n2S(=O)(=O)c2cc(Cl)cc(Cl)c2O)cc1] | [M + H]+: 523.7<br>¹H NMR (400 MHz, DMSO-d₆) δ 3.01 (d, J = 6.4 Hz, 6H), 6.80 (s, 1H), 7.23 (d, J = 2.6 Hz, 1H), 7.34 (d, J = 7.9 Hz, 2H), 7.36-7.45 (m, 3H), 7.73 (d, J = 2.2 Hz, 1H), 7.85 (d, J = 2.6 Hz, 1H), 8.00 (d, J = 8.9 Hz, 1H), 11.44 (s, 1H). |

TABLE 2-continued

| Compound # | Structure | Characterization Data |
|---|---|---|
| I-61 | 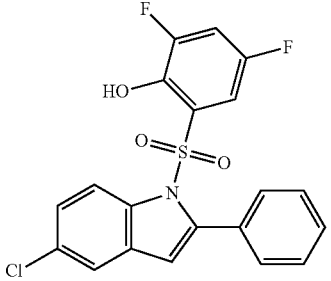 | [M − H]−: 418.4<br>$^1$H NMR (400 MHz, DMSO-d$_6$) δ 6.75 (d, J = 2.8 Hz, 1H), 6.78-6.86 (m, 1H), 7.27 (d, J = 7.4 Hz, 2H), 7.35-7.40 (m, 4H), 7.61 (d, J = 11.0 Hz, 1H), 7.72 (s, 1H), 8.01 (d, J = 9.0 Hz, 1H), 11.30 (brs, 1H). |
| I-62 | 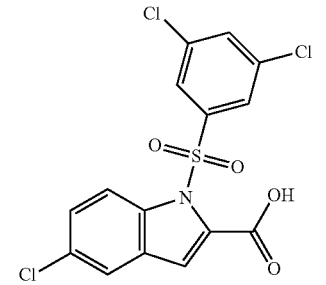 [SMILES: O=C(O)c1cc2cc(Cl)ccc2n1S(=O)(=O)c1cc(Cl)cc(Cl)c1] | [M + H]+: 404.64<br>$^1$H NMR (400 MHz, Chloroform-d) δ 7.44 (s, 1H), 7.54 (d, J = 9.1 Hz, 1H), 7.61-7.71 (m, 2H), 7.97 (s, 2H), 8.14 (d, J = 9.0 Hz, 1H). |
| I-63 | 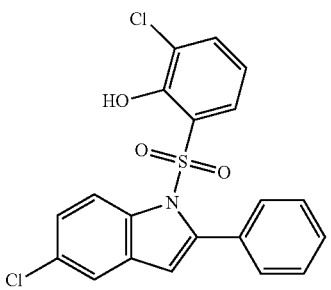 [SMILES: O=S(=O)(c1cccc(Cl)c1O)n1c(-c2ccccc2)cc2cc(Cl)ccc21] | [M − H]−: 416.5<br>$^1$H NMR (400 MHz, DMSO-d$_6$) δ 6.71-6.79 (m, 2H), 7.31-7.39 (m, 7H), 7.63 (s, 1H), 7.70 (s, 2H), 7.96 (d, J = 9.0 Hz, 1H), 10.96 (brs, 1H). |
| I-66 | 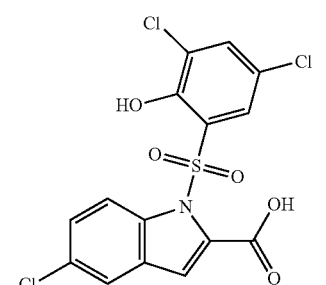 | [M + H]+: 420.2<br>$^1$H NMR (400 MHz, DMSO-d$_6$) δ 7.29-7.36 (m, 2H), 7.52 (d, J = 8.8 Hz, 1H), 7.73 (d, J = 2.7 Hz, 1H), 7.85 (t, J = 4.9 Hz, 2H), 12.30 (brs, 1H). |
| I-67 | 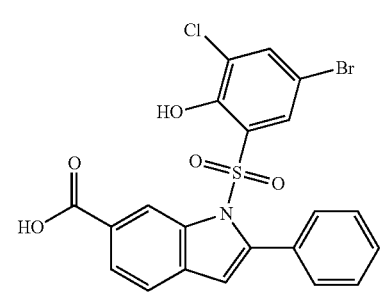 [SMILES: O=C(O)c1ccc2cc(-c3ccccc3)n(S(=O)(=O)c3cc(Br)cc(Cl)c3O)c2c1] | [M + H]+: 506.75<br>$^1$H NMR (400 MHz, DMSO-d$_6$) δ 6.84 (s, 1H), 7.03 (d, J = 2.5 Hz, 1H), 7.18 (d, J = 7.6 Hz, 2H), 7.33 (t, J = 7.6 Hz, 2H), 7.43 (t, J = 7.4 Hz, 1H), 7.71 (d, J = 8.2 Hz, 1H), 7.89 (d, J = 8.0 Hz, 2H), 8.71 (s, 1H), 11.47 (brs, 1H), 12.96 (brs, 1H). |

TABLE 2-continued

| Compound # | Structure | Characterization Data |
|---|---|---|
| I-68 | 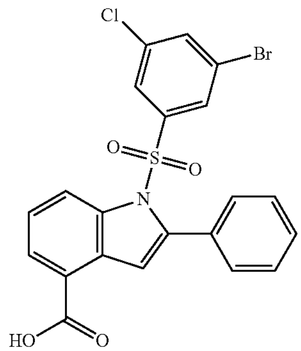 [SMILES: O=C(O)c1cccc2c1cc(-c1ccccc1)n2S(=O)(=O)c1cc(Cl)cc(Br)c1] | [M + H]+: 490.7<br>¹H NMR (400 MHz, DMSO-d₆) δ 7.37 (d, J = 19.4 Hz, 3H), 7.54-7.59 (m, 6H), 7.99 (d, J = 7.7 Hz, 1H), 8.12 (s, 1H), 8.48 (d, J = 8.5 Hz, 1H), 13.28 (brs, 1H). |
| I-69 | 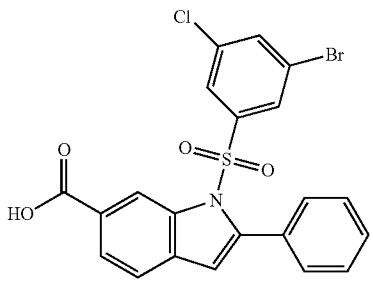 [SMILES: O=C(O)c1ccc2cc(-c3ccccc3)n(S(=O)(=O)c3cc(Cl)cc(Br)c3)c2c1] | [M + H]+: 490.1<br>¹H NMR (400 MHz, DMSO-d₆) δ 7.04 (s, 1H), 7.22 (s, 1H), 7.28 (s, 1H), 7.47-7.59 (m, 5H), 7.72 (d, J = 8.2 Hz, 1H), 7.97 (d, J = 8.2 Hz, 1H), 8.12 (s, 1H), 8.77 (s, 1H), 13.20 (brs, 1H). |
| I-70 | 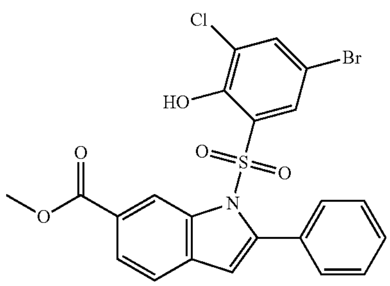 [SMILES: COC(=O)c1ccc2cc(-c3ccccc3)n(S(=O)(=O)c3cc(Br)cc(Cl)c3O)c2c1] | [M + H]+: 520.4<br>¹H NMR (400 MHz, DMSO-d₆) δ 3.93 (d, J = 2.5 Hz, 1H), 6.87 (s, 1H), 7.04 (s, 1H), 7.20 (d, J = 7.7 Hz, 2H), 7.35 (t, J = 7.5 Hz, 2H), 7.45 (d, J = 7.2 Hz, 1H), 7.76 (d, J = 8.5 Hz, 1H), 7.92 (d, J = 9.2 Hz, 2H), 8.75 (s, 1H), 11.48 (brs, 1H) |
| I-71 | 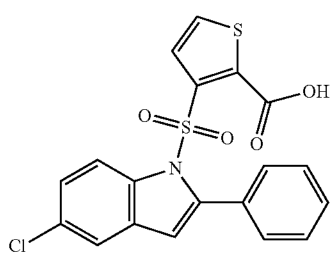 [SMILES: O=C(O)c1sccc1S(=O)(=O)n1c(-c2ccccc2)cc2cc(Cl)ccc21] | [M + H]+: 418.5<br>¹H NMR (400 MHz, DMSO-d₆) δ 6.56 (d, J = 6.7 Hz, 1H), 6.79 (d, J = 6.8 Hz, 1H), 7.29-7.39 (m, 6H), 7.69-7.74 (m, 2H), 7.98 (d, J = 9.2 Hz, 1H), 13.94 (brs, 1H) |
| I-72 | 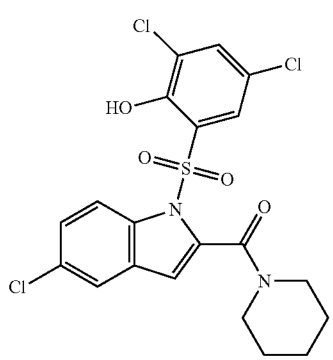 [SMILES: O=C(c1cc2cc(Cl)ccc2n1S(=O)(=O)c1cc(Cl)cc(Cl)c1O)N1CCCCC1] | [M + H]+: 487.4<br>¹H NMR (400 MHz, DMSO-d₆) δ 1.55-1.64 (m, 6H), 3.41 (s, 2H), 3.55 (s, 2H), 6.94 (s, 1H), 7.45 (dd, J = 9.1, 2.2 Hz, 1H), 7.65 (d, J = 2.7 Hz, 1H), 7.77 (d, J = 2.0 Hz, 1H), 7.97 (s, 2H), 11.78 (brs, 1H). |

TABLE 2-continued

| Compound # | Structure | Characterization Data |
|---|---|---|
| I-73 | 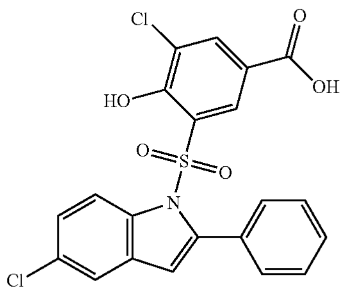 [SMILES: O=C(O)c1cc(Cl)c(O)c(S(=O)(=O)n2c(-c3ccccc3)cc3cc(Cl)ccc32)c1] | [M + H]+: 462.6<br>¹H NMR (400 MHz, DMSO-d$_6$) δ 6.72 (s, 1H), 7.22 (d, J = 7.3 Hz, 2H), 7.26-7.33 (m, 3H), 7.40 (dd, J = 8.9, 2.3 Hz, 1H), 7.65 (d, J = 2.2 Hz, 1H), 7.72 (d, J = 2.3 Hz, 1H), 7.95-8.07 (m, 2H), 11.52 (brs, 1H), 13.09 (brs, 1H). |
| I-74 | 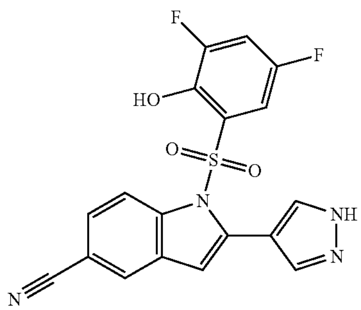 [SMILES: N#Cc1ccc2c(c1)cc(-c1cn[nH]c1)n2S(=O)(=O)c1cc(F)cc(F)c1O] | [M − H]−: 399.3<br>¹H NMR (400 MHz, DMSO-d$_6$) δ 6.80 (s, 1H), 6.93 (d, J = 7.2 Hz, 1H), 7.42 (s, 1H), 7.64 (s, 1H), 7.71-7.81 (m, 2H), 8.15 (s, 1H), 8.21 (d, J = 8.8 Hz, 1H), 11.34 (brs, 1H), 13.10 (brs, 1H). |
| I-75 | 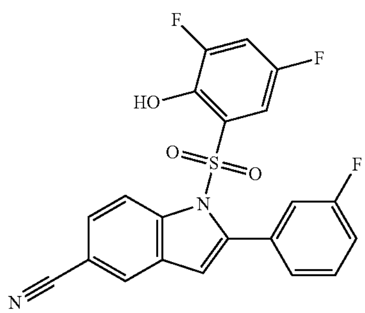 [SMILES: N#Cc1ccc2c(c1)cc(-c1cccc(F)c1)n2S(=O)(=O)c1cc(F)cc(F)c1O] | [M − H]−: 427.2<br>¹H NMR (400 MHz, DMSO-d$_6$) δ 6.91-6.95 (m, 2H), 7.12 (t, J = 9.7 Hz, 2H), 7.25-7.35 (m, 1H), 7.41 (q, J = 7.6 Hz, 1H), 7.67 (s, 1H), 7.78 (d, J = 8.7 Hz, 1H), 8.11-8.23 (m, 2H), 11.47 (brs, 1H). |
| I-76 | 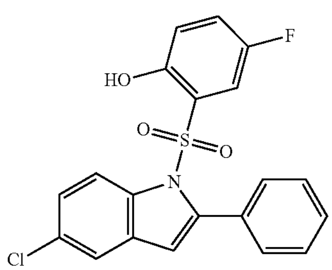 [SMILES: O=S(=O)(c1cc(F)ccc1O)n1c(-c2ccccc2)cc2cc(Cl)ccc21] | [M − H]−: 400.3<br>¹H NMR (400 MHz, DMSO-d$_6$) δ 6.70 (s, 1H), 6.78 (dd, J = 9.1, 4.2 Hz, 1H), 6.90 (dd, J = 8.2, 3.2 Hz, 1H), 7.14-7.24 (m, 2H), 7.26-7.40 (m, 4H), 7.41 (t, J = 7.3 Hz, 1H), 7.68 (d, J = 2.3 Hz, 1H), 8.00 (d, J = 8.9 Hz, 1H), 10.90 (brs, 1H). |
| I-77 | 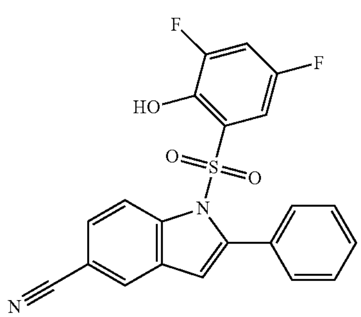 [SMILES: N#Cc1ccc2c(c1)cc(-c1ccccc1)n2S(=O)(=O)c1cc(F)cc(F)c1O] | [M − H]−: 409.3<br>¹H NMR (400 MHz, Chloroform-d) δ 6.65 (dt, J = 7.3, 2.4 Hz, 1H), 6.71 (s, 1H), 7.05 (ddd, J = 10.2, 7.7, 3.0 Hz, 1H), 7.39 (d, J = 7.4 Hz, 2H), 7.41-7.54 (m, 2H), 7.49-7.58 (m, 1H), 7.71 (dd, J = 8.5, 1.7 Hz, 1H), 7.93 (d, J = 1.6 Hz, 1H), 8.39 (d, J = 8.7 Hz, 1H). |

TABLE 2-continued

| Compound # | Structure | Characterization Data |
|---|---|---|
| I-78 | 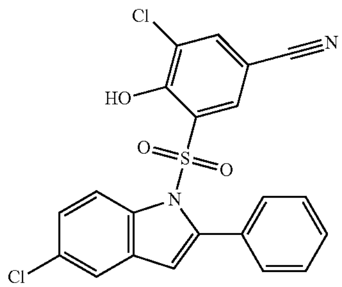 [SMILES: N#Cc1cc(Cl)c(O)c(S(=O)(=O)n2c(-c3ccccc3)cc3cc(Cl)ccc32)c1] | [M − H]−: 441.30<br>¹H NMR (400 MHz, DMSO-d₆) δ 6.64 (s, 1H), 7.23-7.46 (m, 7H), 7.67 (d, J = 2.3 Hz, 1H), 7.80 (s, 1H), 8.03 (d, J = 8.8 Hz, 1H) |
| I-79 | 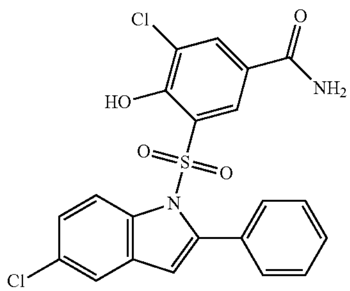 [SMILES: NC(=O)c1cc(Cl)c(O)c(S(=O)(=O)n2c(-c3ccccc3)cc3cc(Cl)ccc32)c1] | [M + H]+: 461.31<br>¹H NMR (400 MHz, DMSO-d₆) δ 6.69 (s, 1H), 7.24-7.38 (m, 8H), 7.68 (d, J = 2.2 Hz, 1H), 7.83 (d, J = 2.3 Hz, 1H), 7.94 (d, J = 8.9 Hz, 1H), 8.06 (s, 1H), 11.81 (brs, 1H). |
| I-80 | 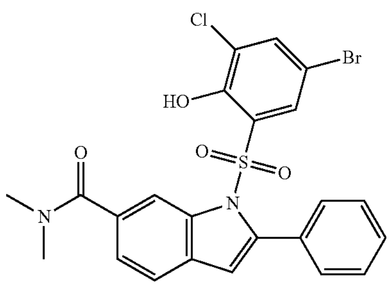 [SMILES: CN(C)C(=O)c1ccc2cc(-c3ccccc3)n(S(=O)(=O)c3cc(Br)cc(Cl)c3O)c2c1] | [M + H]+: 533.82<br>¹H NMR (400 MHz, Chloroform-d) δ 3.12 (s, 3H), 3.22 (s, 3H), 6.68 (s, 1H), 7.16 (d, J = 2.5 Hz, 1H), 7.38 (d, J = 7.5 Hz, 2H), 7.45 (t, J = 8.0 Hz, 3H), 7.51 (d, J = 7.1 Hz, 1H), 7.55-7.63 (m, 2H), 8.36 (s, 1H). |
| I-81 | 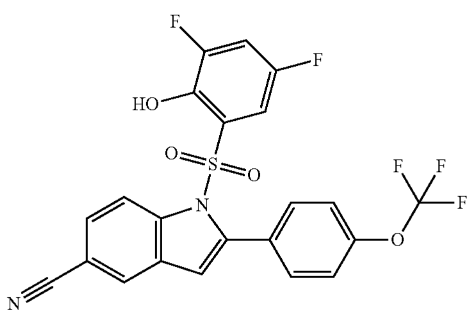 [SMILES: N#Cc1ccc2c(c1)cc(-c1ccc(OC(F)(F)F)cc1)n2S(=O)(=O)c1cc(F)cc(F)c1O] | [M − H]−: 493.3<br>¹H NMR (400 MHz, DMSO-d₆) δ 6.86 (s, 2H), 7.32-7.47 (m, 5H), 7.71 (s, 1H), 8.11-8.15 (m, 2H), 11.49 (brs, 1H) |
| I-82 | 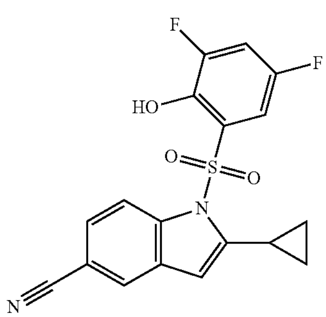 [SMILES: N#Cc1ccc2c(c1)cc(C1CC1)n2S(=O)(=O)c1cc(F)cc(F)c1O] | [M − H]−: 373.27<br>¹H NMR (400 MHz, Chloroform-d) δ 0.62 (dt, J = 6.7, 3.3 Hz, 2H), 0.97-1.07 (m, 2H), 2.27 (td, J = 8.0, 3.9 Hz, 1H), 6.34 (s, 1H), 7.05 (s, 1H), 7.14 (ddd, J = 10.2, 7.7, 3.0 Hz, 1H), 7.59 (dd, J = 8.7, 1.7 Hz, 1H), 7.80 (d, J = 1.7 Hz, 2H), 8.25 (d, J = 8.7 Hz, 1H). |

TABLE 2-continued

| Compound # | Structure | Characterization Data |
|---|---|---|
| I-83 | 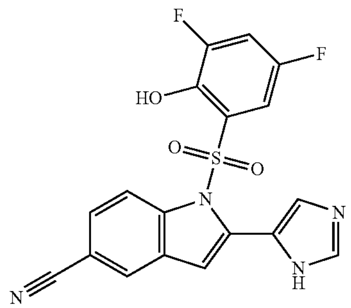 [SMILES: N#Cc1ccc2c(c1)cc(-c1cnc[nH]1)n2S(=O)(=O)c1cc(F)cc(F)c1O] | [M + H]+: 401.2<br>¹H NMR (400 MHz, DMSO-d₆) δ 7.38 (s, 1H), 7.41-7.51 (m, 1H), 7.56 (d, J = 9.0 Hz, 1H), 7.73 (s, 1H), 7.75 (d, J = 17.9 Hz, 1H), 7.83 (d, J = 9.0 Hz, 1H), 7.92 (d, J = 8.8 Hz, 1H), 8.38 (s, 1H). |
| I-84 | 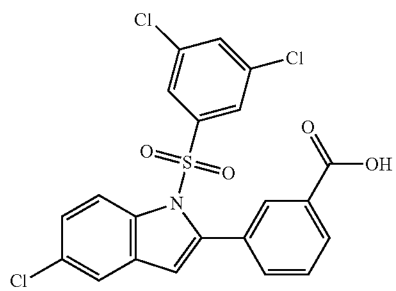 [SMILES: O=C(O)c1cccc(-c2cc3cc(Cl)ccc3n2S(=O)(=O)c2cc(Cl)cc(Cl)c2)c1] | [M + H]+: 480.74<br>¹H NMR (400 MHz, DMSO-d₆) δ 7.01 (s, 1H), 7.25 (d, J = 1.9 Hz, 2H), 7.51 (dd, J = 8.9, 2.3 Hz, 1H), 7.61-7.75 (m, 2H), 7.78 (d, J = 7.7 Hz, 1H), 7.94-8.04 (m, 2H), 8.09 (d, J = 7.8 Hz, 1H), 8.21 (d, J = 8.9 Hz, 1H), 13.23 (brs, 1H). |
| I-85 | 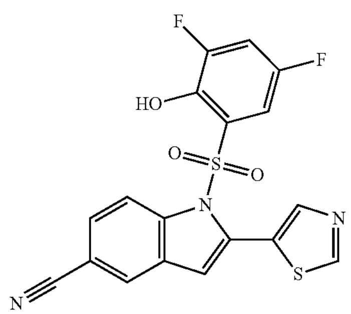 [SMILES: N#Cc1ccc2c(c1)cc(-c1cncs1)n2S(=O)(=O)c1cc(F)cc(F)c1O] | [M − H]−: 416.3<br>¹H NMR (400 MHz, DMSO-d₆) δ 7.05-7.16 (m, 2H), 7.72 (ddd, J = 11.2, 8.4, 3.1 Hz, 1H), 7.79-7.90 (m, 2H), 8.15-8.27 (m, 1H), 8.35 (s, 1H), 9.25 (s, 1H), 11.59 (brs, 1H). |
| I-86 | 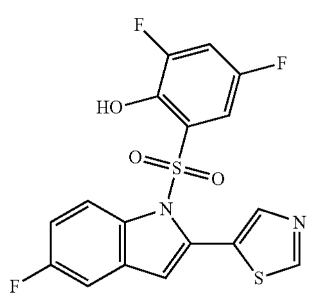 [SMILES: O=S(=O)(c1cc(F)cc(F)c1O)n1c(-c2cncs2)cc2cc(F)ccc21] | [M + H]+: 411.39<br>¹H NMR (400 MHz, DMSO-d₆) δ 7.01 (s, 1H), 7.08-7.16 (m, 1H), 7.26 (td, J = 9.3, 2.8 Hz, 1H), 7.48 (dd, J = 8.9, 2.7 Hz, 1H), 7.68 (s, 1H), 7.88 (s, 1H), 7.98 (dd, J = 9.2, 4.4 Hz, 1H), 9.23 (s, 1H), 11.47 (brs, 1H). |
| I-87 | 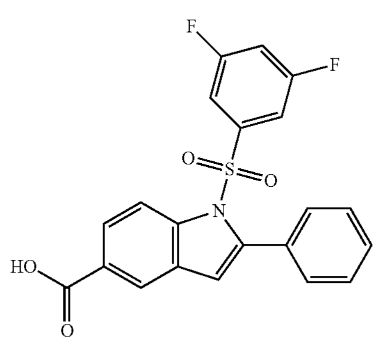 [SMILES: O=C(O)c1ccc2c(c1)cc(-c1ccccc1)n2S(=O)(=O)c1cc(F)cc(F)c1] | [M − H]−: 412.39<br>¹H NMR (400 MHz, DMSO-d₆) δ 7.03 (d, J = 5.9 Hz, 1H), 7.09 (s, 2H), 7.48-7.55 (m, 5H), 7.70 (s, 1H), 8.01 (d, J = 7.4 Hz, 1H), 8.20 (d, J = 5.3 Hz, 1H), 8.26 (s, 1H), 13.06 (brs, 1H). |

TABLE 2-continued

| Compound # | Structure | Characterization Data |
|---|---|---|
| I-88 | 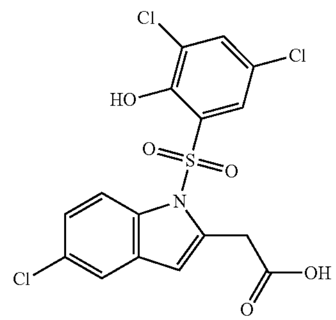 [SMILES: O=C(O)Cc1cc2cc(Cl)ccc2n1S(=O)(=O)c1cc(Cl)cc(Cl)c1O] | [M + H]+: 434.67<br>¹H NMR (400 MHz, DMSO-d₆) δ 4.15 (s, 2H), 6.70 (s, 1H), 7.28 (dd, J = 9.0, 2.2 Hz, 1H), 7.65-7.72 (m, 2H), 7.89-7.99 (m, 2H), 11.90 (brs, 1H), 12.54 (brs, 1H). |
| I-89 | 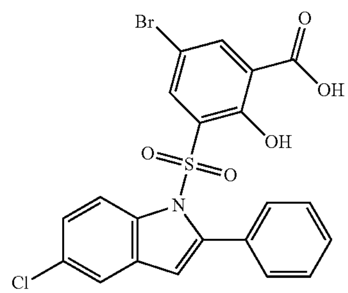 [SMILES: O=C(O)c1cc(Br)cc(S(=O)(=O)n2c(-c3ccccc3)cc3cc(Cl)ccc32)c1O] | (Isolated as the ammonium salt). [M + H]+: 506.75<br>¹H NMR (400 MHz, DMSO-d₆) δ 6.62 (s, 1H), 7.03-9.06 (m, 5H), 7.18 (d, J = 7.6 Hz, 2H), 7.31 (t, J = 7.5 Hz, 3H), 7.41 (t, J = 7.5 Hz, 1H), 7.64 (d, J = 2.3 Hz, 1H), 7.80 (d, J = 2.9 Hz, 1H), 8.05 (d, J = 9.0 Hz, 1H). |
| I-90 | 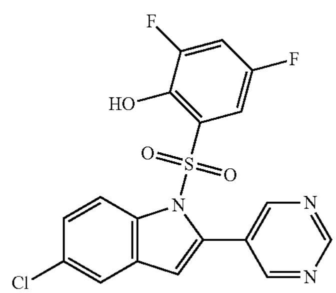 | [M + H]+: 422.2<br>¹H NMR (400 MHz, DMSO-d₆) δ 7.03 (s, 1H), 7.36-7.44 (m, 2H), 7.67 (s, 1H), 7.78 (d, J = 2.1 Hz, 1H), 7.88 (d, J = 8.8 Hz, 1H), 8.91 (s, 2H), 9.25 (s, 1H), 11.49 (brs, 1H). |
| I-91 | 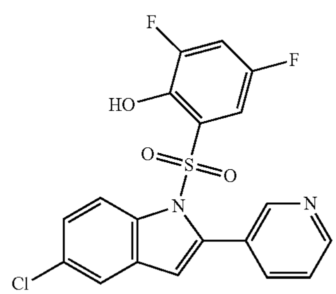 [SMILES: O=S(=O)(c1cc(F)cc(F)c1O)n1c(-c2cccnc2)cc2cc(Cl)ccc21] | [M − H]−: 419.2<br>¹H NMR (400 MHz, DMSO-d₆) δ 6.89 (s, 1H), 7.12 (s, 1H), 7.39 (d, J = 9.3 Hz, 1H), 7.50 (s, 1H), 7.66 (d, J = 10.1 Hz, 1H), 7.75 (s, 1H), 7.86 (d, J = 8.0 Hz, 1H), 7.93 (d, J = 9.0 Hz, 1H), 8.66 (s, 2H), 11.41 (brs, 1H). |
| I-92 | 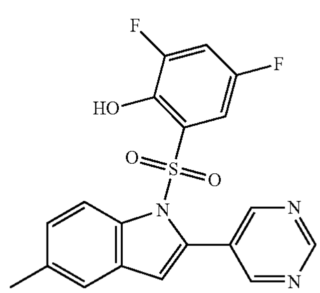 [SMILES: Cc1ccc2c(c1)cc(-c1cncnc1)n2S(=O)(=O)c1cc(F)cc(F)c1O] | [M + H]+: 402.2<br>¹H NMR (400 MHz, DMSO-d₆) δ 2.37 (s, 3H), 6.82 (s, 1H), 7.11 (d, J = 8.5 Hz, 2H), 7.25 (s, 1H), 7.41 (s, 1H), 7.61 (s, 1H), 9.09 (s, 2H), 9.17 (s, 1H), 11.41 (brs, 1H). |

TABLE 2-continued

| Compound # | Structure | Characterization Data |
|---|---|---|
| I-93 | 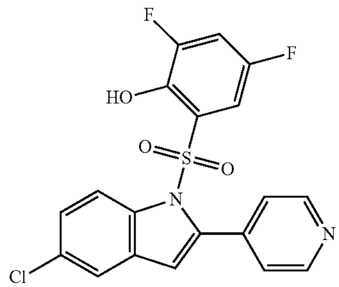 [SMILES: O=S(=O)(c1cc(F)cc(F)c1O)n1c(-c2ccncc2)cc2cc(Cl)ccc21] | [M + H]+: 421.1<br>$^1$H NMR (400 MHz, DMSO-d$_6$) δ 6.97 (s, 1H), 7.25-7.33 (m, 1H), 7.41 (dd, J = 8.9, 2.3 Hz, 1H), 7.52 (d, J = 4.7 Hz, 2H), 7.66 (ddd, J = 11.2, 8.4, 3.2 Hz, 1H), 7.76 (d, J = 2.2 Hz, 1H), 7.92 (d, J = 8.9 Hz, 1H), 8.68 (s, 2H), 11.43 (brs, 1H). |
| I-94 | 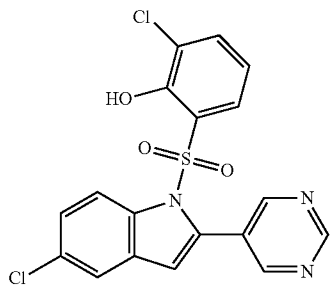 [SMILES: O=S(=O)(c1cccc(Cl)c1O)n1c(-c2cncnc2)cc2cc(Cl)ccc21] | [M − H]−: 420.26<br>$^1$H NMR (400 MHz, DMSO-d$_6$) δ 6.92-7.04 (m, 2H), 7.36 (dd, J = 8.9, 2.2 Hz, 1H), 7.65-7.84 (m, 4H), 8.92 (s, 2H), 9.22 (s, 1H), 11.10 (brs, 1H). |
| I-95 | 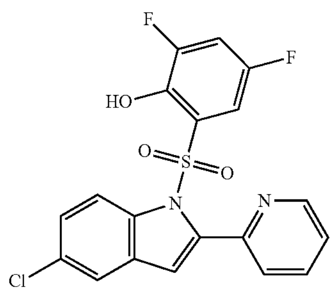 | [M + H]+: 421.2<br>$^1$H NMR (400 MHz, DMSO-d$_6$) δ 7.09 (s, 1H), 7.33 (dt, J = 8.3, 2.4 Hz, 1H), 7.43 (dd, J = 9.0, 2.3 Hz, 1H), 7.48 (dd, J = 7.6, 4.9 Hz, 1H), 7.71 (ddd, J = 11.2, 8.4, 3.2 Hz, 1H), 7.73-7.82 (m, 2H), 7.93-8.04 (m, 2H), 8.47 (d, J = 4.8 Hz, 1H). |
| I-96 | 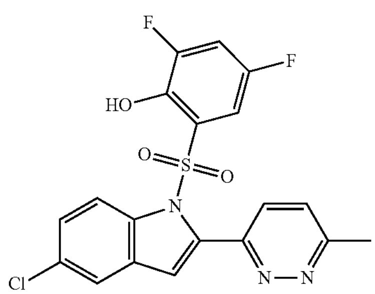 [SMILES: Cc1ccc(-c2cc3cc(Cl)ccc3n2S(=O)(=O)c2cc(F)cc(F)c2O)nn1] | [M + H]+: 436.2<br>$^1$H NMR (400 MHz, DMSO-d$_6$) δ 2.70 (s, 3H), 7.13 (s, 1H), 7.28 (d, J = 8.2 Hz, 1H), 7.44 (dd, J = 8.9, 2.2 Hz, 1H), 7.65-7.75 (m, 2H), 7.82 (d, J = 2.2 Hz, 1H), 7.94 (dd, J = 21.2, 8.5 Hz, 2H), 11.80 (brs, 1H). |
| I-97 | 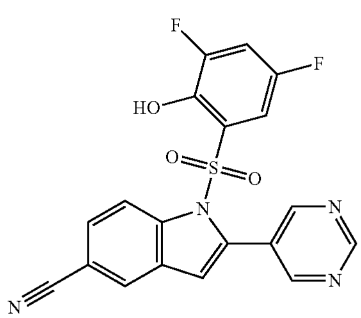 [SMILES: N#Cc1ccc2c(c1)cc(-c1cncnc1)n2S(=O)(=O)c1cc(F)cc(F)c1O] | [M − H]−: 411.29<br>$^1$H NMR (400 MHz, DMSO-d$_6$) δ 7.15 (s, 1H), 7.36 (d, J = 8.0 Hz, 1H), 7.70 (s, 1H), 7.80 (d, J = 8.6 Hz, 1H), 8.07 (d, J = 8.7 Hz, 1H), 8.28 (s, 1H), 8.88 (s, 2H), 9.26 (s, 1H), 11.61 (brs, 1H). |

TABLE 2-continued

| Compound # | Structure | Characterization Data |
|---|---|---|
| I-98 | 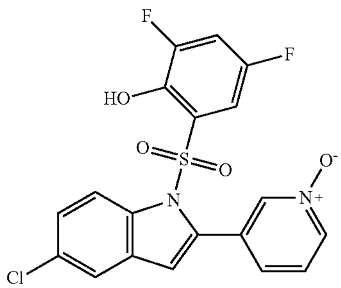 | [M − H]−: 435.33<br>¹H NMR (400 MHz, DMSO-d₆) δ 6.99 (s, 1H), 7.35-7.51 (m, 4H), 7.66 (s, 1H), 7.76 (d, J = 2.2 Hz, 1H), 7.85 (d, J = 8.9 Hz, 1H), 8.27-8.33 (m, 2H), 11.54 (brs, 1H). |
| I-99 | 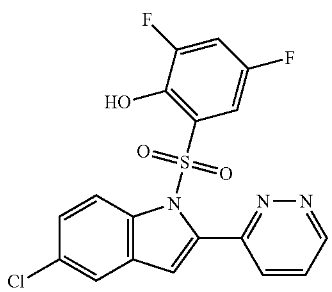 [SMILES: O=S(=O)(c1cc(F)cc(F)c1O)n1c(-c2cccnn2)cc2cc(Cl)ccc21] | [M − H]−: 420.0<br>¹H NMR (400 MHz, DMSO-d₆) δ 7.18 (s, 1H), 7.28 (d, J = 8.1 Hz, 1H), 7.46 (d, J = 9.0 Hz, 1H), 7.69 (s, 1H), 7.80-7.88 (m, 2H), 8.00 (s, 2H), 9.26 (d, J = 4.9 Hz, 1H), 11.65 (brs, 1H). |
| I-100 | 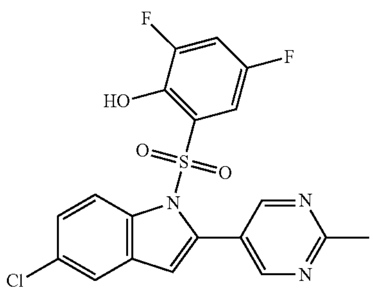 | [M + H]+: 436.13<br>¹H NMR (400 MHz, DMSO-d₆) δ 2.70 (s, 3H), 6.97 (s, 1H), 7.32-7.43 (m, 2H), 7.67 (s, 1H), 7.76 (d, J = 2.2 Hz, 1H), 7.88 (d, J = 8.9 Hz, 1H), 8.74 (s, 2H), 11.44 (brs, 1H). |
| I-101 | 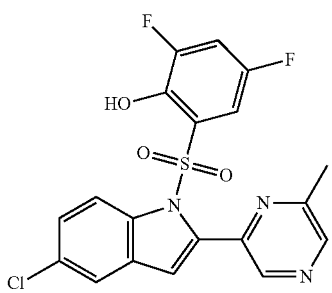 [SMILES: Cc1cncc(-c2cc3cc(Cl)ccc3n2S(=O)(=O)c2cc(F)cc(F)c2O)n1] | [M − H]−: 434.23<br>¹H NMR (400 MHz, DMSO-d₆) δ 2.34 (s, 3H), 7.13 (s, 1H), 7.25-7.33 (m, 1H), 7.45 (dd, J = 9.0, 2.3 Hz, 1H), 7.68-7.82 (m, 2H), 8.05 (d, J = 9.0 Hz, 1H), 8.56 (s, 1H), 8.73 (s, 1H), 11.58 (brs, 1H). |
| I-102 | 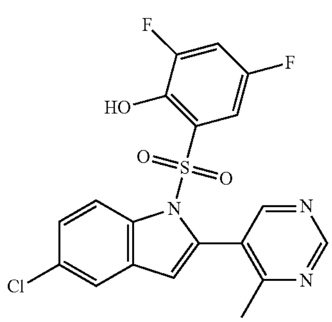 [SMILES: Cc1ncncc1-c1cc2cc(Cl)ccc2n1S(=O)(=O)c1cc(F)cc(F)c1O] | [M − H]−: 434.3<br>¹H NMR (400 MHz, DMSO-d₆) δ 2.26 (s, 3H), 6.94 (s, 1H), 7.13-7.21 (m, 1H), 7.40 (dd, J = 8.9, 2.3 Hz, 1H), 7.70 (s, 1H), 7.77 (d, J = 2.2 Hz, 1H), 7.89 (d, J = 8.9 Hz, 1H), 8.51 (s, 1H), 9.09 (s, 1H), 11.57 (brs, 1H). |

TABLE 2-continued

| Compound # | Structure | Characterization Data |
|---|---|---|
| I-103 | (structure) | [M + H]+: 422.2<br>¹H NMR (400 MHz, Methanol-d₄) δ 7.00 (s, 1H), 7.23 (ddd, J = 10.8, 8.0, 3.1 Hz, 1H), 7.35 (dd, J = 9.0, 2.1 Hz, 1H), 7.45 (dt, J = 8.2, 2.5 Hz, 1H), 7.66 (d, J = 2.1 Hz, 1H), 7.83-7.96 (m, 2H), 9.27 (dd, J = 5.3, 1.2 Hz, 1H), 9.35-9.41 (m, 1H). |
| I-104 | (structure) | (Isolated as the ammonium salt). [M + H]+: 480.4<br>¹H NMR (400 MHz, DMSO-d₆) δ 6.91 (t, J = 7.4 Hz, 2H), 6.98-7.2 (m, 1H), 7.12-7.15 (m, 3H), 7.18-7.23 (m, 2H), 7.28-7.32 (m, 4H), 7.43 (s, 1H), 7.52 (t, J = 9.4 Hz, 2H). |
| I-105 | (structure) | [M − H]−: 420.2<br>¹H NMR (400 MHz, DMSO-d₆) δ 7.16 (s, 1H), 7.35 (d, J = 8.0 Hz, 1H), 7.43 (dd, J = 9.0, 2.2 Hz, 1H), 7.68 (s, 1H), 7.80 (d, J = 2.2 Hz, 1H), 7.95 (d, J = 8.9 Hz, 1H), 8.59 (s, 1H), 8.67 (d, J = 2.6 Hz, 1H), 8.93 (s, 1H), 11.54 (brs, 1H). |
| I-108 | (structure) | [M + H]+: 432<br>¹H NMR (400 MHz, Chloroform-d) δ 1.44 (t, J = 7.2 Hz, 3H), 4.44 (q, J = 7.1 Hz, 2H), 7.21 (s, 1H), 7.48 (dd, J = 9.0, 2.1 Hz, 1H), 7.59-7.67 (m, 2H), 7.98 (d, J = 1.8 Hz, 2H), 8.06 (d, J = 9.0 Hz, 1H). |
| I-109 | (structure) | [M + H]+: 504.78<br>¹H NMR (400 MHz, Chloroform-d) δ 3.98 (s, 3H), 7.27 (t, J = 1.8 Hz, 1H), 7.34-7.43 (m, 2H), 7.47-7.68 (m, 7H), 8.10 (d, J = 7.6 Hz, 1H), 8.54 (d, J = 8.4 Hz, 1H). |

TABLE 2-continued

| Compound # | Structure | Characterization Data |
|---|---|---|
| I-110 | 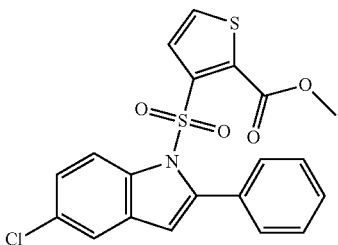 [SMILES: COC(=O)c1sccc1S(=O)(=O)n1c(-c2ccccc2)cc2cc(Cl)ccc21] | [M + H]+: 432.5<br>¹H NMR (400 MHz, DMSO-d₆) δ 3.53 (s, 3H), 6.54 (d, J = 5.3 Hz, 1H), 6.81 (s, 1H), 7.31 (dd, J = 14.9, 7.2 Hz, 3H), 7.33-7.44 (m, 3H), 7.77 (dd, J = 5.2, 3.8 Hz, 2H), 8.01 (d, J = 8.9 Hz, 1H). |
| I-111 | 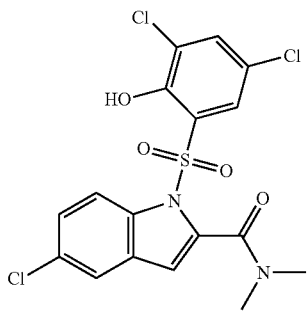 [SMILES: CN(C)C(=O)c1cc2cc(Cl)ccc2n1S(=O)(=O)c1cc(Cl)cc(Cl)c1O] | [M + H]+: 447.2<br>¹H NMR (400 MHz, Chloroform-d) δ 3.29 (d, J = 3.8 Hz, 6H), 6.77 (s, 1H), 7.38 (dd, J = 8.9, 2.1 Hz, 1H), 7.56 (d, J = 8.9 Hz, 1H), 7.64 (dd, J = 13.4, 2.3 Hz, 2H), 8.09 (d, J = 2.6 Hz, 1H), 12.28 (brs, 1H). |
| I-112 | 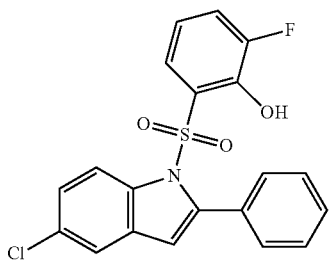 [SMILES: O=S(=O)(c1cccc(F)c1O)n1c(-c2ccccc2)cc2cc(Cl)ccc21] | [M + H]+: 402.33<br>¹H NMR (400 MHz, DMSO-d₆) δ 6.72 (s, 2H), 7.12 (d, J = 8.2 Hz, 1H), 7.25-7.42 (m, 6H), 7.43 (dd, J = 19.6, 9.4 Hz, 1H), 7.70 (d, J = 2.2 Hz, 1H), 7.96 (d, J = 8.9 Hz, 1H), 11.29 (brs, 1H). |
| I-113 | 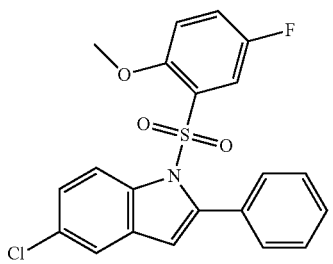 [SMILES: COc1ccc(F)cc1S(=O)(=O)n1c(-c2ccccc2)cc2cc(Cl)ccc21] | [M + H]+: 416.4<br>¹H NMR (400 MHz, Chloroform-d) δ 3.36 (s, 3H), 6.50 (s, 1H), 6.77 (dd, J = 9.1, 3.9 Hz, 1H), 7.00 (dd, J = 7.8, 3.2 Hz, 1H), 7.12-7.25 (m, 3H), 7.30-7.46 (m, 4H), 7.55 (d, J = 2.2 Hz, 1H), 8.15 (d, J = 8.9 Hz, 1H). |
| I-114 | 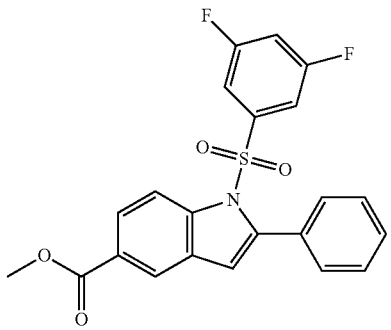 [SMILES: COC(=O)c1ccc2c(c1)cc(-c1ccccc1)n2S(=O)(=O)c1cc(F)cc(F)c1] | [M + H]+: 428.3<br>¹H NMR (400 MHz, DMSO-d₆) δ 3.90 (s, 3H), 7.03-7.14 (m, 3H), 7.46-7.58 (m, 5H), 7.71 (tt, J = 9.0, 2.3 Hz, 1H), 8.03 (dd, J = 8.9, 1.9 Hz, 1H), 8.23-8.34 (m, 2H). |

TABLE 2-continued

| Compound # | Structure | Characterization Data |
|---|---|---|
| I-115 | 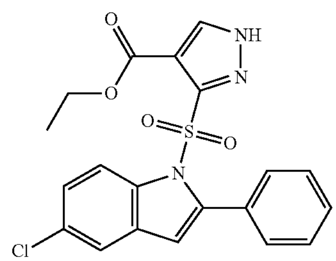 [SMILES: CCOC(=O)c1c[nH]nc1S(=O)(=O)n1c(-c2ccccc2)cc2cc(Cl)ccc21] | [M − H]−: 428.3<br>$^1$H NMR (400 MHz, DMSO-d$_6$) δ 1.22 (t, J = 7.1 Hz, 3H), 4.18 (q, J = 7.1 Hz, 2H), 6.80 (s, 1H), 7.35 (tt, J = 9.6, 4.3 Hz, 5H), 7.74 (d, J = 2.2 Hz, 1H), 7.85 (d, J = 9.0 Hz, 1H), 8.55 (s, 1H), 14.15 (brs, 1H). |
| I-116 | 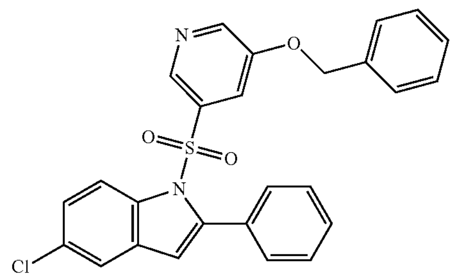 [SMILES: O=S(=O)(c1cncc(OCc2ccccc2)c1)n1c(-c2ccccc2)cc2cc(Cl)ccc21] | [M + H]+: 475.20<br>$^1$H NMR (400 MHz, DMSO-d$_6$) δ 5.13 (s, 2H), 6.87 (s, 1H), 7.21 (t, J = 2.4 Hz, 1H), 7.35-7.43 (m, 5H), 7.44-7.48 (m, 1H), 7.53 (qd, J = 6.9, 5.9, 3.8 Hz, 5H), 7.69 (d, J = 2.2 Hz, 1H), 8.13 (d, J = 2.0 Hz, 1H), 8.18 (d, J = 8.9 Hz, 1H), 8.59 (d, J = 2.8 Hz, 1H). |
| I-117 | 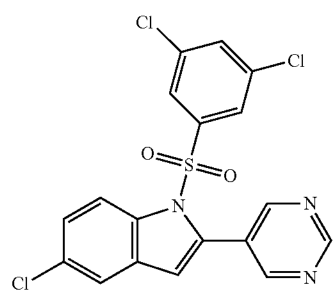 [SMILES: O=S(=O)(c1cc(Cl)cc(Cl)c1)n1c(-c2cncnc2)cc2cc(Cl)ccc21] | [M + H]+: 438.71<br>$^1$H NMR (400 MHz, Chloroform-d) δ 6.78 (s, 1H), 7.24-7.3 (m, 2H), 7.45-7.55 (m, 2H), 7.59 (d, J = 2.0 Hz, 1H), 8.22 (d, J = 8.9 Hz, 1H), 8.92 (s, 2H), 9.36 (s, 1H). |
| I-118 | 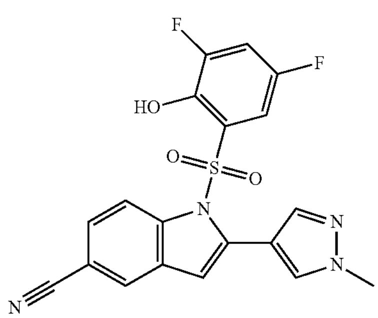 [SMILES: Cn1cc(-c2cc3cc(C#N)ccc3n2S(=O)(=O)c2cc(F)cc(F)c2O)cn1] | [M + H]+: 415.39<br>$^1$H NMR (400 MHz, DMSO-d$_6$) δ 3.83 (s, 3H), 6.79 (s, 1H), 7.02 (s, 1H), 7.36 (s, 1H), 7.67 (d, J = 9.4 Hz, 1H), 7.74 (d, J = 8.1 Hz, 2H), 8.13-8.24 (m, 2H), 11.36 (brs, 1H). |
| I-119 | 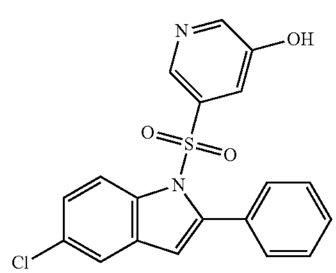 [SMILES: O=S(=O)(c1cncc(O)c1)n1c(-c2ccccc2)cc2cc(Cl)ccc21] | [M − H]−: 383.2<br>$^1$H NMR (400 MHz, DMSO-d$_6$) δ 6.89 (s, 1H), 6.98 (t, J = 2.4 Hz, 1H), 7.44-7.55 (m, 5H), 7.55 (s, 1H), 7.68 (d, J = 2.2 Hz, 1H), 7.99 (d, J = 2.1 Hz, 1H), 8.15 (d, J = 8.9 Hz, 1H), 8.30 (d, J = 2.6 Hz, 1H), 11.07 (brs, 1H). |

TABLE 2-continued

| Compound # | Structure | Characterization Data |
|---|---|---|
| I-120 | 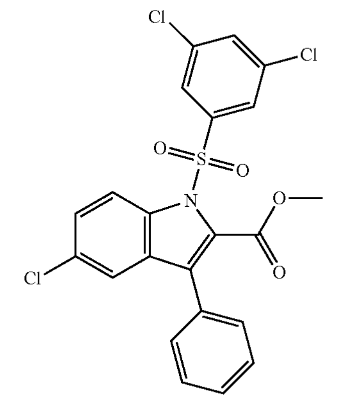 [SMILES: COC(=O)c1c(-c2ccccc2)c2cc(Cl)ccc2n1S(=O)(=O)c1cc(Cl)cc(Cl)c1] | [M + H]+: 496.1<br>¹H NMR (400 MHz, DMSO-d$_6$) δ 3.84 (s, 3H), 7.44-7.59 (m, 6H), 7.61 (dd, J = 8.9, 2.2 Hz, 1H), 8.07 (d, J = 1.9 Hz, 2H), 8.12 (s, 1H), 8.21 (d, J = 9.0 Hz, 1H). |
| I-121 | 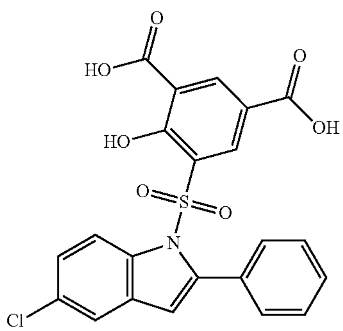 [SMILES: O=C(O)c1cc(C(=O)O)c(O)c(S(=O)(=O)n2c(-c3ccccc3)cc3cc(Cl)ccc32)c1] | [M − H]−: 470.3<br>¹H NMR (400 MHz, DMSO-d$_6$) δ 6.66 (s, 1H), 7.22-7.37 (m, 6H), 7.67 (s, 1H), 7.82 (d, J = 2.4 Hz, 1H), 8.03 (d, J = 9.0 Hz, 1H), 8.39 (d, J = 2.4 Hz, 1H). |
| I-122 | | [M − H]−: 400.3<br>¹H NMR (400 MHz, DMSO-d$_6$) δ 6.77 (s, 1H), 7.35 (s, 6H), 7.73 (s, 1H), 7.83 (d, J = 9.1 Hz, 1H), 8.38 (s, 1H), 13.55 (brs, 2H) |
| I-123 | 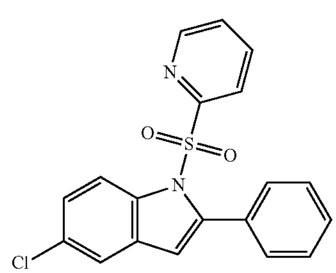 [SMILES: O=S(=O)(c1ccccn1)n1c(-c2ccccc2)cc2cc(Cl)ccc21] | [M + H]+: 368.84<br>¹H NMR (400 MHz, DMSO-d$_6$) δ 6.79 (s, 1H), 7.35-7.50 (m, 6H), 7.64-7.72 (m, 2H), 7.77 (d, J = 7.9 Hz, 1H), 8.04 (t, J = 8.6 Hz, 2H), 8.60 (d, J = 4.7 Hz, 1H). |
| I-124 | 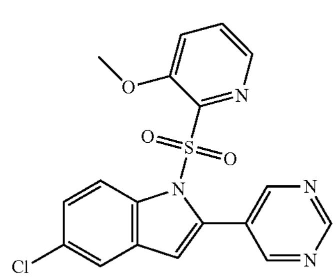 [SMILES: COc1cccnc1S(=O)(=O)n1c(-c2cncnc2)cc2cc(Cl)ccc21] | [M + H]+: 401.2<br>¹H NMR (400 MHz, DMSO-d$_6$) δ 3.77 (s, 3H), 7.08 (s, 1H), 7.39 (dd, J = 8.9, 2.2 Hz, 1H), 7.69 (dd, J = 8.6, 4.4 Hz, 1H), 7.74-7.86 (m, 2H), 7.88 (d, J = 8.9 Hz, 1H), 8.07 (d, J = 4.4 Hz, 1H), 8.86 (s, 2H), 9.21 (s, 1H). |

TABLE 2-continued

| Compound # | Structure | Characterization Data |
| --- | --- | --- |
| I-125 | 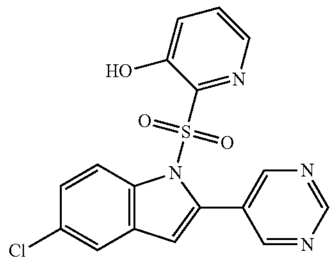 [SMILES: O=S(=O)(c1ncccc1O)n1c(-c2cncnc2)cc2cc(Cl)ccc21] | [M + H]+: 387.2<br>¹H NMR (400 MHz, Methanol-d₄) δ 6.87 (s, 1H), 7.23-7.33 (m, 2H), 7.43 (dd, J = 8.5, 4.4 Hz, 1H), 7.63 (d, J = 2.2 Hz, 1H), 7.92-8.01 (m, 2H), 8.91 (s, 2H), 9.16 (s, 1H). |
| I-126 | 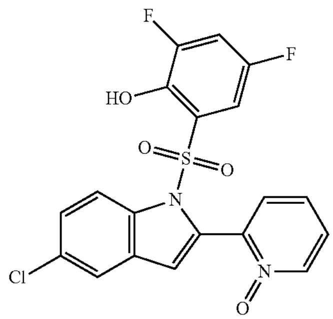 [SMILES: O=S(=O)(c1cc(F)cc(F)c1O)n1c(-c2cccc[n+]2[O-])cc2cc(Cl)ccc21] | [M + H]+: 437.2<br>¹H NMR (400 MHz, Chloroform-d) δ 6.87 (s, 1H), 7.20 (ddd, J = 10.3, 7.7, 3.1 Hz, 1H), 7.32 (d, J = 2.0 Hz, 2H), 7.55-7.70 (m, 2H), 7.66-7.76 (m, 3H), 8.48 (d, J = 6.3 Hz, 1H). |
| I-127 | 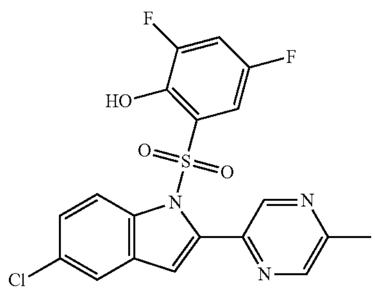 [SMILES: Cc1cnc(-c2cc3cc(Cl)ccc3n2S(=O)(=O)c2cc(F)cc(F)c2O)cn1] | [M − H]−: 434.3<br>¹H NMR (400 MHz, DMSO-d₆) δ 2.58 (s, 3H), 7.12 (s, 1H), 7.35 (d, J = 7.9 Hz, 1H), 7.43 (dd, J = 9.0, 2.3 Hz, 1H), 7.70 (s, 1H), 7.79 (d, J = 2.2 Hz, 1H), 7.97 (d, J = 9.0 Hz, 1H), 8.48 (s, 1H), 8.78 (s, 1H), 11.52 (brs, 1H). |
| I-135 | 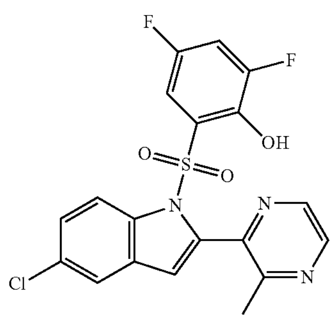 [SMILES: Cc1nccnc1-c1cc2cc(Cl)ccc2n1S(=O)(=O)c1cc(F)cc(F)c1O] | [M − H]−: 434.4<br>¹H NMR (400 MHz, Chloroform-d) δ 2.83 (s, 3H), 7.00 (m, 1H), 7.30 (m, 1H), 7.45 (dq, J = 4.4, 2.5 Hz, 2H), 7.80 (d, J = 9.5 Hz, 1H), 8.17 (s, 1H), 8.51 (d, J = 2.7 Hz, 1H), 8.69 (d, J = 2.6 Hz, 1H), 12.25 (brs, 1H). |
| I-137 | 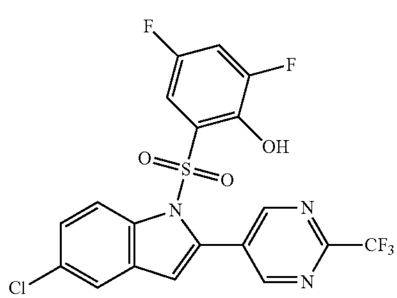 [SMILES: O=S(=O)(c1cc(F)cc(F)c1O)n1c(-c2cnc(C(F)(F)F)nc2)cc2cc(Cl)ccc21] | [M − H]−: 488.4<br>¹H NMR (400 MHz, DMSO-d₆) δ 7.18 (s, 1H), 7.43 (d, J = 8.9 Hz, 1H), 7.53 (d, J = 7.7 Hz, 1H), 7.67 (s, 1H), 7.81-7.93 (m, 2H), 9.24 (s, 2H), 11.52 (brs, 1H). |

TABLE 2-continued
| Compound # | Structure | Characterization Data |
|---|---|---|
| I-138 | 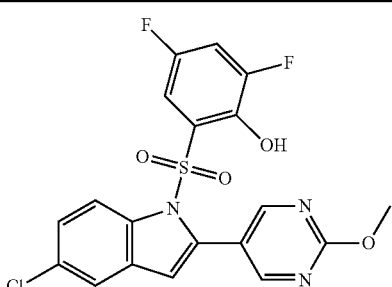 | [M + H]+: 452.5<br>¹H NMR (400 MHz, DMSO-d₆) δ 4.00 (s, 3H), 6.93 (s, 1H), 7.30 (s, 1H), 7.35-7.42 (m, 1H), 7.68 (s, 1H), 7.76 (d, J = 2.2 Hz, 1H), 7.89 (d, J = 8.8 Hz, 1H), 8.63 (s, 2H), 11.46 (brs, 1H). |
| I-139 | 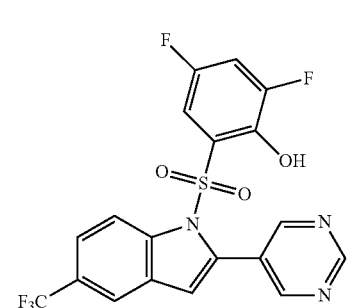 | [M − H]−: 452.5<br>¹H NMR (400 MHz, DMSO-d₆) δ 7.16 (s, 1H), 7.35 (s, 1H), 7.72 (d, J = 9.5 Hz, 1H), 8.08 (s, 1H), 8.14 (s, 1H), 8.90 (s, 2H), 9.25 (s, 1H), 11.58 (brs, 1H). |
| I-140 | 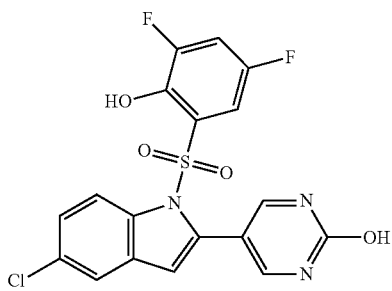 [SMILES: O=S(=O)(c1cc(F)cc(F)c1O)n1c(-c2cnc(O)nc2)cc2cc(Cl)ccc21] | [M + H]+: 438.5;<br>¹H NMR (400 MHz, DMSO-d₆) δ 12.3 (br s, 1H), 11.4 (s 1H), 8.4 (m, 1H), 8.0 (m, 2H), 7.7 (m, 2H), 6.8 (s, 1H), |
| I-142 | 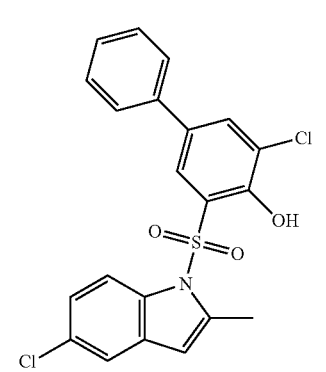 [SMILES: Cc1cc2cc(Cl)ccc2n1S(=O)(=O)c1cc(-c2ccccc2)cc(Cl)c1O] | ¹H NMR (400 MHz, DMSO-d₆) δ 2.59 (s, 3H), 6.56 (s, 1H), 7.24 (d, J = 9.1 Hz, 1H), 7.44 (d, J = 7.3 Hz, 1H), 7.52 (t, J = 7.6 Hz, 2H), 7.60 (s, 1H), 7.72 (d, J = 7.6 Hz, 2H), 7.82 (d, J = 8.8 Hz, 1H), 8.07 (s, 1H), 8.12 (s, 1H), 11.42 (brs, 1H). |
| I-144 | 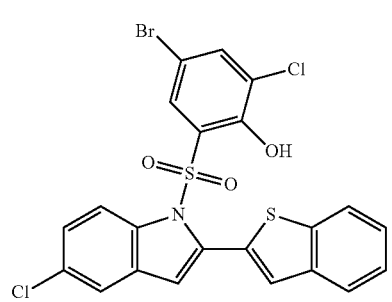 [SMILES: O=S(=O)(c1cc(Br)cc(Cl)c1O)n1c(-c2cc3ccccc3s2)cc2cc(Cl)ccc21] | [M − H]−: 550<br>¹H NMR (400 MHz, DMSO-d₆) δ 3.83 (s, 3H), 6.79 (s, 1H), 7.02 (s, 1H), 7.36 (s, 1H), 7.67 (d, J = 9.4 Hz, 1H), 7.74 (d, J = 8.1 Hz, 2H), 8.13-8.24 (m, 2H), 11.36 (brs, 1H). |

TABLE 2-continued

| Compound # | Structure | Characterization Data |
|---|---|---|
| I-146 | 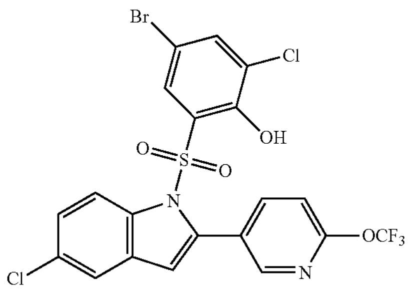 [SMILES: O=S(=O)(c1cc(Br)cc(Cl)c1O)n1c(-c2ccc(OC(F)(F)F)nc2)cc2cc(Cl)ccc21] | [M + H]+: 581.99<br>$^1$H NMR (400 MHz, DMSO-d$_6$) $^1$H NMR (400 MHz, DMSO-d$_6$) δ 6.94 (s, 1H), 7.33-7.46 (m, 2H), 7.50 (d, J = 2.5 Hz, 1H), 7.77 (d, J = 2.2 Hz, 1H), 7.89-7.99 (m, 2H), 8.08 (dd, J = 8.5, 2.5 Hz, 1H), 8.32 (d, J = 2.5 Hz, 1H), 11.51 (brs, 1H). |
| I-147 | 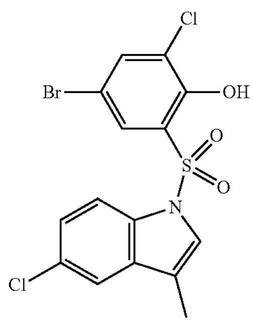 [SMILES: Cc1cn(S(=O)(=O)c2cc(Br)cc(Cl)c2O)c2ccc(Cl)cc12] | [M + H]+: 434.2<br>$^1$H NMR (400 MHz, DMSO-d$_6$) δ 2.22 (s, 3H), 7.33 (dd, J = 8.8, 2.2 Hz, 1H), 7.53 (s, 1H), 7.59 (s, 1H), 7.64-7.75 (m, 1H), 7.98-8.07 (m, 2H), 11.63 (brs, 1H). |
| I-148 | 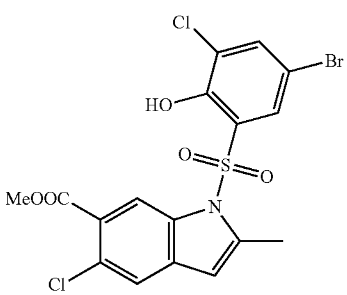 [SMILES: COC(=O)c1cc2c(cc1Cl)cc(C)n2S(=O)(=O)c1cc(Br)cc(Cl)c1O] | [M + H]+: 492.2<br>$^1$H NMR (400 MHz, DMSO-d$_6$) δ 2.55 (s, 3H), 3.89 (s, 3H), 6.62 (s, 1H), 7.75 (s, 1H), 8.02 (s, 2H), 8.32 (s, 1H), 11.86 (brs, 1H). |
| I-149 | 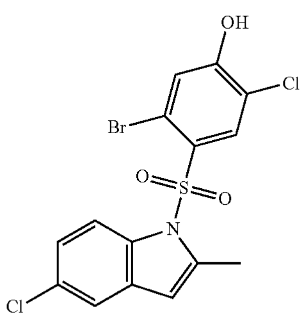 [SMILES: Cc1cc2cc(Cl)ccc2n1S(=O)(=O)c1cc(Cl)c(O)cc1Br] | [M + H]+: 434.2<br>$^1$H NMR (400 MHz, DMSO-d$_6$) δ 2.45 (s, 3H), 6.60 (s, 1H), 7.22-7.30 (m, 2H), 7.63 (d, J = 2.3 Hz, 1H), 7.72 (d, J = 8.9 Hz, 1H), 8.01 (s, 1H), 12.27 (brs, 1H). |
| I-150 | 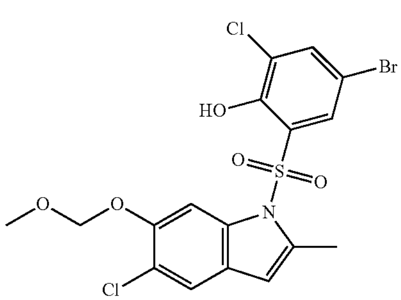 [SMILES: COCOc1cc2c(cc1Cl)cc(C)n2S(=O)(=O)c1cc(Br)cc(Cl)c1O] | [M + H]+: 494.26<br>$^1$H NMR (400 MHz, DMSO-d6) δ 2.46 (s, 3H), 6.37 (s, 1H), 7.44 (d, J = 11.0 Hz, 2H), 7.91 (d, J = 2.5 Hz, 1H), 8.02 (d, J = 2.5 Hz, 1H), 10.16 (brs, 1H), 11.60 (brs, 1H). |

TABLE 2-continued

| Compound # | Structure | Characterization Data |
|---|---|---|
| I-151 | 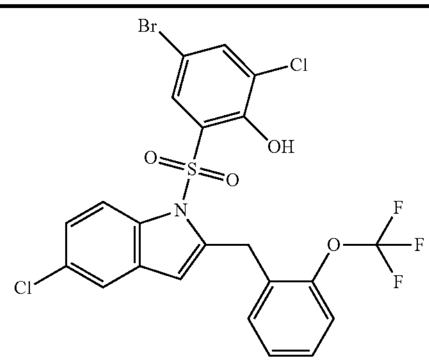 | [M + H]+: 594.14<br>¹H NMR (400 MHz, DMSO-d6) δ 4.39 (s, 2H), 6.20 (s, 1H), 7.23 (d, J = 7.7 Hz, 1H), 7.31 (td, J = 9.0, 8.6, 4.5 Hz, 2H), 7.41 (d, J = 7.9 Hz, 2H), 7.62 (d, J = 2.2 Hz, 1H), 7.86 (d, J = 8.9 Hz, 1H), 7.93 (s, 2H), 11.75 (brs, 1H). |
| I-152 | 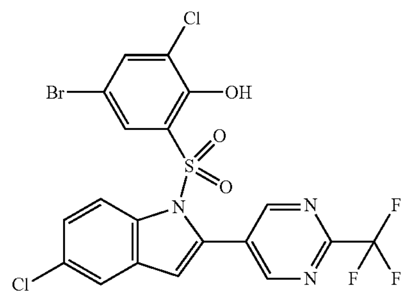 [SMILES: O=S(=O)(c1cc(Br)cc(Cl)c1O)n1c(-c2cnc(C(F)(F)F)nc2)cc2cc(Cl)ccc21] | [M + H]+: 566.12<br>¹H NMR (400 MHz, DMSO-d$_6$) δ 7.15 (s, 1H), 7.43 (d, J = 9.0 Hz, 1H), 7.82 (s, 2H), 7.86 (d, J = 8.9 Hz, 1H), 7.96 (s, 2H), 9.24 (s, 2H), 11.43 (brs, 1H). |
| I-153 | 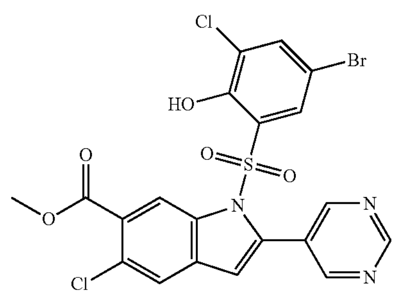 | MS(ES): m/z 542.3 [M − H]⁻.<br>LCMS purity: 96.18%, 1H NMR (400 MHz, DMSO-d6) δ 7.08 (s, 1H), 7.46 (s, 1H), 7.90 (s, 1H), 7.97 (s, 1H), 8.38 (s, 1H), 8.84 (s, 2H), 9.26 (s, 1H), 13.43 (brs, 2H) |
| I-154 | 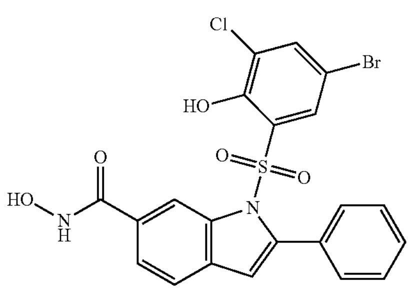 [SMILES: O=C(NO)c1ccc2cc(-c3ccccc3)n(S(=O)(=O)c3cc(Br)cc(Cl)c3O)c2c1] | MS(ES): m/z 521.1 [M − H]⁺.<br>LCMS purity: 100%, 1H NMR (400 MHz, DMSO-d6) δ 6.77 (s, 1H), 7.06 (s, 1H), 7.21 (d, J = 7.5 Hz, 2H), 7.32 (t, J = 7.5 Hz, 2H), 7.42 (t, J = 7.4 Hz, 1H), 7.65 (s, 2H), 7.83 (s, 1H), 8.51 (s, 1H), 9.05 (brs, 1H), 11.28 (brs, 2H) |
| I-155 | 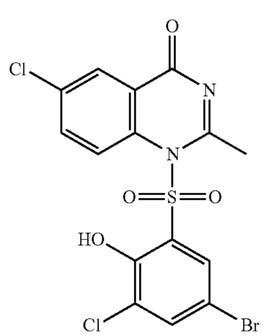 [SMILES: Cc1nc(=O)c2cc(Cl)ccc2n1S(=O)(=O)c1cc(Br)cc(Cl)c1O] | MS(ES): m/z 465.2 [M + H]⁺.<br>LCMS purity: 98.55%, 1H NMR (400 MHz, Methanol-d4) δ 2.55 (s, 3H), 7.82-7.92 (m, 3H), 8.07 (d, J = 2.4 Hz, 1H), 8.51 (d, J = 2.4 Hz, 1H). |

TABLE 2-continued

| Compound # | Structure | Characterization Data |
|---|---|---|
| I-156 | 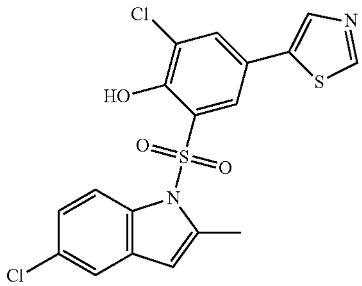 [SMILES: Cc1cc2cc(Cl)ccc2n1S(=O)(=O)c1cc(-c2cncs2)cc(Cl)c1O] | MS (ES): m/z 437.2 [M − H]−. LCMS purity: 95.7%, 1H NMR (400 MHz, DMSO-d6) δ 2.60 (s, 3H), 6.48 (s, 1H), 7.19 (d, J = 8.9 Hz, 1H), 7.56 (s, 1H), 7.76 (d, J = 8.8 Hz, 1H), 7.97 (s, 2H), 8.29 (s, 1H), 9.06 (s, 1H) |
| I-157 | 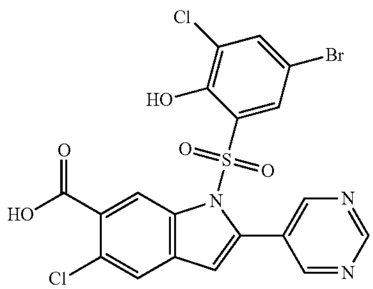 [SMILES: O=C(O)c1cc2c(cc1Cl)cc(-c1cncnc1)n2S(=O)(=O)c1cc(Br)cc(Cl)c1O] | MS(ES): m/z 542.3 [M + H]+. LCMS purity: 96.18%, 1H NMR (400 MHz, DMSO-d6) δ 7.08 (s, 1H), 7.46 (s, 1H), 7.90 (s, 1H), 7.97 (s, 1H), 8.38 (s, 1H), 8.84 (s, 2H), 9.26 (s, 1H), 13.43 (brs, 2H) |
| I-158 | 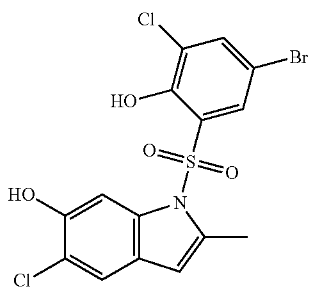 [SMILES: Cc1cc2cc(Cl)c(O)cc2n1S(=O)(=O)c1cc(Br)cc(Cl)c1O] | MS (ES): m/z 449.8 [M + H]+, LCMS purity: 98.58%, $^1$H NMR (400 MHz, DMSO-d6) δ 2.46 (s, 3H), 6.37 (s, 1H), 7.44 (d, J = 11.0 Hz, 2H), 7.91 (d, J = 2.5 Hz, 1H), 8.02 (d, J = 2.5 Hz, 1H), 10.16 (brs, 1H), 11.60 (brs, 1H). |
| I-159 | 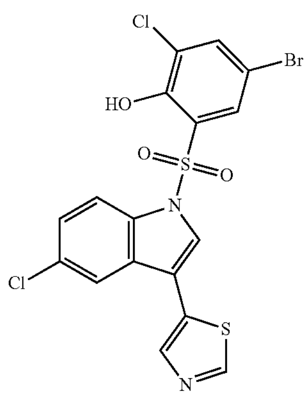 [SMILES: O=S(=O)(c1cc(Br)cc(Cl)c1O)n1cc(-c2cncs2)c2cc(Cl)ccc21] | MS (ES): m/z 504.97 [M + H]+, LCMS purity: 100%, $^1$H NMR (400 MHz, DMSO-d$_6$) 7.40 (d, J = 8.4 Hz, 1H), 7.84 (d, J = 8.8 Hz, 1H), 7.92 (s, 1H), 7.96 (s, 1H), 8.1 (s, 1H), 8.26 (s, 1H), 8.44 (s, 1H), 9.19 (s, 1H) |
| I-160 | 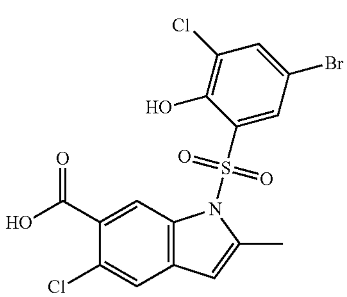 [SMILES: Cc1cc2cc(Cl)c(C(=O)O)cc2n1S(=O)(=O)c1cc(Br)cc(Cl)c1O] | MS(ES): m/z 478.8 [M − H]−. $^1$H NMR (400 MHz, DMSO-d$_6$) δ 2.5 (s, 3H), 6.62 (s, 1H), 7.75 (s, 1H), 8.02 (s, 2H), 8.32 (s, 1H), 11.86 (brs, 1H), 13.23 (brs, 1H) |

TABLE 2-continued

| Compound # | Structure | Characterization Data |
|---|---|---|
| I-161 | 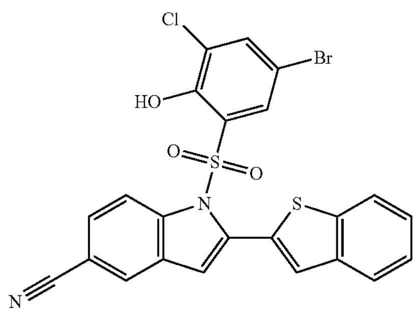 [SMILES: N#Cc1ccc2c(c1)cc(-c1cc3ccccc3s1)n2S(=O)(=O)c1cc(Br)cc(Cl)c1O] | (ES, m/z): [M − H]⁻ = 540.9: (400 MHz, Methanol-d₄) δ 8.44 (d, J = 8.8 Hz, 1H), 8.05 (d, J = 1.7 Hz, 1H), 7.87 -7.79 (m, 2H), 7.74-7.66 (m, 1H), 7.55 (d, J = 2.5 Hz, 1H), 7.43-7.37 (m, 3H), 7.15 (d, J = 2.5 Hz, 1H), 6.93 (s, 1H). |
| I-162 | 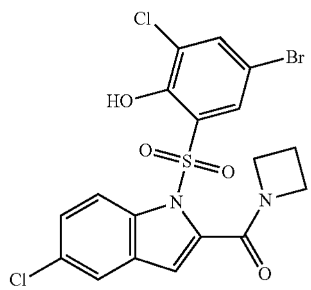 [SMILES: O=C(c1cc2cc(Cl)ccc2n1S(=O)(=O)c1cc(Br)cc(Cl)c1O)N1CCC1] | MS (ES): m/z 503.23 [M − H]⁺ LC-MS purity 100%, ¹H NMR (400 MHz, DMSO-d₆) 2.32 (t, J = 7.2 Hz, 2H), 4.08 (s, 2H), 4.50 (s, 2H), 7.39 (d, J = 8.8 Hz, 2H), 7.25 (d, J = 8.8 Hz, 1H), 7.94 (d, J = 24 Hz, 1H), 8.12 (d, J = 10 Hz, 2H), 11.1 (brs, 1H). |
| I-163 | 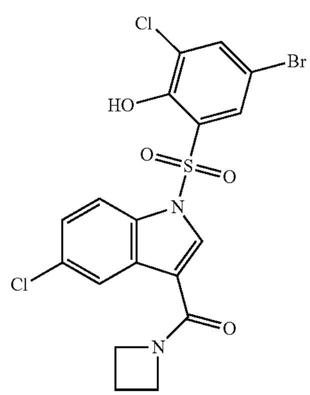 [SMILES: O=C(c1cn(S(=O)(=O)c2cc(Br)cc(Cl)c2O)c2ccc(Cl)cc12)N1CCC1] | MS (ES): m/z 503.23 [M − H]⁺, ¹H NMR (400 MHz, DMSO-d₆) 2.32 (t, J = 7.2 Hz, 2H), 4.08 (s, 2H), 4.50 (s, 2H), 7.39 (d, J = 8.8 Hz, 2H), 7.25 (d, J = 8.8 Hz, 1H), 7.94 (d, J = 24 Hz, 1H), 8.12 (d, J = 10 Hz, 2H), 11.1 (brs, 1H). |
| I-164 | 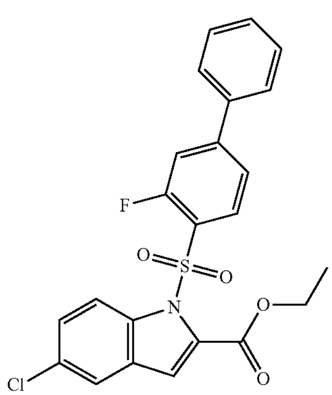 [SMILES: CCOC(=O)c1cc2cc(Cl)ccc2n1S(=O)(=O)c1ccc(-c2ccccc2)cc1F] | [M + H]⁺ = 458.0 ¹H NMR: (300 MHz, DMSO-d₆): δ 8.08 (t, J = 8.0 Hz, 2H), 7.89 (d, J = 2.4 Hz, 1H), 7.91-7.76 (m, 4H), 7.64-7.51 (m, 2H), 7.52 (s, 3H), 4.29 (m, 2H), 1.26 (t, J = 7.1 Hz, 3H). |

TABLE 2-continued
| Compound # | Structure | Characterization Data |
|---|---|---|
| I-165 | 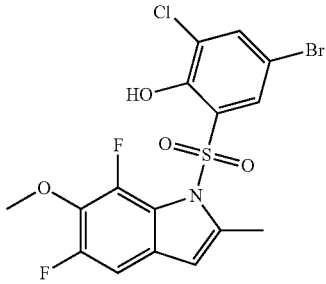 [SMILES: COc1c(F)cc2cc(C)n(S(=O)(=O)c3cc(Br)cc(Cl)c3O)c2c1F] | [M − H]−: 463.9<br>¹H NMR (400 MHz, methano-d₄) δ 2.77 (s, 3H) 3.83 (s, 3H), 6.26 (s, 1H), 6.95 (d, 1H), 7.52 (s, 1H), 7.88 (s, 1H) |
| I-6 | 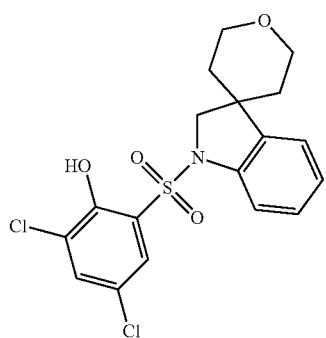 [SMILES: O=S(=O)(c1cc(Cl)cc(Cl)c1O)N1CC2(CCOCC2)c2ccccc21] | [M − H]−: 411.9 |
| I-7 | 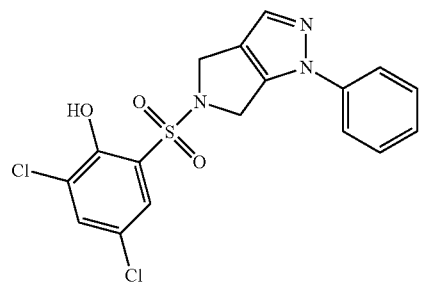 [SMILES: O=S(=O)(c1cc(Cl)cc(Cl)c1O)N1Cc2cnn(-c3ccccc3)c2C1] | [M + H]+: 410 |
| I-8 | 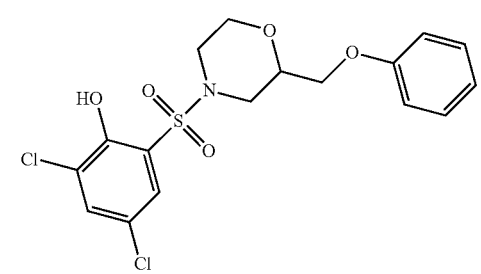 [SMILES: O=S(=O)(c1cc(Cl)cc(Cl)c1O)N1CCOC(COc2ccccc2)C1] | [M + H]+: 417.8 |
| I-9 | 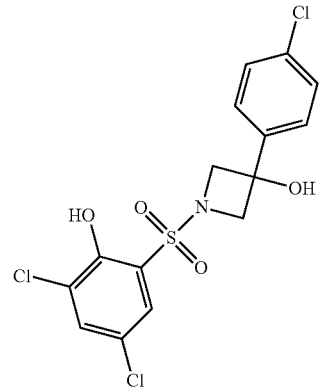 [SMILES: O=S(=O)(c1cc(Cl)cc(Cl)c1O)N1CC(O)(c2ccc(Cl)cc2)C1] | [M + H]+: 410 |

TABLE 2-continued

| Compound # | Structure | Characterization Data |
|---|---|---|
| I-10 | 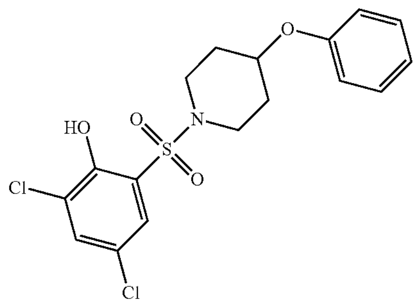 [SMILES: O=S(=O)(c1cc(Cl)cc(Cl)c1O)N1CCC(Oc2ccccc2)CC1] | [M + H]+: 402 |
| I-11 | 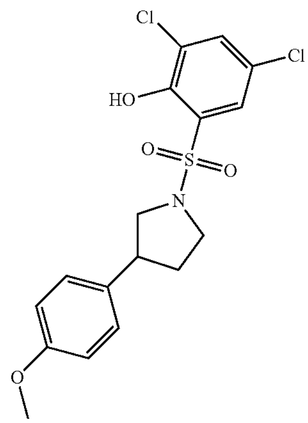 [SMILES: COc1ccc(C2CCN(S(=O)(=O)c3cc(Cl)cc(Cl)c3O)C2)cc1] | [M + H]+: 402 |
| I-12 | 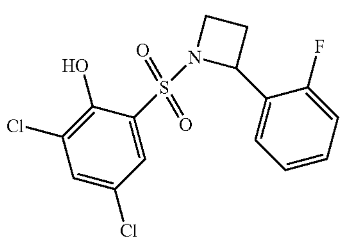 [SMILES: O=S(=O)(c1cc(Cl)cc(Cl)c1O)N1CCC1c1ccccc1F] | [M − H]−: 374 |
| I-13 | 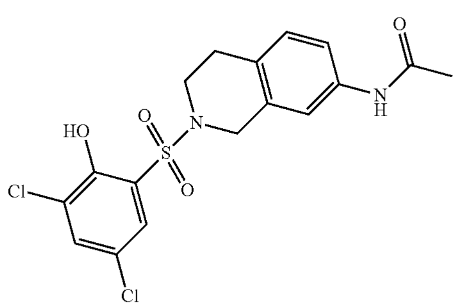 [SMILES: CC(=O)Nc1ccc2c(c1)CN(S(=O)(=O)c1cc(Cl)cc(Cl)c1O)CC2] | [M + H]+: 415 |
| I-14 | 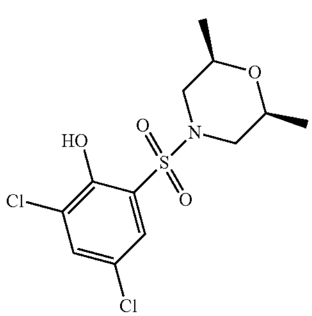 [SMILES: C[C@@H]1CN(S(=O)(=O)c2cc(Cl)cc(Cl)c2O)C[C@H](C)O1] | [M + H]+: 340 |

TABLE 2-continued
| Compound # | Structure | Characterization Data |
|---|---|---|
| I-15 | 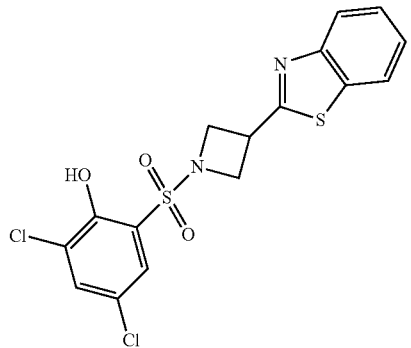 [SMILES: O=S(=O)(c1cc(Cl)cc(Cl)c1O)N1CC(c2nc3ccccc3s2)C1] | [M + H]+: 415 |
| I-16 | 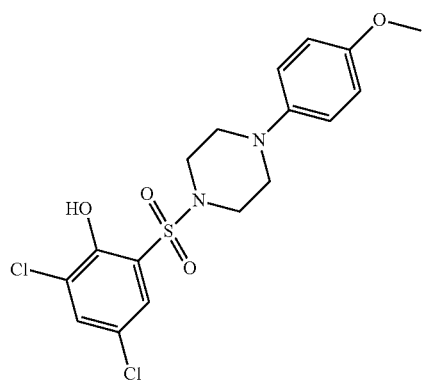 [SMILES: COc1ccc(N2CCN(S(=O)(=O)c3cc(Cl)cc(Cl)c3O)CC2)cc1] | [M + H]+: 417 |
| I-17 | 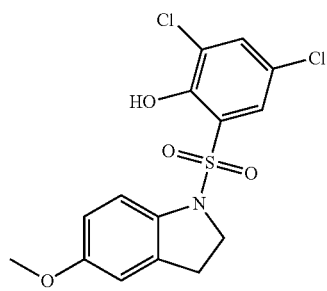 [SMILES: COc1ccc2c(c1)CCN2S(=O)(=O)c1cc(Cl)cc(Cl)c1O] | [M − H]−: 371.9 |
| I-18 | 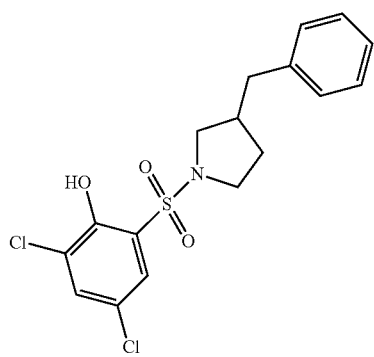 [SMILES: O=S(=O)(c1cc(Cl)cc(Cl)c1O)N1CCC(Cc2ccccc2)C1] | [M + H]+: 386 |

TABLE 2-continued
| Compound # | Structure | Characterization Data |
|---|---|---|
| I-19 | 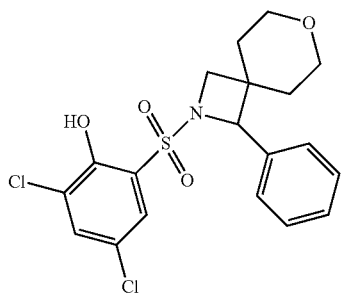 [SMILES: O=S(=O)(c1cc(Cl)cc(Cl)c1O)N1CC2(CCOCC2)C1c1ccccc1] | [M − H]−: 426 |
| I-20 | 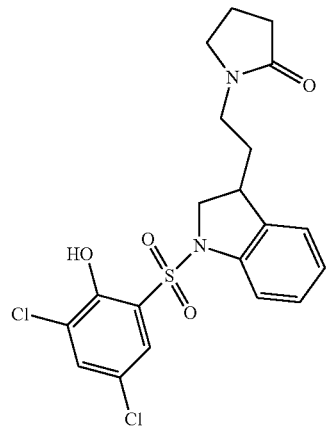 [SMILES: O=C1CCCN1CCC1CN(S(=O)(=O)c2cc(Cl)cc(Cl)c2O)c2ccccc21] | [M − H]−: 428 |
| I-21 | 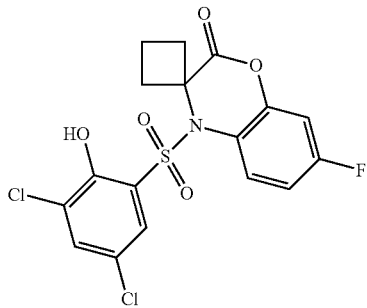 [SMILES: O=C1Oc2cc(F)ccc2N(S(=O)(=O)c2cc(Cl)cc(Cl)c2O)C12CCC2] | [M − H]−: 428 |
| I-22 | 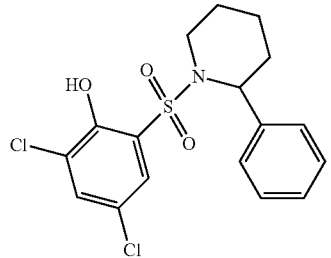 [SMILES: O=S(=O)(c1cc(Cl)cc(Cl)c1O)N1CCCCC1c1ccccc1] | [M − H]−: 384 |

TABLE 2-continued

| Compound # | Structure | Characterization Data |
|---|---|---|
| I-2 | (structure) | [M − H]⁻ 442.0; 1H NMR (400 MHz, DMSO, ppm): δ8.36-8.35 (d, J = 2.0 Hz, 1H), δ7.93-7.92 (d, J = 2.0 Hz, 1H), δ7.46-7.41 (m, 4H), δ7.39-7.33 (m, 1H), δ7.26-7.23 (m, 2H), δ7.17-7.15 (m, 1H), δ7.10-6.97 (m, 1H), δ4.37-4.33 (t, J = 8.4 Hz, 2H), δ3.82 (s, 3H), δ3.13-3.09 (t, J = 8.4 Hz, 2H) |
| I-5 | (structure) | (ES, m/z): [M − H]⁻ 428.0 1H NMR: (300 MHz, DMSO, ppm): δ11.88 (brs, 1H), δ8.25 (s, 1H), δ7.60 (s, 1H), δ7.30-7.42 (m, 5H), δ7.16-7.09 (m, 3H), δ7.49-7.51 (m, 2H), δ3.05-3.10 (m, 2H) |

Example 28. ADP-Glo Assay

Compounds of the present invention were evaluated in an ADP-GLO assay as follows:

a) Dilute cpd 1:3 in succession in DMSO by hand for each cpds for 12 pts b) Add 0.1 μL diluted cpd solution to assay plate, each dose with 2 replicates c) Centrifuge 1000 RPM for 1 min d) Add 5 μL ACL working solution to 384-well assay plate, centrifuge 1000 RPM for 1 min e) Incubate at 25° C. for 15 min f) Add 5 μL substrate working solution to initiate reaction g) Final ACL reaction concentrations: 3 nM ACL, 15 μM ATP, 3 μM CoA, 300 μM Citrate, 0.01% Brij35, 4 mM DTT, 1% DMSO;

h) Reference final conc: 30 uM starting Conc, 3× dilution, 11+0 points. Test cpd conc: 30/100 uM starting Conc, 3× dilution, 11+0 points.

i) Incubate at 25° C. for 60 min j) Add 10 μL ADP Glo reagent, centrifuge 1000 RPM for 1 min k) Incubate at 25° C. for 40 min l) Add 20 μL kinase detection reagent, centrifuge 1000 RPM for 1 min m) Incubate at 25° C. for 40 min n) Read on Envision for US LUM as RLU Results of the ADP-Glo Assay are provided in Table 3 below. Compounds that had an IC$_{50}$ result of <0.50 μM in the assay are labeled "A"; compounds that had an IC$_{50}$ result of ≥0.50 μM and <20.0 μM in the assay are labeled "B; and compounds that had an IC$_{50}$ result of ≥20 μM are labeled "C."

TABLE 3

ADP-Glo Assay results.

| Compound Number | ACL-ADP-Glo (IC50) [μM] |
|---|---|
| I-1 | B |
| I-2 | B |
| I-3 | B |
| I-4 | B |
| I-5 | B |
| I-6 | B |
| I-7 | B |
| I-8 | B |
| I-9 | B |
| I-10 | B |
| I-11 | B |
| I-12 | B |
| I-13 | B |
| I-14 | B |
| I-15 | B |
| I-16 | B |
| I-17 | B |
| I-18 | B |
| I-19 | B |
| I-20 | B |
| I-21 | B |
| I-22 | B |
| I-23 | B |
| I-24 | A |
| I-25 | B |
| I-26 | B |
| I-27 | B |
| I-28 | B |
| I-29 | B |
| I-30 | B |
| I-31 | B |
| I-32 | B |
| I-33 | B |
| I-34 | A |
| I-35 | B |
| I-36 | B |
| I-37 | B |
| I-38 | B |
| I-39 | B |
| I-40 | B |
| I-41 | B |
| I-42 | B |

TABLE 3-continued

ADP-Glo Assay results.

| Compound Number | ACL-ADP-Glo (IC50) [μM] |
|---|---|
| I-43 | B |
| I-44 | A |
| I-45 | B |
| I-46 | B |
| I-47 | B |
| I-48 | B |
| I-49 | B |
| I-50 | B |
| I-51 | B |
| I-52 | B |
| I-53 | B |
| I-54 | B |
| I-55 | A |
| I-56 | B |
| I-57 | B |
| I-58 | B |
| I-59 | B |
| I-60 | B |
| I-61 | B |
| I-62 | A |
| I-63 | B |
| I-64 | B |
| I-65 | B |
| I-66 | B |
| I-67 | B |
| I-68 | B |
| I-69 | B |
| I-70 | B |
| I-71 | B |
| I-72 | B |
| I-73 | B |
| I-74 | B |
| I-75 | B |
| I-76 | B |
| I-77 | B |
| I-78 | B |
| I-79 | B |
| I-80 | B |
| I-81 | B |
| I-82 | B |
| I-83 | B |
| I-84 | B |
| I-85 | B |
| I-86 | B |
| I-87 | B |
| I-88 | B |
| I-89 | B |
| I-90 | B |
| I-91 | B |
| I-92 | B |
| I-93 | B |
| I-94 | B |
| I-95 | B |
| I-96 | B |
| I-97 | B |
| I-98 | B |
| I-99 | B |
| I-100 | B |
| I-101 | B |
| I-102 | B |
| I-103 | B |
| I-104 | B |
| I-105 | B |
| I-106 | C |
| I-107 | C |
| I-108 | C |
| I-109 | C |
| I-111 | B |
| I-112 | B |
| I-114 | C |
| I-117 | C |
| I-118 | C |
| I-119 | C |
| I-120 | C |
| I-121 | B |
| I-126 | C |
| I-127 | B |
| I-135 | B |
| I-136 | B |
| I-137 | B |
| I-138 | B |
| I-139 | B |
| I-140 | B |
| I-141 | B |
| I-142 | B |
| I-143 | B |
| I-144 | B |
| I-145 | B |
| I-146 | B |
| I-147 | B |
| I-148 | B |
| I-149 | B |
| I-150 | B |
| I-151 | B |
| I-152 | B |
| I-153 | B |
| I-154 | B |
| I-155 | C |
| I-156 | B |
| I-157 | B |
| I-158 | B |
| I-159 | A |
| I-160 | B |
| I-161 | B |
| I-162 | B |
| I-163 | B |
| I-164 | C |
| I-165 | B |

Example 29. ACLY Coupled Assay

TABLE 4

Materials and Instruments

| | Vendor | Cat No. |
|---|---|---|
| Materials | | |
| ACL | XT AL | |
| CoANa2 | Sigma | C3144 |
| Potassium Citrate | Sigma | 89306 |
| ATP | Promega | V915B |
| NADH | Sigma | N8129 |
| MDH from porcine heart | Sigma | M2634 |
| HEPES | Life technolgies | 15630080 |
| MgCl2 | Sigma | M1028 |
| Brij 35 detergent | Merck | 203728 |
| DTT | Sigma | 646563 |
| DMSO | MP | 196055 |
| Corning ® 96 Well Clear Flat Bottom UV-Transparent Microplate | Corning | 3635 |
| 384 dilution plate | Corning | 3657 |
| Top seal A | Perkin Elmer | E5341 |
| 96-well plate | Nunc | 249944 |
| Instrument | | |
| Plate reader | Perkin Elmer | Envision 2104 |
| Centrifuge | Eppendorf | 5810R |

Compounds of the present invention were evaluated in an ACLY Coupled Assay.

The assay protocol for the Coupled Assay (below) was followed:

a) Add 49 μL (ACL+Citrate+CoA Na) to 96 assay plate (final concentration: 8 nM ACL, 60 CoA Na2, 85 μM Citrate)

b) Add 1 μL cpds to 96 assay plate, Test cpd conc: 100/30/10 μM top dose, 3 folds diltion, 10+0+control (control: buffer without ACL+DMSO) points, 1000 rpm for 1 min, incubation at 25° C. for 60 min c) Add 50 μL substrate mixture to 96 assay plate (final conc: 250 μM ATP, 250 μM NADH, 0.1 units MDH), 1000 rpm for 1 min.

d) Read OD 340 nm value on Envision 2104, 1 min/point for 30 min.

Results of the Coupled Assay are provided in Table 5 below. All compounds listed had an $IC_{50}$ result of ≤3 μM

TABLE 5

ACLY Coupled Assay Results.
Compound Number

I-1
I-4
I-23
I-24
I-25
I-26
I-27
I-28
I-30
I-31
I-32
I-33
I-34
I-35
I-36
I-37
I-39
I-40
I-41
I-42
I-43
I-44
I-45
I-46
I-47
I-48
I-51
I-54
I-59
I-60
I-61
I-62
I-63
I-65
I-81
I-90
I-91
I-142
I-143
I-144
I-146
I-147
I-148
I-150
I-151
I-152
I-154
I-156
I-159
I-161
I-163

Example 30. ACLY HepG2 $^{14}$C-Pyruvate Incorporation Assay with Serum

TABLE 6

Materials and Instruments

| | Vendor | Cat No. |
|---|---|---|
| Materials | | |
| HepG2 cell | ATCC | HB-8065 ™ |
| DMEM(without pyruvate, 25 mM Glucose) | Invitrogen | 11965-092 |
| DMEM(without pyruvate, no Glucose) | Invitrogen | 11966-025 |
| FBS | Biowest | S1820-500 |
| TrypLE ™ Express | Invitrogen | 12604-01 |
| Pen/Strep | Biosera | L0022 |
| Acetic acid [2-14C] sodium salt | Perkin Elmer | NEC085H001MC |
| DPBS | Invitrogen | 14190-144 |
| NaOH | Sigma | 484024 |
| KOH | Sigma | 484016 |
| Micro Scint-20 | PerkinElmer | 6013621 |
| DMSO | MP | D8371 |
| Petroleum ether | Sigma | 32299 |
| 96- DEEP well plate | Coming | 3960 |
| 96- well plate | Coming | 3610 |
| Instrument | | |
| Plate reader | Perkin Elmer | Microbeta-2450 |
| Centrifuge | Eppendorf | 5810R |

Compounds of the invention were also assayed in an ACLY HepG2 $^{14}$C-pyruvate incorporation assay with serum ($IC_{50}$ Cholesterol) and ($IC_{50}$ Fatty Acid). The protocol of the assay (below) was followed:

1. Cell Culture

HepG2 cells were seed at 5 k cells/well in 96-well cell culture plate in DMEM with 10% FBS (heat inactivated and 25 mM glucose). After 48 hours, the medium was replaced with fresh medium containing 10% FBS (heat inactivated and 25 mM glucose).

2. Adding Compounds

After 18 hours, the medium was replaced with 200 uL of DMEM (5.5 mM glucose without pyruvate) with or without FBS containing compounds (30, 10, 3.33, 1.11, 0.370, 0.123, 0.041 uM). DMSO concentration was 0.5%. The cells were incubated with compounds at 37° C. for 1 hour.

3. Adding 14C-Pyruvate

2 μci of [14C]-pyruvate was added per well and the cell samples were incubated at 37° C., 5% CO2 for 5 hours.

4. Cell Treatment

The medium was removed and placed into a 96-well polypropylene deep well plate. 200 uL of 0.1N NaOH was added to each well at room temperature to dissolve cell monolayer. The remaining cell suspension was pooled with medium in a 96-well polypropylene deep well plate. 68 uL of 50% KOH was added to the plate containing medium and cell suspensions and capped.

5. Saponification

Cells were incubated at 70° C. for 1 hour, and then cooled to room temperature.

6. Cholesterol Extraction 1 mL petroleum ether was added per well to extract non-saponifyable lipids (primarily sterols such as cholesterol), shaken vigorously, and centrifuged at 1000 rpm for 5 minutes. 500 μL of the petroleum ether layer was then transferred to a 96 well plate and 200 ul of $H_2O$ was added, shaken vigorously, and centrifuged at 1000 rpm for 5 minutes. The petroleum ether layer 500 ul was transferred to a new 96-well plate and evaporated to dryness with Speed-Vac overnight. 200 µL of scintillation cocktail was then added and shaken and transferred to a 96 well optiplate and counted using the Microbeta Liquid Scintillation Counter.

7. Acidification 400 ul of the remaining 500 ul petroleum ether layer was removed and discard. 1 mL petroleum ether was added to the well, shaken vigorously, and centrifuged at 1000 rpm for 5 minutes. All 1100 ul of the petroleum ether layer removed and discarded. The aqueous phase was then acidified with 500 uL of concentrated HCl, checking pH of one or two extracts to make sure pH below 1 (critical, check by PH paper).

8. Fatty acids extraction 1 mL of petroleum ether was added per well to extract saponifyable lipids (extracted as fatty acids originating from saponified lipids such as triglycerides and phospholipids), shaken vigorously, centrifuged at 1000 rpm for 5 min, and 500 uL of the petroleum ether layer was then transferred to a new 96-well deep well plate. Repeat petroleum ether extraction step one more time and pool the petroleum ether extracts. Evaporate to dryness with SpeedVac overnight. 200 µL of scintillation cocktail was added and shaken and transferred to a 96 well optiplate and counted using the Microbeta Liquid Scintillation Counter.

Results of the HepG2 Cholesterol Assay are provided in Table 7 below. Compounds which had an $IC_{50}$ result of ≤10 µM in the assay are labeled "A" and compounds which had an $IC_{50}$ result of >10 µM and <30 µM in the assay are labeled "B"

TABLE 7

ACLY HepG2 $^{14}$C-Pyruvate incorporation assay with serum ($IC_{50}$ Cholesterol) results.

| Compound Number | ACLY HepG2 $^{14}$C- Pyruvate Assay with serum IC50 Fatty Acid 96 well ($IC_{50}$) [µM] |
|---|---|
| I-1 | A |
| I-25 | A |
| I-26 | A |
| I-28 | A |
| I-30 | A |
| I-33 | A |
| I-40 | A |
| I-42 | A |
| I-47 | A |
| I-48 | A |
| I-61 | A |
| I-81 | A |

Results of the HepG2 Fatty Acid Assay are provided in Table 8 below. Compounds which had an $IC_{50}$ result of ≤10 µM in the assay are labeled "A" and compounds which had an $IC_{50}$ result of >10 µM and <30 µM in the assay are labeled "B"

TABLE 8

ACLY HepG2 $^{14}$C-Pyruvate incorporation assay with serum ($IC_{50}$ Fatty Acid) results.

| Compound Number | ACLY HepG2 $^{14}$C- Pyruvate Assay with serum IC50 Fatty Acid 96 well ($IC_{50}$) [µM] |
|---|---|
| I-1 | A |
| I-25 | A |
| I-26 | A |
| I-28 | A |

TABLE 8-continued

ACLY HepG2 $^{14}$C-Pyruvate incorporation assay with serum ($IC_{50}$ Fatty Acid) results.

| Compound Number | ACLY HepG2 $^{14}$C- Pyruvate Assay with serum IC50 Fatty Acid 96 well ($IC_{50}$) [µM] |
|---|---|
| I-30 | A |
| I-33 | A |
| I-40 | A |
| I-42 | A |
| I-47 | A |
| I-48 | A |
| I-61 | A |
| I-81 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

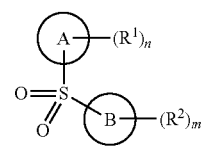

or a pharmaceutically acceptable salt thereof, wherein:

Ring A is

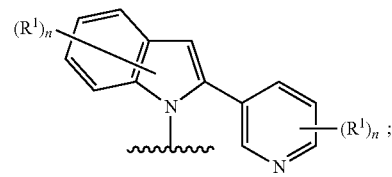

Ring B is a ring selected from phenyl or 5-6 membered heteroaryl having 1-3 heteroatoms independently selected from nitrogen, oxygen, and sulfur;

each $R^1$ is independently hydrogen, —$R^3$, halogen, —CN, —$NO_2$, —OR, —SR, —$NR_2$, —$S(O)_2R$, —$S(O)_2NR_2$, —$S(O)R$, —C(O)R, —C(O)OR, —$C(O)NR_2$, —C(O)N(R)OR, —OC(O)R, —$OC(O)NR_2$, —OPh, —$C(R)_2Ph$, —$C(R)_2OR$, —$C(R)_2C(O)OR$, —$C(R)_2C(O)NR_2$,—$CH_2C(R)_2C(O)OR$, —$CH_2C(R)_2C(O)NR_2$, —$CH_2OPh$, —N(R)C(O)OR, —N(R)C(O)R, —N(R)C(O)NR_2, —N(R)S(O)_2R, or —N(R)S(O)_2NR_2;

or two instances of $R^1$ are optionally taken together to form an oxo;

or $R^1$ at N forms an N-oxide;

each R is independently hydrogen, or an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently —$R^3$, halogen, —$NO_2$, —OR, —$OC(R)_2Ph$, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —$C(R)_2OR$, —$C(R)_2C(O)OR$, —$C(R)_2C(O)NR_2$, —$CH_2C(R)_2C(O)OR$, —$CH_2C(R)_2C(O)NR_2$, —N(R)C(O)OR, —N(R)C(O)R, —$N(R)C(O)NR_2$, —$N(R)S(O)_2R$, or —$N(R)S(O)_2NR_2$;

or two instances of $R^2$ are optionally taken together to form an oxo;

each $R^3$ is independently an optionally substituted group selected from $C_{1-6}$ aliphatic, phenyl, a 3-7 membered saturated or partially unsaturated carbocyclic ring, a 4-7 membered saturated or partially unsaturated heterocyclic ring having 1-2 heteroatoms independently selected from nitrogen, and sulfur, and a 5-6 membered heteroaryl ring having 1-4 heteroatoms independently selected from nitrogen, and sulfur;

each n is 0, 1, 2, 3, or 4; and
each m is 0, 1, 2, 3, or 4.

2. The compound of claim 1, wherein each $R^1$ is independently hydrogen, —$R^3$, halogen, —CN, —$NO_2$, —OR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —OPh, —$C(R)_2Ph$, —$C(R)_2OR$, —$C(R)_2C(O)OR$, —$C(R)_2C(O)NR_2$, —$CH_2C(R)_2C(O)OR$, —$CH_2C(R)_2C(O)NR_2$, —$CH_2OPh$, —N(R)C(O)R, —N(R)C(O)OR, —$N(R)C(O)NR_2$, —$N(R)S(O)_2R$, or —$N(R)S(O)_2NR_2$.

3. The compound of claim 1, wherein each $R^1$ is independently selected from —$CH_3$, -cyclopropyl, —$C(CH_3)_2OH$, —$CH_2CO_2H$, —CN, —F, —Cl, —Br, —I, —$N(H)C(O)CH_3$, —OH, —OMe, -$OCF_3$, —$CO_2H$, —$CO_2CH_3$, —$C(O)NH_2$, —$C(O)N(CH_3)_2$,

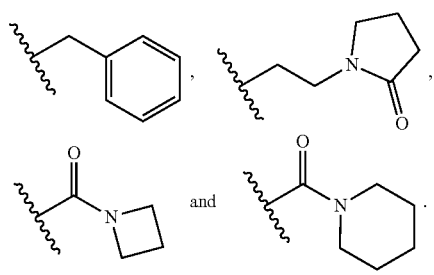

and .

4. The compound of claim 1, wherein each $R^2$ is independently $R^3$, halogen, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —OPh, —$C(R)_2Ph$, —$C(R)_2OR$, —$C(R)_2C(O)OR$, —$C(R)_2C(O)NR_2$, —$CH_2C(R)_2C(O)OR$, —$CH_2C(R)_2C(O)NR_2$, —$CH_2OPh$, —N(R)C(O)R, —N(R)C(O)OR, —$N(R)C(O)NR_2$, —$N(R)S(O)_2R$, or —$N(R)S(O)_2NR_2$.

5. The compound of claim 1, wherein each $R^2$ is independently selected from —$CH_3$, -cyclopropyl, —$C(CH_3)_2OH$, —$CH_2CO_2H$, —F, —Cl, —Br, —I, —N(H)C(O)$CH_3$, —OH, —$OCH_3$, —$OCF_3$, —$CO_2H$, —$CO_2CH_3$, —C(O)OEt, —$C(O)NH_2$, —$C(O)N(CH_3)_2$, -Ph,

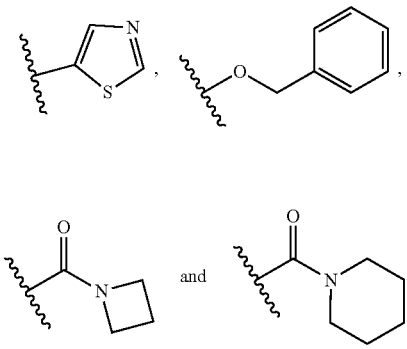

6. The compound of claim 5, wherein each $R^2$ is independently selected from —C(O)OEt, -Ph, and

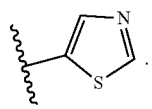

7. A compound selected from:

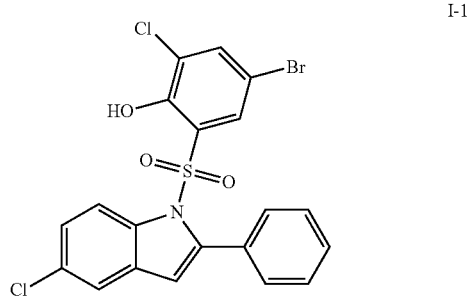

I-1

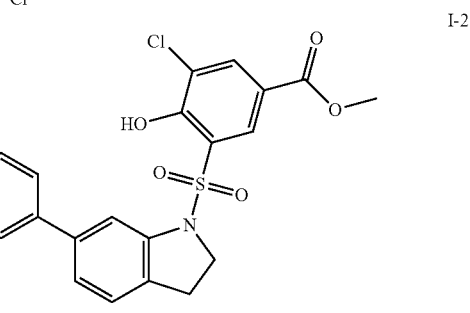

I-2

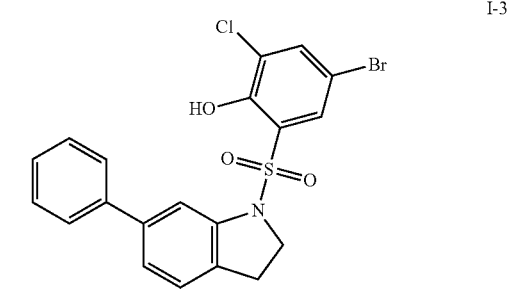

I-3

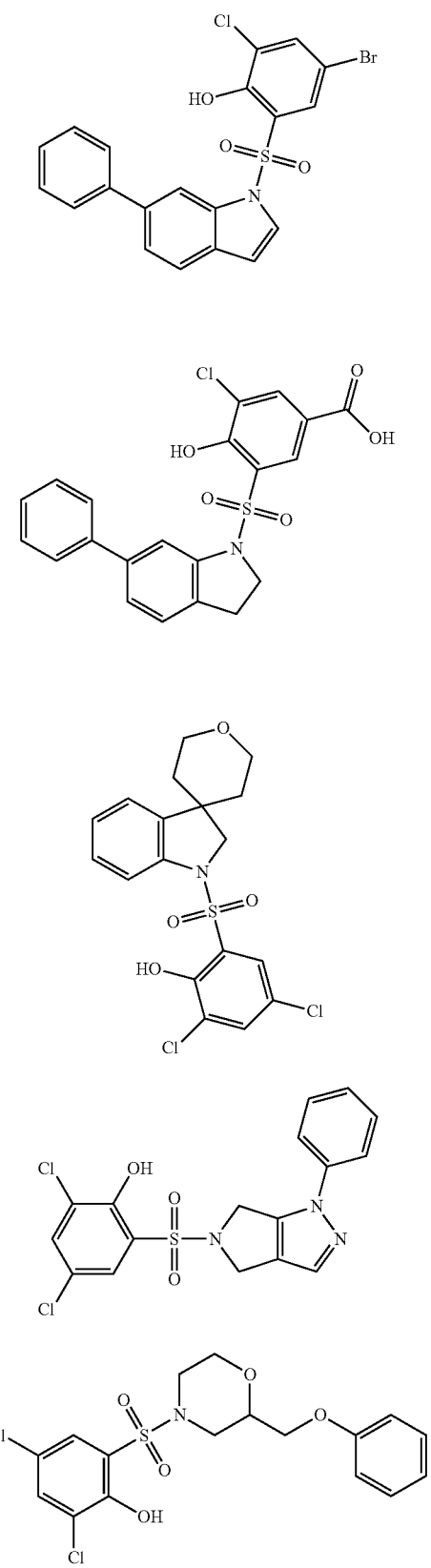

-continued
I-16
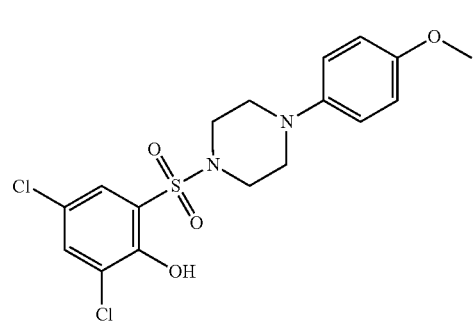
I-17
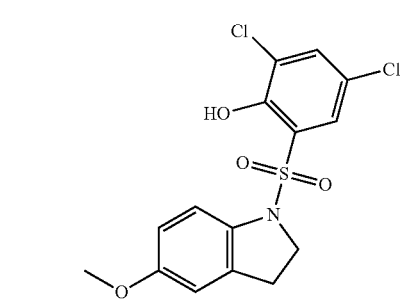
I-18
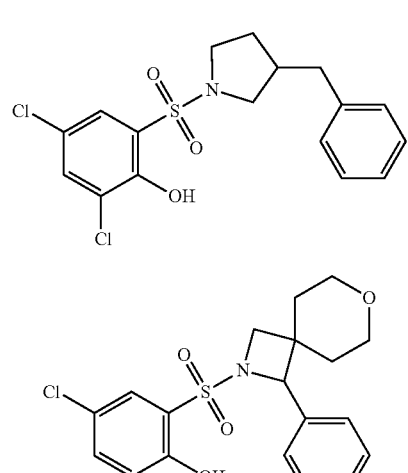
I-19
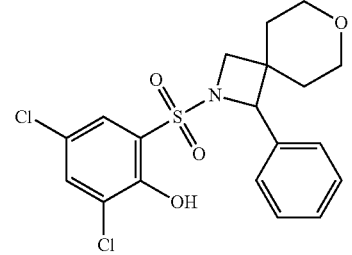
I-20
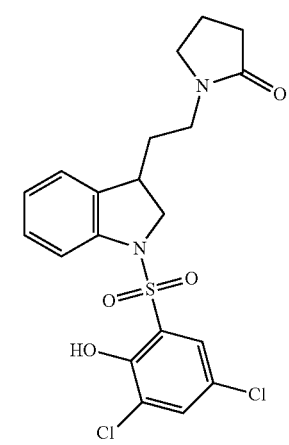
-continued
I-21
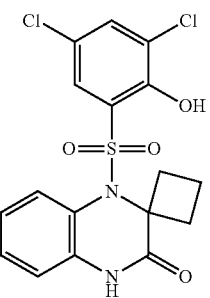
I-22
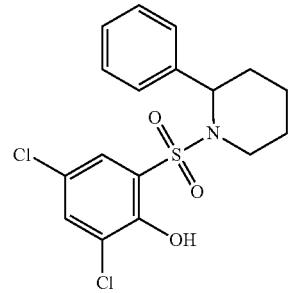
I-23
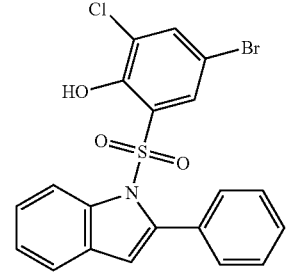
I-24
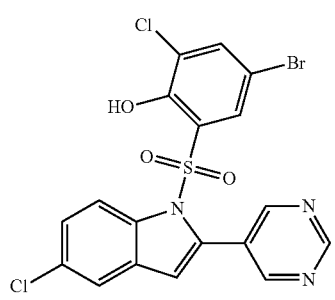
I-25
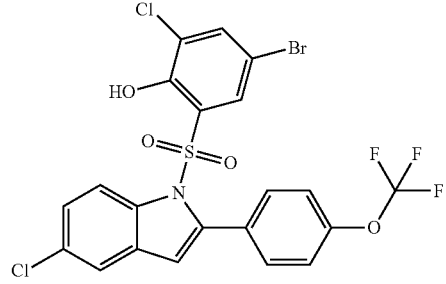

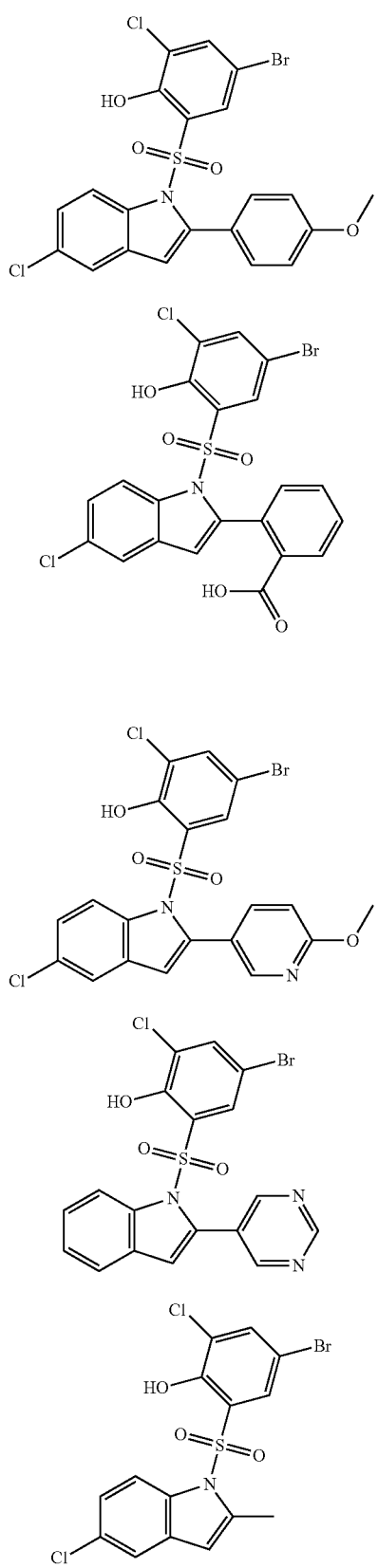
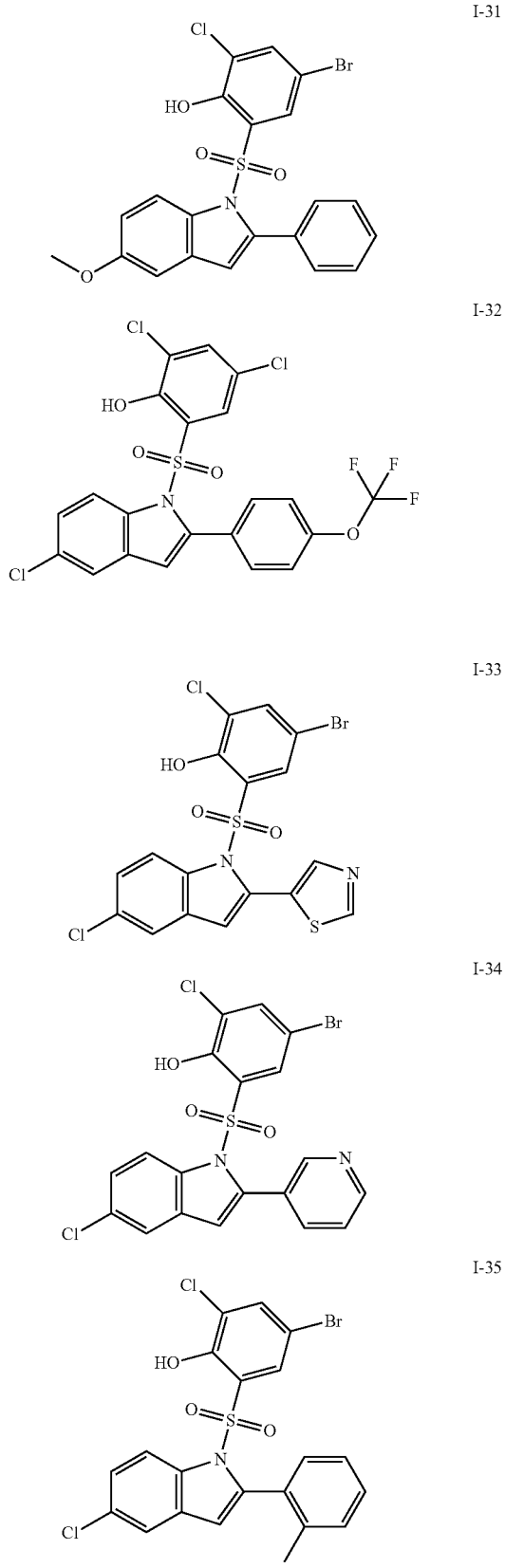

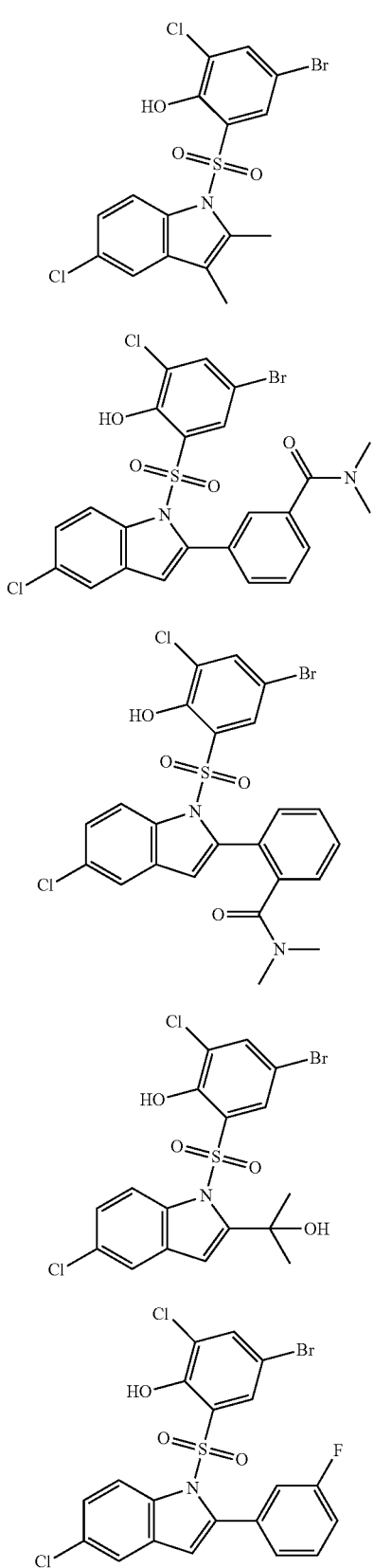
I-36
I-37
I-38
I-39
I-40
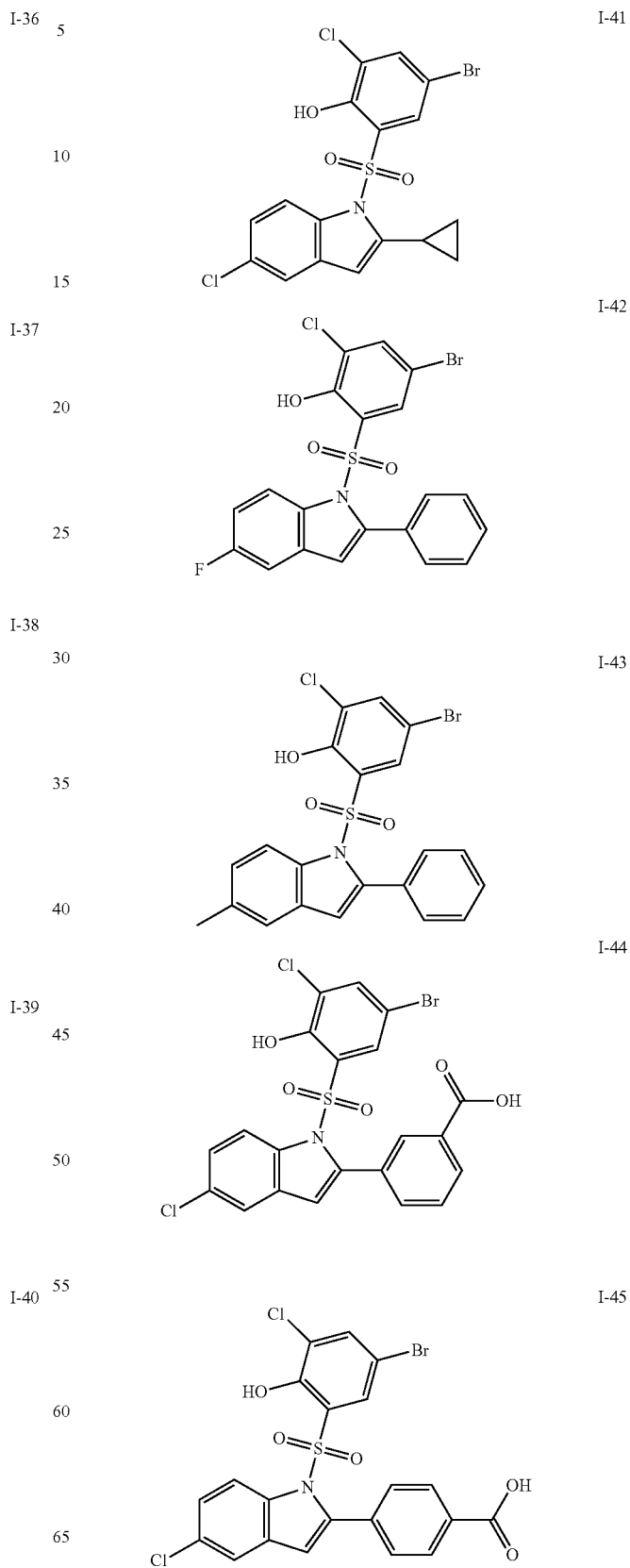
I-41
I-42
I-43
I-44
I-45

I-46
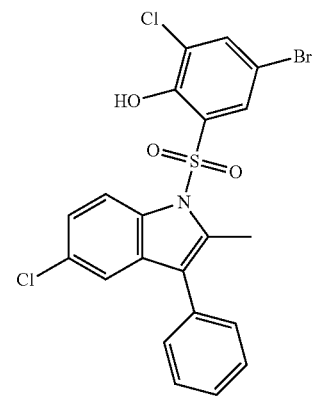
I-47
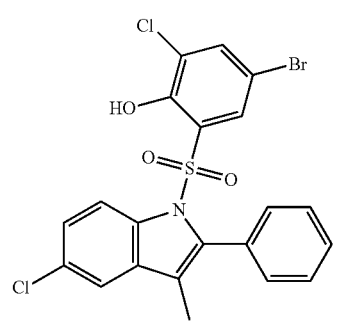
I-48
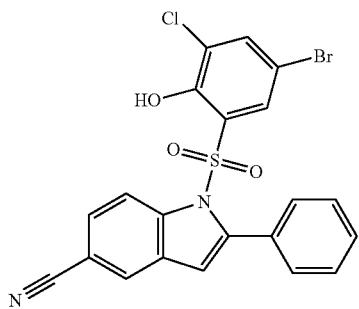
I-49
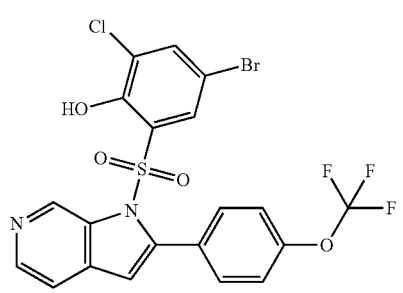
I-50
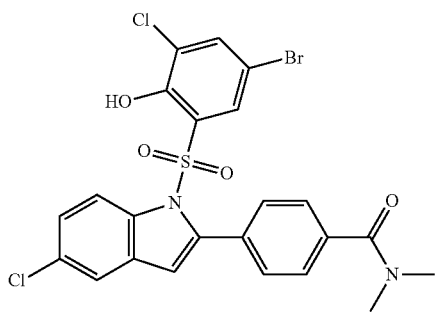
I-51
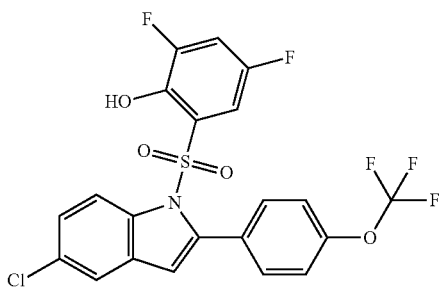
I-52
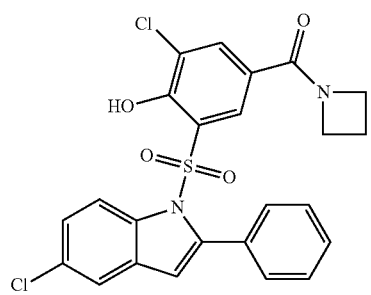
I-53
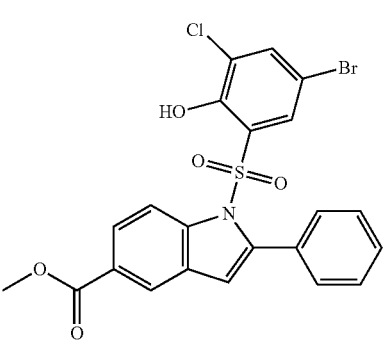
I-54
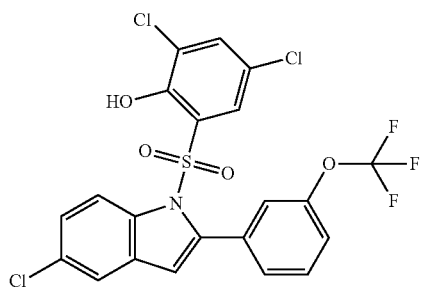
I-55
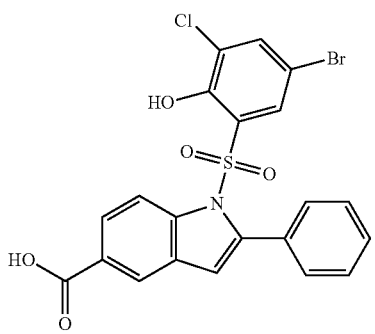

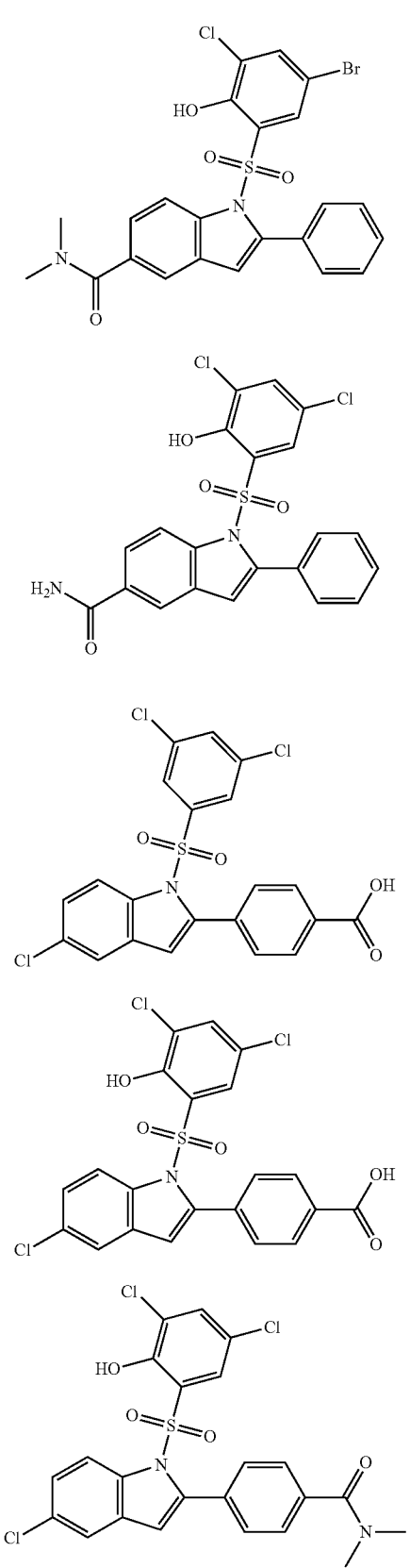
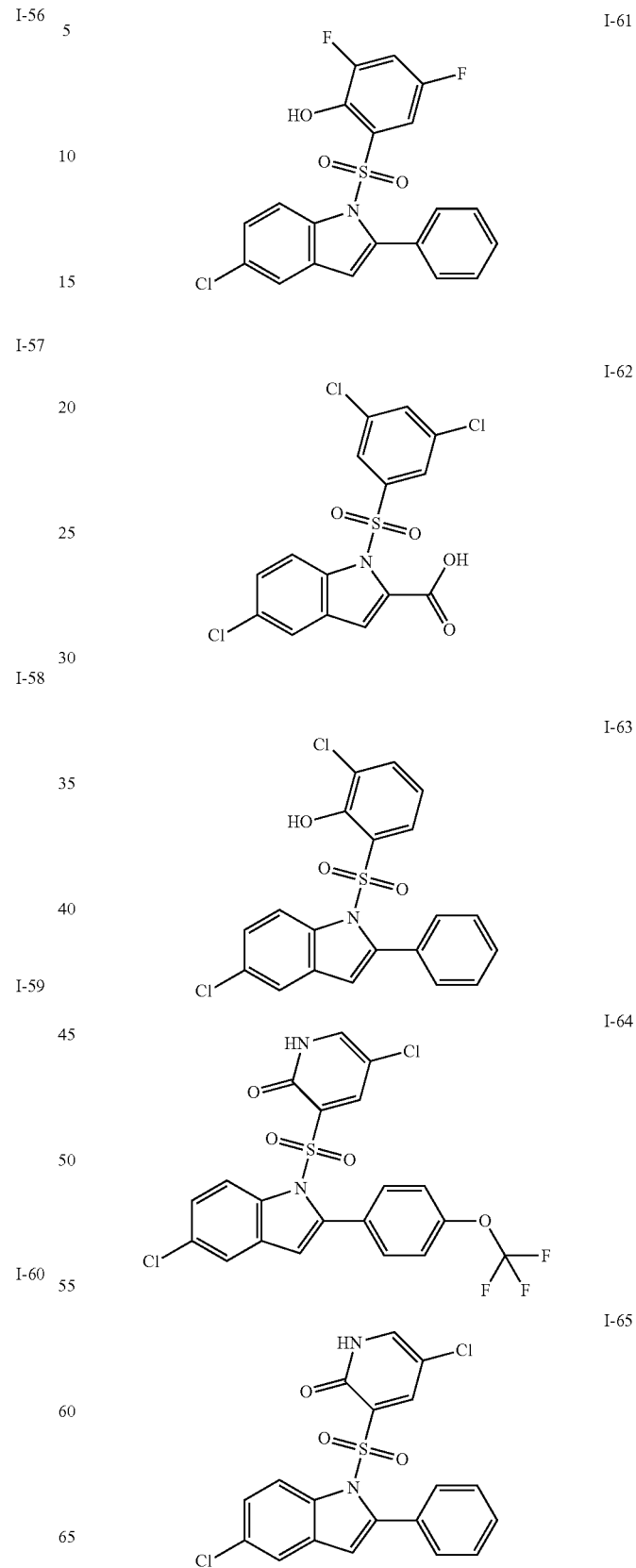

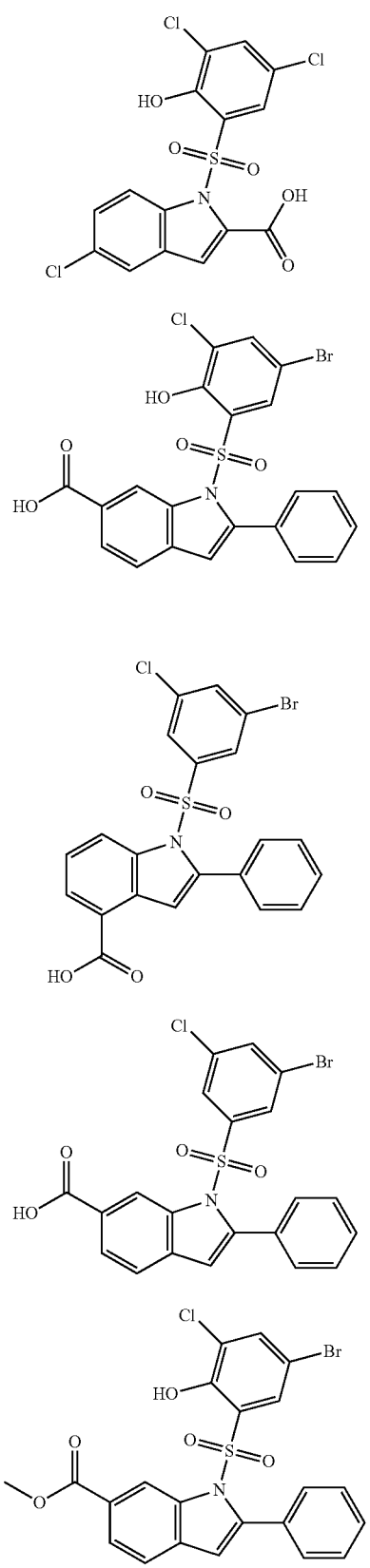
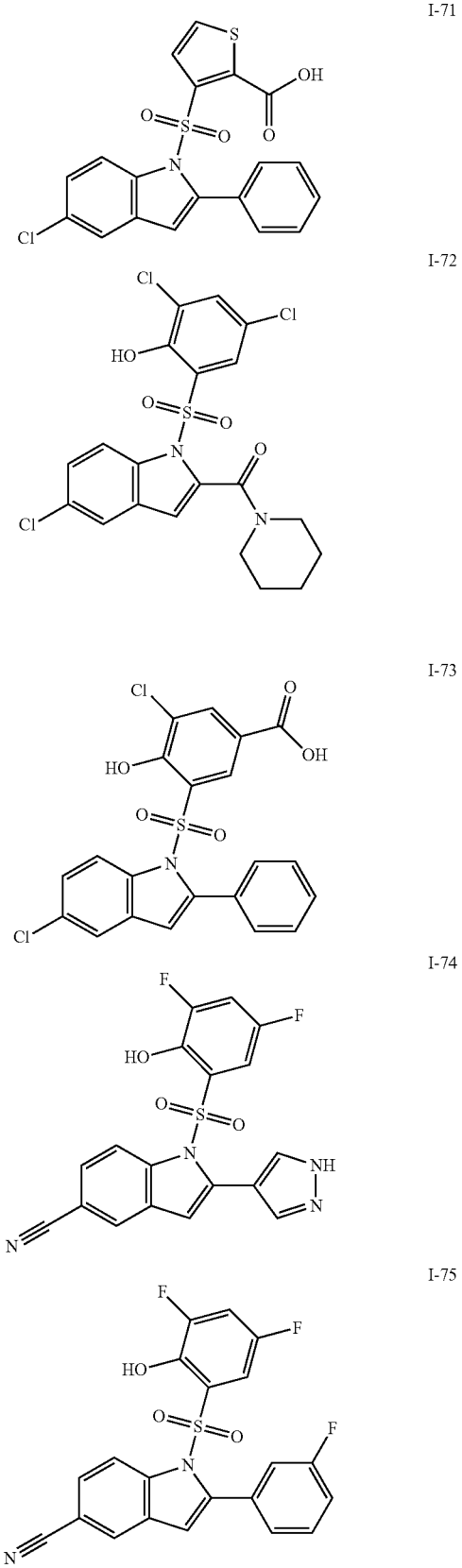

233
-continued
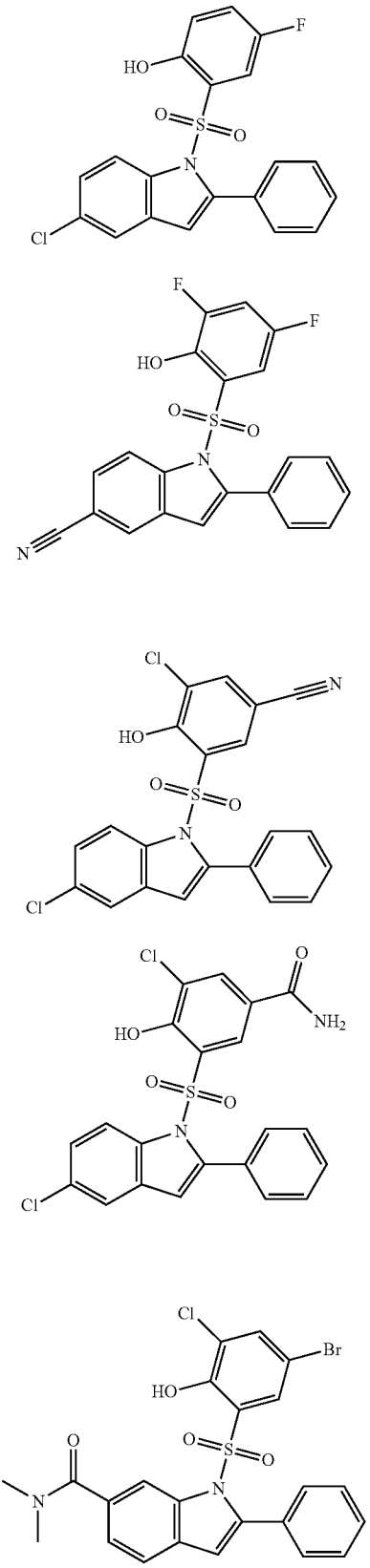
I-76
I-77
I-78
I-79
I-80
234
-continued
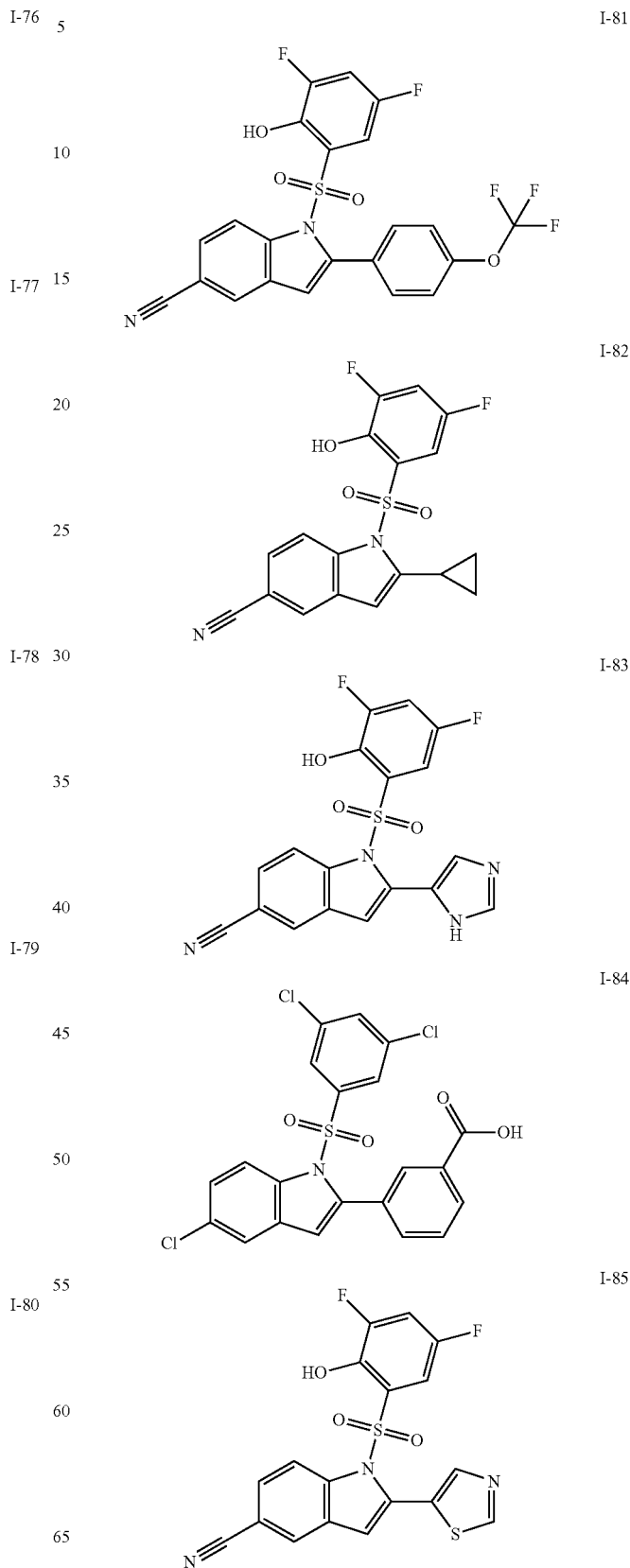
I-81
I-82
I-83
I-84
I-85

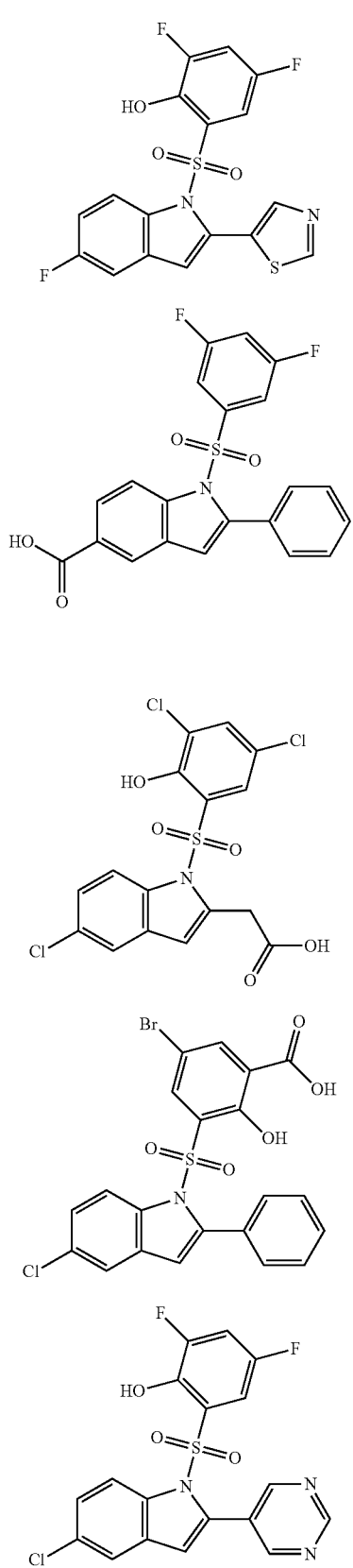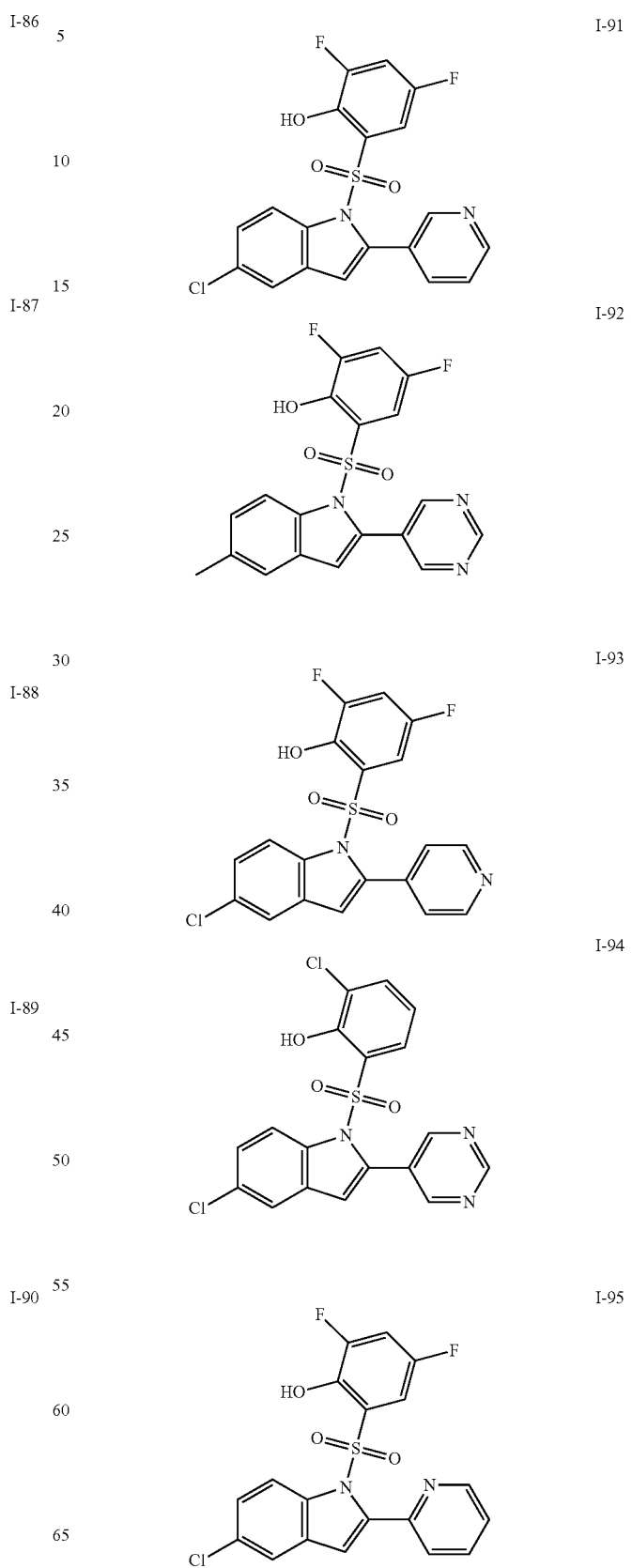

I-96
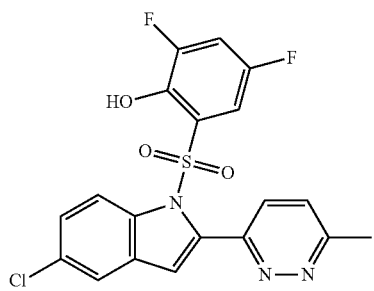
I-97
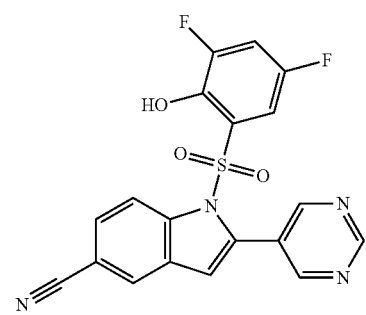
I-98
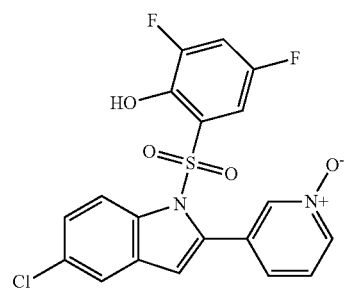
I-99
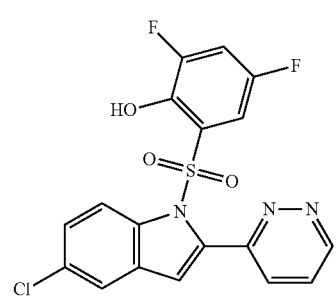
I-100
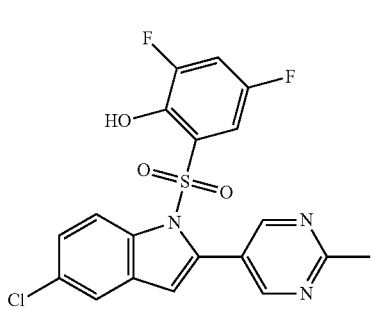
I-101
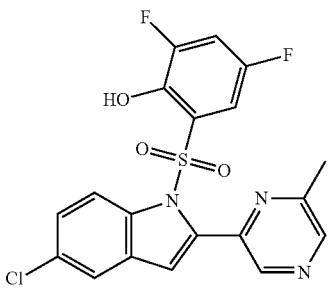
I-102
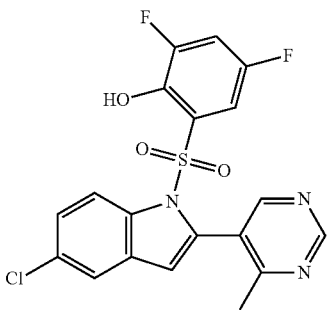
I-103
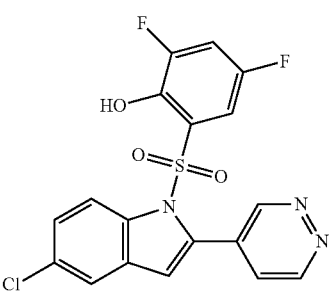
I-104
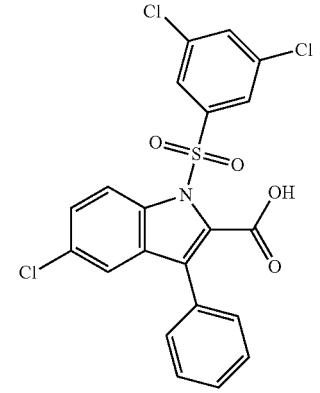
I-105
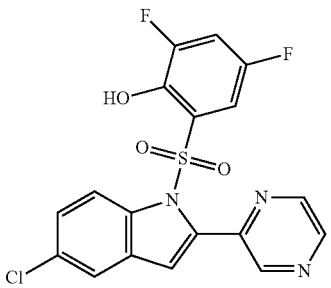

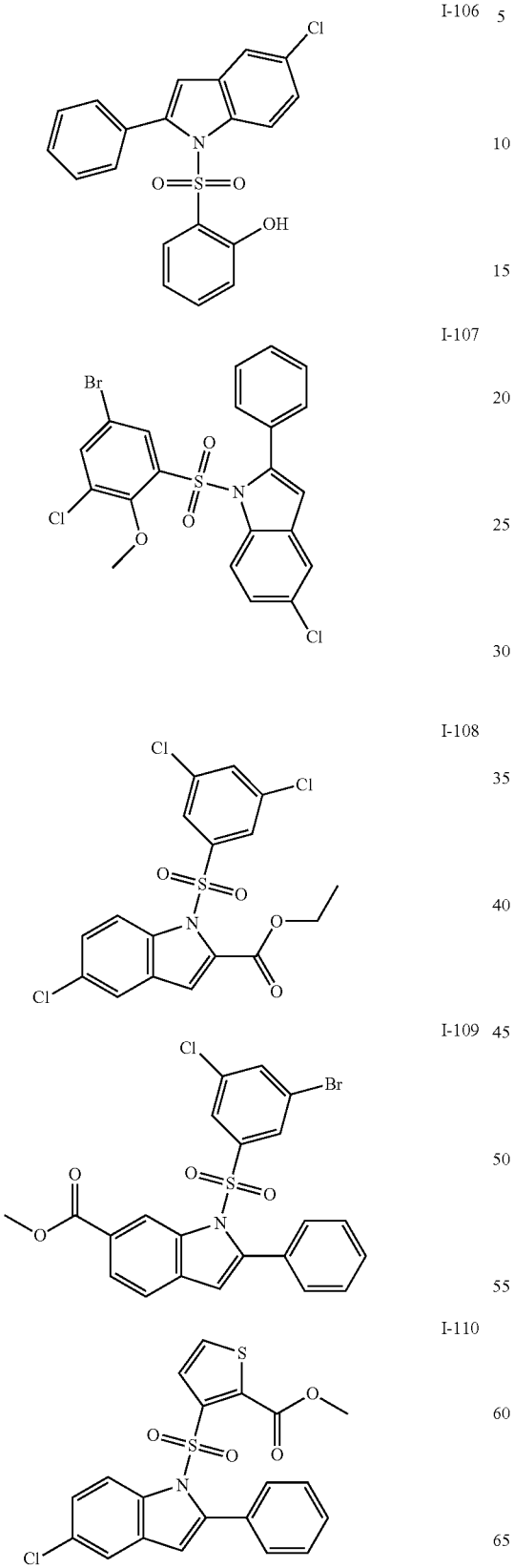

I-116
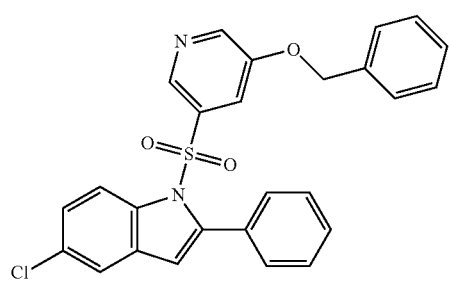
I-117
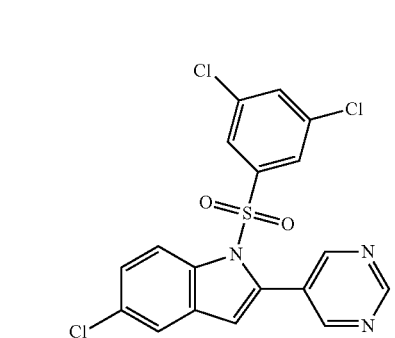
I-118
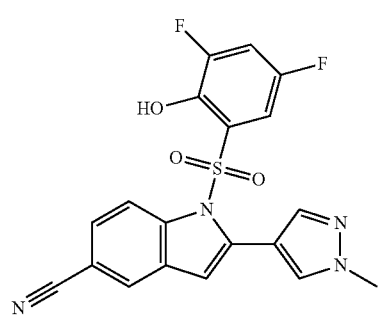
I-119
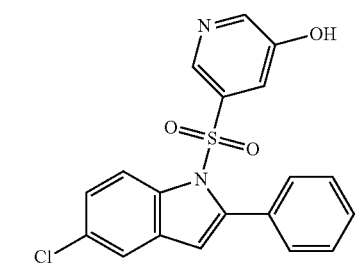
I-120
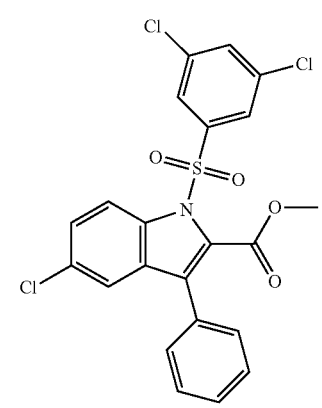
I-121
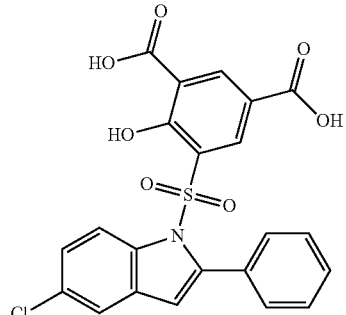
I-122
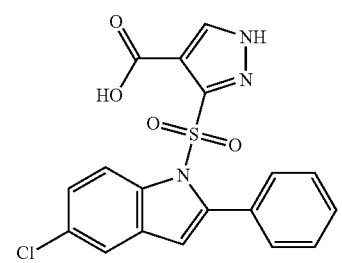
I-123
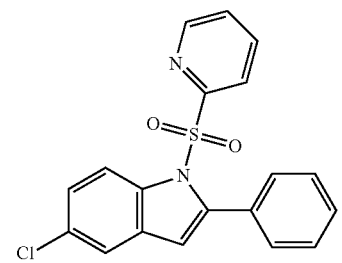
I-124
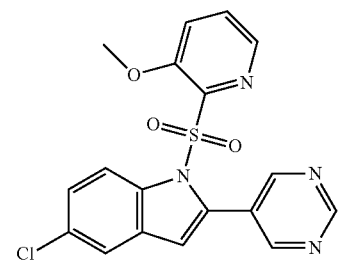
I-125
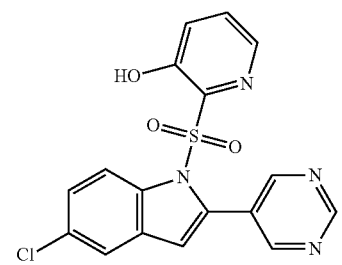

I-126 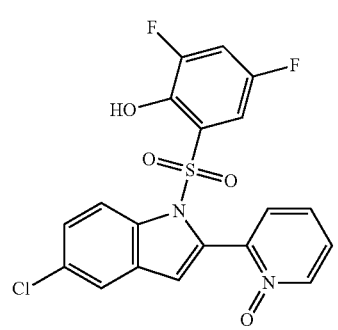
I-127 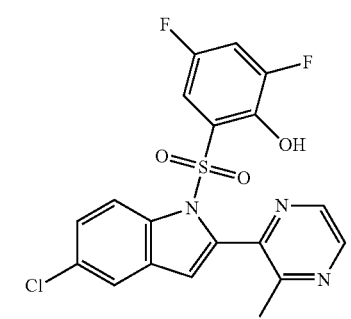
I-135 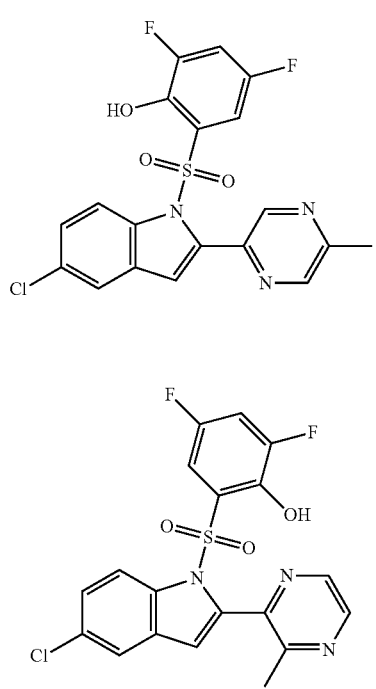
I-136 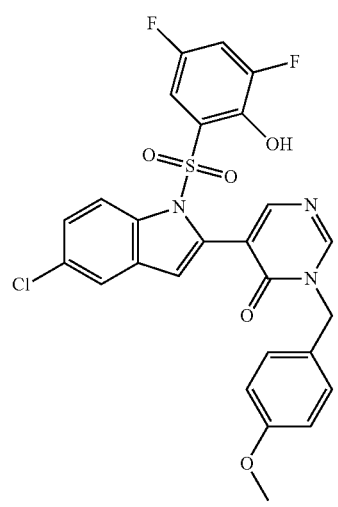
I-137 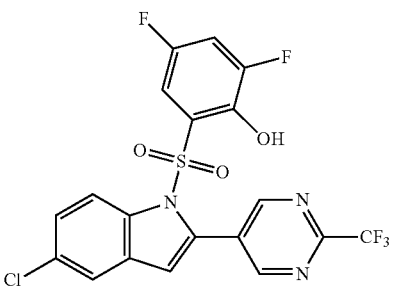
I-138 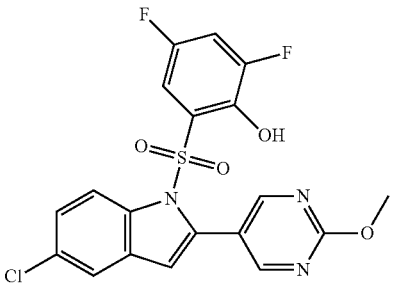
I-139 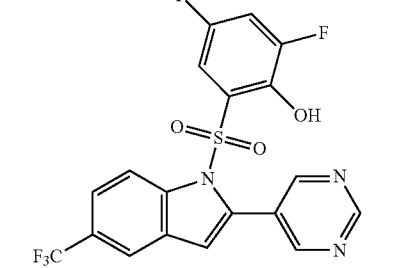
I-140 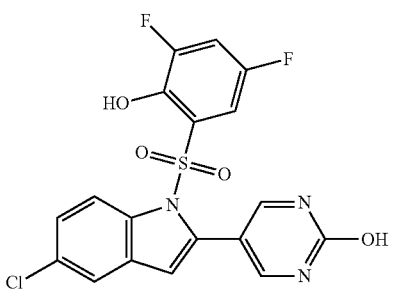
I-141 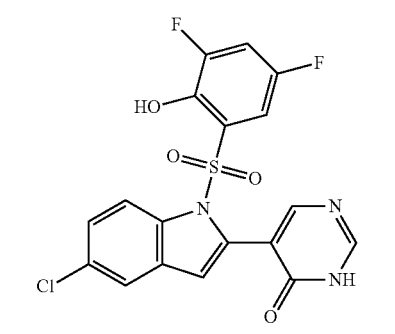

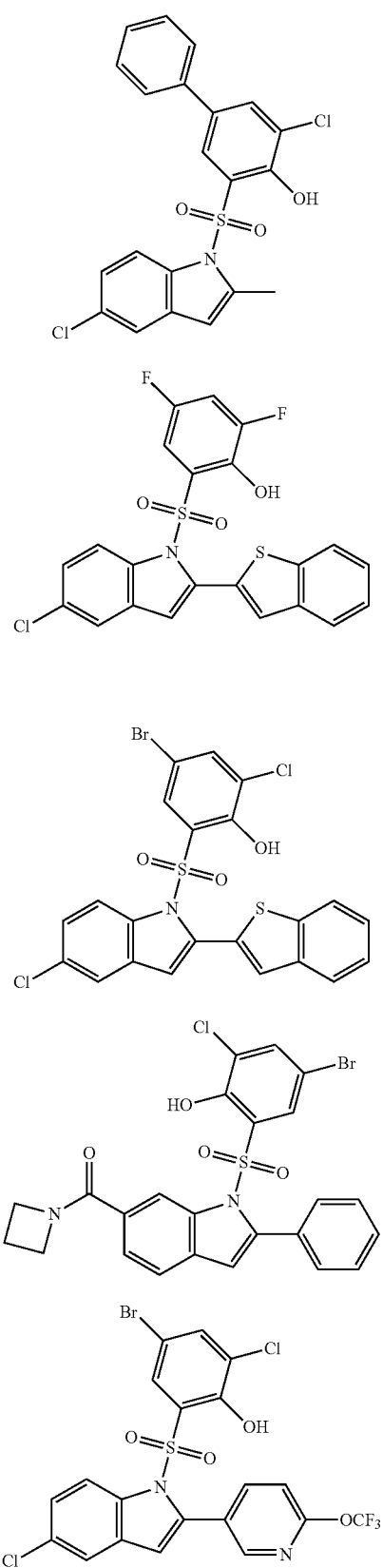
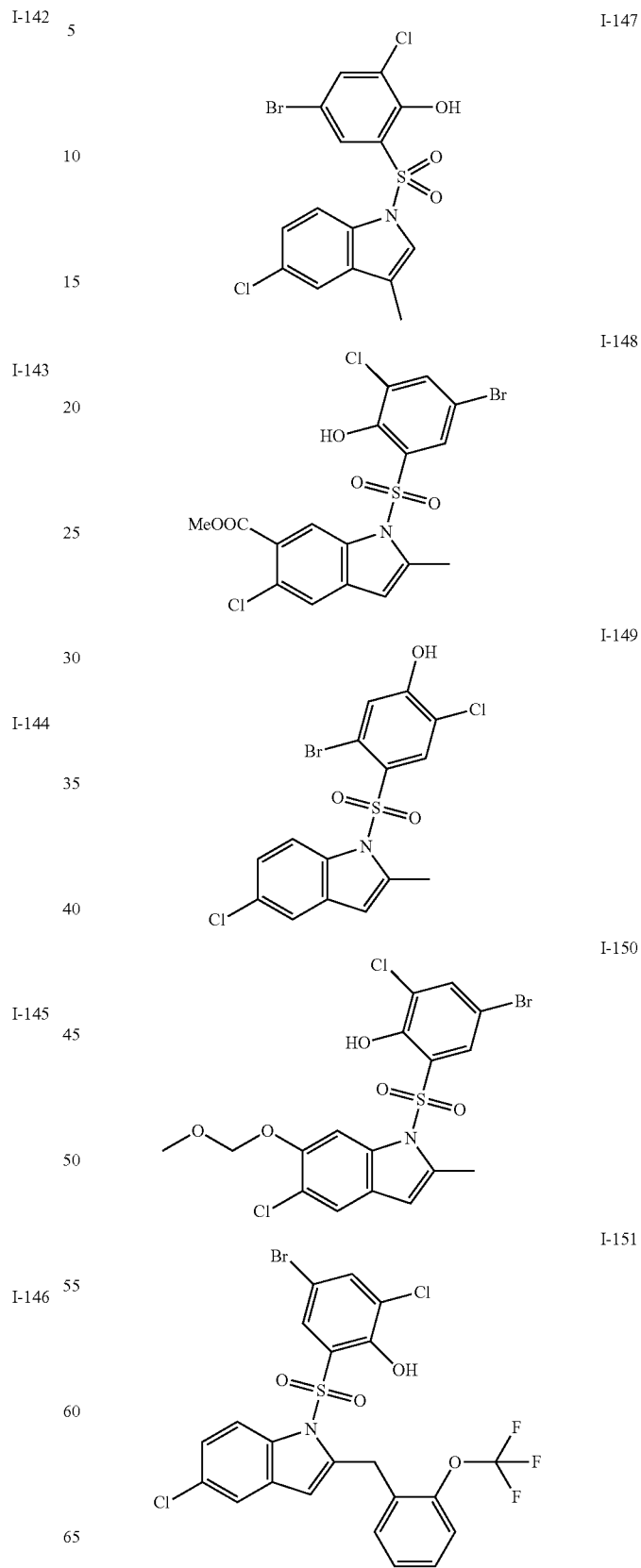

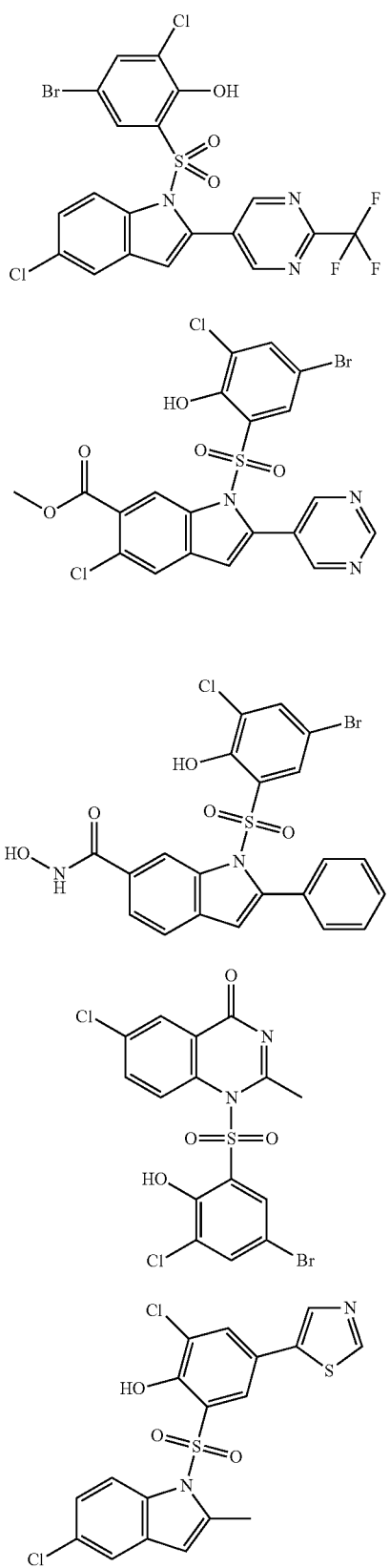
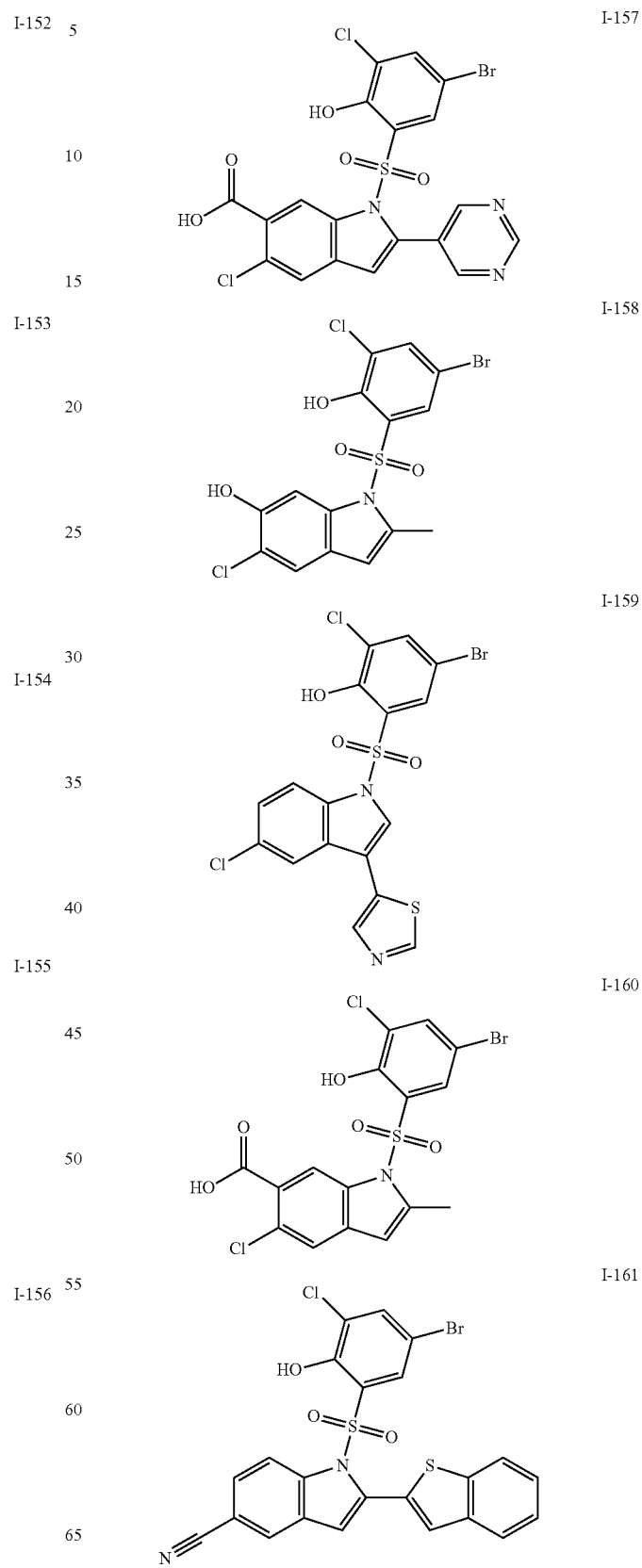

I-162
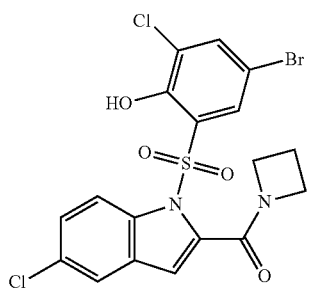
I-163
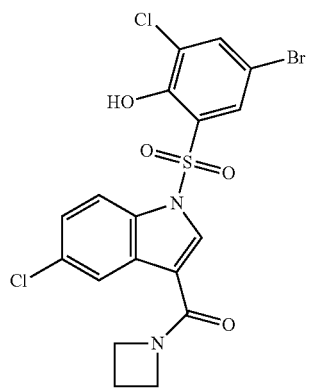
I-164
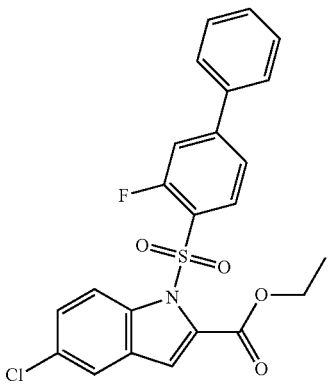
I-165
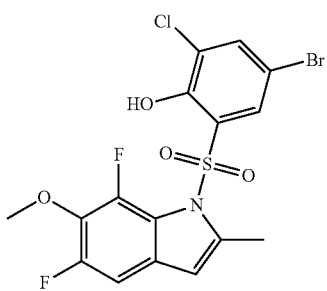
or a pharmaceutically acceptable salt thereof.
8. A composition comprising a compound according to any one of claim 1 or 7 and a pharmaceutically acceptable carrier, adjuvant, or vehicle.
* * * * *